United States Patent
Cai et al.

(10) Patent No.: US 12,421,540 B2
(45) Date of Patent: Sep. 23, 2025

(54) SEQUENTIAL PROBING OF MOLECULAR TARGETS BASED ON PSEUDO-COLOR BARCODES WITH EMBEDDED ERROR CORRECTION MECHANISM

(71) Applicant: CALIFORNIA INSTITUTE OF TECHNOLOGY, Pasadena, CA (US)

(72) Inventors: Long Cai, Pasadena, CA (US); Chee Huat Eng, Pasadena, CA (US); Sheel Shah, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 912 days.

(21) Appl. No.: 16/322,462

(22) PCT Filed: Aug. 1, 2017

(86) PCT No.: PCT/US2017/044994
§ 371 (c)(1),
(2) Date: Jan. 31, 2019

(87) PCT Pub. No.: WO2018/026873
PCT Pub. Date: Feb. 8, 2018

(65) Prior Publication Data
US 2021/0017587 A1 Jan. 21, 2021

Related U.S. Application Data

(63) Continuation-in-part of application No. 15/225,820, filed on Aug. 1, 2016, now abandoned, and a
(Continued)

(51) Int. Cl.
*C12Q 1/6841* (2018.01)

(52) U.S. Cl.
CPC ..... *C12Q 1/6841* (2013.01); *C12Q 2525/161* (2013.01); *C12Q 2537/143* (2013.01);
(Continued)

(58) Field of Classification Search
CPC ............ C12Q 1/6841; C12Q 2525/161; C12Q 2537/143; C12Q 2537/149; C12Q 2563/179; C12Q 2565/102
See application file for complete search history.

(56) References Cited

U.S. PATENT DOCUMENTS 5,364,763 A 11/1994 Kacian
5,367,066 A 11/1994 Urdea et al.
(Continued)

FOREIGN PATENT DOCUMENTS

CN 105392898 A 3/2016
EP 0611828 A1 8/1994
(Continued)

OTHER PUBLICATIONS

Chen et al. Science. 2015. 348(6233): 16 pages and Supplemental Material. (Year: 2015).*
(Continued)

*Primary Examiner* — Joseph G. Dauner
(74) *Attorney, Agent, or Firm* — SQUIRE PATTON BOGGS (US) LLP

(57) ABSTRACT

The present invention, among other things, provides technologies for detecting and/or quantifying nucleic acids in cells, tissues, organs, or organisms. Pre-designed barcodes are associated with specific molecular targets through sequential hybridization experiments. A pseudo-color based barcoding scheme is described that overcomes the limitations in the previous generation of the technology. The current method can be applied to both in vitro and in situ analysis.

27 Claims, 69 Drawing Sheets

Related U.S. Application Data continuation-in-part of application No. 15/298,219, filed on Oct. 19, 2016, now Pat. No. 10,510,435.

(60) Provisional application No. 62/428,910, filed on Dec. 1, 2016, provisional application No. 62/456,291, filed on Feb. 8, 2017, provisional application No. 62/523,127, filed on Jun. 21, 2017.

(52) U.S. Cl.
CPC . *C12Q 2537/149* (2013.01); *C12Q 2563/107* (2013.01); *C12Q 2563/179* (2013.01); *C12Q 2565/102* (2013.01); *C12Q 2565/514* (2013.01); *C12Q 2565/518* (2013.01)

(56) References Cited

U.S. PATENT DOCUMENTS

| | | | |
|---|---|---|---|
| 5,424,413 | A | 6/1995 | Hogan et al. |
| 5,629,147 | A | 5/1997 | Asgari et al. |
| 5,866,331 | A | 2/1999 | Singer et al. |
| 5,955,272 | A | 9/1999 | Lawrence et al. |
| 6,194,146 | B1 | 2/2001 | Utermohlen et al. |
| 6,534,266 | B1 | 3/2003 | Singer |
| 6,537,755 | B1 | 3/2003 | Drmanac |
| 7,189,509 | B2 | 3/2007 | Shao et al. |
| 7,727,720 | B2 | 6/2010 | Dhallan |
| 8,309,306 | B2 | 11/2012 | Nolan et al. |
| 10,457,980 | B2 | 10/2019 | Cai et al. |
| 2001/0019835 | A1 | 9/2001 | Usui |
| 2001/0026918 | A1 | 10/2001 | Collins et al. |
| 2002/0172950 | A1 | 11/2002 | Kenny et al. |
| 2003/0087279 | A1 | 5/2003 | Shao et al. |
| 2003/0129611 | A1 | 7/2003 | Bao et al. |
| 2003/0152490 | A1 | 8/2003 | Trulson et al. |
| 2003/0170613 | A1 | 9/2003 | Straus |
| 2004/0171075 | A1 | 9/2004 | Flynn et al. |
| 2004/0229253 | A1 | 11/2004 | Hyldig-Nielsen et al. |
| 2005/0069895 | A1 | 3/2005 | Woudenberg et al. |
| 2006/0275782 | A1 | 12/2006 | Gunderson et al. |
| 2008/0269068 | A1 | 10/2008 | Church et al. |
| 2009/0081688 | A1 | 3/2009 | Luo et al. |
| 2010/0221708 | A1 | 9/2010 | Yamada et al. |
| 2010/0304994 | A1 | 12/2010 | Wu et al. |
| 2010/0323348 | A1 | 12/2010 | Hamady et al. |
| 2011/0104676 | A1 | 5/2011 | Pierce et al. |
| 2012/0021410 | A1 | 1/2012 | Yin et al. |
| 2012/0046178 | A1 | 2/2012 | Van Den Boom et al. |
| 2012/0142014 | A1 | 6/2012 | Cai |
| 2012/0301886 | A1 | 11/2012 | Farrell et al. |
| 2014/0031243 | A1 | 1/2014 | Cai et al. |
| 2014/0073520 | A1 | 3/2014 | Cai et al. |
| 2014/0099637 | A1 | 4/2014 | Nolan et al. |
| 2014/0171338 | A1 | 6/2014 | Terbrueggen et al. |
| 2015/0005188 | A1* | 1/2015 | Levner ................ C12Q 1/6837 506/9 |
| 2015/0225801 | A1 | 8/2015 | Cai et al. |
| 2016/0019334 | A1 | 1/2016 | Cai et al. |
| 2016/0369329 | A1 | 12/2016 | Cai et al. |
| 2018/0142307 | A1 | 5/2018 | Cai et al. |
| 2023/0212658 | A1 | 7/2023 | Cai et al. |
| 2023/0295697 | A1 | 9/2023 | Cai et al. |

FOREIGN PATENT DOCUMENTS

| | | | |
|---|---|---|---|
| EP | 2992115 B1 | 3/2020 | |
| JP | H09168399 A | 6/1997 | |
| JP | 2002542793 A | 12/2002 | |
| JP | 2003527075 A | 9/2003 | |
| WO | WO00/65094 A | 11/2000 | |
| WO | WO 03/027640 A2 | 4/2003 | |
| WO | WO 2003/083440 A2 | 10/2003 | |
| WO | WO 03/102239 A2 | 12/2003 | |
| WO | WO 2007/001986 A2 | 1/2007 | |
| WO | WO2010/148039 A3 | 12/2010 | |
| WO | WO 2011/038403 A1 | 3/2011 | |
| WO | WO 2011/048184 A1 | 4/2011 | |
| WO | WO 2011/112634 A2 | 9/2011 | |
| WO | WO2012/0158967 A1 | 11/2012 | |
| WO | WO 2013/096851 A1 | 6/2013 | |
| WO | WO 2014/182528 A2 | 11/2014 | |
| WO | WO 2016/018960 A1 | 2/2016 | |

OTHER PUBLICATIONS

Eng et al. Nature Methods. 2017. 14(12):1153-115 and Online Methods. (Year: 2017).*
Examination Report dated Mar. 26, 2021 issued for Canadian Patent Application No. 2,907,493, 5 pages.
Final Preliminary Rejection dated Aug. 6, 2021 issued for Korean Patent Application No. 10-2015-7033924, with English translation, 7 pages.
Communication Pursuant to 94(3) EPC dated Aug. 2, 2021 issued for European Patent Application No. 19206244.6, 5 pages.
Non-Final Office Action mailed Aug. 4, 2021 for U.S. Appl. No. 16/572,511, 18 pages.
Ahern, "Biochemical, Reagents KitsOffer Scientists Good Return On Investment", The Scientist; Jul. 24, 1995; vol. 9(15), pp. 1-7.
Giestas, et al: "Multiplexed spectral coding for simultaneous detection of DNA hybridization reactions based on FRET", Sensors and Actuators B: Chemical; May 2, 2008; vol. 134, pp. 146-157.
Lassauniere, et al: "A novel multiplex real-time RT-PCR assay with FRET hybridization probes for the detection and quantitation of 13 respiratory viruses", Journal of Virological Methods; Feb. 11, 2010; vol. 165, pp. 254-260.
Notice of Reasons for Refusal mailed Dec. 15, 2020 for Japanese Patent Application No. 2019-189650, English translation 10 pages.
Communication of a notice of Opposition mailed Dec. 18, 2020 for European Patent No. EP2992115, 148 pages.
Communication of notices of Opposition (R.79(1) EPC) mailed Dec. 21, 2020 for European Patent No. EP2992115, 1 page.
Consolidated list of references for notice of Opposition mailed Dec. 18, 2020 for European Patent No. EP2992115, 2 pages.
Notice of Reasons for Rejection/Notice To File A Response mailed Dec. 29, 2020 for Korean Patent Application No. 10-2015-7033924, with English translation, 9 pages.
Almstrand, et al: "New methods for analysis of spatial distribution and coaggregation of microbial populations in complex biofilms", Applied and Environmental Microbiology; Oct. 2013; vol. 79(19), pp. 5978-5987.
Almstrand, et al: D21 Supplement—additional documents (from Consolidated list of references for notice of Opposition mailed Dec. 18, 2020).
Choi, et al: "Next Generation in Situ Hybridization Chain Reaction: higher gain, lower cost, greater durability", ACS Nano; May 27, 2014; vol. 8(5), pp. 4284-4294.
Daphnis, et al: "Detailed FISH analysis of day 5 human embryos reveals the mechanisms leading to mosaic aneuploidy", Human Reproduction 2005; Nov. 26, 2004; vol. 20(1), pp. 129-137.
Kris, et al: "High-throughput, high-sensitivity analysis of gene expression in *Arabidopsis*", Plant Physiology; Jul. 2007; vol. 144, pp. 1256-1266.
Lubeck, et al: "Single-cell in situ RNA profiling by sequential hybridization", Nature Methods 2014; Mar. 28, 2014; vol. 11(4), pp. 360-361. (D2 from Consolidated list of references for notice of Opposition mailed Dec. 18, 2020).
Lubeck, et al.: D2a Supplementary Information (from Consolidated list of references for notice of Opposition mailed Dec. 18, 2020); FIGURES 1-10 Supplementary Methods and Supplementary Note.
Mokros, et al: "Identification of chromosomal fusion sites in *Arabidopsis* mutants using sequential bicolour Bac-FISH", Genome; Aug. 2006; vol. 49(8), pp. 1036-1042.
Player, et al: "Single-copy gene detection using branched DNA (bDNA) In Situ Hybridization", Journal of Histochemistry & Cytochemistry 2001; vol. 49(5), pp. 603-611.

(56) References Cited

OTHER PUBLICATIONS

Uher, et al: "Non-informative results and monosomies in PGD: the importance of a third round of re-hybridization", Reproductive Bio Medicine Online; Aug. 12, 2009; vol. 19(4), pp. 539-546.
VYSIS MultiVysion PGT Multi-color FISH Probe Kit, Abbott Laboratories; Sep. 2014 (D5a from Consolidated list of references for notice of Opposition mailed Dec. 18, 2020).
Wang, et al: "A novel in situ RNA analysis platform for Formalin-fixed, Paraffin-embedded tissues", The Journal of Molecular Diagnostics; Jan. 1, 2012; vol. 14(1); pp. 22-29.
First Office Action and Search Report issued Jan. 4, 2022 for Chinese Patent Application No. 201780061639.2, with English translation, 51 pages.
Notice of Reasons For Refusal issued Nov. 2, 2021 for Japanese Patent Application No. 2019-189650, with English translation, 5 pages.
Communication forwarding the extended European Search Report dated Jun. 26, 2020 issued for European Patent Application No. 17837577.0, 10 pages.
Blanco, Ana, et al., "A FRET-based assay for characterization of alternative splicing events using peptide nucleic acid fluorescence in titu hybridization", Nucleic Acids Research, vol. 37, No. 17, e116 (Jun. 26, 2009).
Choi, Harry M.T., et al., "Programmable in situ amplification for multiplexed imaging of mRNA expression", Nat Biotechnol, vol. 28, No. 11, pp. 1208-1212 (Nov. 2010).
Collins, et al., A branched DNA signal amplification assay for quantification of nucleic acid targets below 100 molecules/ml, *Nucleic Acids Research 1997*, vol. 25, No. 15, pp. 2979-2984.
Eng, et al., Profiling the transcriptome with RNA SPOTs *Nature Methods* Published Online Nov. 13, 2017; doi:10.1038/NMETH. 4500, 6 pages.
Epstein, Lucy, et al., "Reutilization fo previously hybridized slides for fluorescence in situ hybridization", Cytometry vol. 21, pp. 378-381 (Year: 1995).
Femino, Andrea, et al., "Visualization of signle RNA transcript", Science 280: 585 (Year: 1998).
Fernandez-Suarez, Marta, et al., "Fluorescent probes for super-resolution imaging in living cells", Molecular Cell Biology, vol. 9, pp. 929-943 (Dec. 2008).
Flagella, et al., A multiplex branched DNA assay for parallel quantitative gene expression profiling, Analytical Biochemistry, Mar. 2006, vol. 352, pp. 50-60.
Ioannou, D., et al., "Multicolour interphase cytogenetics: 24 chromosome probes, 6 colours, 4 layers", Molecular and Cellular Probes, vol. 25, pp. 199-205 (Aug. 2011).
Kitayama, Yasuhiko, et al., "Repeated fluorescence in situ hybridization by microwave-enhanced protocol", Pathology International 2006, vol. 56, pp. 490-493.
Levesque, Marshall J., et al., "Single-chromosome transcriptional profiling reveals chromosomal gene expression regulation", Nature Methods, vol. 10, No. 3, pp. 246-248 (Mar. 2013).
Levesque, Marshall J., et al., "Visualizing SNVs to quantify allele-specific expression in single cells", Nature Methods, vol. 10, No. 9, pp. 865-867 (Sep. 2013).
Levsky, Jeffrey M., et al., "Single-cell gene expression profiling", Science 297 : 836 (Year: 2002).
Liehr, T., et al., "Multicolor FISH probe sets and their applications", Histology and Histopathology, vol. 19, pp. 229-237 (Year: 2004).
Linton, et al., Microarray Gene Expression Analysis of Fixed Archival Tissue Permits Molecular Classification and Identification of Potential Therapeutic Targets in Diffuse Large B-Cell Lymphoma, Journal Of Molecular Diagnostics, May 2012, vol. 14, No. 3, pp. 223-232.
Lu, Jing, et al., "Quantification of mIRNA Abundance in single cells using locked nucleic acid-FISH and enzyme-labeled fluorescence", Methods in Molecular Biology 680:77 (Year: 2011).
Lubeck, Eric, et al., "Single-cell in situ RNA profiling by sequential hybridization", Nature Methods, vol. 1, No. 4, pp. 360-361 (Apr. 2014).

Lubeck, Eric, et al., "Single-cell systems biology by super-resolution imaging and combinatorial labeling", Nature Methods, vol. 9, No. 7, pp. 743-748 (Jul. 2012).
Mali, Prashant, et al., "Barcoding cells using cell-surface programmable DNA-binding domains", Nature Methods vol. 10, No. 5, pp. 403-406 (May 2013).
Moffitt, Jeffrey R., et al., "High-throughput single-cell gene-expression profiling with multiplexed error-robust fluorescence in situ hybridization", PNAS Sep. 27, 2016, vol. 113, No. 39, pp. 11046-11051.
Muller, Stefan, et al., "Towards unlimited colors for fluorescence in situ hybridization (FISH)", Chromosome Research, vol. 10, pp. 223-232 (Year: 2002).
Muller, Stefan, et al., "A nonredundant multicolor bar code as a screening tool for rearrangements in neoplasia", Genes Chromosomes & Cancer, vol. 39, No. 1, pp. 59-70 (Jan. 2004).
Pon, et al., Tandem oligonucleotide synthesis using linker phosphoramidites, Nucleic Acids Research, Apr. 6, 2005, vol. 33, No. 6, pp. 1940-1948.
Shah, et al., Dynamics and Spatial Genomics of the Nascent Transcriptome by Intron seqFISH Cell (2018) doi.org/10.1016/j. cell.2018.05.035, 15 pages.
Sinclair, et al., Improved Sensitivity of BCR-A BL Detection: A Triple Probe Three-Color Fluorescence In Situ Hybridization System, *Blood*, Aug. 15, 1997, vol. 90, No. 4, pp. 1395-1402.
Theodosiou, Zenonas, et al., "Automated analysis of FISH and immunohistochemistry images: a review", Cytometry Part A, vol. 71A, pp. 439-450 (Year: 2007).
Urdea, et al., A comparison of non-radioisotopic hybridization assay methods using fluorescent, chemilluminescent and enzyme labeled synthetic oligodeoxyribonucleotide probes, *Nucleic Acids Research 1988*, vol. 16, No. 11, pp. 4937-4956.
Velculescu, et al., "Analysis of human transcriptomes", Nature Dec. 1999, vol. 23, pp. 387-388.
Zhen, D.K., et al., "Poly-FISH: A technique of repeated hybridizations that improves cytogenetic analysis of fetal cells in maternal blood", Prenatal Diagnosis, vol. 18, pp. 1181-1185 (Year: 1998).
Communication under Rule 164 EPC with supplementary partial European Search Report dated Jan. 29, 2020 issued for European Patent Application No. 17837577.0, 11 pages.
Office Action dated Mar. 6, 2020 issued for Canadian Patent Application No. 2,907,493, 7 pages.
Communication forwarding the extended European Search Report dated Feb. 7, 2020 issued for European Patent Application No. 19206244.6, 8 pages.
Shah, et al., "In Situ Transcription Profiling of Single Cells Reveals Spatial Organization of Cells in the Mouse Hippocampus", J. Neuron., NeuroResource Oct. 19, 2019, vol. 92, No. 2, pp. 342-357.
Summons to Attend Oral Proceedings under Rule 115(1) EPC dated Nov. 17, 2022 for European Patent Application No. 14795452.3, with updated listing of references; 13 pages.
Brief Communication dated Dec. 5, 2022 regarding video-conference for Oral Proceedings for European Patent Application No. 14795452.3; 1 page.
First Office Action dated Nov. 2, 2022 for Chinese Patent Application No. 201910951092.4; with English translation (Machine Translation); 16 pages.
Miner, et al: "Molecular barcodes detect redundancy and contamination in the hairpin-bisulfite PCR", Nucleic Acids Research; published online Sep. 30, 2004; vol. 32, No. 17; e35.
Weremowicz, et al: "Validation of DNA probes for preimplantation genetic diagnosis (PGD) by fluorescence in situ hybridization (FISH)R1", Prenat Diagn; published online Sep. 4, 2006; vol. 26; pp. 1042-1050.
Opponent's Final Submissions for Oral Proceedings for European Patent Application No. 14795452.3 filed Apr. 14, 2023; 39 pages.
Nederlof, et al: "Multiple Fluorescence In Situ Hybridization", Cytometry 1990; vol. 11, pp. 1126-1131.
Office Action dated Feb. 24, 2023 for Korean Patent Application No. 10-2022-7005979; with English translation, 15 pages.
Communication Pursuant to Article 94(3)EPC dated Mar. 28, 2023 forwarding the Examination Report for European Patent Application No. 17837577.0; 5 pages.

(56) References Cited

OTHER PUBLICATIONS

Notification of Reasons for Refusal dispatched May 9, 2023 for Japanese Patent Application No. 2022-074240; with English translation, 13 pages.
Office Action for Canadian Patent Application No. 2,907,493 dated May 11, 2023; 5 pages.
U.S. Appl. No. 61/817,651 application claimed in PCT/2014/036258, Filed Apr. 30, 2013, Cai, et al.
U.S. Appl. No. 61/971,974 application claimed in PCT/2014/036258, Filed Mar. 28, 2014, Cai, et al.
Examination Report for Canadian Patent Application No. 3,032,649 dated Jul. 21, 2023; 4 pages.
Lee, et al., "Highly multiplexed subcellular RNA sequencing in situ", Science; Mar. 21, 2014; vol. 343(6177); pp. 1360-1363.
20230414 Submission in Opposition Proceedings for EP2992115: Submission List, 2 pages.
20230414 Submission in Opposition Proceedings for EP2992115: Letter to EPO Summary of Requests; 7 pages.
20230414 Submission in Opposition Proceedings for EP2992115: Letter to EPO Attendee List for Oral Proceedings; 2 pages.
20230414 Submission in Opposition Proceedings for EP2992115: Published Evidence 1; Takei, et al., Nature 2021; 53 pages.
20230414 Submission in Opposition Proceedings for EP2992115: Published Evidence 2; Eng, et al., Nature 2019; 37 pages.
20230414 Submission in Opposition Proceedings for EP2992115: Published Evidence 4; Shah, et al., Cell 2018; 35 pages.
20230414 Submission in Opposition Proceedings for EP2992115: New First Auxiliary Request 1 through New Twelfth Auxiliary Request (clean and marked); 71 pages.
04142023 EPO Acknowledgment of Receipt (Submission No. 11947234) for written submissions filed for EP2992115; 2 pages.
20230614 Opponent additional submission in advance of Oral Proceedings; 23 pages.
20230614 Opponent additional submission in Opposition Proceedings made following summons to attend Oral Proceedings; 2 pages.
20230614 EPO Acknowledgment of Receipt (Submission No. 12129203) for written submissions filed by opponent; 1 pages.
20230614 Letter to EPO; Request For Adjournment of Oral Proceedings; 1 page.
20230622 Summons to Oral Proceedings canceled (adjournment granted); 1 page.
20230626 Postponement; Summons To Attend Oral Proceedings pursuant to Rule 115(1) EPC; 6 pages.
20231005 Submission for Oral Proceedings by Opponent; Letter to EPO; EPO Acknowledgment of Receipt (Submission No. 12497872); Opponent's reply to examination report in opposition proceedings for EP2992115; 5 pages.
20231006 Submission in Opposition Proceedings for EP2992115: Letter to EPO; EPO Form 1038; 1 page.
20231006 Submission in Opposition Proceedings for EP2992115: Letter to EPO; EPO Form 1038 Description of Documents filed; 2 pages.
20231006 Submission in Opposition Proceedings for EP2992115: Letter to EPO; Attendee List for Oral Proceedings; 2 pages.
20231006 Submission in Opposition Proceedings for EP2992115: Letter to EPO; Summary of Requests; 17 pages.
20231006 Submission in Opposition Proceedings for EP2992115: D31 Declaration by Michael B. Elowitz, 16 pages.
20231006 Submission in Opposition Proceedings for EP2992115: D32 Declaration by Arjun Raj, 14 pages.
20231006 Submission in Opposition Proceedings for EP2992115: D33 Precautions for Handling of RNA; Roche Life Science Products Education Center, https://lifescience.roche.com/global/en/article-listing/article/precaustions-for-handling-of-rna.html; 7 pages.
20231006 Submission in Opposition Proceedings for EP2992115: Main Request (clean); 3 pages.
20231006 Submission in Opposition Proceedings for EP2992115: Main Request (marked); 3 pages.
20231006 Submission in Opposition Proceedings for EP2992115: New Auxiliary Request 1 through New Auxiliary Request 21 (clean and marked); 136 pages.
20231006 EPO Acknowledgment of Receipt (Submission No. 12505217) for written submissions filed for EP2992115; 1 page.
20231006 EPO Acknowledgment of Receipt (Submission No. 12505057) for written submissions filed for EP2992115; 3 pages.
Decision of Rejection dated Jun. 27, 2024 for Chinese Patent Application No. 201910951092.4; with English translation, six pages.
Examination Report for Canadian Patent Application No. 3,032,649 dated Nov. 19, 2024; 4 pages.
20240422 Notification of Appeal Number; Commencement of Proceedings before the Board of Appeal for EP2992115; 7 pages.
20240610 Internal EPO Communication regarding Withdrawal of Appeal for EP2992115; 4 pages.
20240612 Withdrawal of Appeal for EP2992115; 4 pages.
20240613 Closure of Appeal Proceedings EP2992115; 1 page.
20240614 Communication Pursuant to Rule 82(2) EPC for EP2992115; 4 pages.
EPO Communication Pursuant to 94(3) EPC dated Dec. 20, 2023 forwarding the Examination Report for European Patent Application No. 19206244.6; 6 pages.
Notice of Final Rejection dated Nov. 27, 2023 for Korean Patent Application No. 10-2022-7005979; with English translation, 7 pages.
Decision To Refuse dated Dec. 26, 2023 for Japanese Patent Application No. 2022-074240; with English translation, 13 pages.
EPO Communication dated Feb. 13, 2024 forwarding Interlocutory Decision in Opposition Proceedings for EP2992115; 112 pages.

* cited by examiner

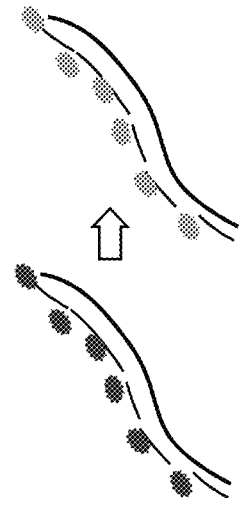
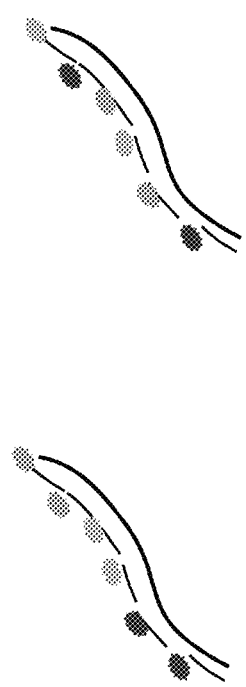
| | A spatial barcodes | B spectral barcodes | C temporal sequential barcodes |
|---|---|---|---|
| Scales: | $_FP_N$ | $_FC_N$ | seqFISH $F^N$ |
| Max capacity: (assuming 5 dyes) Coding scheme | 720 | 31 | $5^7=78,125$ $5^3=125$ 4-5 colors |
| Probes needed | 20-40 | 20-40 | 10-20 rehybs probes |
FIG. 1

| Serial Hyb | Barcoding Hyb1 | Barcoding Hyb2 | Barcoding Hyb3 | Barcoding Hyb4 |
|---|---|---|---|---|
| 1 | Readout 1 (Red) | Readout 13 (Red) | Readout 25 (Red) | Readout 37 (Red) |
|   | Readout 2 (Green) | Readout 14 (Green) | Readout 26 (Green) | Readout 38 (Green) |
|   | Readout 3 (Blue) | Readout 15 (Blue) | Readout 27 (Blue) | Readout 39 (Blue) |
| 2 | Readout 4 (Red) | Readout 16 (Red) | Readout 28 (Red) | Readout 40 (Red) |
|   | Readout 5 (Green) | Readout 17 (Green) | Readout 29 (Green) | Readout 41 (Green) |
|   | Readout 6 (Blue) | Readout 18 (Blue) | Readout 30 (Blue) | Readout 42 (Blue) |
| 3 | Readout 7 (Red) | Readout 19 (Red) | Readout 31 (Red) | Readout 43 (Red) |
|   | Readout 8 (Green) | Readout 20 (Green) | Readout 32 (Green) | Readout 44 (Green) |
|   | Readout 9 (Blue) | Readout 21 (Blue) | Readout 33 (Blue) | Readout 45 (Blue) |
| 4 | Readout 10 (Red) | Readout 22 (Red) | Readout 34 (Red) | Readout 46 (Red) |
|   | Readout 11 (Green) | Readout 23 (Green) | Readout 35 (Green) | Readout 47 (Green) |
|   | Readout 12 (Blue) | Readout 24 (Blue) | Readout 36 (Blue) | Readout 48 (Blue) |

FIG. 10

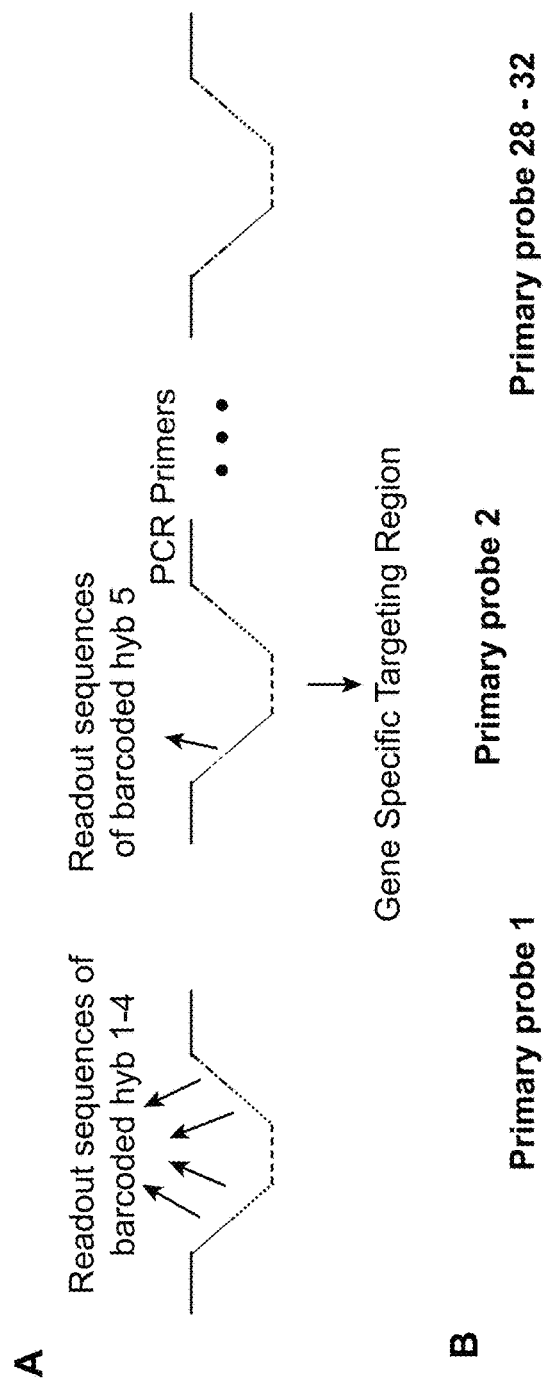
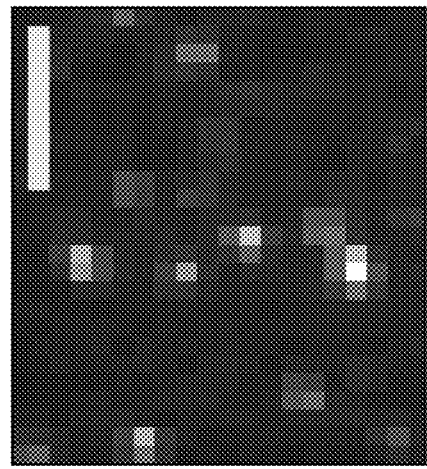
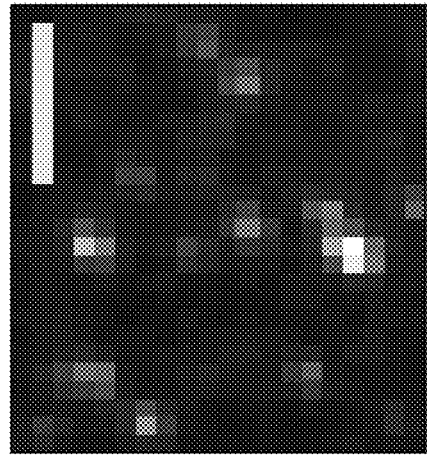
FIG. 17

A
readout probe 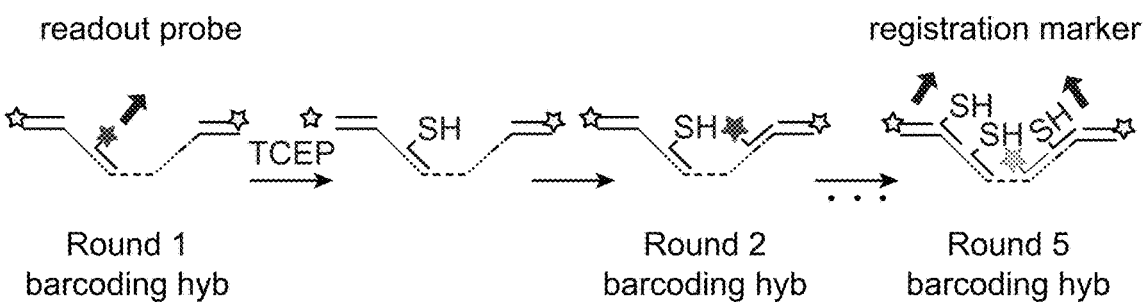 registration marker
Round 1 barcoding hyb   Round 2 barcoding hyb   Round 5 barcoding hyb
B
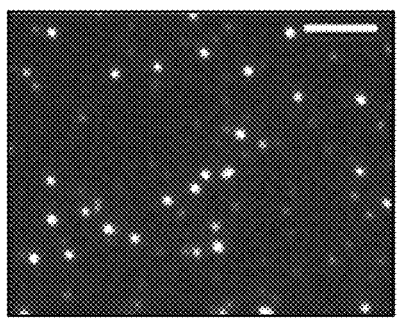 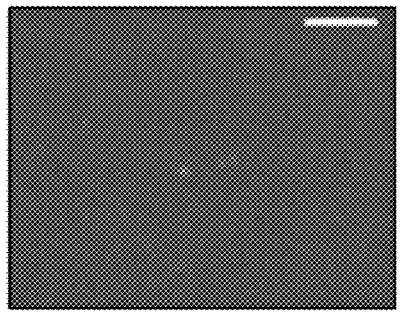
Channel 647
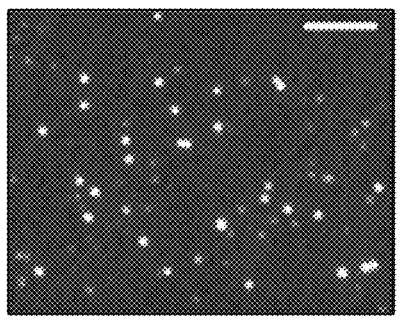 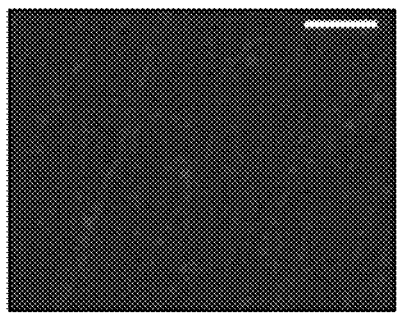
Channel 594
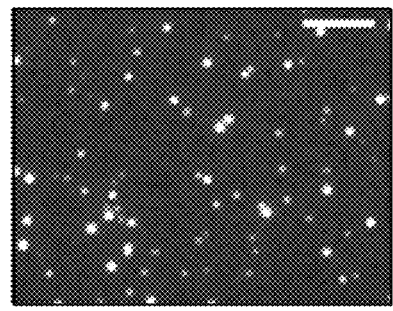 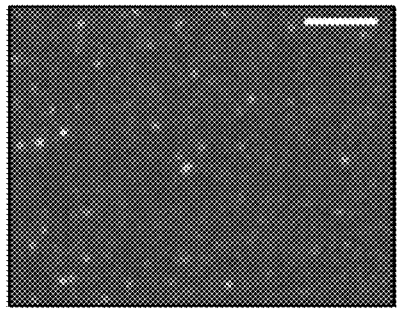
Channel 532
FIG. 18

A
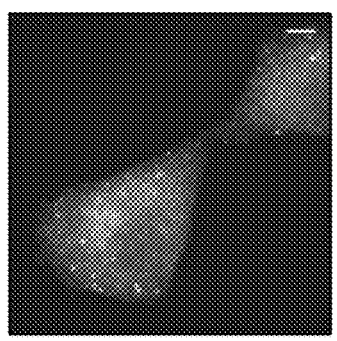
Aurka
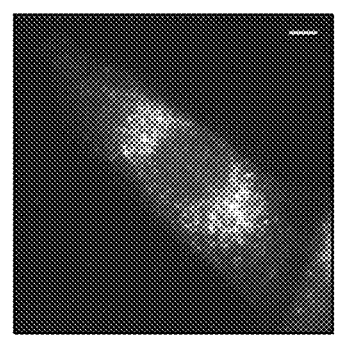
Bgn
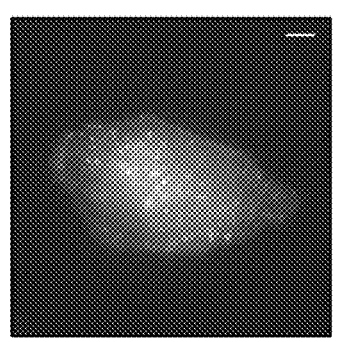
Ccna2
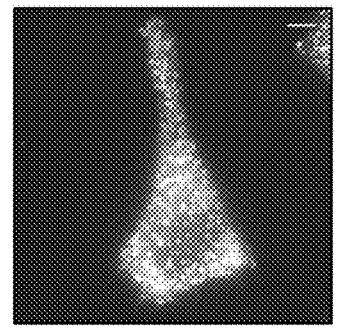
Eef2
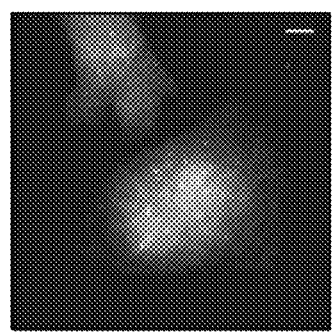
Igsf8
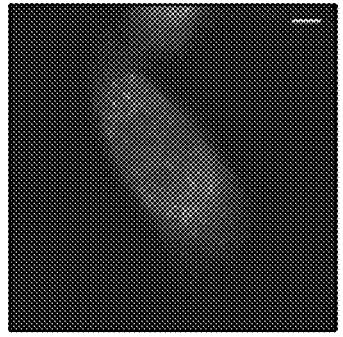
Tfrc
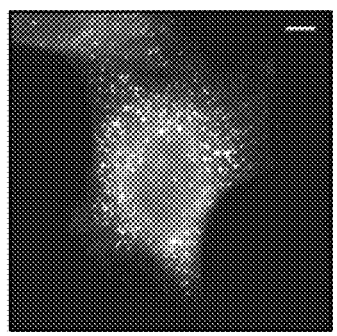
Tubb5
B
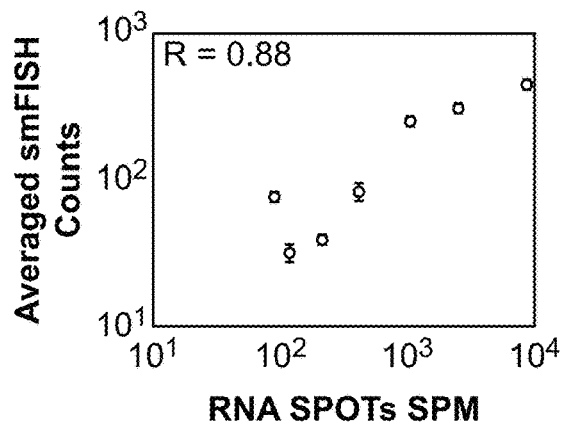
FIG. 23

A
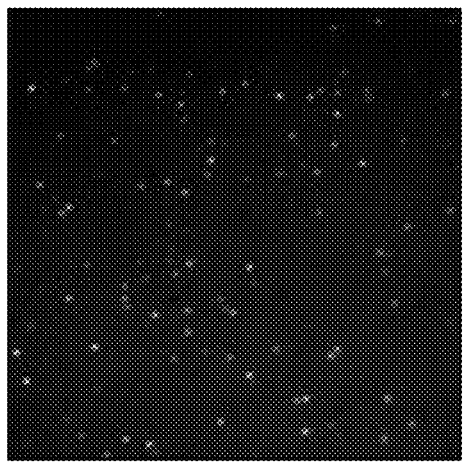
Hyb1 - Channel 647
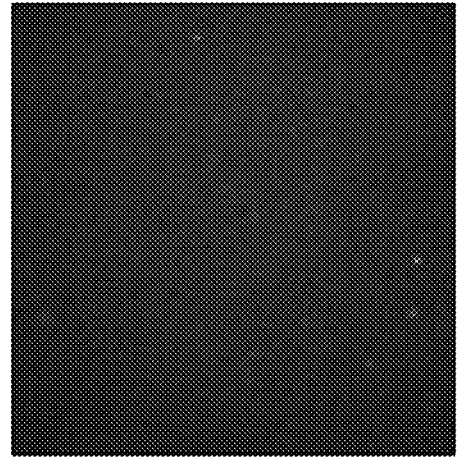
Hyb1 - Channel 594
B
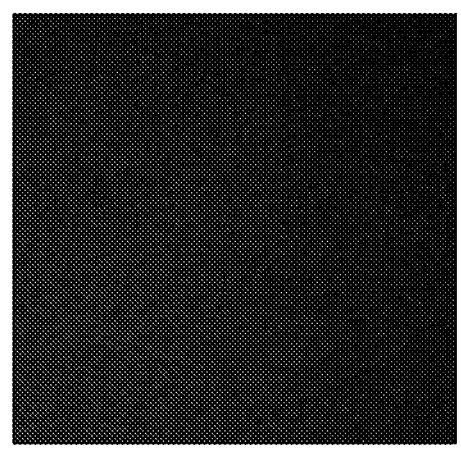
Channel 647 after TCEP treatment and washed
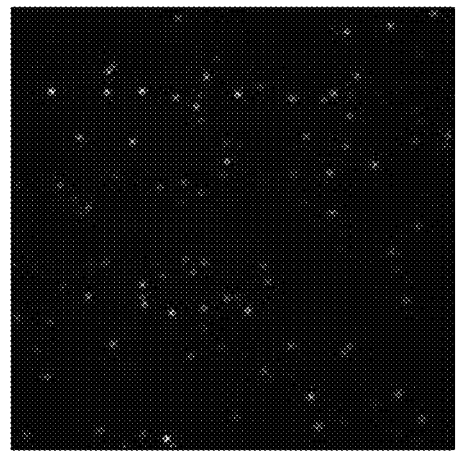
Hyb2 - Channel 594
FIG. 29

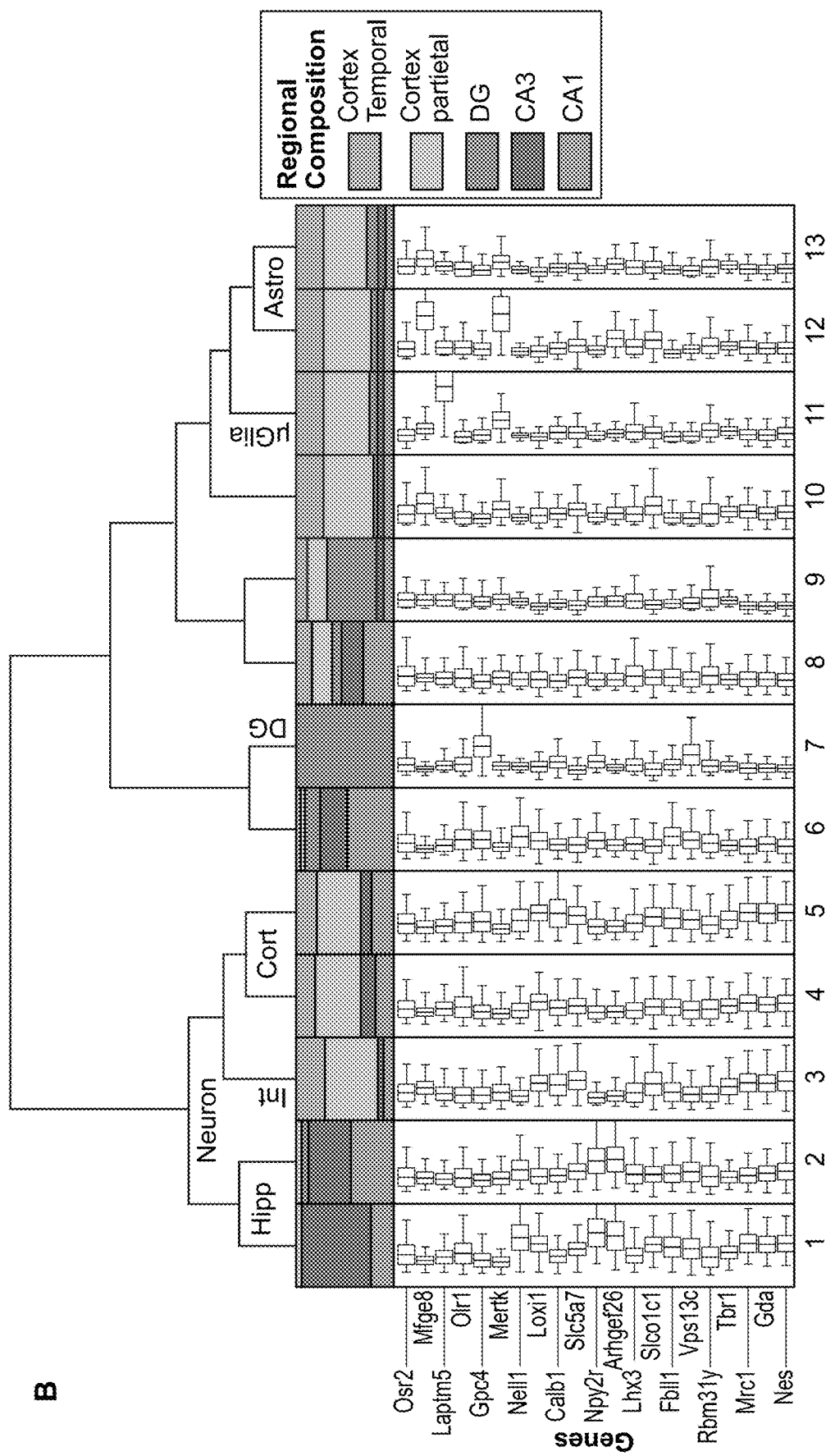
FIG. 34 (Cont. 1)

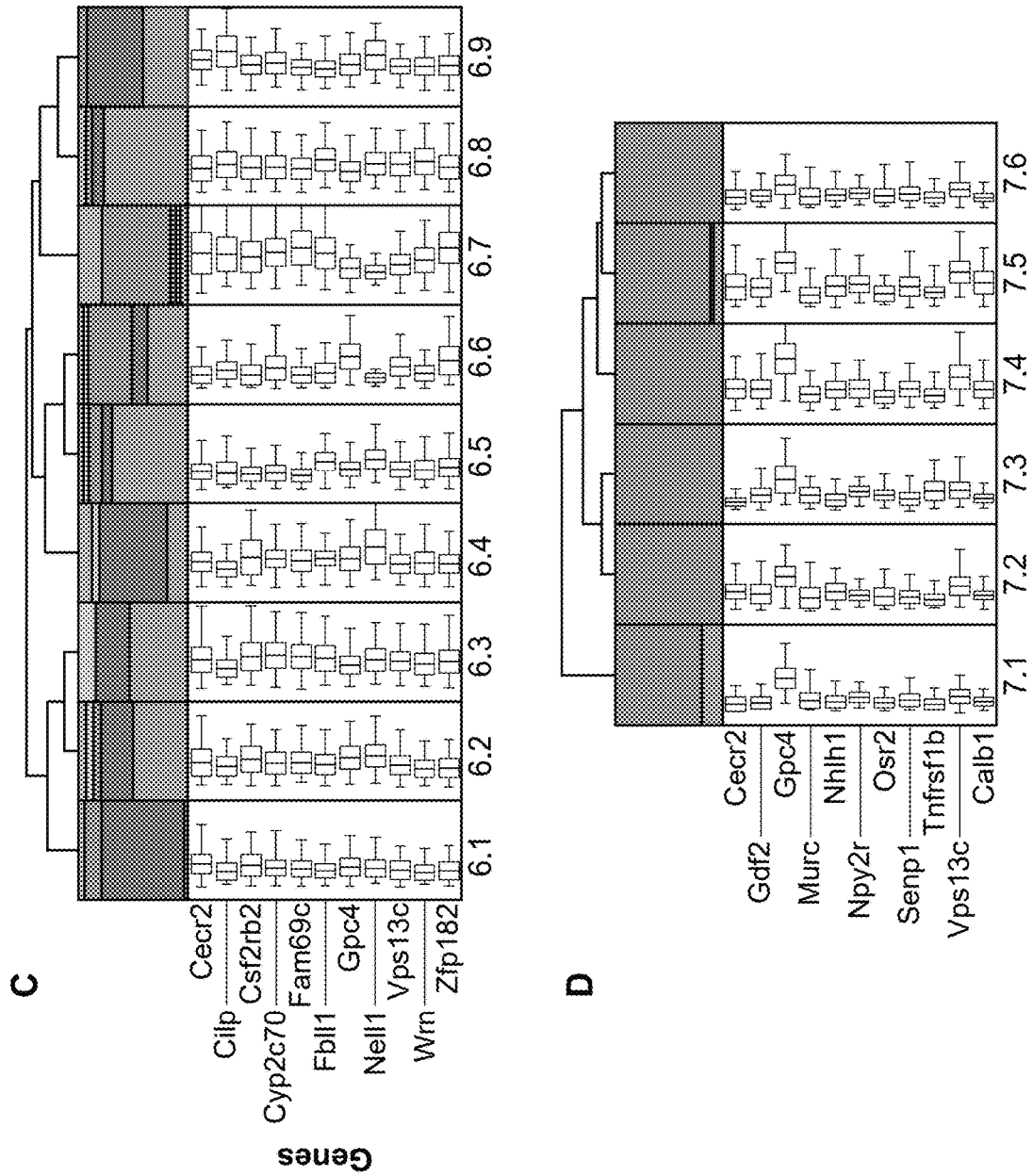
FIG. 34 (Cont. 2)

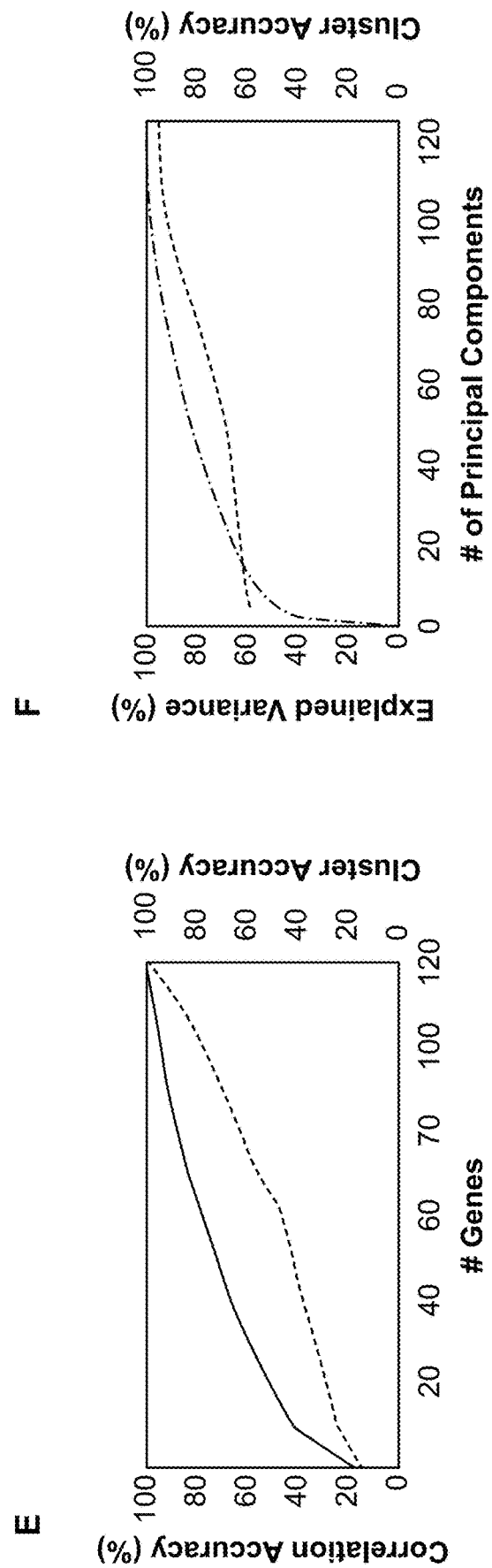
FIG. 34 (Cont. 3)

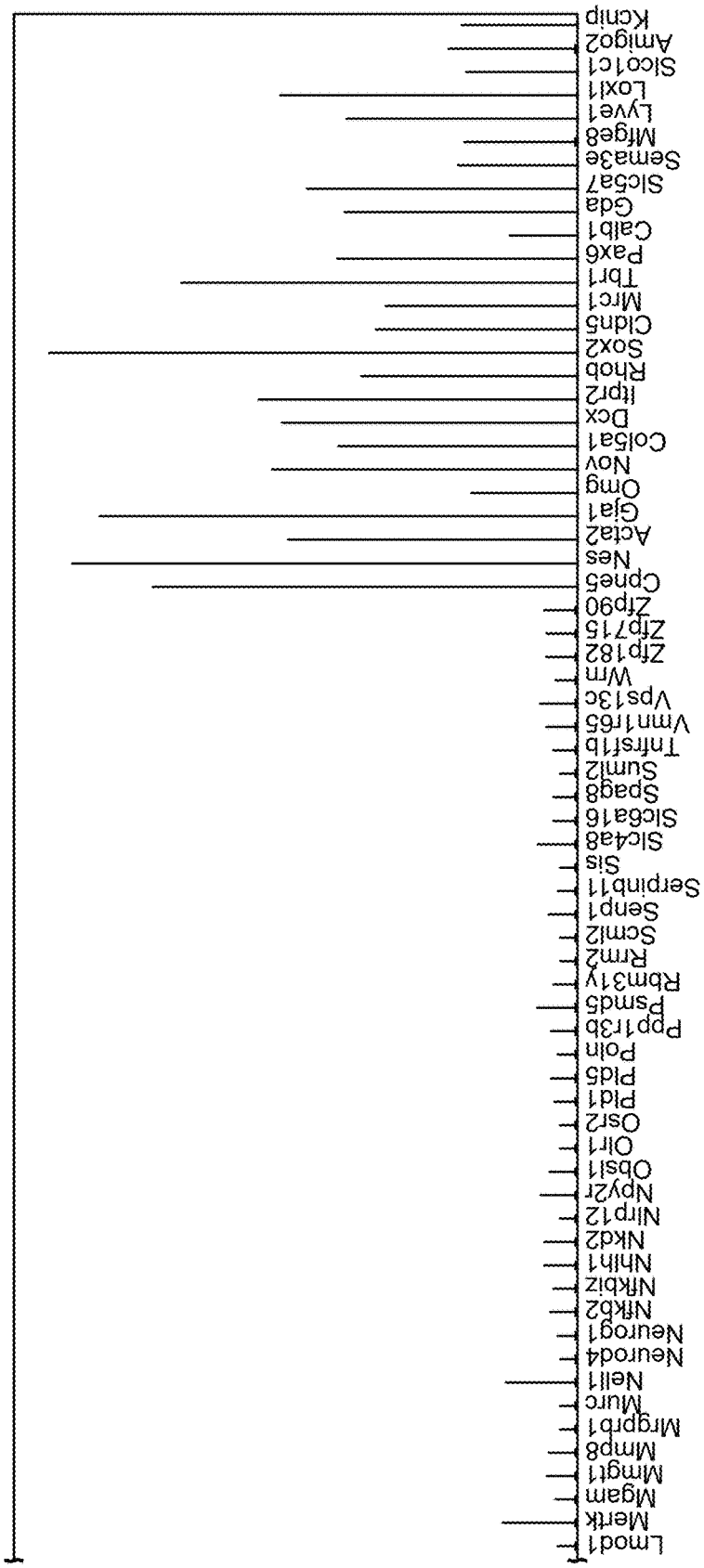
FIG. 43 (Cont. 1)

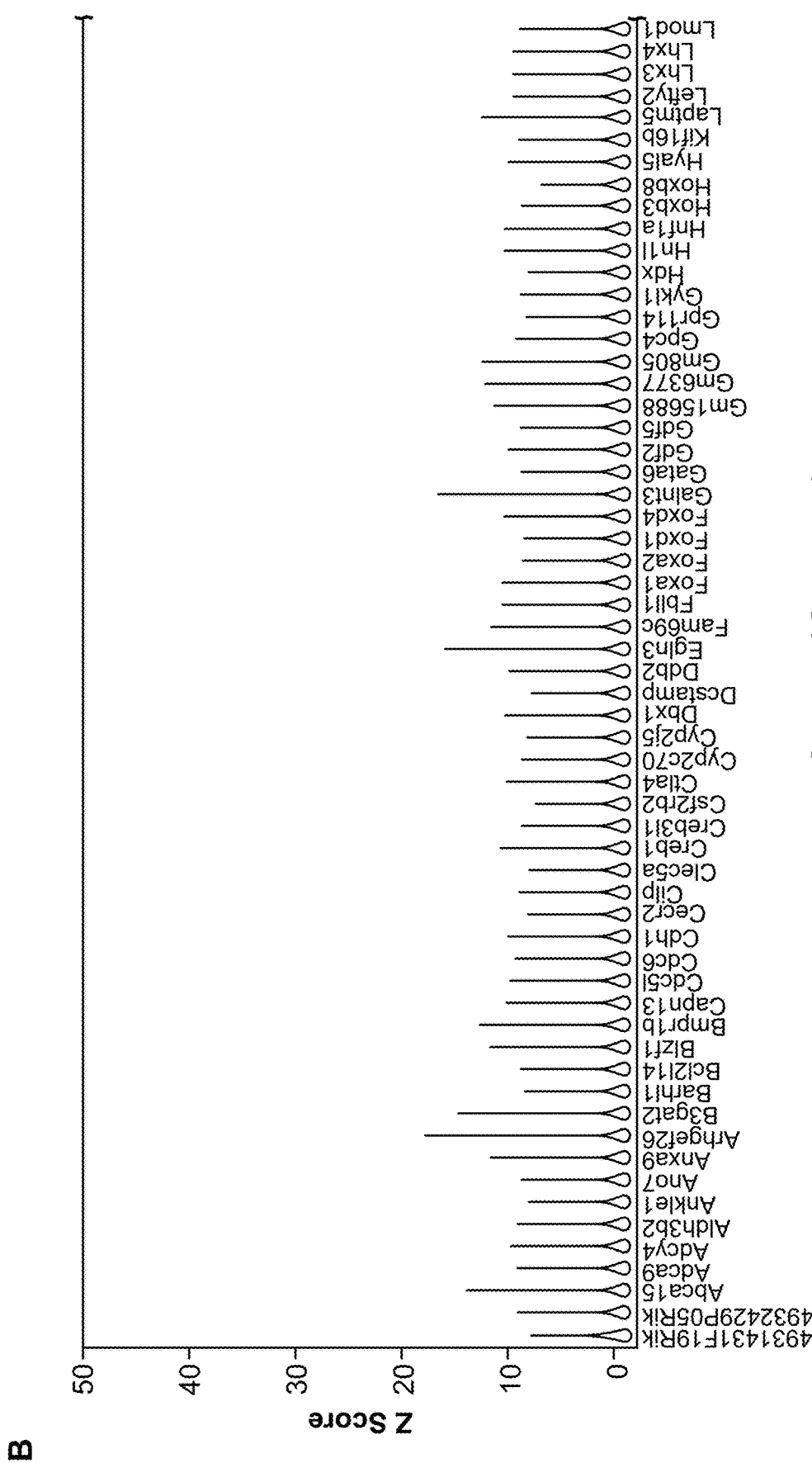
FIG. 43 (Cont. 2)

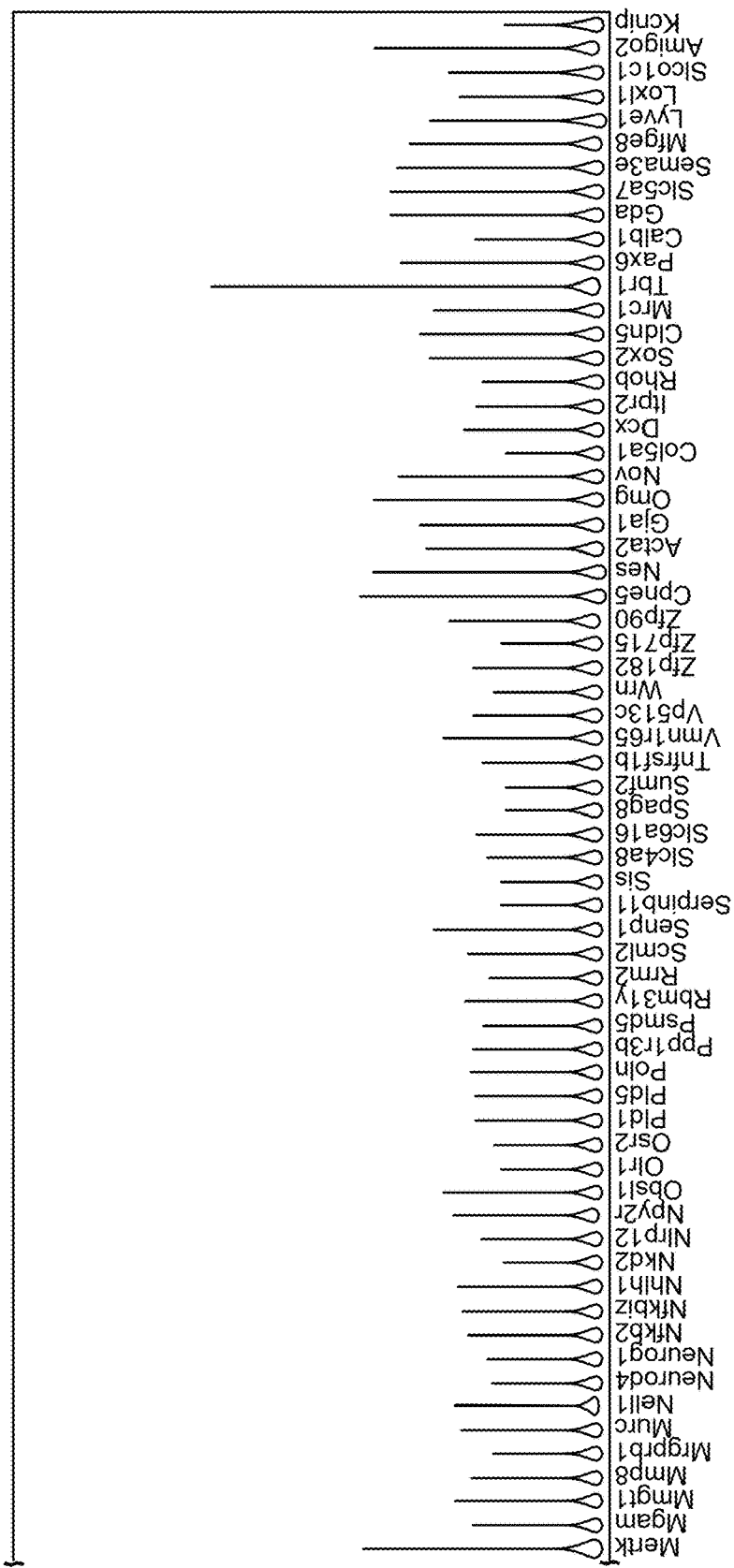
FIG. 43 (Cont. 3)

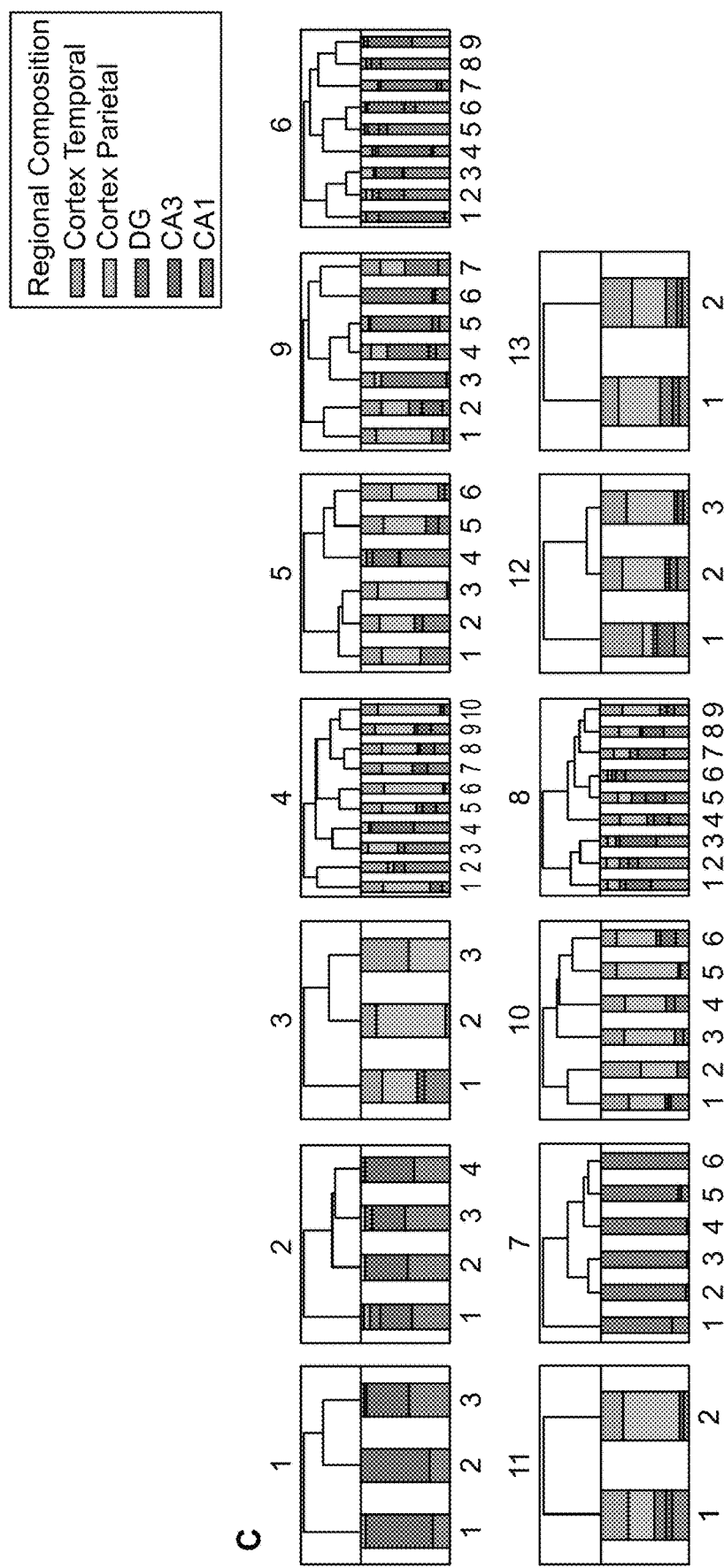
FIG. 43 (Cont. 4)

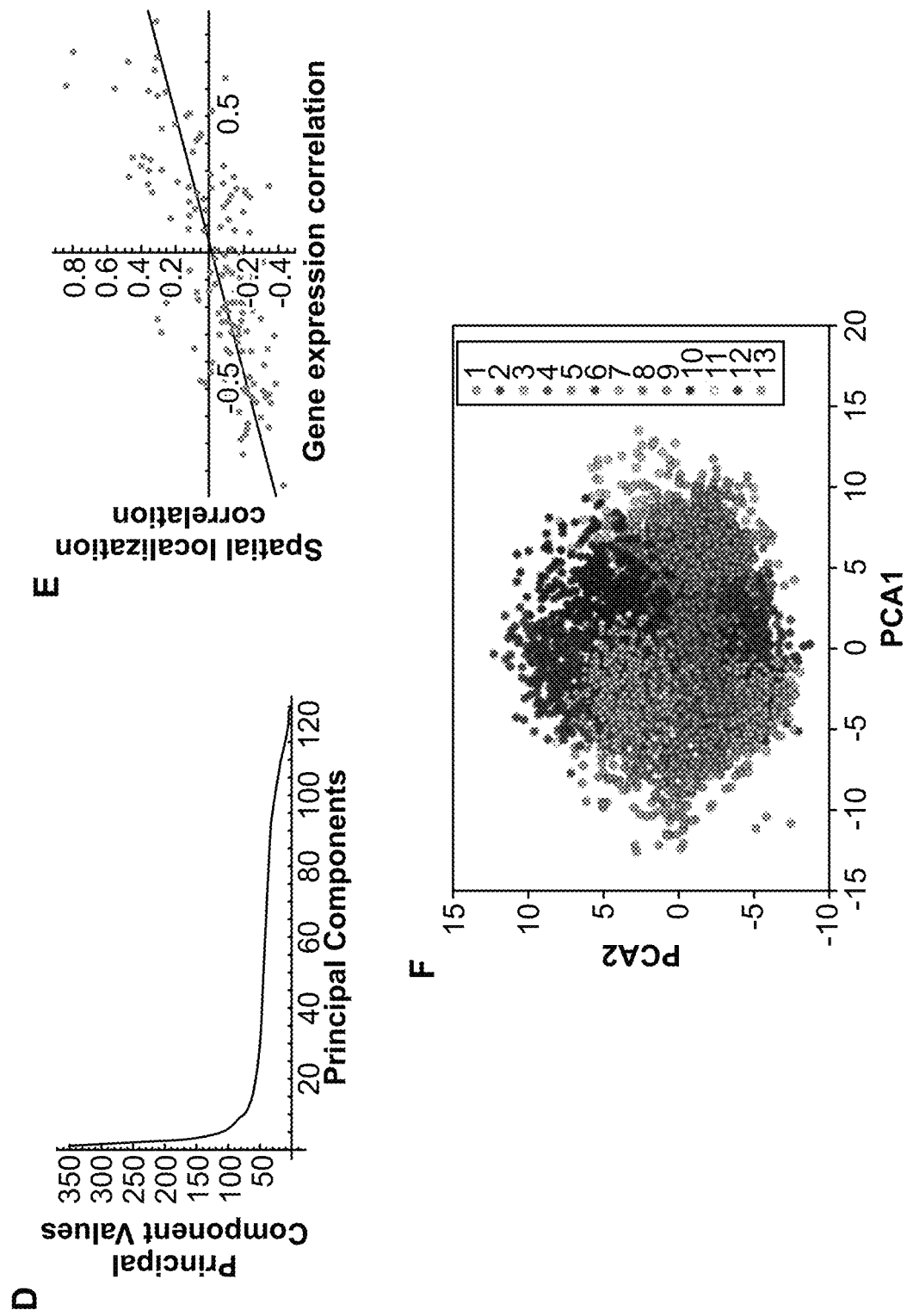
FIG. 43 (Cont. 5)

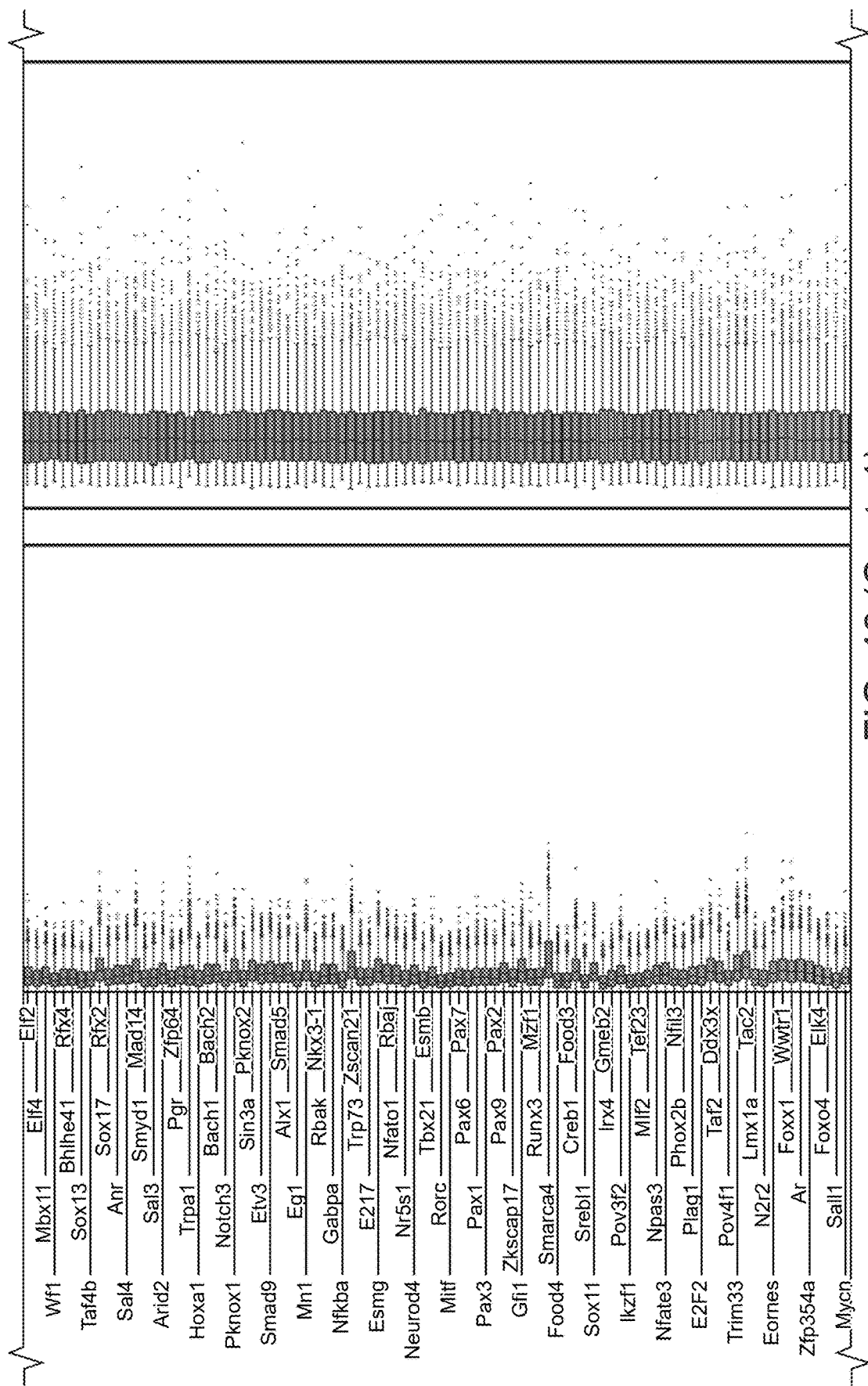
FIG. 46 (Cont. 1)

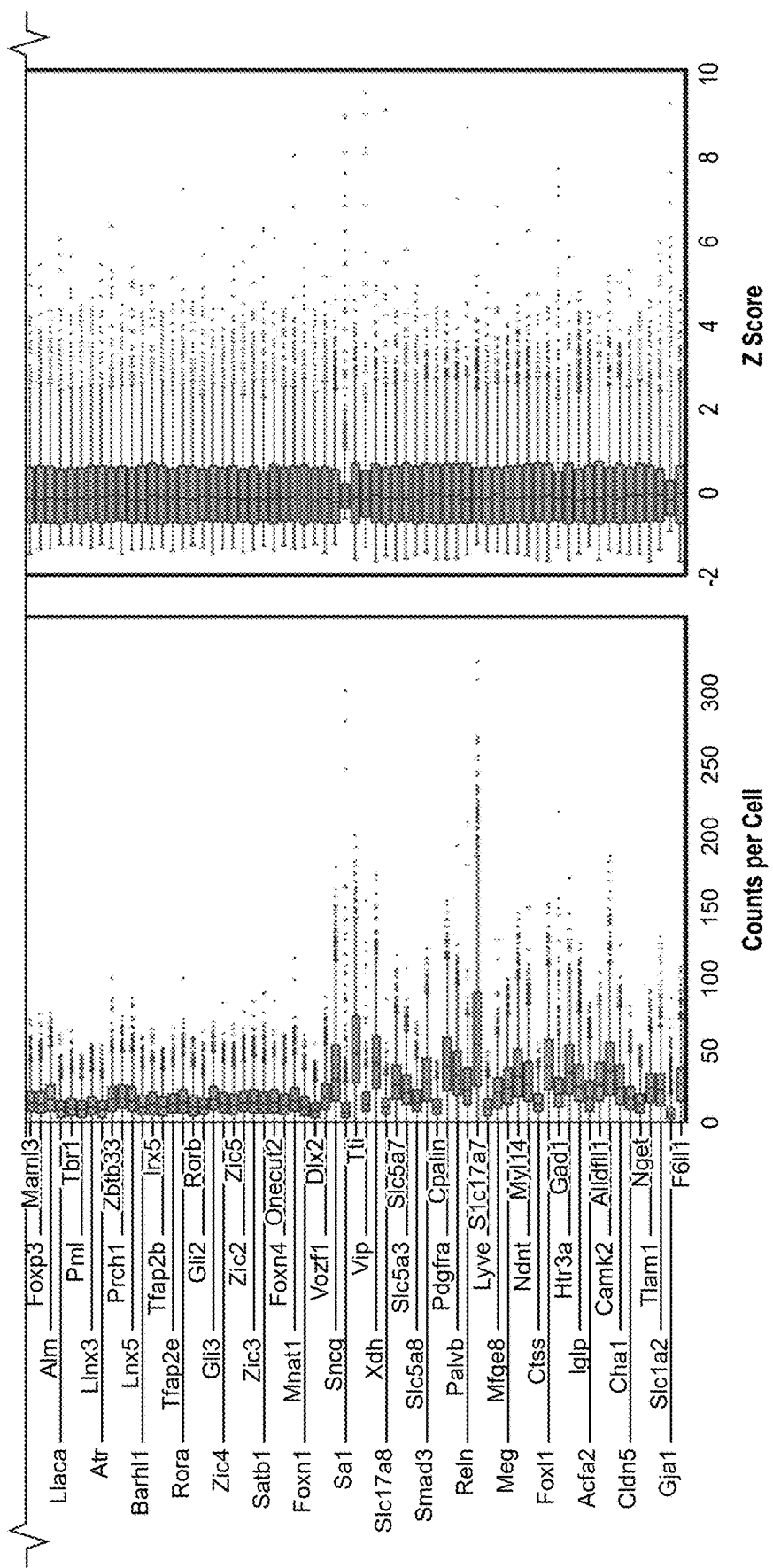
FIG. 46 (Cont. 2)

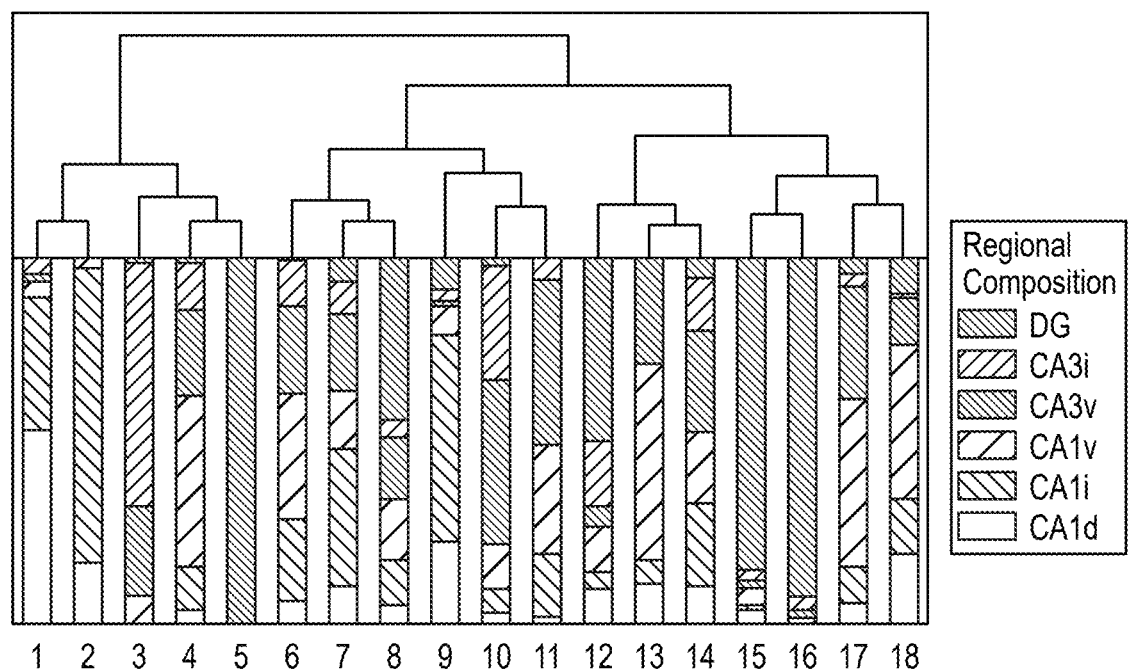
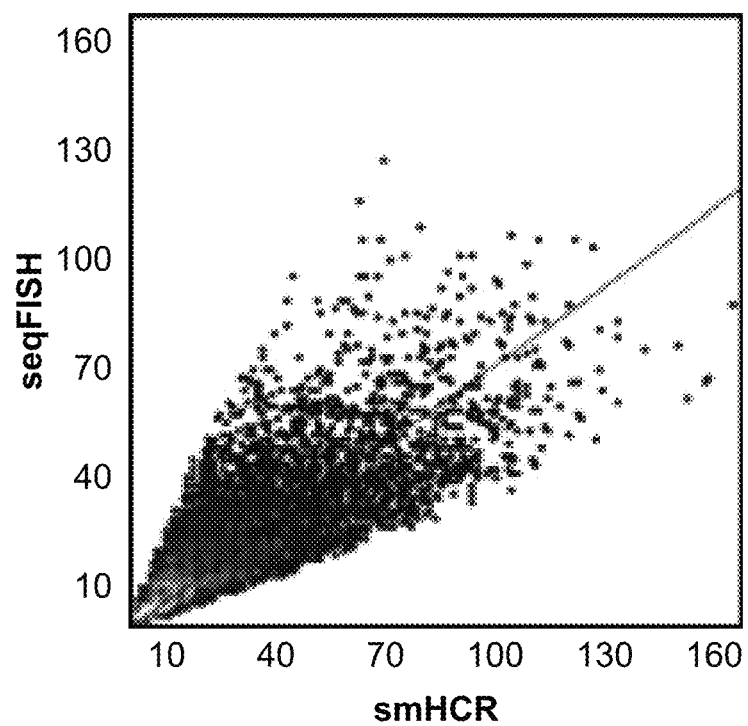
FIG. 46 (Cont. 3)

E
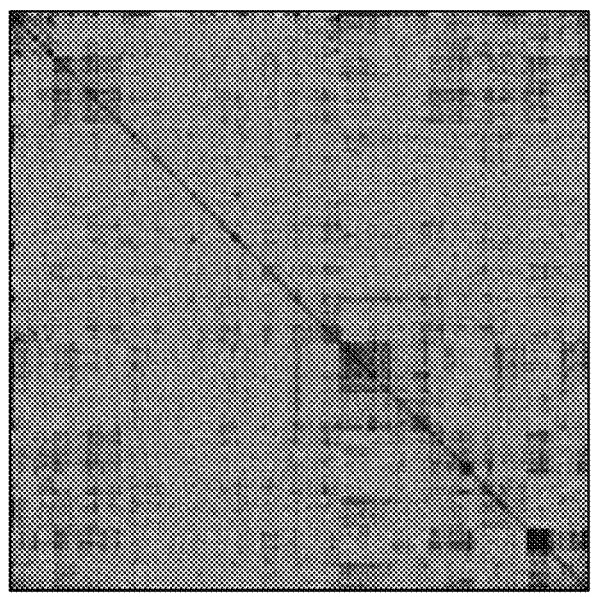
F
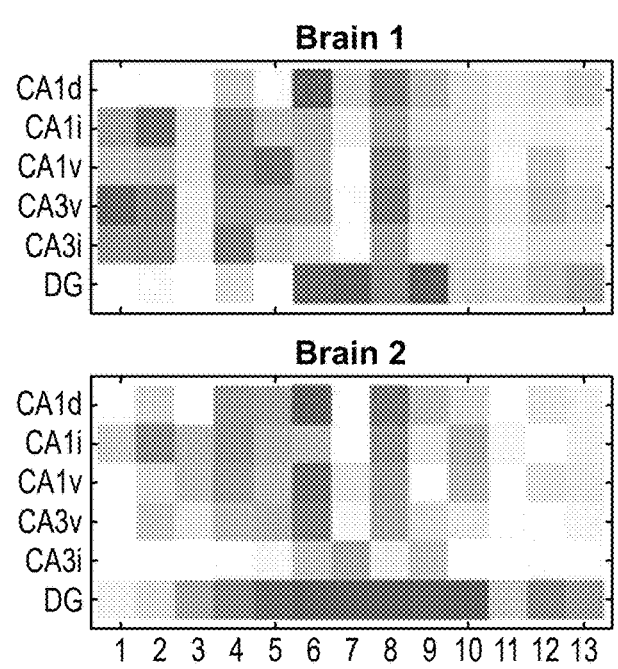
G
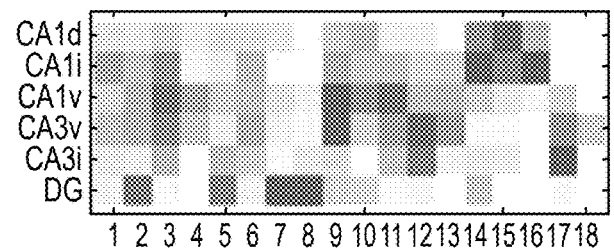
FIG. 46 (Cont. 4)

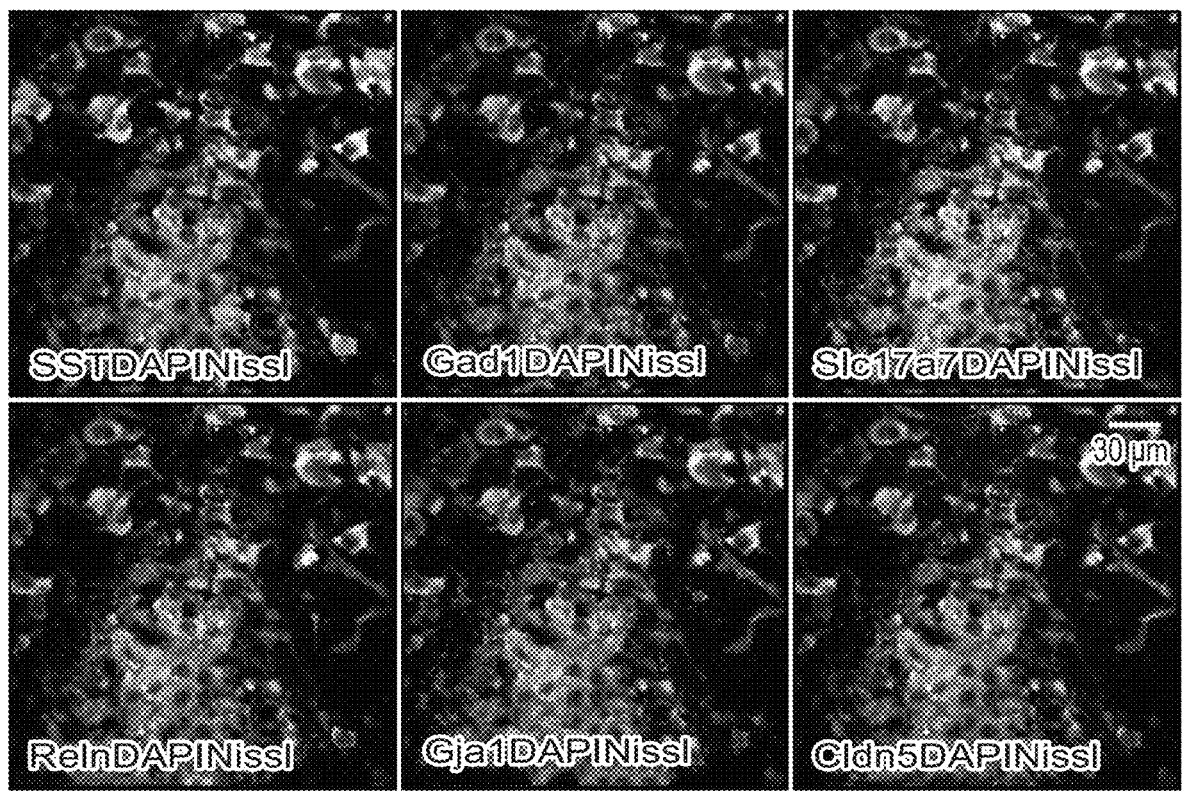
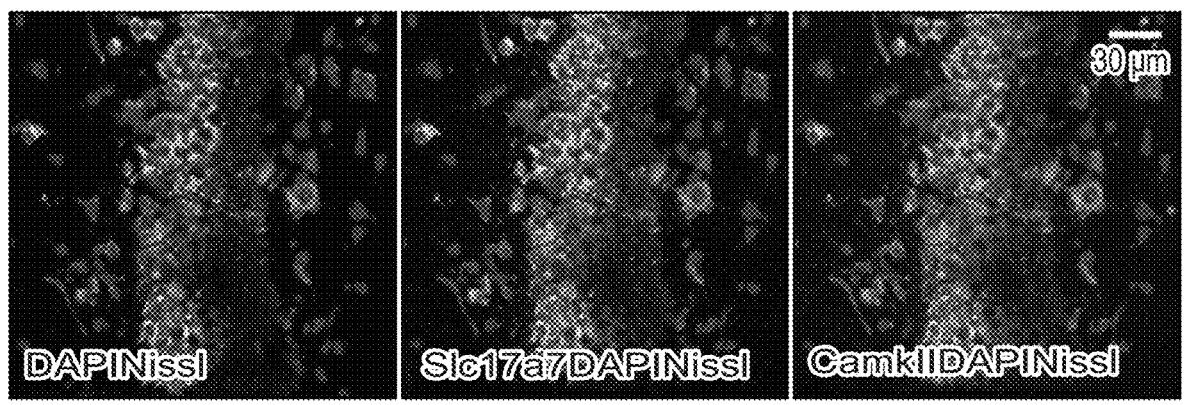
FIG. 47

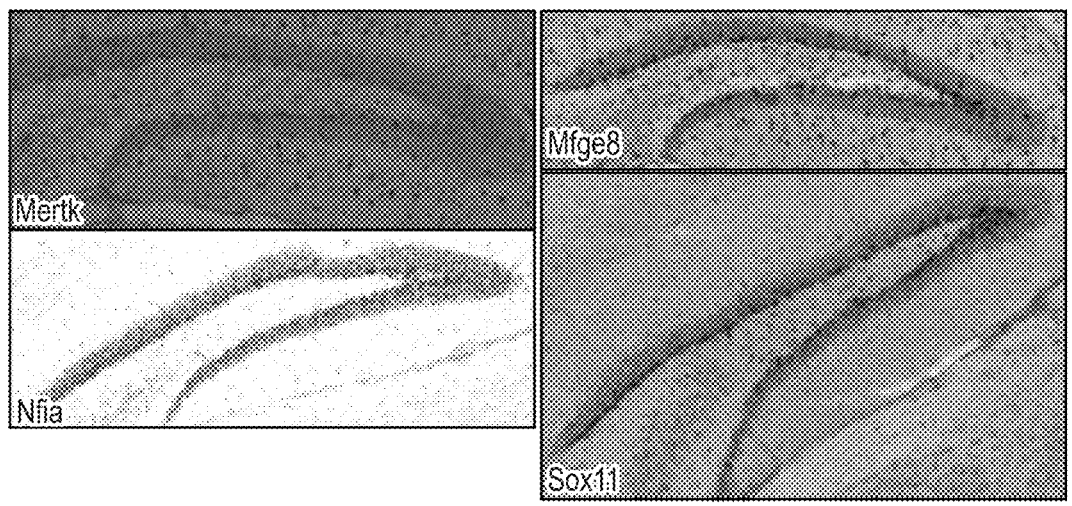
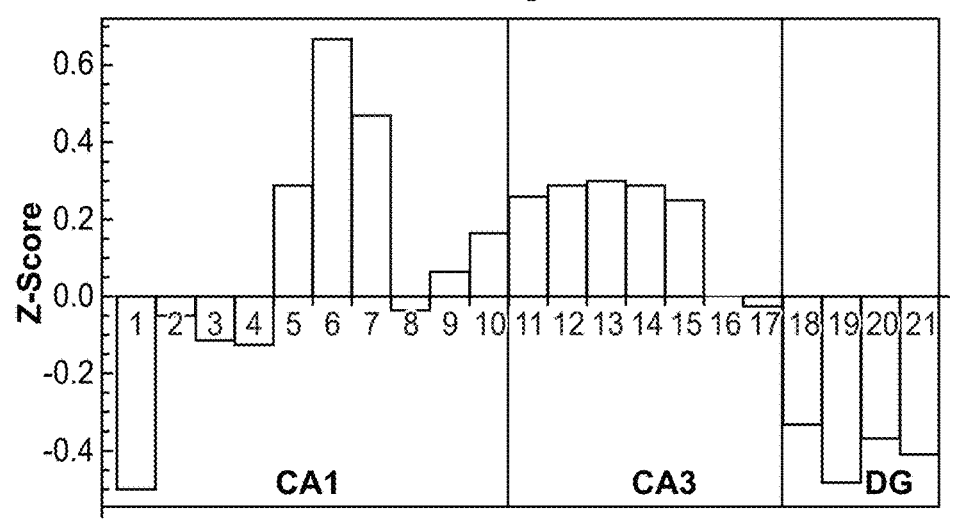
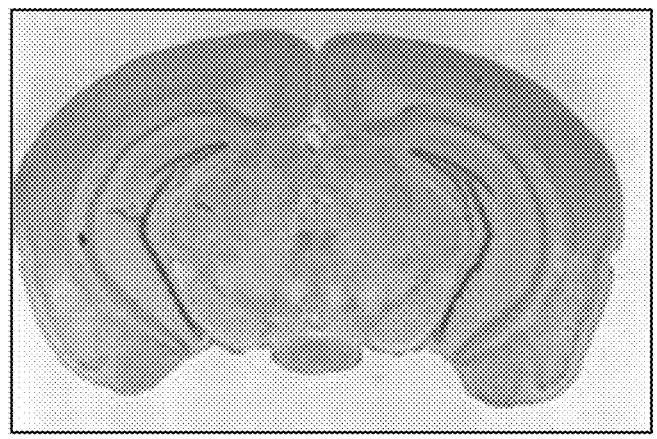
FIG. 48

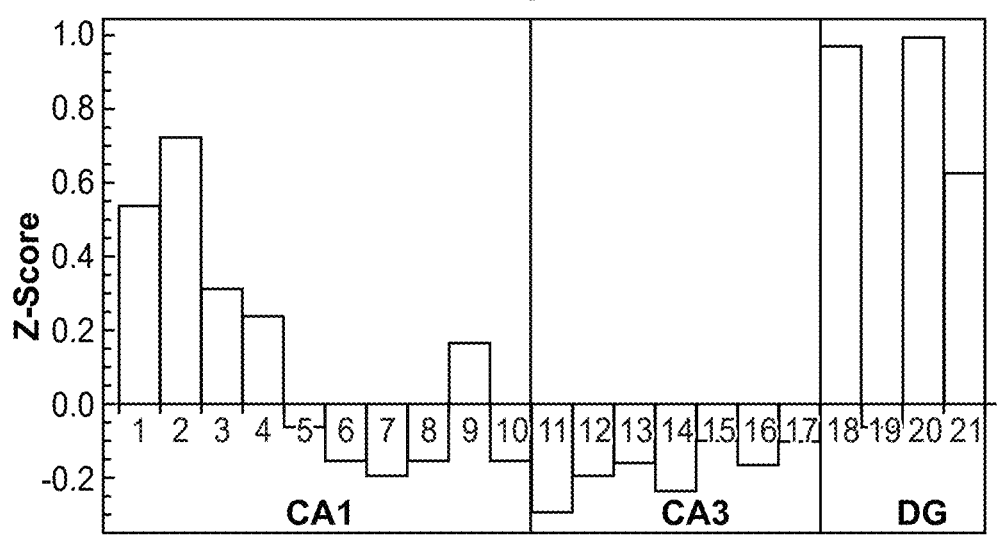
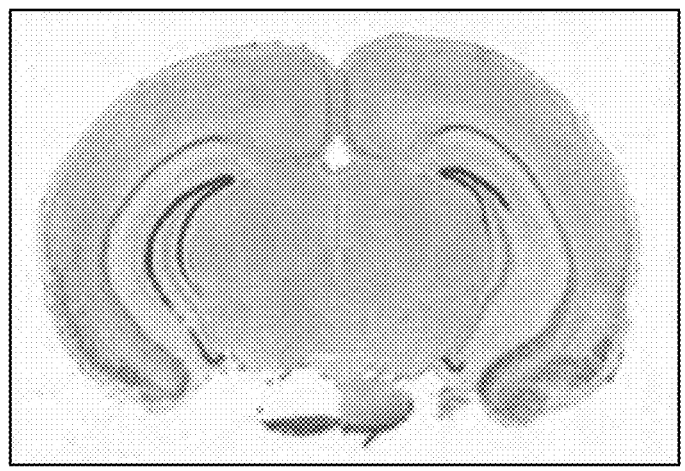
FIG. 48 (Cont.)

SEQUENTIAL PROBING OF MOLECULAR TARGETS BASED ON PSEUDO-COLOR BARCODES WITH EMBEDDED ERROR CORRECTION MECHANISM

CROSS-REFERENCE TO RELATED APPLICATIONS

This application is the U.S. National Stage of International Application No. PCT/US17/44994, filed Jan. 8, 2017, which claims priority to U.S. patent application Ser. No. 15/225,820, filed on Aug. 1, 2016 and entitled "Multiplex Labeling of Molecules by Sequential Hybridization Barcoding Using Probes With Cleavable Linkers," U.S. patent application Ser. No. 15/298,219, filed on Oct. 19, 2016 and entitled "Error Correction of Multiplex Imaging Analysis by Sequential Hybridization," U.S. Patent Provisional Application No. 62/428,910, filed on Dec. 1, 2016 and entitled "Single Molecule Profiling Through Serial and Barcoded Hybridization," U.S. Patent Provisional Application No. 62/456,291, filed on Feb. 8, 2017 and entitled "Imaging-based Transcriptomic and Translational Profiling of 1000 Genes with in vitro seqFISH," and U.S. Patent Provisional Application No. 62/523,127, filed on Jun. 21, 2017 and entitled "Transcriptome Profiling of 10,000 mRNAs by RNA SPOTs," each of which is hereby incorporated by reference herein in its entirety.

STATEMENT REGARDING FEDERALLY SPONSORED RESEARCH OR DEVELOPMENT

This invention was made with government support under Grant No. HD075605 and under Grant No. OD008530 awarded by the National Institutes of Health. The government has certain rights in the invention.

FIELD OF THE INVENTION

The methods provided herein generally relate to the field of molecular biology.

BACKGROUND OF THE INVENTION

Transcription profiling of cells are essential for many purposes. Microscopy imaging which can resolve multiple mRNAs in single cells can provide valuable information regarding transcript abundance and localization, which are important for understanding the molecular basis of cell identify and developing treatment for diseases. Molecular profiling such as transcriptomic profiling of biological samples is essential for various purposes. For example, it would allow one to assess gene expression levels to detect and identify abnormal growth states such as cancers. Using nucleic acid detection as an example, current nucleic acid-based assays such as qPCR and microarrays have been useful, but they do not reach single molecule sensitivity. Next generation sequencing, on the other hand, involves amplification of the sample and reverse transcription of mRNA which can introduce biases and inaccuracies in quantification. Moreover, sample preparation and sequencing can be time-consuming and economically costly. Despite the fact that imaging has been used for mRNA transcripts quantification, it is limited to a few hundreds of genes. Many scientific questions require thousands of genes or even the whole transcriptome to be quantified.

What is needed in the are better methods and systems for carrying out imaging based transcriptomic profiling at a single molecule sensitivity with high accuracy in a time efficient manner.

SUMMARY OF THE INVENTION

The present invention provides certain insights into challenges or defects associated with existing technologies for profiling transcripts or DNA loci in cells, particularly for single cells. Moreover, the present invention provides new technologies for achieving effective such profiling, including of single cells. Provided technologies are broadly useful, including for example for profiling of isolated cells, cells in tissues, cells in organs, and/or cells in organisms.

For example, the present invention provides the insight that existing technologies such as single cell RNA-seq or qPCR require single cells to be isolated and put into multi-well format, which is a multiple step process that can be cost prohibitive, labor intensive and prone to artifacts. Furthermore, the present invention recognizes that existing in situ sequencing technologies that use enzymatic reactions to convert the mRNA into a DNA template first can be highly inefficient (for example in the mRNA to DNA conversion process), so that, often, only a small fraction of the RNAs are converted and detected. The present invention provides the particular insight that one major downside of such low efficiency, which is estimated at 1% for RT and 10% for PLA, is that it can introduce significant noise ad bias in the gene expression measurements. The present invention further recognizes that existing spectral mRNA barcoding technologies that utilize single molecule fluorescence in situ hybridization (smFISH) require distinct fluorophores for scale up, and may be limited in the number of barcodes that can be generated. smFISH also requires splitting probes into barcoding subsets during hybridization. Because smFISH often uses two or more colors for a target, it produces high density of objects in the image, which can increase the complexity of data analysis.

Among other things, the present inventions provides new technologies for profiling, for example, transcripts and/or DNA loci, that overcome one or more or all of the problems associated with methods prior to the present invention. In some embodiments, the present invention provides methods for detecting multiple targets, e.g., transcripts or DNA loci, in a cell through a sequential barcoding scheme that permits multiplexing of different targets.

In one aspect, disclosed herein is a method of barcoding molecular targets. The method comprises: identifying N molecular targets in a biological sample, wherein the N molecular targets are immobilized; associating a unique barcode to each molecular target via n sequential barcoding rounds (where n≥2), wherein each barcoding round comprises m serial hybridizations of probes collectively bound to the N molecular targets (where m≥2), and optionally removing probes between two barcoding rounds. In some embodiments, each serial hybridization in turn further comprises: contacting one or more groups of probes to a subset of the N molecular targets, the total number of groups of probes corresponding to the number of molecular targets in the subset, where probes in each group comprise one or more binding sequences specifically targeting a molecular target in the subset, where each probe is capable of generating at least one detectable visual signal representing binding of the probe to a molecular target in the subset, and where probes in the one or more groups generate one or more different detectable visual signals corresponding to the number of molecular targets in the subset; detecting the detectable visual signals that reflect the binding between the one or more groups of probes and the subset of the N molecular targets; and removing the visual signals, when applicable, prior to the next serial hybridization; wherein the unique barcode to each molecular target consists of n components, each component is assigned from S unique symbols, where S is an integer that equal to or greater than $\sqrt[n]{N}$. N and n are both integer.

In some embodiments, the detecting the detectable visual signals comprises: capturing, for each serial hybridization round, an image of the detectable visual signals that reflect the binding between the one or more groups of probes and the subset of the N molecular targets.

In some embodiments, the method further comprises: generating, for each barcoding round, a composite image by superimposing m images corresponding to the m serial hybridizations, wherein the m images are aligned based on one or more alignment references whose positions remain constant relative to the biological sample.

In some embodiments, the method further comprises: applying Gaussian analysis to super-localize the detectable visual signals in an image.

In some embodiments, the method further comprises: decoding the detectable visual signals in each composite image based on the unique barcodes for the N molecular targets and the S unique symbols.

In some embodiments, the method further comprises: detecting reference visual signals associated with the one or more alignment reference.

In some embodiments, the one or more alignment references comprise one or more selected from the group consisting of an oligonucleotide sequence immobilized on the coverslips and detected by a complementary oligo, a common sequence embedded in all probes, a microscopic object, a metal bead, a gold bead, a polystyrene bead, a PCR handle sequence on a primary binding probe, and combinations thereof.

In some embodiments, the n sequential barcoding rounds includes x round for error correction, where x is an integer equal or greater than 1; and wherein assigning unique barcodes for each of N molecular targets requires S unique symbols, where S is an integer equal or greater than $\sqrt[n-x]{N}$.

In some embodiments, the biological sample comprises a tissue sample, a cell sample, a cell extract sample, a nucleic acid sample, an RNA transcript sample, a protein sample, an mRNA sample, DNA molecules, protein molecules, RNA and DNA isoform molecules, single nucleotide polymorphism molecules, or combinations thereof.

In some embodiments, the method further comprises: determining a secondary molecular target that are associated with the N molecular targets by contacting the biological sample with molecules specifically binding to the secondary molecular target.

In some embodiments, the secondary molecular target comprises one selected from the group consisting of a RNA binding protein molecule, ribosome, a DNA binding protein molecule, a transcription factor, a chromatin binding protein, a protein binding molecule, a scaffold protein, and combinations thereof.

In some embodiments, probes in the one or more groups of probes further comprise: one or more binding sequences each specifically targeting one or more sites within a molecular target in the biological sample; and n unique readout sequences associated with the one or more binding sequences, wherein, in each barcoding round, only one unique readout sequence is associated with a detectable visual signal for a particular molecular target.

In some embodiments, the one or more binding sequences target multiple different sites within the same molecular target. In some embodiments, the one or more binding sequences target multiple different sites within different molecular targets.

In some embodiments, each probe comprises one or more of the n unique readout sequences.

In some embodiments, at least one of the n unique readout sequences is located in an overhang sequence directly connected to the binding sequence of a probe.

In some embodiments, at least one of the n unique readout sequences is indirectly connected to the binding sequence of a probe via one or more intermediate molecules.

In some embodiments, the one or more intermediate molecules comprise an RNA bridge probe, a DNA bridge probe, a protein bridge probe, a probe for hybridization chain reaction (HCR), a hairpin nucleic acid probe, an HCR initiator, an HCR polymer, or combinations thereof.

In some embodiments, the one or more binding sequences specifically target one or more non-nucleic acid sites in the molecular target, and wherein the n unique readout sequences comprising nucleic acid sequences that are directly or indirectly connected to the binding sequences of the probes.

In some embodiments, the detectable visual signal is connected to the binding sequence of a probe or an intermediate molecule via a cleavable linker.

In some embodiments, the one or more binding sequences comprises a peptide sequence binding to a specific antigen within a particular molecular target, an aptmer, or click chemistry group.

In some embodiments, the S unique symbols comprise colors, numbers, letters, shapes, or combinations thereof.

In some embodiments, for each serial hybridization, the one or more groups of probes to a non-overlapping subset of the N molecular targets.

In one aspect, disclosed herein is a method of hybridization analysis of binding between labeled probes and molecular targets in a biological sample. The method comprises: generating multiple composite images of labeled probes bound to a plurality of molecular targets in the biological sample, wherein each composite image is generated from a plurality of images of labeled probes collectively bound to the plurality of molecular targets, wherein the plurality of molecular targets are immobilized within the biological sample, and wherein each image of the plurality of images reveals: labeled probes bound to a subset of molecular targets within the plurality of molecular targets, wherein the labeled probes comprise one or more groups of probes, the total number of groups of probes corresponding to the number of molecular targets in the subset, wherein probes in each group comprise one or more binding sequences specifically targeting a molecular target in the subset, and wherein each labeled probe is capable of generating a visual signal representing binding of the probe to a molecular target; and one or more reference targets whose positions remain constant in the biological sample for aligning the plurality of images.

In some embodiments, the biological sample comprises a tissue sample, a cell sample, a cell extract sample, a nucleic acid sample, an RNA transcript sample, a protein sample, an mRNA sample, DNA molecules, protein molecules, RNA and DNA isoform molecules, single nucleotide polymorphism molecules, or combinations thereof.

In some embodiments, in each image, the labelled probes bind to a non-overlapping subset of molecular targets within the plurality of molecular targets.

In some embodiments, the method further comprises: contacting the one or more groups of probes with the subset of molecular targets of the plurality of molecular targets; detecting visual signals that reflect the binding between the one or more groups of probes and molecular targets in the subset; and removing the visual signals, when applicable, prior to a next round of hybridization of labeled probes binding to a new subset of molecular targets within the plurality of molecular targets.

In some embodiments, the method further comprises: detecting reference visual signals associated with the one or more alignment references.

In some embodiments, the method further comprises: aligning the plurality of images based on the positions of the one or more alignment references.

In one aspect, disclosed herein is a sequential hybridization method that comprises the steps of: identifying a plurality of target genes; and associating, via sequential hybridization of binding probes to the plurality of target genes, a first plurality of unique codes with the plurality of target genes, where each target gene in the plurality of target genes is represented by a unique code in the first plurality of unique codes, where the sequential hybridization comprises n rounds of hybridization (where n≥2). Here, each round of hybridization in n rounds of hybridization in turn comprises the steps of contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes; and removing the visual signals, when applicable, prior to the next round of hybridization. In some embodiments, probes used in the n rounds of hybridization are capable of emitting at least F types of detectable visual signals (where F≥2 and $F^n$ is greater than the number of target genes in the plurality of target genes). In some embodiments, a unique code in the first plurality of unique codes for a target gene consists of n components. In some embodiments, each component is determined by visual signals that reflect the binding between binding probes and the target gene during one of the n rounds of hybridization. In some embodiments, the n rounds of hybridization include m error correction round (m≥1). In some embodiments, a second plurality of unique codes for the plurality of target genes is generated after the m error correction round is removed from the n rounds of hybridization. In some embodiments, each unique code in the second plurality of unique codes consists of (n−m) components and uniquely represents a target gene in the plurality of target genes.

In some embodiments, the plurality of target genes are located on immobilized nucleic acids selected from the group consisting of mRNAs, chromosomal DNAs and combinations thereof. In some embodiments, n is 4 or greater, 5 or greater, or 10 or greater. In some embodiments, the m error correction round comprises one round of the n rounds of hybridization. In some embodiments, the one round of the n rounds of hybridization is a repeat of one of the remaining one or more (n−1) rounds of the n rounds of hybridization. In some embodiments, where m≤0.5n.

In some embodiments, the at least F types of detectable visual signals comprises one selected from the group consisting of a fluorescence signal, a color signal, a red signal, a green signal, a yellow signal, a combined color signal representing two or more colors, and combinations thereof.

In some embodiments, a probe in the plurality of binding probes further comprises a signal moiety that emits a detectable visual signal upon binding of the probe to a target sequence.

In some embodiments, the signal moiety is connected to the binding sequence of the probe via a cleavable linker.

In some embodiments, each component of a n-component unique code in the first plurality of unique codes is assigned a numerical value that corresponds to one of the at least F types of detectable visual signals; and where at least one component of the n-component unique code is determined based on the numerical values of all or some of the other n−1 components.

In some embodiments, the n-component unique code is determined as:

$\{j_1, j_2, \ldots (a_1*j_1+a_2*j_2 \ldots +a_n*j_n+C) \bmod F, \ldots, j_n\}$, where $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization; and where $j_1, j_2, \ldots j_n, a_1, a_2, \ldots a_n$ and n are none zero integers and C is an integer.

In some embodiments, m, n, F, i, j and k are all integers.

In one aspect disclosed herein is a hybridization method that comprises the steps of: identifying a plurality of target genes; performing sequential hybridization of binding probes to the plurality of target genes, where the sequential hybridization comprises n rounds of hybridization (where n≥2). Here, each round of hybridization in n rounds of hybridization in turn comprises: contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes, where each target gene in the plurality of target genes is represented by visual signals that are unique for the target gene, and where probes used in the n rounds of hybridization are capable of emitting at least F types of detectable visual signals (where F≥2, and $F^n$ is greater than the number of target genes in the plurality of target genes); and removing the visual signals, when applicable, prior to the next round of hybridization; and performing serial hybridizations against one or more serial target genes, where the expression level of each serial target gene is above a predetermined threshold value, and where each serial hybridization in turn comprises: contacting the one or more serial target genes with a plurality of binding probes, where each probe in the plurality of binding probes comprises: a binding sequence that specifically binds a target sequence in a serial target gene in the one or more serial target genes, where one or more serial target genes are spatially transfixed from each other, where each probe is capable of emitting a detectable visual signal upon binding of the probe to the target sequence, and where probes binding to target sequences in the same serial target gene emit the same detectable visual signals; and detecting visual signals that reflect the binding between the plurality of binding probes and the one or more serial target gene.

In some embodiments, the n rounds of hybridization generate a first plurality of unique codes, where each target gene in the plurality of target genes is represented by a unique code in the first plurality of unique codes.

In some embodiments, where a unique code in the first plurality of unique codes for a target gene consists of n components, and where each component is determined by visual signals that reflect the binding between binding probes and the target gene during one of the n rounds of hybridization.

In some embodiments, the n rounds of hybridization include m error correction round (m≥1), where a second plurality of unique codes for the plurality of target genes is generated after the m error correction round is removed from the n rounds of hybridization, and where each unique code in the second plurality of unique codes consists of (n-m) components and uniquely represents a target gene in the plurality of target genes.

In some embodiments, the method of hybridization further comprises the step of: identifying the one or more serial target genes based on expression levels of candidate target genes.

In some embodiments, the plurality of target genes are located on immobilized nucleic acids selected from the group consisting of mRNAs, chromosomal DNAs and combinations thereof.

In some embodiments, the one or more serial target genes are located on immobilized nucleic acids selected from the group consisting of mRNAs, chromosomal DNAs and combinations thereof.

In some embodiments, each unique code in the first plurality of unique codes consists of n component, where each component of a n-component unique code in the first plurality of unique codes is assigned a numerical value that corresponds to one of the at least F types of detectable visual signals; and where at least one component of the n-component unique code is determined based on the numerical values of all or some of the other n−1 components.

In some embodiments, the n-component unique code is determined as:

$\{j_1, j_2, \ldots (a_1*j_1+a_2*j_2 \ldots +a_n*j_n+C) \bmod F, \ldots, j_n\}$, where $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization; and where $j_1, j_2, \ldots j_n, a_1, a_2, \ldots$ an are none zero integers and C is an integer.

In one aspect, disclosed herein is a non-transitory computer-readable medium containing instructions that, when executed by a computer processor, cause the computer processor to: associate, via sequential hybridization of binding probes to a plurality of target genes, a first plurality of unique codes with the plurality of target genes, where each target gene in the plurality of target genes is represented by a unique code in the first plurality of unique codes, where the sequential hybridization comprises n rounds of hybridization (where n≥2). Here each round of hybridization in n rounds of hybridization in turn comprises: contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes; and removing the visual signals, when applicable, prior to the next round of hybridization.

In some embodiments, probes used in the n rounds of hybridization are capable of emitting at least F types of detectable visual signals (where F≥2 and $F^n$ is greater than the number of target genes in the plurality of target genes). In some embodiments, a unique code in the first plurality of unique codes for a target gene consists of n components. In some embodiments, each component is determined by visual signals that reflect the binding between binding probes and the target gene during one of the n rounds of hybridization. In some embodiments, the n rounds of hybridization include m error correction round (m≥1). In some embodiments, a second plurality of unique codes for the plurality of target genes is generated after the m error correction round is removed from the n rounds of hybridization. In some embodiments, each unique code in the second plurality of unique codes consists of (n−m) components and uniquely represents a target gene in the plurality of target genes.

In one aspect, disclosed herein is a non-transitory computer-readable medium containing instructions that, when executed by a computer processor, cause the computer processor to: perform sequential hybridization of binding probes to a plurality of target genes, where the sequential hybridization comprises n rounds of hybridization (where n≥2).

Here, each round of hybridization in n rounds of hybridization comprises: contacting the plurality of target genes with a plurality of binding probes, where each probe in the plurality of binding probes comprises: a binding sequence that specifically binds a target sequence in a gene in the plurality of target genes, where target genes from the plurality of target genes are spatially transfixed from each other, and where each probe is capable of emitting a detectable visual signal upon binding of the probe to a target sequence; detecting visual signals that reflect the binding between the plurality of binding probes and the plurality of target genes, where each target gene in the plurality of target genes is represented by visual signals that are unique for the target gene, and where probes used in the n rounds of hybridization are capable of emitting at least F types of detectable visual signals (where F≥2, and $F^n$ is greater than the number of target genes in the plurality of target genes); and removing the visual signals, when applicable, prior to the next round of hybridization; and perform serial hybridizations against one or more serial target genes, where the expression level of each serial target gene is above a predetermined threshold value, where each serial hybridization comprises: contacting the one or more serial target genes with a plurality of binding probes, where each probe in the plurality of binding probes comprises: a binding sequence that specifically binds a target sequence in a serial target gene in the one or more serial target genes, where one or more serial target genes are spatially transfixed from each other, where each probe is capable of emitting a detectable visual signal upon binding of the probe to the target sequence, and where probes binding to target sequences in the same serial target gene emit the same detectable visual signals; and detecting visual signals that reflect the binding between the plurality of binding probes and the one or more serial target gene.

In any of the embodiments disclosed herein, m, n, F, i, j and k are all integers. Embodiments disclosed herein can be applied individually or in combination in any aspect disclosed herein.

In one aspect, disclosed herein is a composition comprising a plurality of primary probes, a first plurality of bridge probes, and first plurality of readout probes.

In some embodiments, each primary probe in the plurality of primary probes comprises: a primary binding sequence that binds to a complementary target sequence in a target nucleic acid molecule, and a first overhang sequence connected to one end of the primary binding sequence.

In some embodiments, each bridge probe in the first plurality of bridge probes comprises a binding sequence that specifically binds to all or a part of the first overhang sequence of a primary probe of the plurality of primary probes, and one or more readout binding targets connected in series and linked to the binding sequence.

In some embodiments, each readout probe in the first plurality of readout probes comprises: a readout binding sequence that specifically binds to a first readout binding target of the one or more readout binding targets of a bridge probe of the first plurality of bridge probes, and a signal moiety linked to the readout binding sequence via a cleavable linker.

In these embodiments, the signal moiety is capable of emitting a first detectable visual signal upon binding of each readout probe from the first plurality of readout probes to the first readout binding target of one of the one or more readout binding targets.

In some embodiments, the composition further comprises: a second plurality of readout probes, wherein each readout probe comprises: a readout binding sequence that specifically binds to a second readout binding target of the one or more readout binding targets in a bridge probe of the first plurality of bridge probes, and a signal moiety linked to the readout binding sequence via a cleavable linker.

In these embodiments, the signal moiety is capable of emitting a second detectable visual signal upon binding of each readout probe from the second plurality of readout probes to the second readout binding target of the one or more readout binding targets.

In some embodiments, the composition further comprises: a second overhang sequence, linked to the other end of the primary binding sequence.

In some embodiments, the composition further comprises: a second plurality of bridge probes, wherein each bridge probe comprises: a binding sequence that specifically binds to all or a part of the second overhang sequence of a primary probe of the plurality of primary probes, and one or more additional readout binding targets connected in series and linked to the binding sequence.

In some embodiments, the composition further comprises: a third plurality of readout probes, wherein each readout probe comprises: a readout binding sequence that specifically binds to a first additional readout binding target of the one or more additional readout binding targets in a bridge probe of the second plurality of bridge probes, and a signal moiety linked to the readout binding sequence via a cleavable linker.

In these embodiments, the signal moiety is capable of emitting a third detectable visual signal upon binding of each readout probe from the third plurality of readout probes to the first additional readout binding target of the one or more additional readout binding targets.

In some embodiments, the composition further comprises: a fourth plurality of readout probes. Each readout probe in the fourth plurality of readout probes comprises: a readout binding sequence that specifically binds to a second additional readout binding target of the one or more additional readout binding targets in a bridge probe of the second plurality of bridge probes, and a signal moiety linked to the readout binding sequence via a cleavable linker.

In these embodiments, the signal moiety is capable of emitting a fourth detectable visual signal upon binding of each readout probe from the fourth plurality of readout probes to the second additional readout binding target of the one or more additional readout binding targets.

In some embodiments, the cleavable linker is selected from the group consisting of an enzyme cleavable linker, a nucleophile/base sensitive linker, reduction sensitive linker, a photo-cleavable linker, an electrophile/acid sensitive linker, a metal-assisted cleavable linker, and an oxidation sensitive linker.

In some embodiments, the cleavable linker is a disulfide bond or a nucleic acid restriction site. In some embodiments, the one or more readout binding targets comprises three or more readout binding targets.

In some embodiments where second overhang is present, the additional one or more readout binding targets comprises three or more readout binding targets.

In one aspect, disclosed herein is a sequential hybridization method utilizing a plurality of primary probes, a first plurality of bridge probes, and first plurality of readout probes. In some embodiments, the method comprises the steps of: a) contacting a target nucleic acid molecule with a plurality of primary probes, where each primary probe comprises: a primary binding sequence that binds to a complementary target sequence within the target nucleic acid molecule, and a first overhang sequence connected to one end of the primary binding sequence; b) contacting, after step a) the target nucleic acid molecule with a first plurality of bridge probes, where each bridge probe comprises: a binding sequence that specifically binds to all or a part of the first overhang sequence of a primary probe of the plurality of primary probes, and one or more readout binding targets connected in series and linked to the binding sequence; and c) contacting, after step b) the target nucleic acid molecule with a first plurality of readout probes, wherein each readout probe comprises: a readout binding sequence that specifically binds to a first readout binding target of the one or more readout binding targets of a primary probe of the plurality of primary probes, and a signal moiety linked to the readout binding sequence via a cleavable linker.

In these embodiments, the signal moiety is capable of emitting a first detectable visual signal upon binding of each readout probe from the first plurality of readout probes to the first readout binding target of the one or more readout binding targets of a bridge probe of the first plurality of bridge probes.

In some embodiments, the method further comprises the steps of: c1) imaging the target nucleic acid molecule after step c) so that interactions between the first plurality of readout probes and the first readout binding target of the one or more readout binding targets of a primary bridge probe are detected by the presence of first detectable visual signal; and c2) applying, after step c1) a cleaving agent to cleave the linker, thereby eliminating the signal moiety from each readout probe in the first plurality of readout probes.

In some embodiments, the method further comprises: d) contacting, after step c), the target nucleic acid molecule with a second plurality of readout probes. Each readout probe comprises: a readout binding sequence that specifically binds to a second readout binding target of the one or more readout binding targets of a bridge probe, and a signal moiety linked to the readout binding sequence via a cleavable linker.

In these embodiments, the signal moiety is capable of emitting a second detectable visual signal upon binding of each readout probe from the second plurality of readout probes to the second readout binding target of the one or more readout binding targets of a bridge probe of the first plurality of bridge probes.

In some embodiments, the method further comprises: d1) imaging the target nucleic acid molecule after step d) so that interactions between the second plurality of readout probes and the second readout binding target of the one or more readout binding targets of a bridge probe are detected by the presence of second detectable visual signal; and d2) applying a cleaving agent to cleave the linker, thereby eliminating the signal moiety from each readout probe in the second plurality of readout probes.

In some embodiments, each primary probe in the plurality of primary probes further comprises: a second overhang sequence connected to the other end of the primary binding sequence.

In some embodiments, the method further comprises: e) contacting, after step d), the target nucleic acid molecule with a second plurality of bridge probes. Each bridge probe comprises: a binding sequence that specifically binds to all or a part of the second overhang sequence of a primary probe of the plurality of primary probes, and one or more additional readout binding targets connected in series and linked to the binding sequence.

In some embodiments, the method further comprises: f) contacting, after step e), the target nucleic acid molecule with a third plurality of readout probes. Each readout probe comprises: a readout binding sequence that specifically binds to a first additional readout binding target of the one or more additional readout binding targets of a bridge probe in the second plurality of bridge probes, and a signal moiety linked to the readout binding sequence via a cleavable linker.

In these embodiments, the signal moiety is capable of emitting a third detectable visual signal upon binding of each readout probe from the third plurality of readout probes to the first additional readout binding target of the one or more additional readout binding targets.

In some embodiments, the method further comprises: f1) imaging the target nucleic acid molecule after step f) so that interactions between the third plurality of readout probes and the first additional readout binding target of the one or more additional readout binding targets of a bridge probe in the second plurality of bridge probes are detected by the presence of the third detectable visual signal; and f2) applying a cleaving agent to cleave the linker, thereby eliminating the signal moiety from each readout probe in the third plurality of readout probes.

In some embodiments, the method further comprises: g) contacting, after step f), the target nucleic acid molecule with a fourth plurality of readout probes. Each readout probe comprises: a readout binding sequence that specifically binds to a second additional readout binding target of the one or more additional readout binding targets of a bridge probe in the second plurality of bridge probes, and a signal moiety linked to the readout binding sequence via a cleavable linker.

In these embodiments, the signal moiety is capable of emitting a fourth detectable visual signal upon binding of each readout probe from the fourth plurality of readout probes to the second additional readout binding target of the one or more additional readout binding targets.

In some embodiments, the method further comprises: h1) imaging the target nucleic acid molecule after step g) so that interactions between the fourth plurality of readout probes and the second additional readout binding target of the one or more additional readout binding targets of a bridge probe in the second plurality of bridge probes are detected by the presence of the fourth detectable visual signal; and h2) applying a cleaving agent to cleave the linker, thereby eliminating the signal moiety from each readout probe in the fourth plurality of readout probes.

In some embodiments, the target nucleic acid molecule is an mRNA or a DNA. In some embodiments, the target nucleic acid molecule is within an intact mammalian cell. In some embodiments, the intact mammalian cell is a human cell.

In these embodiments, the cleavable linker is selected from the group consisting of an enzyme cleavable linker, a nucleophile/base sensitive linker, reduction sensitive linker, a photo-cleavable linker, an electrophile/acid sensitive linker, a metal-assisted cleavable linker, and an oxidation sensitive linker. In these embodiments, the cleavable linker is a disulfide bond or a nucleic acid restriction site. In these embodiments, the one or more readout binding targets comprises three or more readout binding targets.

In these embodiments where a second overhang is present, the additional one or more readout binding targets comprises three or more readout binding targets.

In one aspect, disclosed herein is a composition that comprises a plurality of primary probes and a first plurality of readout probes. In these embodiments, each primary probe comprises: a primary binding sequence that binds to a complementary target sequence in a target nucleic acid molecule, and a first overhang sequence connected to one end of the primary binding sequence, wherein the first overhang sequence comprises one or more readout binding targets connected in series. Also in these embodiments, each readout probe comprises: a readout binding sequence that specifically binds to a first readout binding target of the one or more readout binding targets in a first overhang sequence, and a signal moiety linked to the readout binding sequence via a cleavable linker. In these embodiments, the signal moiety is capable of emitting a first detectable visual signal upon binding of each readout probe from the first plurality of readout probes to the first readout binding target of one of the one or more readout binding targets.

In some embodiments, the composition further comprises: a second plurality of readout probes, where each readout probe comprises: a readout binding sequence that specifically binds to a second readout binding target of the one or more readout binding targets in a first overhang sequence, and a signal moiety linked to the readout binding sequence via a cleavable linker. In these embodiments, the signal moiety is capable of emitting a second detectable visual signal upon binding of each readout probe from the second plurality of readout probes to the second readout binding target of the one or more readout binding targets.

In some embodiments, a primary probe further comprises: a second overhang sequence, linked to the other end of the primary binding sequence, where the second overhang sequence comprises one or more additional readout binding targets connected in series.

In some embodiments, the composition further comprises a third plurality of readout probes, where each readout probe comprises: a readout binding sequence that specifically binds to a first additional readout binding target of the one or more additional readout binding targets in a second overhang sequence, and a signal moiety linked to the readout binding sequence via a cleavable linker. In these embodiments, the signal moiety is capable of emitting a third detectable visual signal upon binding of each readout probe from the third plurality of readout probes to the first additional readout binding target of the one or more additional readout binding targets.

In some embodiments, the composition further comprises a fourth plurality of readout probes, where each readout probe comprises: a readout binding sequence that specifically binds to a second additional readout binding target of the one or more additional readout binding targets in a second overhang sequence, and a signal moiety linked to the readout binding sequence via a cleavable linker. In these embodiments, the signal moiety is capable of emitting a fourth detectable visual signal upon binding of each readout probe from the fourth plurality of readout probes to the second additional readout binding target of the one or more additional readout binding targets.

In any embodiments disclosed herein, the cleavable linker is selected from the group consisting of an enzyme cleavable linker, a nucleophile/base sensitive linker, reduction sensitive linker, a photo-cleavable linker, an electrophile/acid sensitive linker, a metal-assisted cleavable linker, and an oxidation sensitive linker.

In any embodiments disclosed herein, the cleavable linker is a disulfide bond or a nucleic acid restriction site.

In any embodiments disclosed herein, the one or more readout binding targets comprises three or more readout binding targets.

In embodiments where a second overhang sequence is present, the additional one or more readout binding targets comprises three or more readout binding targets.

In some embodiments, the target nucleic acid molecule is an mRNA or a DNA. In some embodiments, the target nucleic acid molecule is within an intact mammalian cell. In some embodiments, the intact mammalian cell is a human cell.

In one aspect, disclosed herein is a sequential hybridization method utilizing with a plurality of primary probes and a first plurality of readout probes. The method comprises the steps of: a) contacting a target nucleic acid molecule with a plurality of primary probes. Each primary probe comprises: a primary binding sequence that binds to a complementary target sequence within the target nucleic acid molecule, and a first overhang sequence connected to one end of the primary binding sequence, wherein the first overhang sequence comprises one or more readout binding targets connected in series; and b) contacting, after step a) the target nucleic acid molecule with a first plurality of readout probes. Each readout probe comprises: a readout binding sequence that specifically binds to a first readout binding target of the one or more readout binding targets of a primary probe of the plurality of primary probes, and a signal moiety linked to the readout binding sequence via a cleavable linker.

In these embodiments, the signal moiety is capable of emitting a first detectable visual signal upon binding of each readout probe from the first plurality of readout probes to the first readout binding target of one of the one or more readout binding targets.

In some embodiments, the method further comprises the steps of: b1) imaging the target nucleic acid molecule after step b) so that interactions between the first plurality of readout probes and the first readout binding target of the one or more readout binding targets of a primary bridge probe are detected by the presence of the first detectable visual signal; and b2) applying a cleaving agent to cleave the linker, thereby eliminating the signal moiety from each readout probe in the first plurality of readout probes.

In some embodiments, the method further comprises the steps of: c) contacting, after step b), the target nucleic acid molecule with a second plurality of readout probes. Each readout probe comprises: a readout binding sequence that specifically binds to a second readout binding target of the one or more readout binding targets of a primary probe, and a signal moiety linked to the readout binding sequence via a cleavable linker.

In these embodiments, the signal moiety is capable of emitting a second detectable visual signal upon binding of each readout probe from the second plurality of readout probes to the second readout binding target of the one or more readout binding targets.

In some embodiments, the method further comprises the steps of: c1) imaging the target nucleic acid molecule after step c) so that interactions between the second plurality of readout probes and the second readout binding target of the one or more readout binding targets of a primary probe are detected by the presence of the second detectable visual signal; and c2) applying a cleaving agent to cleave the linker, thereby eliminating the signal moiety from each readout probe in the second plurality of readout probes.

In some embodiments, each primary probe in the plurality of primary probes further comprises: a second overhang sequence connected to the other end of the primary binding sequence, wherein the second overhang sequence comprises one or more additional readout binding targets connected in series.

In some embodiments, the method further comprises the steps of: d) contacting, after step c), the target nucleic acid molecule with a third plurality of readout probes. Each readout probe comprises: a readout binding sequence that specifically binds to a first additional readout binding target of the one or more additional readout binding targets of a primary probe, and a signal moiety linked to the readout binding sequence via a cleavable linker.

In these embodiments, the signal moiety is capable of emitting a third detectable visual signal upon binding of each readout probe from the third plurality of readout probes to the first additional readout binding target of the one or more additional readout binding targets.

In some embodiments, the method further comprises the steps of: d1) imaging the target nucleic acid molecule after step d) so that interactions between the second plurality of readout probes and the second readout binding target of the one or more readout binding targets of a primary probe are detected by the presence of the second detectable visual signal; and d2) applying a cleaving agent to cleave the linker, thereby eliminating the signal moiety from each readout probe in the second plurality of readout probes.

In some embodiments, the method further comprises the steps of: e) contacting, after step d), the target nucleic acid molecule with a fourth plurality of readout probes. Each readout probe comprises: a readout binding sequence that specifically binds to a second additional readout binding target of the one or more additional readout binding targets of a primary probe, and a signal moiety linked to the readout binding sequence via a cleavable linker, In these embodiments, the signal moiety is capable of emitting a fourth detectable visual signal upon binding of each readout probe from the fourth plurality of readout probes to the second additional readout binding target of the one or more additional readout binding targets.

In some embodiments, the method further comprises the steps of: e1) imaging the mRNA after step d) so that interactions between the fourth plurality of readout probes and the second additional readout binding target of the one or more additional readout binding targets of a primary probe are detected by the presence of the fourth detectable visual signal; and e2) applying a cleaving agent to cleave the linker, thereby eliminating the signal moiety from each readout probe in the fourth plurality of readout probes.

In some embodiments, the target nucleic acid molecule is an mRNA or a DNA. In some embodiments, the target nucleic acid molecule is within an intact mammalian cell. In some embodiments, the intact mammalian cell is a human cell.

In some embodiments, the cleavable linker is selected from the group consisting of an enzyme cleavable linker, a nucleophile/base sensitive linker, reduction sensitive linker, a photo-cleavable linker, an electrophile/acid sensitive linker, a metal-assisted cleavable linker, and an oxidation sensitive linker. In some embodiments, the cleavable linker is a disulfide bond or a nucleic acid restriction site.

In some embodiments, the one or more readout binding targets comprises three or more readout binding targets.

In some embodiments where the second overhang sequence is present, the additional one or more readout binding targets comprises three or more readout binding targets.

In one aspect, disclosed herein is a composition comprising a first plurality of nucleic acid detection probes and an extendible signal motif formed by a first plurality populations of extender probes $\{EP_1, EP_2, \ldots, EP_n\}$. In some embodiments, each nucleic acid detection probe in the first plurality of nucleic acid detection probes comprises: a binding region comprising a binding sequence that binds to a first target sequence; and an initiator sequence linked to the binding region with a cleavable linker. In some embodiments, each population of extender probes is represented by $EP_1, EP_2, \ldots, EP_n$, respectively, where each extender probe in $EP_1$ comprises: a binding sequence that binds to all or a part of the initiator sequence; one or more target sequences for extender probes in $EP_2$ and subsequent populations of extender probes, and a signal moiety capable of emitting a first detectable signal. In some embodiments, each probe in $EP_2$ and subsequent populations of extender probes comprises: a binding sequence that binds to all or a part of the previous extender sequence; one or more target sequences for probes in subsequent populations of extender probes; and a signal moiety capable of emitting the first detectable signal.

In some embodiments, the first target sequence is within a primary probe that directly binds to a target nucleic acid molecule. In some embodiments, the first target sequence is within a secondary probe that binds to a primary probe that directly binds to a target nucleic acid molecule. In some embodiments, the first target sequence is within a tertiary probe that binds to a secondary probe that binds to a primary probe that directly binds to a target nucleic acid molecule.

In some embodiments, the target nucleic acid molecule is an mRNA or a DNA. In some embodiments, the target nucleic acid molecule is within an intact mammalian cell. In some embodiments, the intact mammalian cell is a human cell.

In some embodiments, the cleavable linker is selected from the group consisting of an enzyme cleavable linker, a nucleophile/base sensitive linker, reduction sensitive linker, a photo-cleavable linker, an electrophile/acid sensitive linker, a metal-assisted cleavable linker, and an oxidation sensitive linker. In some embodiments, the cleavable linker is a disulfide bond or a nucleic acid restriction site.

In some embodiments, each extender probe of the plurality of extender probes comprises a binding sequence that is complementary to all or a part of the initiator sequence in the nucleic acid detection probe, wherein each extender probe forms a hairpin structure, and wherein the presence of the initiator sequence causes the hairpin structure to unfold and initiates a hybridization chain reaction.

In some embodiments, the composition further comprises a second plurality of nucleic acid detection probes and an extendible signal motif formed by a second plurality populations of extender probes $\{EP_{1'}, EP_{2'}, \ldots, EP_{n'}\}$. In some embodiments, each nucleic acid detection probe in the second plurality of nucleic acid detection probes comprises: a binding region comprising a binding sequence that binds to a second target sequence; and an initiator sequence linked to the binding region with a cleavable linker. In some embodiments, each population of extender probes is represented by $EP_{1'}, EP_{2'}, \ldots, EP_{n'}$, respectively, wherein each extender probe in $EP_{1'}$ comprises: a binding sequence that binds to all or a part of the initiator sequence; one or more target sequences for extender probes in $EP_{2'}$ and subsequent populations of extender probes; and a signal moiety capable of emitting a second detectable signal. In some embodiments, each probe in $EP_{2'}$ and subsequent populations of extender probes comprises: a binding sequence that binds to all or a part of the previous extender sequence; one or more target sequences for probes in subsequent populations of extender probes; and a signal moiety capable of emitting the second detectable signal.

In one aspect, disclosed herein is a sequential hybridization method. The method comprises the steps of: a) contacting a target nucleic acid molecule with a first plurality of nucleic acid detection probes and b) contacting, after step a) the target nucleic acid molecule with a first plurality populations of extender probes $\{EP_1, EP_2, \ldots, EP_n\}$. In some embodiments, each nucleic acid detection probe in the first plurality of nucleic acid detection probes comprises: a binding region comprising a binding sequence that binds to a first target sequence; and an initiator sequence linked to the binding region with a cleavable linker. In some embodiments, each population of extender probes is represented by $EP_1, EP_2, \ldots, EP_n$, respectively, where each extender probe in $EP_1$ comprises: a binding sequence that binds to all or a part of the initiator sequence; one or more target sequences for extender probes in $EP_2$ and subsequent populations of extender probes; and a signal moiety capable of emitting a first detectable signal. In some embodiments, each probe in $EP_2$ and subsequent populations of extender probes comprises: a binding sequence that binds to all or a part of the previous extender sequence; one or more target sequences for probes in subsequent populations of extender probes; and a signal moiety capable of emitting the first detectable signal.

In some embodiments, the method further comprises: b1) imaging the target nucleic acid molecule after step b) so that interactions between the first plurality of nucleic acid detection probes and first target sequences are detected by the presence of the first detectable visual signal; and b2) applying a cleaving agent to cleave the linker, thereby eliminating the extendible signal motif.

In some embodiments, the method further comprises: c) contacting an target nucleic acid molecule with a second plurality of nucleic acid detection probes. In some embodiment, each nucleic acid detection probe in the second plurality of nucleic acid detection probes comprises: a binding region comprising a binding sequence that binds to a second target sequence; and an initiator sequence linked to the binding region with a cleavable linker.

In some embodiments, the method further comprises: d) contacting, after step c) the target nucleic acid molecule with a second plurality populations of extender probes {$EP_{1'}$, $EP_{2'}$, ..., $EP_{n'}$}, where each population of extender probes is represented by $EP_{1'}$, $EP_{2'}$, ..., and $EP_{n'}$, respectively. In some embodiments, each extender probe in $EP_1$ comprises: a binding sequence that binds to all or a part of the initiator sequence; one or more target sequences for extender probes in $EP_{2'}$ and subsequent populations of extender probes; and a signal moiety capable of emitting a second detectable signal. In some embodiments, each probe in $EP_{2'}$ and subsequent populations of extender probes comprises: a binding sequence that binds to all or a part of the previous extender sequence; one or more target sequences for probes in subsequent populations of extender probes; and a signal moiety capable of emitting the second detectable signal.

In some embodiments, the method further comprises: d1) imaging the target nucleic acid molecule after step d) so that interactions between the second plurality of nucleic acid detection probes and second target sequences are detected by the presence of the second detectable visual signal; and d2) applying a cleaving agent to cleave the linker, thereby eliminating the extendible signal motif.

In some embodiments, the second target sequence is within a primary probe that directly binds to a target nucleic acid molecule. In some embodiments, the second target sequence is within a secondary probe that binds to a primary probe that directly binds to a target nucleic acid molecule. In some embodiments, the second target sequence is within a tertiary probe that binds to a secondary probe that binds to a primary probe that directly binds to a target nucleic acid molecule.

In some embodiments, the target nucleic acid molecule is an mRNA or a DNA. In some embodiments, the target nucleic acid molecule is within an intact mammalian cell. In some embodiments, the intact mammalian cell is a human cell.

In some embodiments, the cleavable linker is selected from the group consisting of an enzyme cleavable linker, a nucleophile/base sensitive linker, reduction sensitive linker, a photo-cleavable linker, an electrophile/acid sensitive linker, a metal-assisted cleavable linker, and an oxidation sensitive linker. In some embodiments, the cleavable linker is a disulfide bond or a nucleic acid restriction site.

In some embodiments, each extender probe of the plurality of extender probes comprises a binding sequence that is complementary to all or a part of the initiator sequence in the nucleic acid detection probe, where each extender probe forms a hairpin structure, and where the presence of the initiator sequence causes the hairpin structure to unfold and initiates a hybridization chain reaction.

The compositions and methods disclosed herein can be used in sequential hybridizations to identify any suitable cellular targets within an intact cell or in an in vitro setting. In some embodiments, the cellular targets can be mRNAs or DNAs. In some embodiments, the cellular targets can be proteins. For example, the initial target-binding primary probe can be an antibody conjugated with nucleic acid sequence for subsequent bindings.

One of skill in the art would understand that embodiments disclosed herein can be applied or combined in any aspect when applicable.

Definitions

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, word length=12 to obtain nucleotide sequences homologous to nucleic acid molecules of the invention. In some embodiments, to obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing:

Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12 (1): 387 (1984)), BLASTP, BLASTN, and FASTA (Altschul, S. F. et al., J. Molec. Biol. 215:403-410 (1990) and Altschul et al. Nuc. Acids Res. 25:3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm can also be used to determine identity.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Oligonucleotide: the term "oligonucleotide" refers to a polymer or oligomer of nucleotide monomers, containing any combination of nucleobases, modified nucleobases, sugars, modified sugars, phosphate bridges, or modified bridges.

Oligonucleotides of the present invention can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Predetermined: By predetermined is meant deliberately selected, for example as opposed to randomly occurring or achieved. A composition that may contain certain individual oligonucleotides because they happen to have been generated through a process that cannot be controlled to intentionally generate the particular oligonucleotides is not a "predetermined" composition. In some embodiments, a predetermined composition is one that can be intentionally reproduced (e.g., through repetition of a controlled process).

Probe: As used herein, the term "probe" or "probes" refers to any molecules, synthetic or naturally occurring, that can attach themselves directly or indirectly to a molecular target (e.g., an mRNA sample, DNA molecules, protein molecules, RNA and DNA isoform molecules, single nucleotide polymorphism molecules, and etc.). For example, a probe can include an nucleic acid molecule, an oligonucleotide, a protein (e.g., an antibody or an antigen binding sequence), or combinations thereof. For example, a protein probe may be connected with one or more nucleic acid molecules to for a probe that is a chimera. As disclosed herein, in some embodiments, a probe itself can produce a detectable signal. In some embodiments, a probe is connected, directly or indirectly via an intermediate molecule, with a signal moiety (e.g., a dye or fluorophore) that can produce a detectable signal.

Sample: As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Subject: As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

BRIEF DESCRIPTION OF THE DRAWINGS

Those of skill in the art will understand that the drawings, described below, are for illustrative purposes only. The drawings are not intended to limit the scope of the present teachings in any way.

FIG. 1 depicts exemplary embodiments of known methods for coding molecular targets.

FIG. 10 depicts a table showing possible barcodes obtained using the pseudo-color barcode scheme.

FIG. 17 illustrates results of gene specific primary probes design. (a) Each primary probe comprises a 25-nt gene specific sequences complementary to the mRNA, 4 readout sequences, and 2 primers binding sites. Each gene is targeted by a minimum of 28 to 32 primary probes. (b) Both priming regions (grey in the probe schematic) used in synthesizing gene specific primary probes are also used as a registration marker through the hybridization of ALEXA FLUOR™ 488 conjugated readout probes. Majority of the fluorescent spots stay even after 20 rounds of hybridizations. (Scale bars: 2 μm.)

FIG. 18 illustrates fluorescent switching through cleavage of disulfide conjugate dye on readout probes is highly efficient (a) 20 rounds of hybridization are accomplished by extinguishing fluorescent signals through reduction of disulfide conjugated dye to readout probes using TCEP, followed by re-hybridization of next unique secondary readout probes. The amide bond between the ALEXA FLUOR™ 488 dye (shown in yellow) and primer readout probes used as a registration marker is not affected by TCEP. (b) The fluorescent signals in each channel after treatment of 50 mM of TCEP for 5 minutes at room temperature is reduced to minimal to none. (Scale bars: 5 μm.)

FIG. 23 depicts smFISH measurement in single cells correlates with RNA SPOTs measurement in NIH/3T3 cells. (a) Raw images of the 7 genes measured by smFISH in NIH/3T3 cells. (Scale bars: 5 μm.) (b) The averaged RNA smFISH counts agrees with RNA SPOTs SPM (spots per million) with a Pearson correlation coefficient of 0.88, indicating RNA SPOTs quantitation is accurate. Error bars represents the standard error of the mean (SEM) across different single cells.

We also capture in vitro transcribed polyA-tailed dCAS9-EGFP mRNA on a dT20 Locked Nucleic Acid (LNA) surface-modified coverslips to show the rehybridization scheme works on the coverslips.

FIG. 29 depicts an exemplary embodiments illustrating rehybridization on mRNA captured on a dT20 LNA surface-modified coverslips. (a) (Left) First round of hybridization with tertiary probes conjugated with A647. (Right) No fluorescent spots are observed in channel 594 during first hybridization. (b) (Left) Channel 647 has minimal to no leftover fluorescent signals. (Right) Fluorescent spots from second round of hybridization which appear as the same positions as first hybridization.

Figure 30:
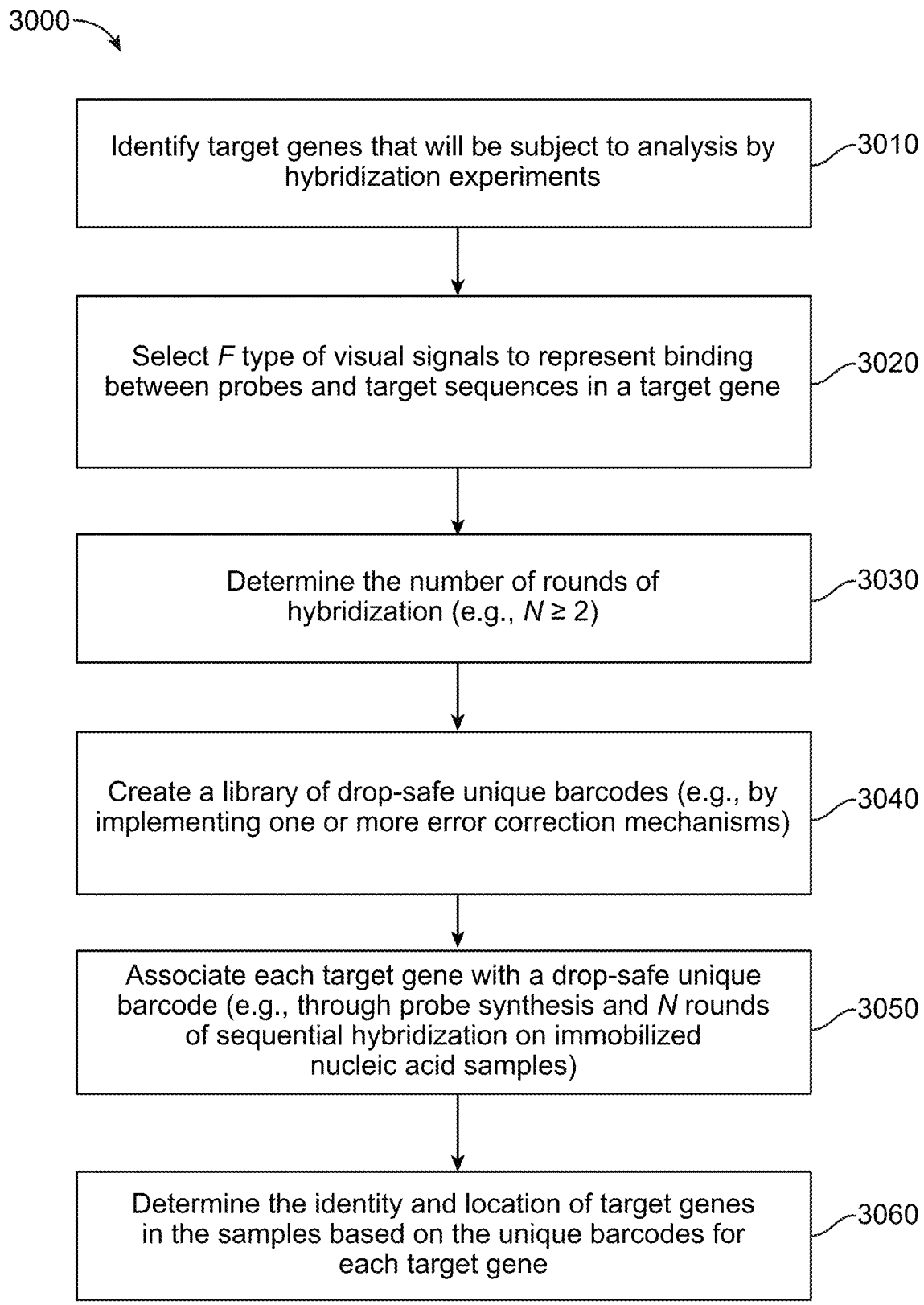

FIG. 30 illustrates an exemplary process for error correction.

Figure 31:
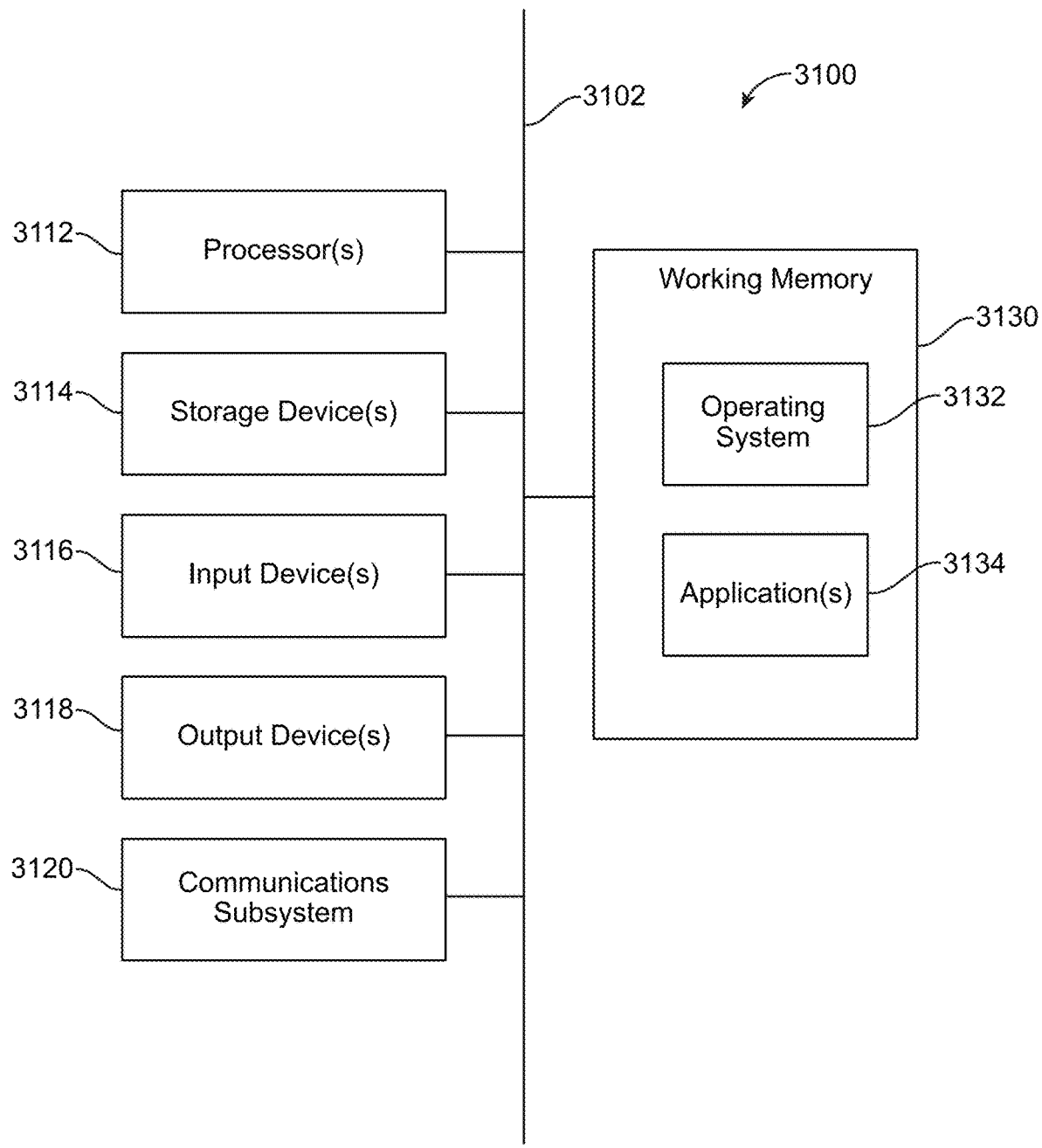

FIG. 31 illustrate an exemplary computer system for implementing the error correction methods disclosed herein.

Figure 32:
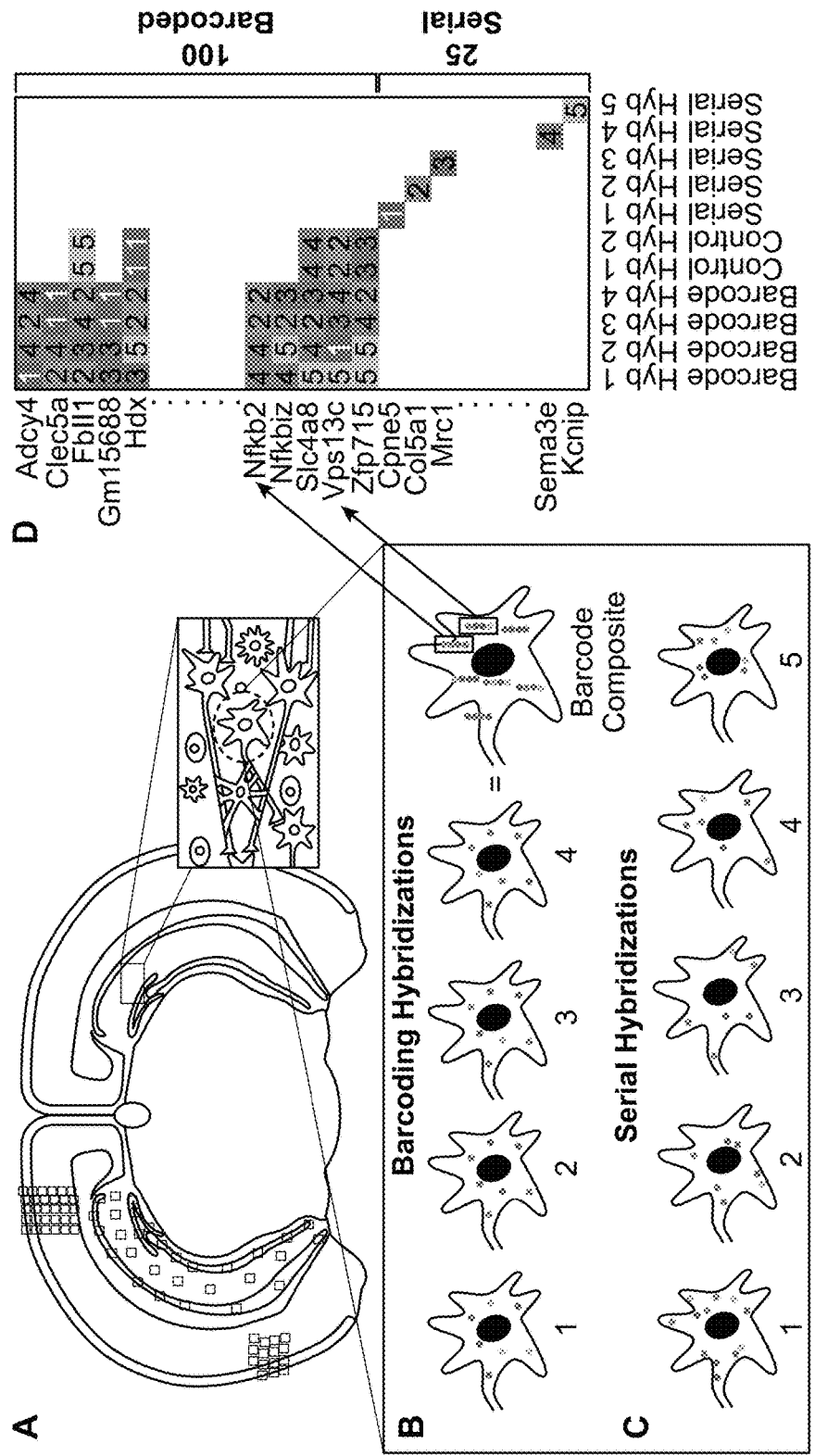

FIG. 32 depicts an overview of the Sequential barcode FISH (seqFISH) in brain slices. A). A coronal section from a mouse brain was mounted on a slide and imaged in all boxed areas. Each image was taken at 60× magnification. B). Example of barcoding hybridizations from one cell in field from A. The same points are re-probed through a sequence of 4 hybridizations (numbered). The sequence of colors at a given location provides a barcode readout for that mRNA ("barcode composite"). These barcodes are identified through referencing a lookup table abbreviated in D and quantified to obtain single cell expression. In principle, the maximum number of transcripts that can be identified with this approach scales to $F^N$, where F is the number of fluorophores and N is the number of hybridizations. Error correction adds another round of hybridization. C). Serial smHCR is an alternative detection method where 5 genes are quantified in each hybridization and repeated N times. Serial hybridization scales as F*N. D). Schematic for multiplexing 125 genes in single cells. 100 genes are multiplexed in 4 hybridizations by seqFISH barcoding. This barcode scheme is tolerant to loss of any round of hybridization in the experiment. 25 genes are serially hybridized 5 genes at a time by 5 rounds of hybridization. Each number represents a color channel in single molecule HCR. As a control, 5 genes are measured both by double rounds of smHCR as well as barcoding in the same cell. E. SmHCR amplifies signal from individual mRNAs. After imaging, DNAse strips the smHCR probes from the mRNA, enabling rehybridization on the same mRNA (step a). The "color" of an mRNA can be modulated by hybridizing probes that trigger HCR polymers labeled with different dyes (step b). mRNA are amplified following hybridization by adding the complementary hairpin pair (step c). The DNAse smHCR cycle is repeated on the same mRNAs to construct a predefined barcode over time.

Figure 33:
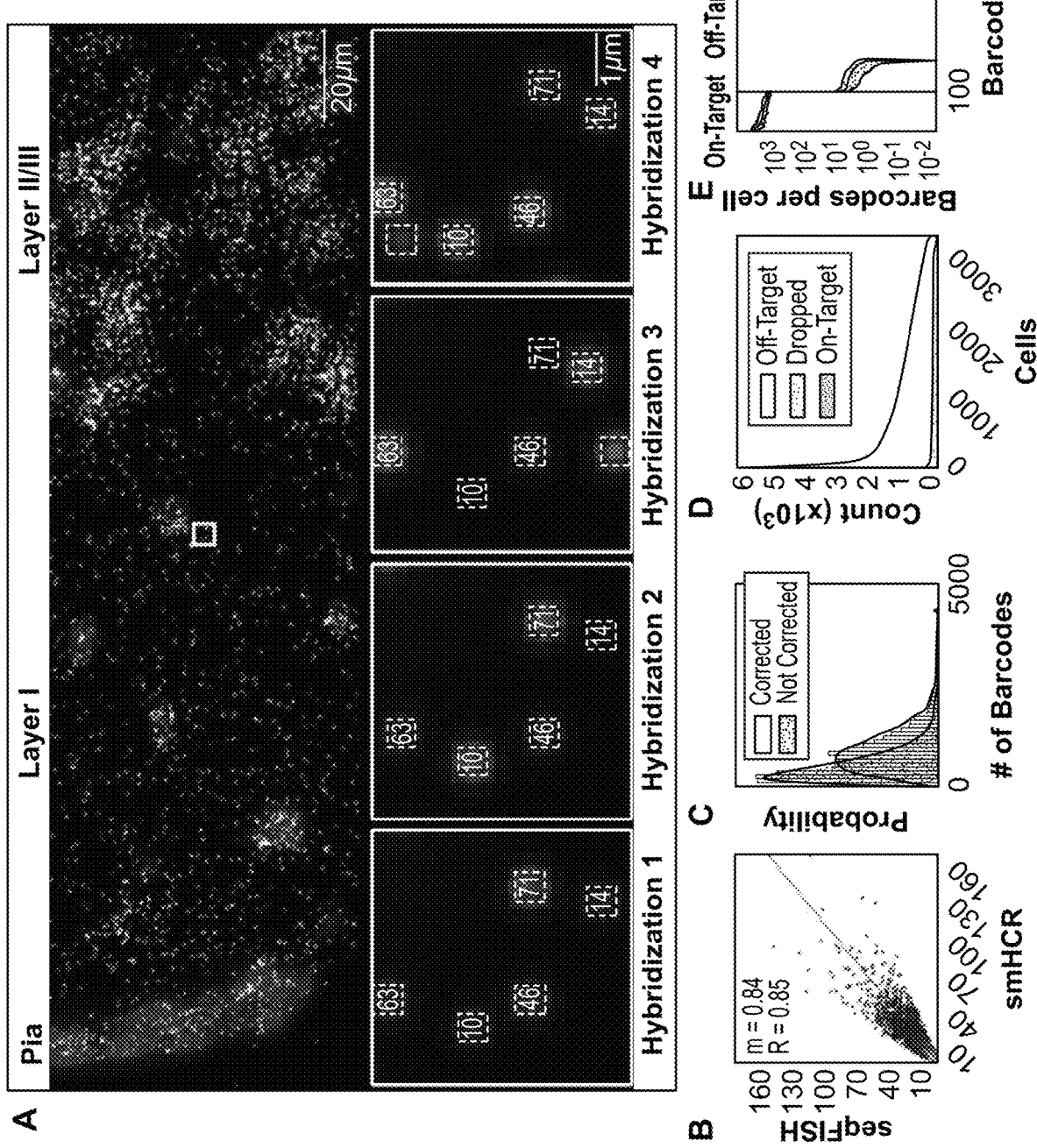

FIG. 33 illustrates an example accurate in situ quantification of mRNA levels generated by seqFISH. A). Image of seqFISH barcoding 100 genes in the outer layer of the mouse cortex. RNA dots in the image are z projected over 15 μm. Individual mRNA points are shown across 4 hybridizations in the inset images. White squares correspond to identified barcodes, yellow squares correspond to missing transcripts in a particular hybridization, red squares correspond to spurious false positives and are not counted in any barcode measurements. Numbers in the squares correspond to barcode indices. B). seqFISH correlates with smHCR counts. After barcoding, 5 target mRNAs were measured twice by smHCR in the same cells, providing absolute counts of the transcripts. The two techniques correlate with an R=0.85 and a slope (m) of 0.84 (n=3851 measurements). The 2D histogram intensity shows the distribution of points around the regression line. A high density of points is seen along the regression line. The density falls off steeply around the regression line. C). Error correction results in a median gain of 373 (25%) counts per cell (n=3497). Red and blue curves correspond to the total barcode counts per cell before and after error correction. D). Dropped and off-target barcodes represent a small source of error in seqFISH. 100 on-target barcodes and 525 off-target barcodes are measured per cell. Dropped barcodes are due to at least two overlapping dots appearing within the same region. E. Off-target barcodes are rarely observed and contribute minimally to the expression profile in single cells. Each of the 100 on-target barcodes (blue) and 525 off-target barcodes (red) are quantified per cell. The mean is shown with shaded regions corresponding to 1 SD (N=41 imaged regions).

Figure 34:
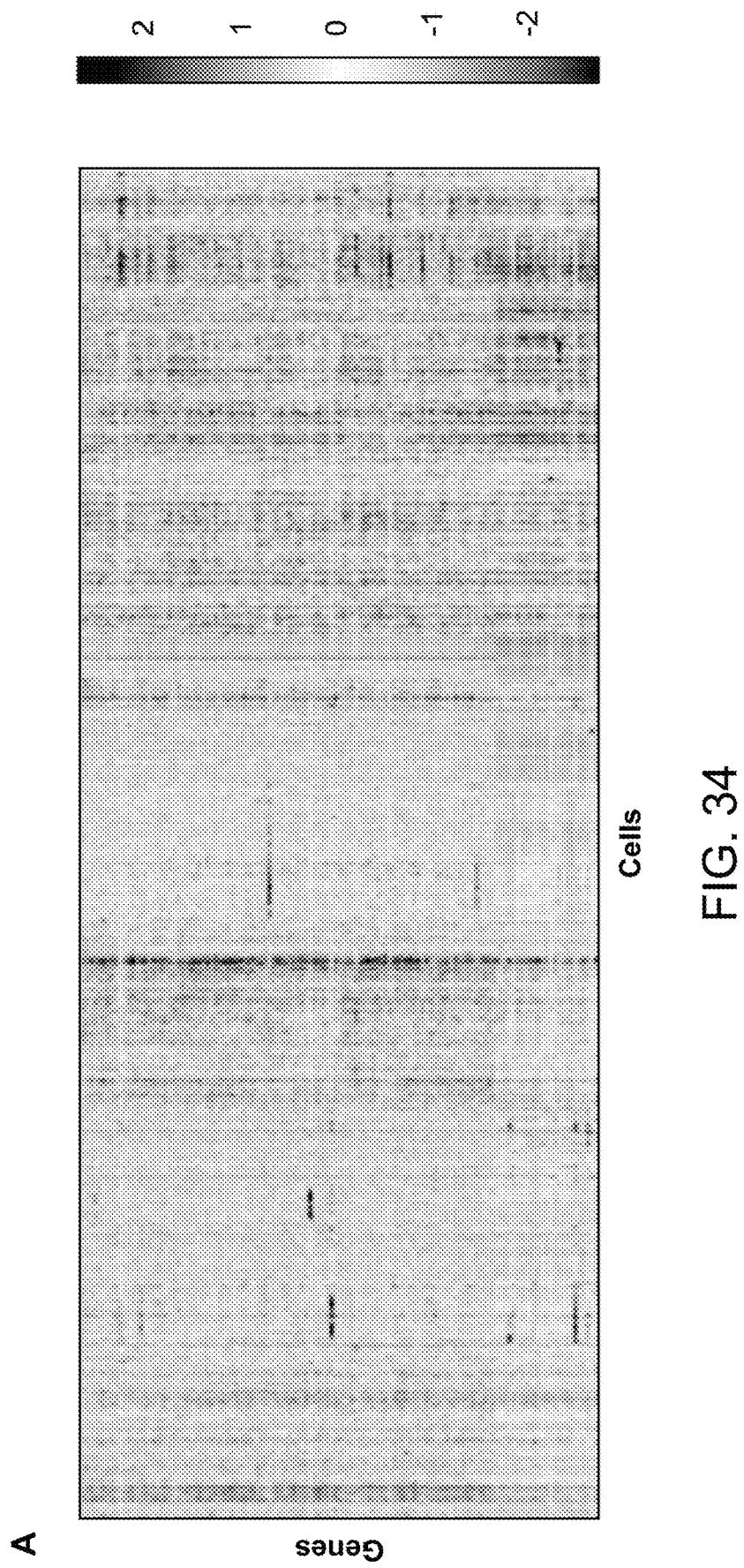

FIG. 34 depicts an example illustrating that distinct clusters of cells exhibit different regional localization in the brain. A). Gene expression of 14,908 cells presented as a Z-score normalized heatmap. B). Regional compositions of 13 cell clusters are visualized as stacked bar plots with the area corresponding the number of cells in each region. Hippocampal regions are: CA3, CA1, Dentate Gyrus (DG). Cortical regions: parietal and temporal. Box plot of the Z scores of 21 representative genes are plotted for each cell class. The major tick marks correspond to Z score 0 while every minor tick is a z score interval of 1. Cell type assignments are shown on the dendrogram. Abbreviations: Hippocampus pyramidal (Hipp), cortex (Cort), Dentate Gyrus (DG), Interneurons (Int), Astrocyes (Astro), Microglia (μGlia). C). Subclusters of cluster 6 cells and their regional localization and gene expression profile displayed under the dendrogram. Subcluster 6.1 is enriched in the CA3, while 6.7 is enriched in the DG. D). Subclusters of cluster 7 cells are shown. Almost all cells are localized in the GCL but have different combinatorial expression profiles. Note Calb1 expression, which marks out granule cell maturation, differs amongst subclusters. E). Any random subset of 25 genes can recapitulate approximately 50% of the information in the correlation amongst cells (red), but a larger number of genes are required to accurately assign cells to cluster using a random forest algorithm (blue) (n=10 bootstrap replicates; shading is 95% CI), indicating that fine structures in the data require quantitative measurements of combinatorial expression of many genes. F). Similar to E, while the first ten PCs explain the coarse structure, a larger number of principal components (PCs) are required to describe the full data. Expected variation (green) and accuracy in predicting cell identity using a random forest model (blue).

Figure 35:
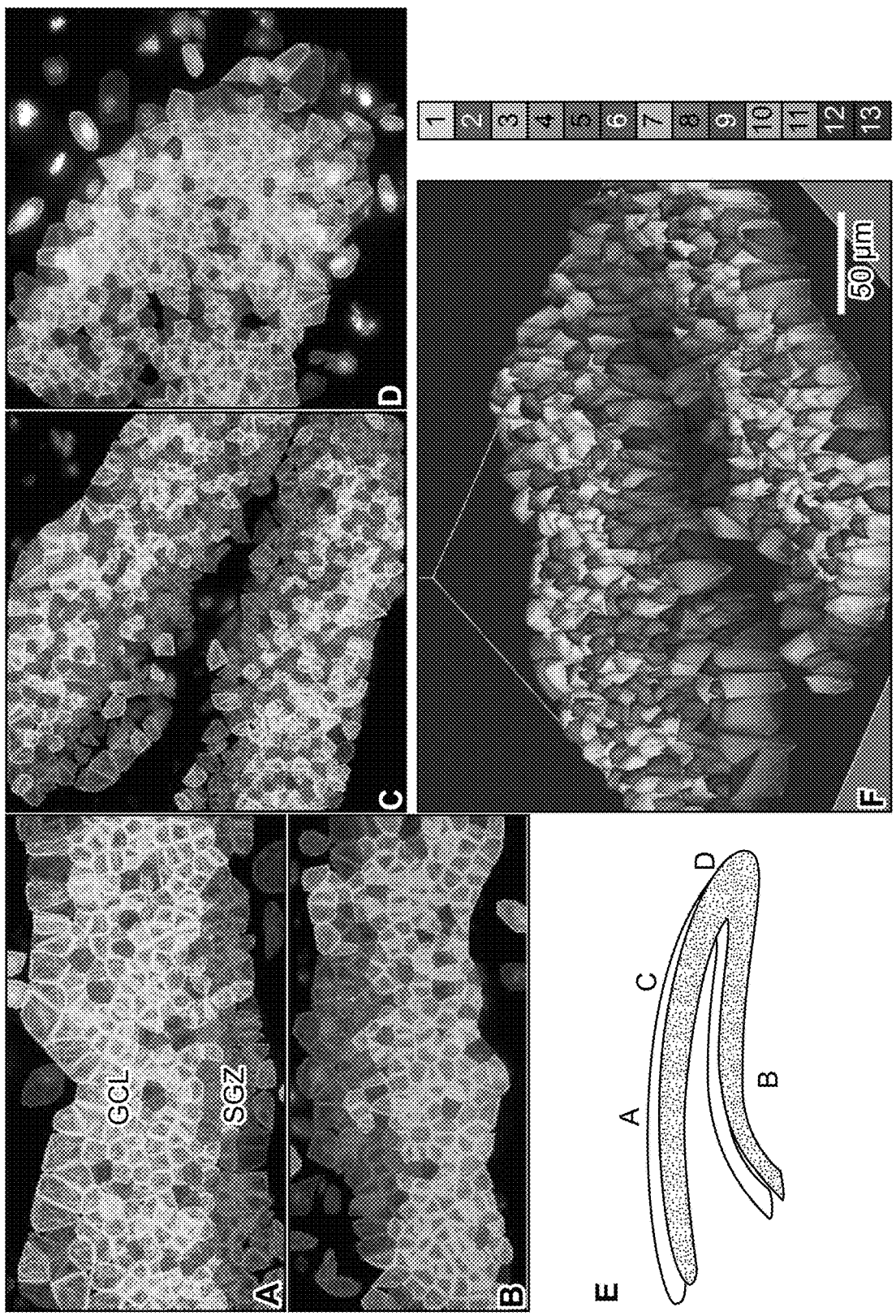

FIG. 35 depicts an example embodiment, illustrating spatial layering of cell classes in the Dentate Gyrus (DG). A-B). Suprapyramidal and infrapyramidal blades of DG. Cells of the subgranular zone (SGZ) and granule cell layer (GCL) are arranged in lamina layers in mirror symmetric patterns on the upper and lower blades. C). The SGZ stays on the inner layer of the DG fork. D). Cells are patterned in the crest. Numbered color key corresponds to cluster numbers in FIG. 34, b. E). Letters in the cartoon of DG correspond to images. F). 3D image of the fork region shown in C).

Figure 36:
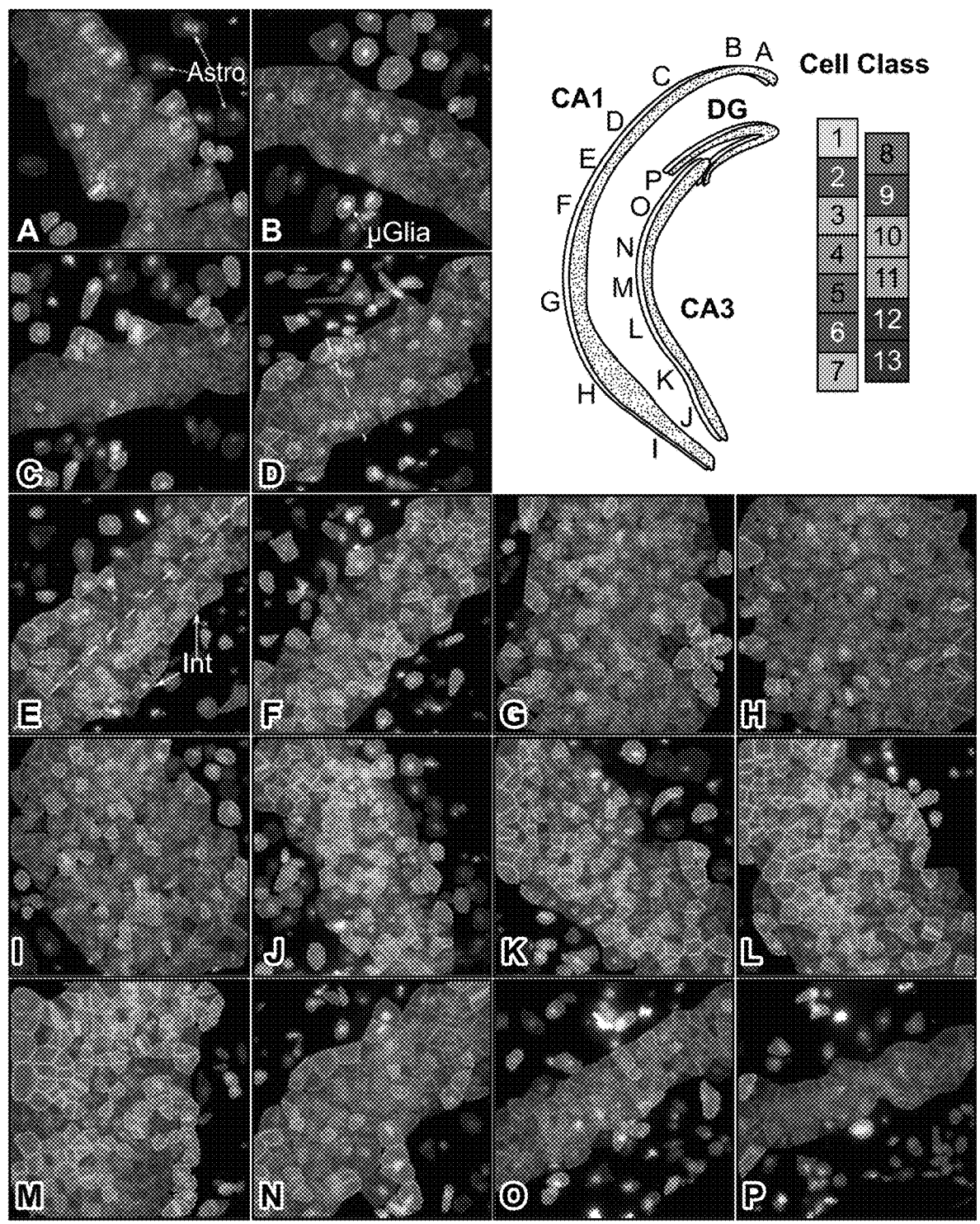

FIG. 36 depicts an example embodiment, illustrating that subregions of the hippocampus are composed of distinct compositions of cell classes based on the first 125 gene experiment. Upper right panel. Cartoon of hippocampus with imaged regions labeled. Color key corresponds to the classes in FIG. 39, b. A-D). These images are regions from the CA1d. Astrocytes (Astro) are marked in image A) and a microglia cell (μGlia) is marked in image B). Moving along the hippocampus from CA1 dorsal to ventral, cell classes transition from a homogenous dorsal population (C to D) to a mixed population in the CA1 intermediate (E-F) to regions of even larger cellular diversity in the CA1 ventral region (G-I). The dotted line in D) marks the transition point of the CA1d to the CA1i. E) shows two laterally segregated cell classes (marked by a dotted line) in the CA1i along with cholinergic interneurons (Int) on the interior surface of the CA1i. The ventral (J-K) and intermediate CA3 (L-M) have similar cell classes compositions to the CA1v and CA1i. The two last regions (O-P) of the dorsal CA3 shows distinct cell classes compositions that are relatively homogeneous within a field but are different than other fields of CA3. The cell class composition of field P is similar to that of the CA1d, but these cluster 6 cells are grouped into a distinct subcluster.

Figure 37:
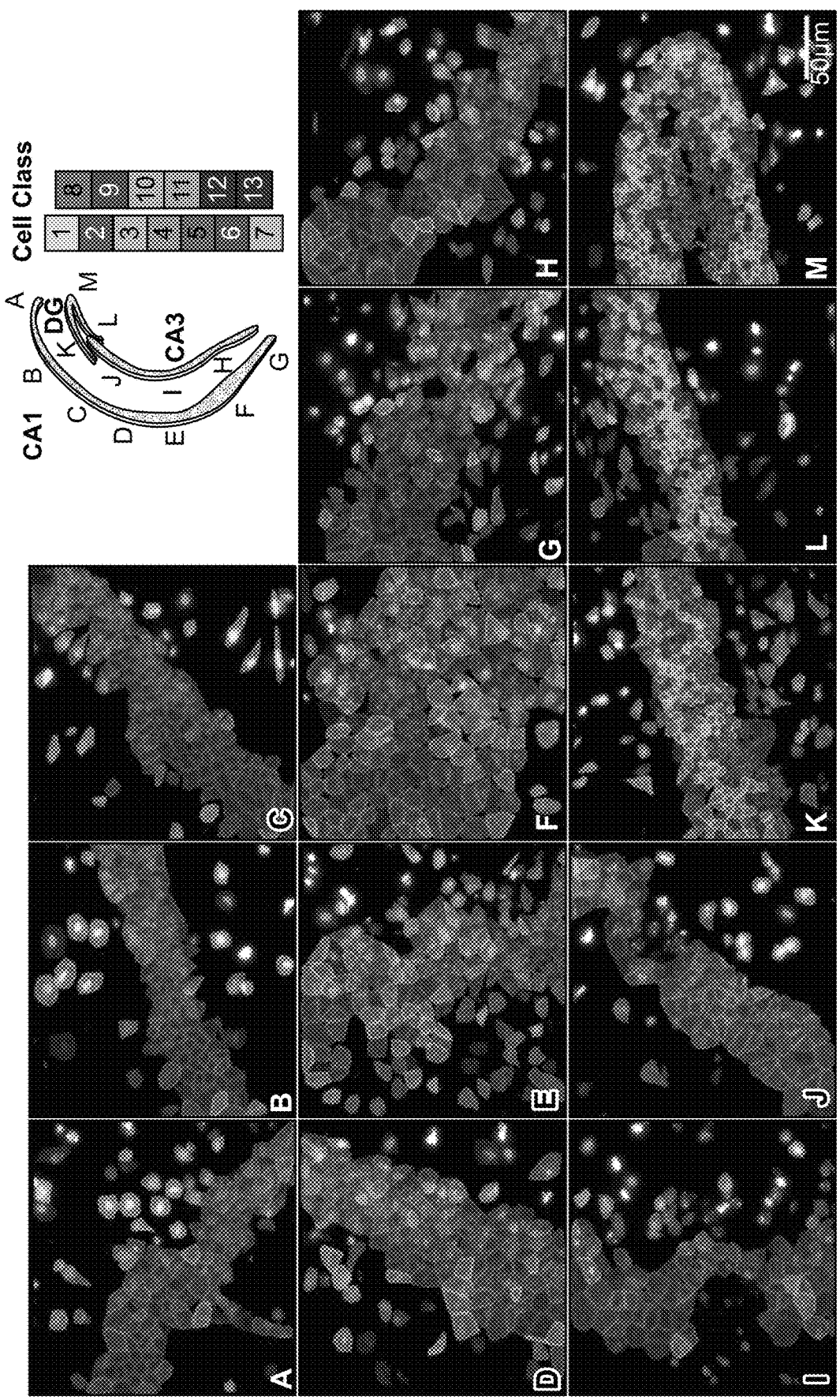

FIG. 37 depicts an example embodiment, showing mapping of cell types to a second brain slice with 125 genes. Upper right panel. Cartoon of hippocampus with imaged regions labeled. Color key corresponds to the classes in FIG. 34, b. A-D. Similar to the cell class compositions shown for the hippocampus in FIG. 36, CA1d in this second coronal section from a second mouse is composed of mostly cluster 6 cells. (E) CA1i region and (F-G) the CA1 ventral regions are again composed of similar cell classes to that shown in FIG. 36 with increasing diversity of cell class compositions from the CA1d to the CA1i to finally the CA1v. (H-J) CA3 regions. (K-M) DG regions showing the same cell classes and layer pattern of the GCL and SGZ shown in FIG. 35.

Figure 38:
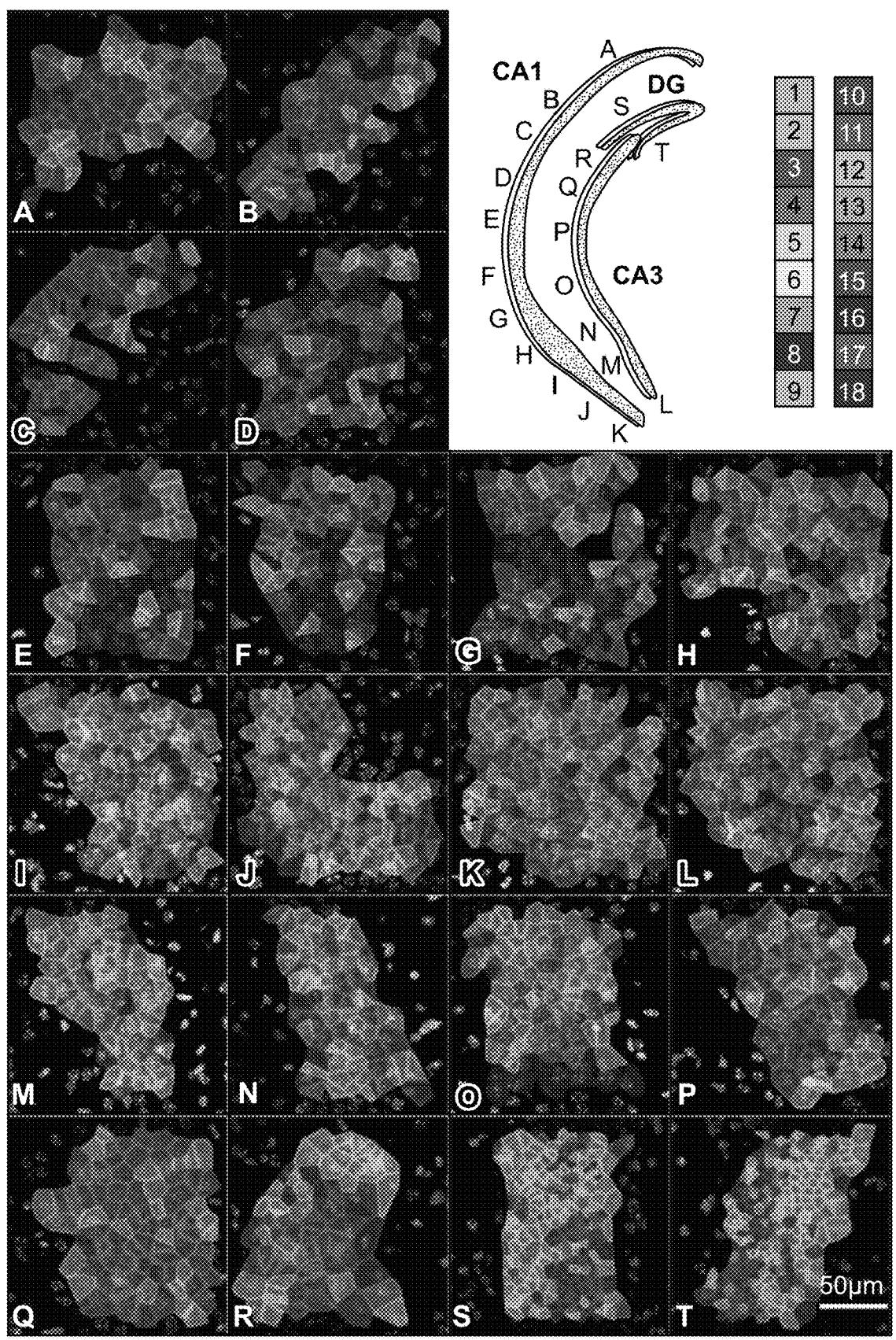

FIG. 38 depicts an example embodiments, showing mapping of cell types to a third brain slice with 249 genes. Upper right panel. Cartoon of hippocampus with imaged regions labeled. Color key corresponds to the classes in FIG. 46, C. A-C). Similar to the slice shown in FIGS. 36 and 37, CA1d is relatively homogenous in cell cluster composition. D-G). Images from the CA1i region show that the cell class composition is different from that of the CA1d. H-K). Again, similar to FIGS. 36 and 37, images from the CA1 ventral regions shows a much more complicated cellular composition and a high degree of cellular heterogeneity. L-R). Images from the CA3 region show that the cellular compositions also creates 3-4 subregions within the CA3. The cellular heterogeneity of the CA3 subregions mirrors that of the CA1, where the ventral region of the CA3 is very heterogenous while the dorsal region of the CA3 is relatively homogenous. S-T). The DG regions show the distinct SGZ versus GCL layering pattern seen in the previous two brains.

Figure 39:
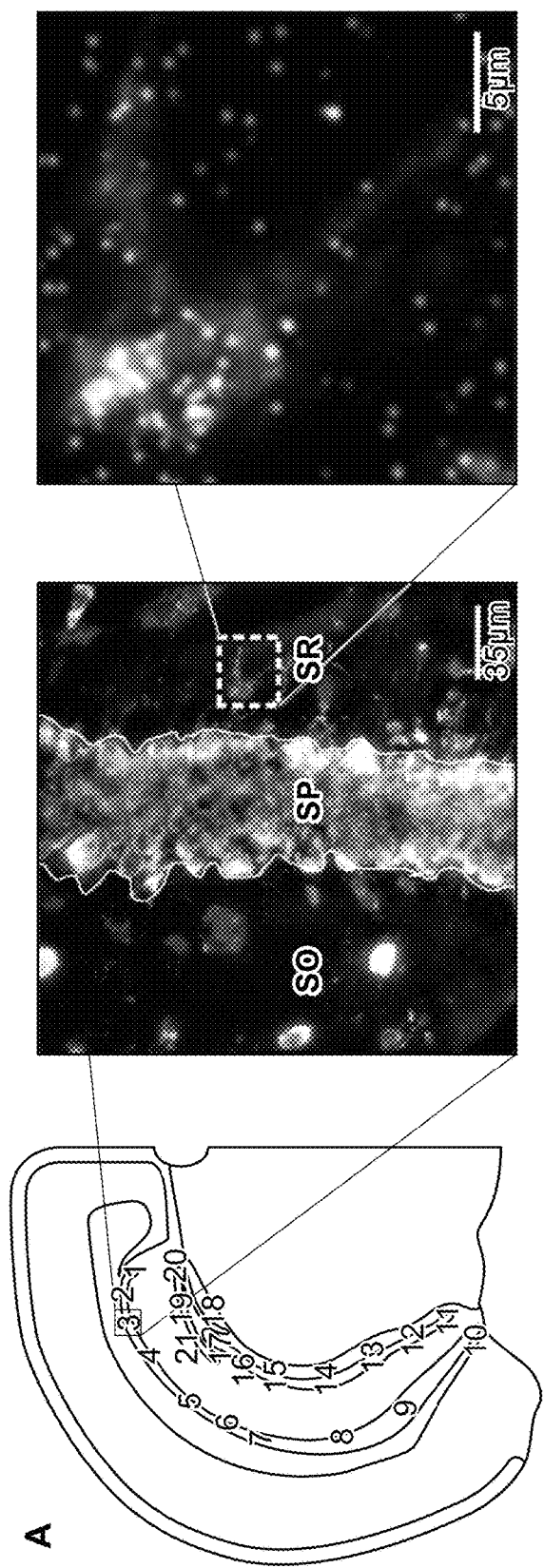

FIG. 39 depicts an example embodiment, showing correlations of the transcription profile across the pyramidal layer A). mRNA counts in the cell bodies in the Stratum Pyramidale (SP) are grouped within each field of view. A single cell in the Stratum Radiatum (SR) is shown to illustrate individual mRNA localization. Stratum Oriens (SO) is labeled for orientation. B). mRNAs in different subregions of pyramidal layer show both long-distance spatial correlations as well as local correlations between neighboring fields. Both CA1 and Dentate Gyrus (DG) show high regional correlations. Correlation is calculated based on the 125 gene experiment. C). Illustration of regional and long distance correlation patterns observed in B. Correlated regions are colored and long distance correlations are shown as dotted lines with their median correlation coefficient written over the dotted line.

Figure 40:
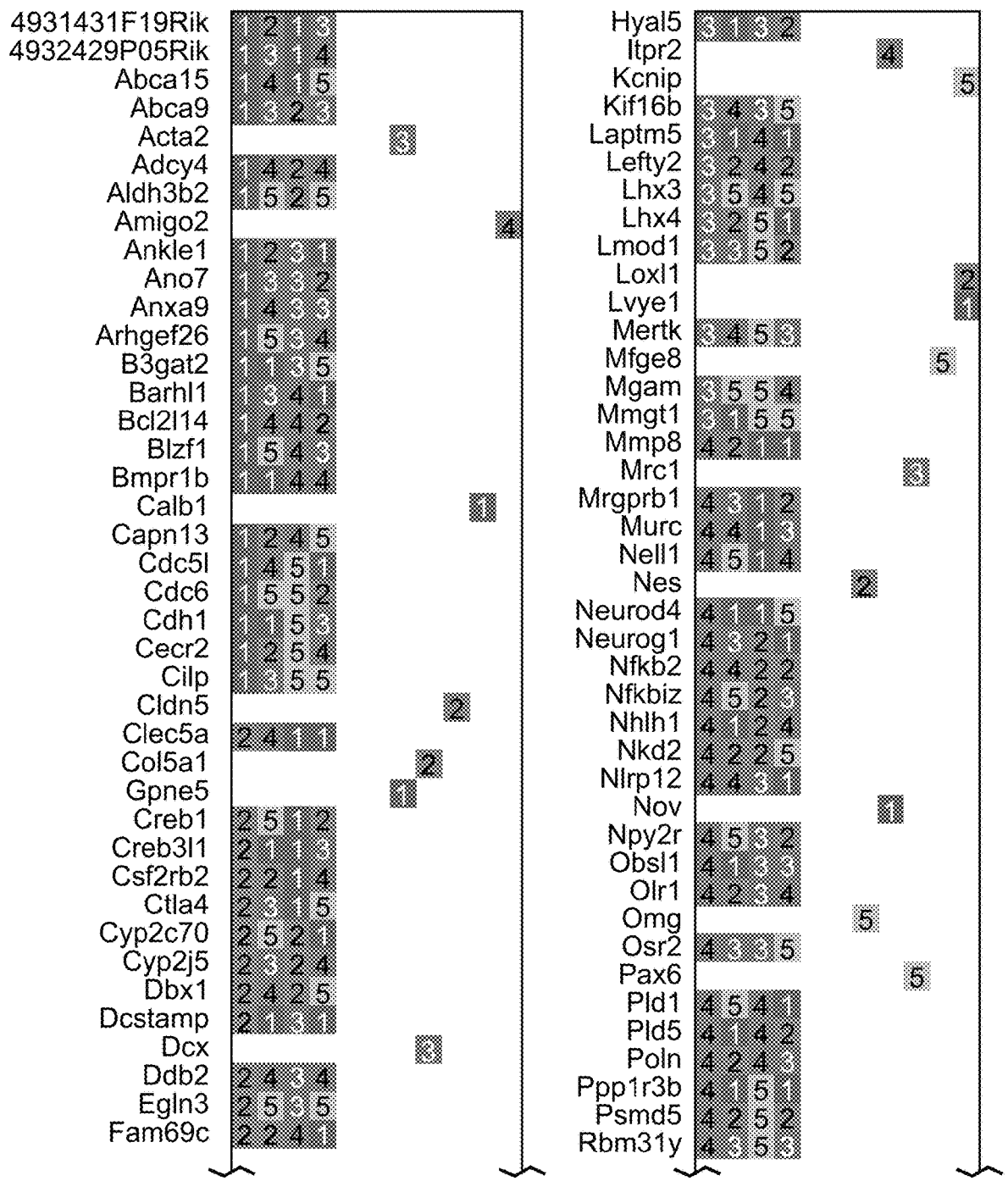
Figure 40:
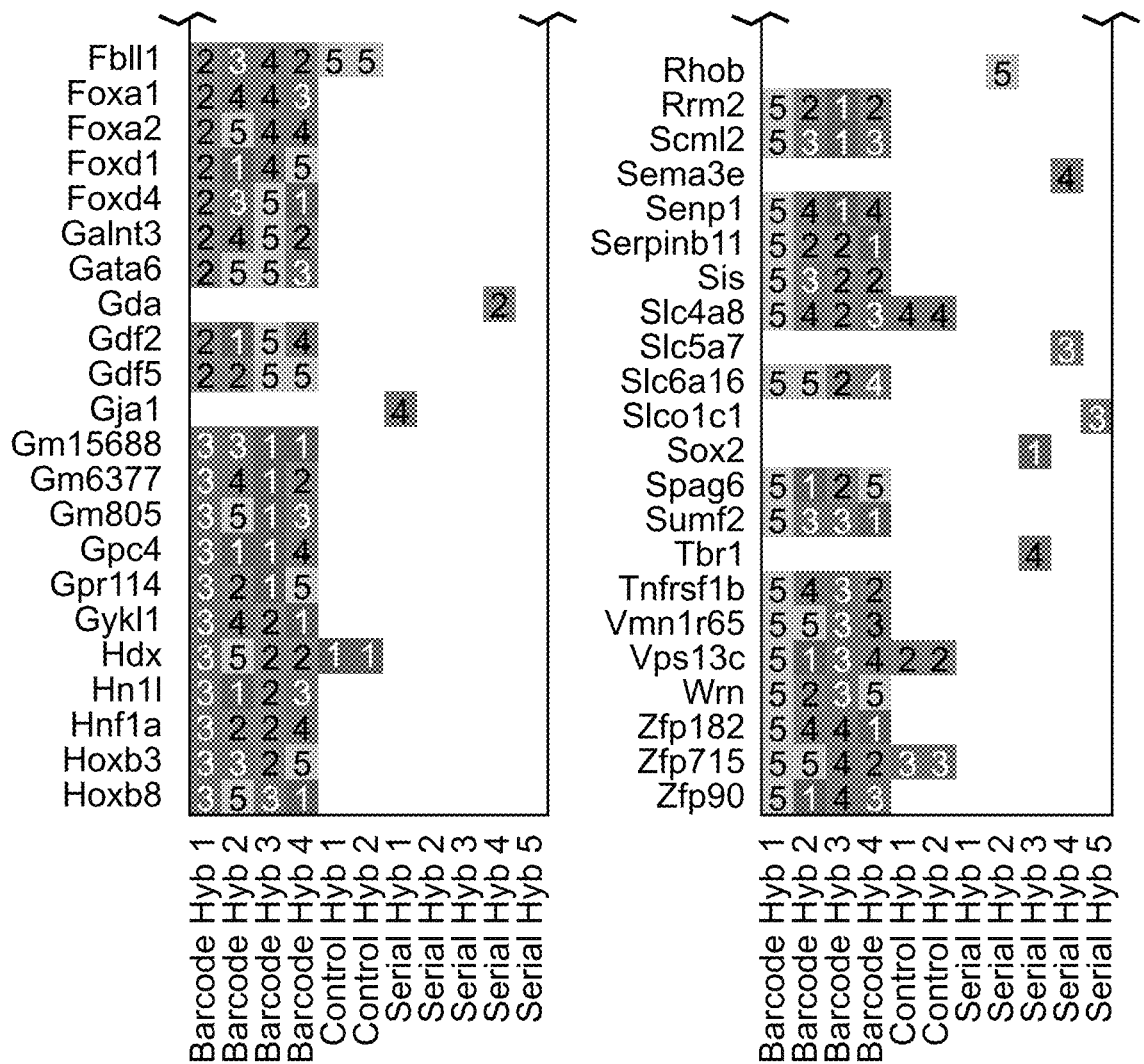

FIG. 40 depicts an example embodiment, showing barcode assignments for all genes in the combined hybridization experiment (FIG. 32). Barcode assignments in the 125-gene seqFISH and serial experiment (FIG. 32). 125 genes are profiled, 100 of which are barcoded and 25 are identified by serial smHCR hybridizations. Five control genes (Hdx, Vps13c, Zfp715, Fbl11, Slc4a8) were quantified by both techniques. The smHCR round of hybridization of control genes were performed twice to co-localize signal to obtain an absolute count.

Figure 41:
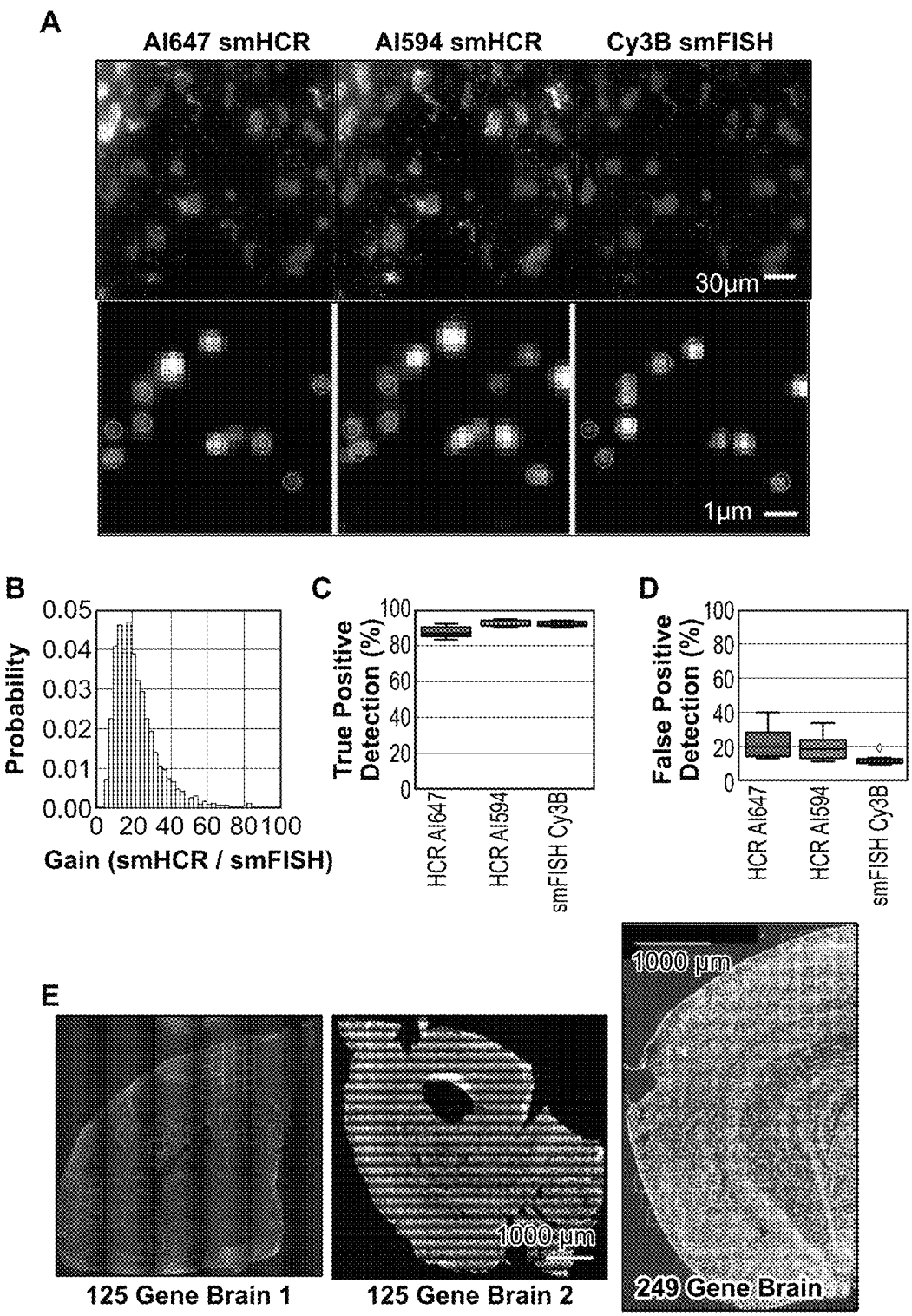

FIG. 41 depicts an example embodiment, showing smHCR performance metrics as compared to smFISH, (related to FIG. 32). A). Raw data of Pgk1 transcripts imaged in a brain slice. The transcript was targeted with 2 hcr probes sets and 1 smFISH probe set, each consisted of 24 oligonucleotide probes. The probe sets were hybridized together and were imaged in 3 different channels. Green circles are transcripts detected in all channels, yellow circles signify transcripts detected in 2 out of 3 channels, and red circles represent signal found in only 1 channel (false positives due to nonspecific binding). These images show that smHCR and smFISH have similar sensitivity, specificity, and spot size. B). Gain of smHCR vs smFISH. The mean gain of smHCR is 22.1±11.55 vs smFISH (n=1338). C). True positive detection rate of smHCR and smFISH per channel. The percent of true positives (transcripts detected with at least 2 out of 3 probe sets) detected with each probe set (n=1338). D). False positive rate of smHCR and smFISH. Percent of total dots in a channel not detected in any other channel for 3 color Pgk1 (n=1338). E). All the regions imaged in the coronal section are boxed. Each box represents a field of 216 um×216 um. The brain section used for FIGS. 32 and 33 is shown on the left. The middle section is used for FIG. 34 and the right section is used for FIG. 38.

Figure 42:
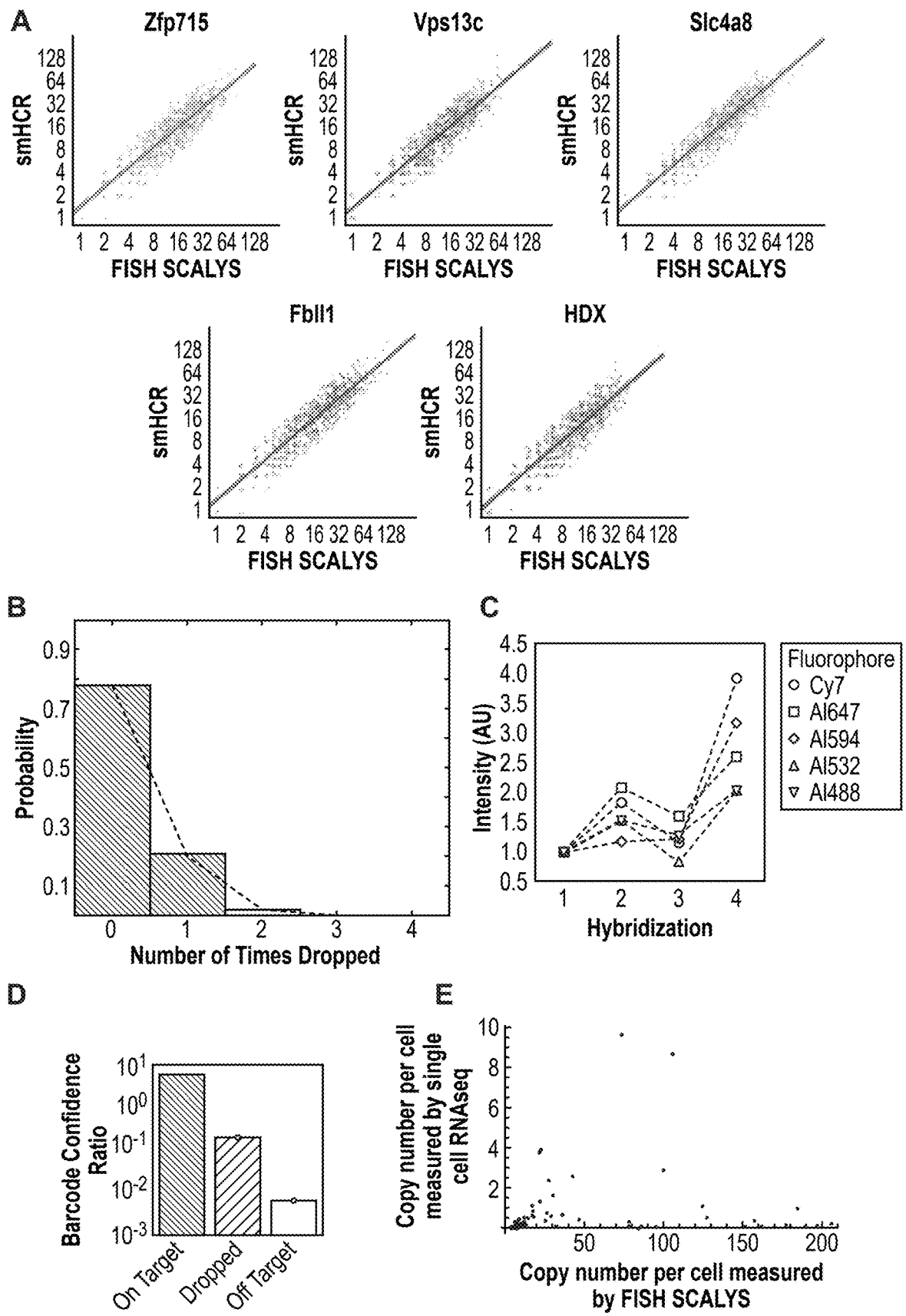

FIG. 42 depicts an example embodiment, showing quantitation of seqFISH (related to FIG. 33). A). All control genes show high correlations between seqFISH and smHCR. B). Number of dropped hybridizations from the barcode. Blue bars represent measured probability and the red bars represent inferred values from binomial distribution fitting of measured probability. The ratio of the full barcodes (4 hybridizations) vs 3 hybridization barcodes indicate that transcripts that are mis-hybridized in 2 rounds are rare. Transcripts missed in 2 or more hybridizations (red bars) could not be recovered from the error-correction algorithm and would be dropped from our quantifications (N=2,115, 477 total barcodes). C). Intensity of barcode hybridizations overtime. All dots belonging to barcodes are quantified in each hybridization and their mean intensity is plotted over time normalized to the first hybridization. 99% CI ratio of mean is plotted as a bar over points, but is not visible due to its small size (n=60143 to 111284 points per channel). D). Barcoding confidence ratio. Barcode classes in D) are compared to a null model of barcode observations where random chance observation should give a ratio of 1. Off target barcodes are observed 0.005 times less than expected, suggesting that seqFISH has high accuracy in correctly counting barcoded transcripts (n=3493 cells). Dark bars on top of bar plots correspond to 99.999% confidence interval determined by bootstrap resampling. E). Comparison of average copy numbers per gene as measured by Zeisel et al. and seqFISH. Single cell RNA-seq underestimates copy numbers compared to seqFISH.

Figure 43:
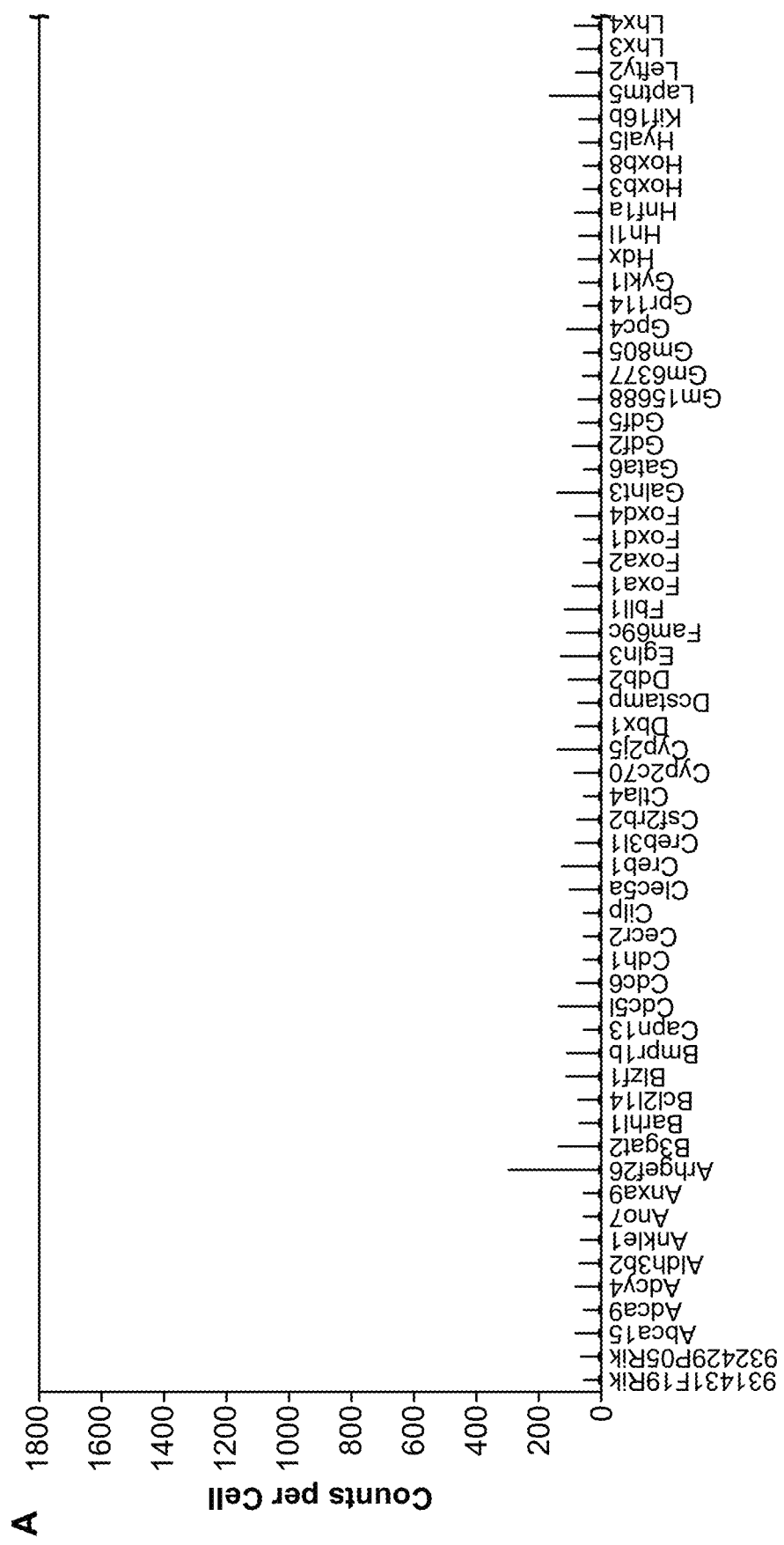

FIG. 43 depicts an example embodiment, showing gene expression patterns and clustering of the 125-gene dataset (related to FIG. 34). A). Overview of 125 gene expression. Plots show the distribution of each transcript in all 14,908 imaged cells. Note the last 25 genes have higher expression and were imaged with serial hybridization. B). Violin plots of Z-score distribution for 125 genes. C). Sub-cluster hierarchy of each of the 13 clusters identified in FIG. 34B. D). PCA eigenvalue analysis of the cell-to-cell correlation matrix. First 125 PC and their eigenvalues are shown. As observed in FIG. 31, the first 10 PCs explain 59.5% of the variation in the data, while the remaining 115 PCs are needed to explain remaining data. Reflecting this, the eigenvalues of the first 10 components are high, while the remaining eigenvalues are uniform. E). Correlation between gene expression and spatial localization. Each dot represents a pair of cell classes and their correlations in gene expression space (x) and spatial localization patterns (y) (N=153 pairwise correlations between classes, R=0.67). Classes that are similar in expression have similar localization patterns. F). PCA decomposition separates cells into coherent clusters corresponding to cell classes. Cells are colored according to the clusters displayed in the dendrogram.

Figure 44:
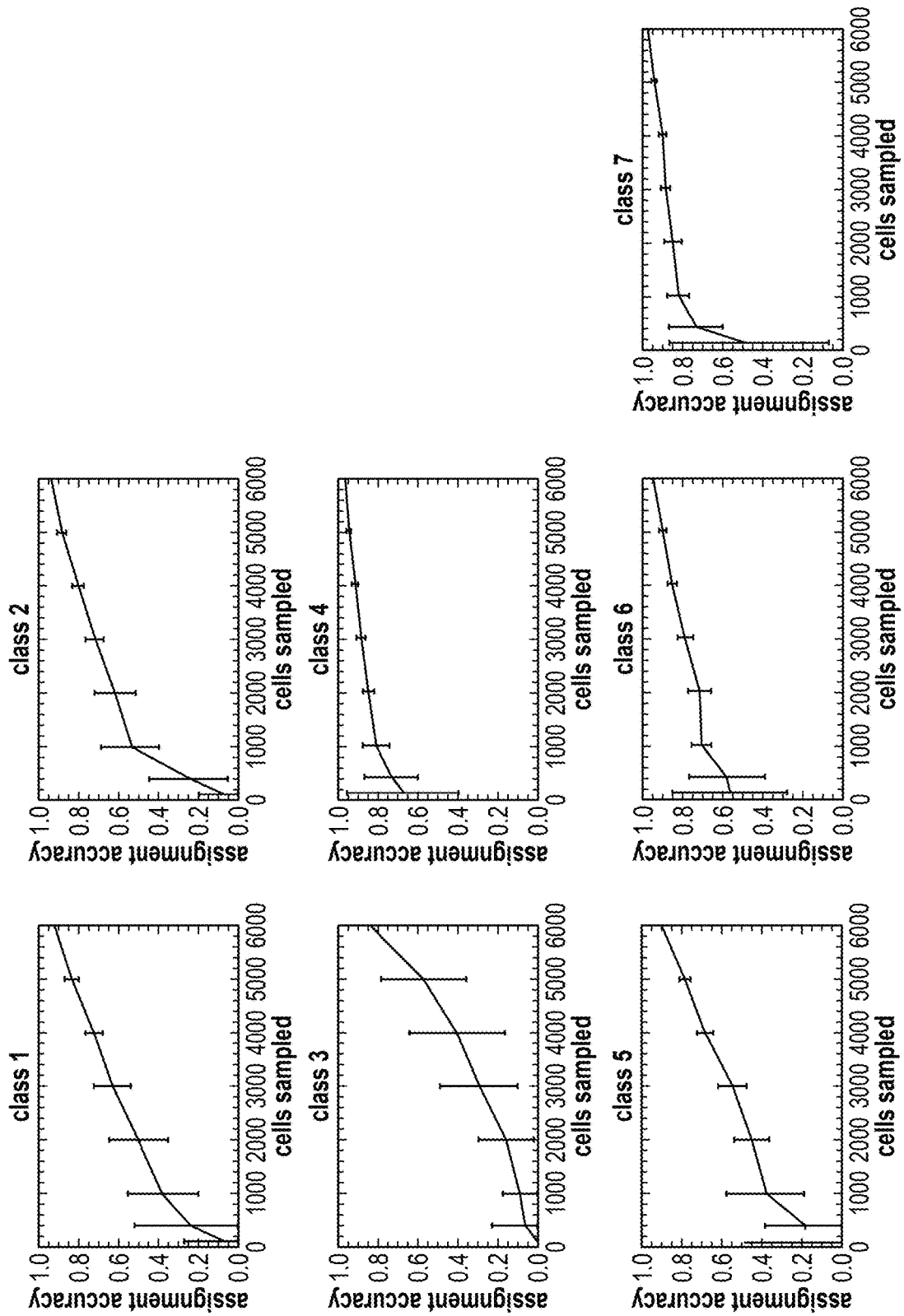
Figure 44:
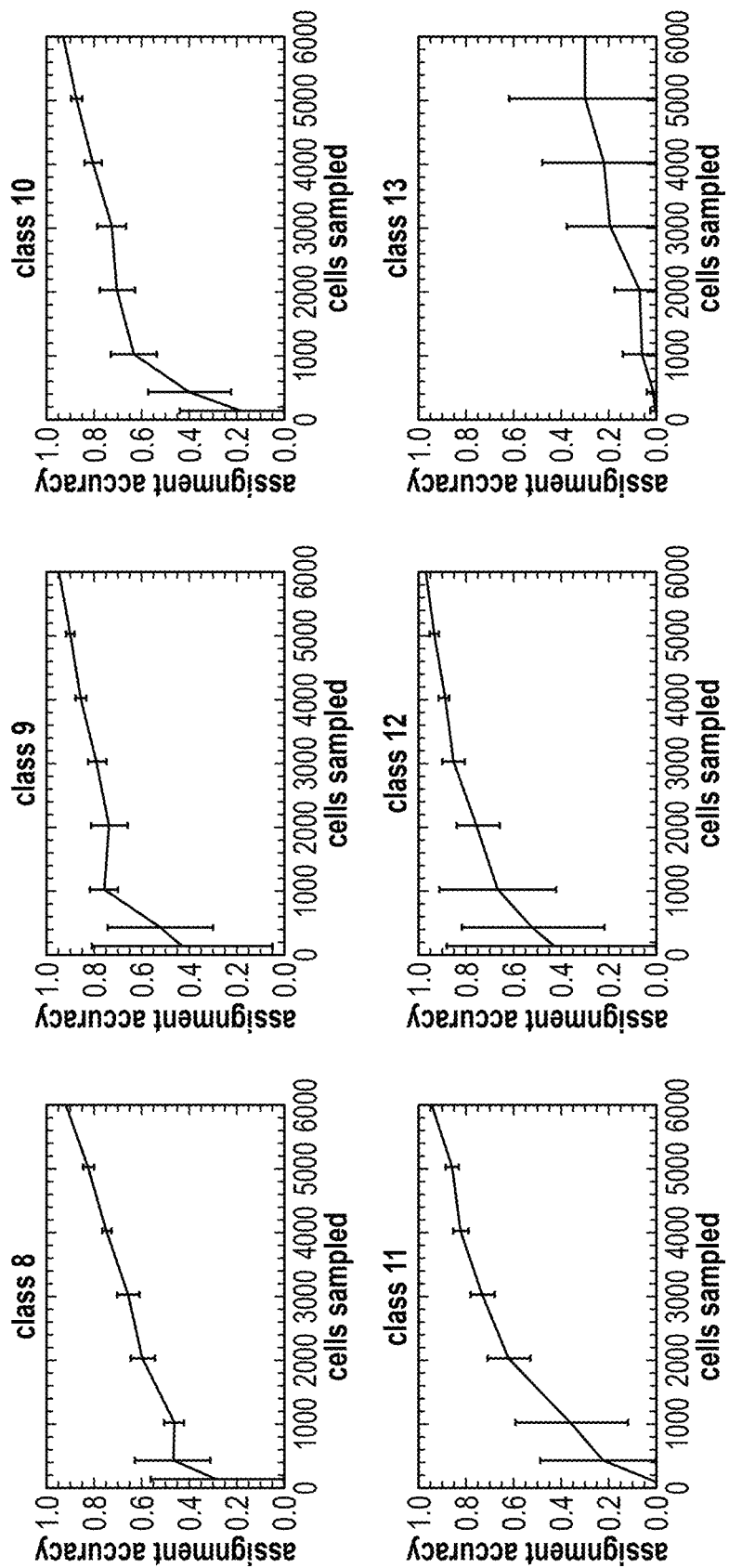

FIG. 44 depicts an example embodiment, showing robustness of cell classes to downsampling of cells (related to FIG. 34). To measure how well cluster assignments perform with a limited number of cells, a random forest model was trained on the cell-to-cell correlation matrix of the 6872 cells in the center field of view. The robustness of the clusters was calculated by applying this model to classify the remaining cells and determining the percent accuracy of correct assignment to the clusters presented in FIG. 34, b. While some classes can be assigned accurately even with a small number of cells as the initial training set, several classes require large number of cells to accurately assign (n=10 bootstrap replicates, S.E.)

Figure 45:
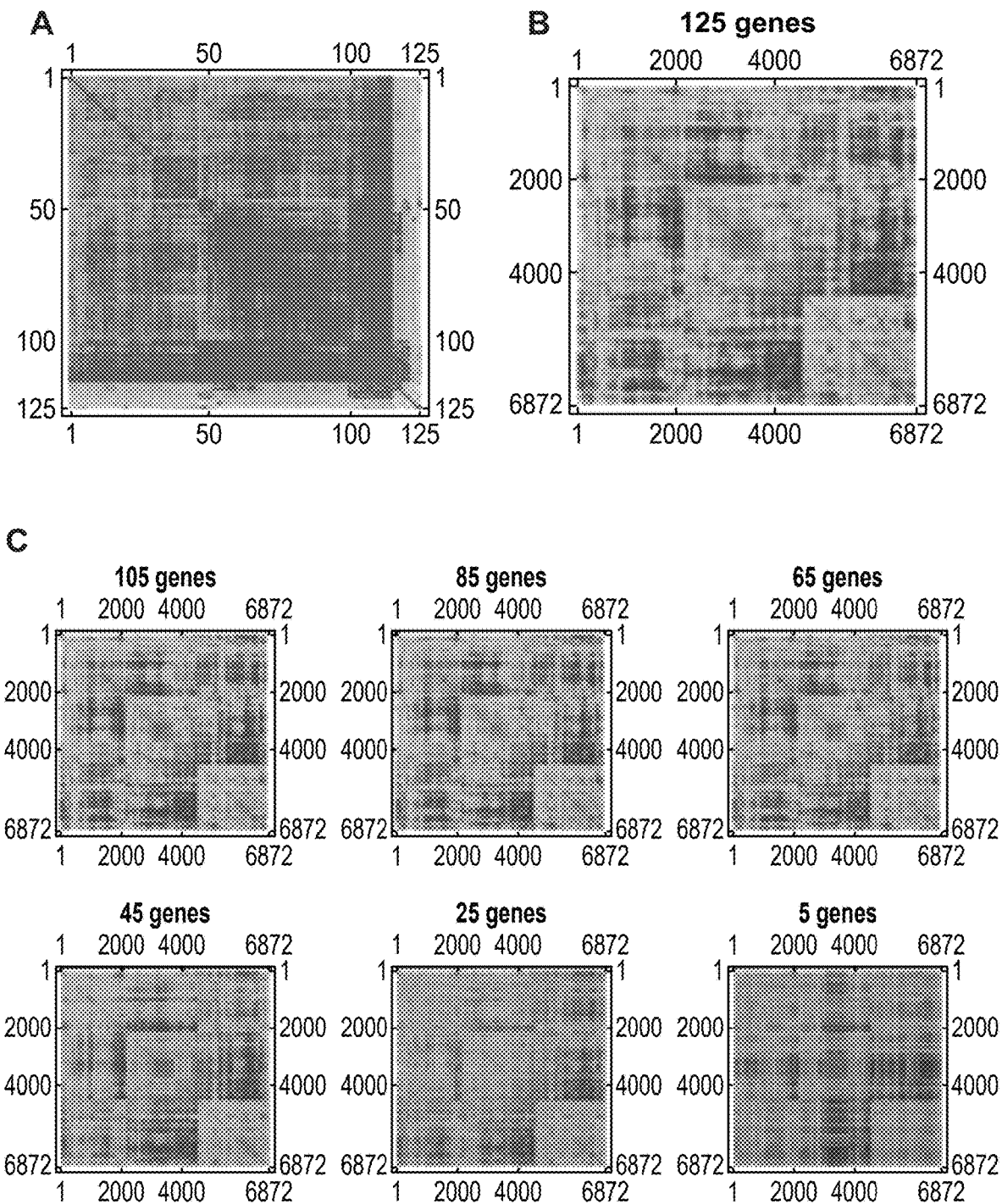

FIG. 45 depicts an example embodiment, showing cell-to-cell correlation analysis as a function of dropping genes (related to FIG. 34). A). Clustered gene to gene correlation map for all 125 genes. There are many blocks of highly correlated genes. A few genes do not fall into any blocks. B). The full cell-to-cell correlation map using all genes in the data set. C). Representative cell-to-cell correlation with the indicated number of genes used to construct the matrix indicated above each plot. Dropping genes from the data results in degradation of the fine structure of the correlation map.

Figure 46:
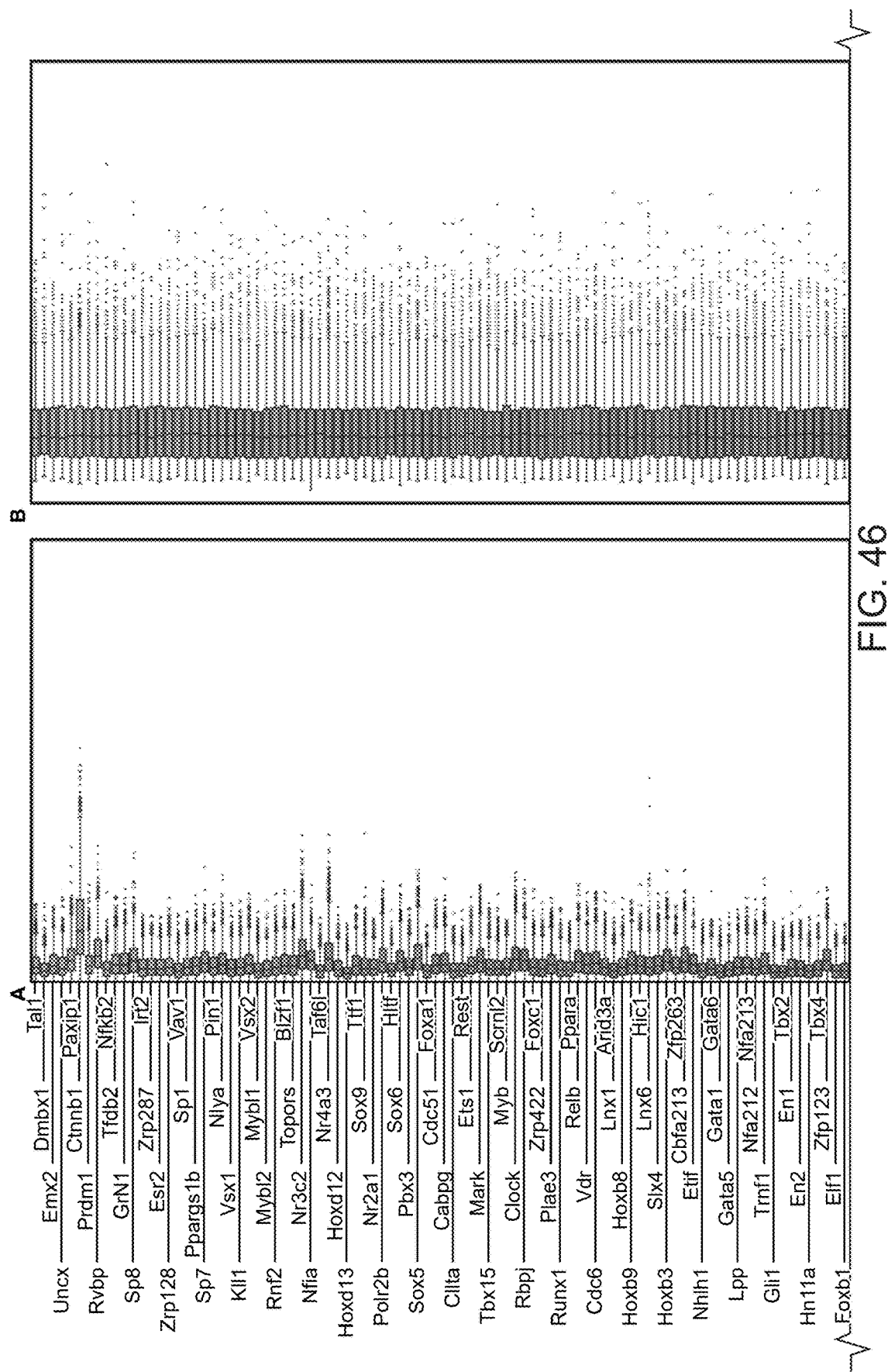

FIG. 46 depicts an example embodiment, showing gene expression patterns and clustering of the 249-gene dataset (related to FIG. 38). A). Overview of 249-gene expression. Plots show the distribution of each transcript in all 2050 imaged cells in the hippocampus. Note the last 35 genes have higher expression and were imaged with serial hybridization. B). Violin plots of Z-score distribution for 249 genes. C). Dendogram with regional localization of the 18 cell clusters for the 249-gene experiment. D). Correlation of seqFISH counts to smHCR counts for the 249-gene experiment. The 2D density histogram shows a high density of points around the regression line that fall off towards the edges of the distribution. E). Cell-to-cell correlation for all 2050 cells in the 249-gene dataset. F). Heat map of the percentage of each cell class in each region of the hippocampus for both the 125-gene experiments. These heat maps show that in both 125-gene experiments the same cell classes are used in roughly the same proportions in each subregion. G). Heat map of the percentage of each cell class in each region of the hippocampus for the 249-gene experiment. The same patterns are seen as the 125 gene experiment (i.e., different regions use different cell classes in varying amounts).

FIG. 47 depicts an example embodiment, showing marker genes expression in the hippocampus (related to FIG. 38). A). The top panel outlines the region of the hippocampus being shown in a yellow box. The images show the raw gene expression patterns seen using smHCR in our data at the dorsal most tip of the CA3 for a representative set of cell identity markers used in the 249 gene experiment. The transcript expression profile is shown in red, Nissl staining is shown in green, and DAPI staining is shown in blue. Each image shown is the full field of view and a maximum intensity projection over 15 um. B). Set of images showing the distinction between the GCL and SGZ. The GCL shows a high level of Nissl staining and expression of neuronal genes such as slc17a$_7$ and camkII. The SGZ shows an absence of Nissl staining and terminal neuron marker genes. The transcript expression profile is shown in red, Nissl staining is shown in green, and DAPI staining is shown in blue. Each image shown is the full field of view (216 um×216 um) and a maximum intensity projection over 15 um.

FIG. 48 depicts an example embodiment, showing comparison of SeqFISH expression data to Allen Brain Atlas expression data (related to FIG. 39). A). ISH data from the Allen Brain Atlas for genes seen to be enriched in the SGZ in the 125 and 249 gene seqFISH experiments. In the 125 gene experiment, mertk and mfge8 were found to be enriched in the SGZ. In the 249 gene experiment, nfia and sox11 were seen to be enriched in the SGZ. ABA ISH data shows similar patterns to those observed with seqFISH for the SGZ. B-C). Comparison of averaged z-score values per cell from seqFISH to ABA data across hippocampus. B). Amigo2 Z-score profile found across the different fields of the hippocampus using seqFISH is shown on top and the ABA ISH image for Amigo2 is shown on the bottom. C). Gpc4 Z-score profile found across the different fields of the hippocampus using seqFISH is shown on top and ABA ISH image for Gpc4 is shown on the bottom.

DETAILED DESCRIPTION OF CERTAIN EMBODIMENTS

Among other things, the present invention provides new methods, compositions and/or kits for profiling nucleic acids (e.g., transcripts and/or DNA loci) in cells.

In some embodiments, the present invention provides methods for profiling nucleic acids (e.g., transcripts and/or DNA loci) in cells. In some embodiments, provide methods profile multiple targets in single cells. Provided methods can, among other things, profile a large number of targets (transcripts, DNA loci or combinations thereof), with a limited number of detectable labels through sequential barcoding.

Pseudo-Color Based Barcoding

In one aspect, disclosed herein are pseudo-color based barcoding method. For example, pre-designed barcodes are associated specific molecular targets through sequential hybridization experiments. A pseudo-color based barcoding scheme is developed to overcome limitations in the previous generation of the technology such as lack of visual signals that can be associated with the probes or small internal within cell when carrying out in situ experiments. The current method can be applied to both in vitro and in situ analysis. According to the method, each barcoding round comprises multiple serial hybridizations where a small number of colored signals (that are associated with probes) are used in each hybridization experiment within a serial hybridization round. Images from each serial hybridization experiment within the same serial hybridization round are combined to form a composite image for each barcoding round. In each barcoding round, the same set of molecular targets are analyzed. After all barcoding rounds are completed, associated of the barcode with these molecular targets is completed.

To distinguish from existing FISH methods, the currently pseudo-color based barcoding methods is referred to as Sequential Probing Of Targets ("SPOTs").

SPOTs offers numerous advantageous over existing barcoding methods. For example, it does not require a user to have a large number of detectable label molecules, which can save time and money.

Pseudo-color scheme can overcome this density problem in both in situ and in vitro applications. In the in vitro cases, implemented with SPOTS, capturing transcripts onto an oligonucleotide dT surface and adjusting the dilution factors can easily remove the optical crowding problems and allow the transcriptome to be imaged by seqFISH.

In addition, pseudo-color is more efficient in terms of imaging time than all existing imaging methods including expansion microscopy. For example, with 3 fluorophores, it takes $3^{(10-1)}=19,683$ to code for the transcriptome with one round of error correction. Thus, a total of 30 frames of imaging is required. In the pseudo color scheme, 20 pseudo-colors can be used for 4 rounds of hybridization to code for $20^{(4-1)}=8000$ genes in each of the three fluorophore channels for a total of 24,000 genes. This requires 3×20×4-240 frames to image, a 8 fold increase in the imaging time. However, because the density of mRNA is effectively diluted into 3×20-60 pseudo-channels instead of 3 fluorophore without pseudo-color coding, the density problem is alleviated with a factor of 20. The target spots can be localized to nanometer precision by Gaussian fitting to decrease the density in each pseudo-color channel before barcode alignment. Thus, the benefit of pseudo-color coding is to decrease the density of the target spots in the cell, while saving imaging time compared to expansion microscopy, where expanding the sample by 20 folds requires an additional 20 fold increase in imaging time. Since imaging time is rate limiting in any sequential imaging method, pseudo-color solves a major problem in implementing transcriptome profiling in situ.

Overview

In fluorescence in situ hybridization (FISH) methods, fluorescence labels that are capable of producing different visual signals are used to detect multiple molecular targets (such as mRNA transcripts) at the same time in one hybridization experiment.

FIG. 1 illustrates three types of hybridization methods, where combinations of visual signals (barcoding schemes) are used to specifically encode individual molecular targets. FIG. 1, a) shows a spatial barcode scheme where different colored probes are bound to the same target. The probes of the same color are grouped and spatially separated from another color.

FIG. 1, b) depicts a spectral barcode scheme where different colored probes are no longer separated in groups according to their respective colors. Probes bound along a target are resolved by spectral methods to create a barcode.

The approaches in FIG. 1, a) and b) both rely on combinations of signals (colors) and are heavily limited by the types of signals that are available and the resolution at which microscopic instruments can resolve such signals.

As noted in FIG. 1, when 5 different color dyes are associated with probes to identify different molecular targets, the spatial barcoding scheme in FIG. 1, a) of FIG. 1 will lead a barcoding capacity of 720; i.e., up to 720 molecular targets can be uniquely coded. Using the approach of FIG. 1, b), only a maximum of 31 molecular targets can be uniquely coded.

The approach in FIG. 1, c), known seqFISH, greatly expanded coding capacity. Here, instead of cramming all coding signals into a single hybridization experiment, barcodes are formed via temporally separately sequential hybridization experiments. The color of probes binding to a target can remain the same or change to a different color in different rounds. The barcode for a target is determined by the order by which each color appears during sequential rounds of hybridization. Details of this barcoding scheme are depicted in FIG. 2 and can be found in International Patent Publication No. WO 2014/182528, which hereby incorporate by reference in its entirely.

This method involves lysing cells and immobilized the mRNA on a surface for single molecule quantification. However, this technology is not limited to profiling only the mRNA species, but also applicable to other molecules such as DNA and proteins.

Since mRNAs are immobilized on a surface, they can be barcoded by introducing several rounds of hybridizations, imaging the fluorescent spots, and extinguishing the signal for the next round of hybridization. The number of barcodes available scales as FN where F is the number of fluorophores and N is the number of barcoding hybridization rounds. For example, with 3 fluorophores and 9 rounds of hybridizations, the available barcodes are $3^9=19683$. This method achieves single molecule sensitivity which allows the determination of gene expression through counting each identified mRNA molecules on the surface.

Figure 2:
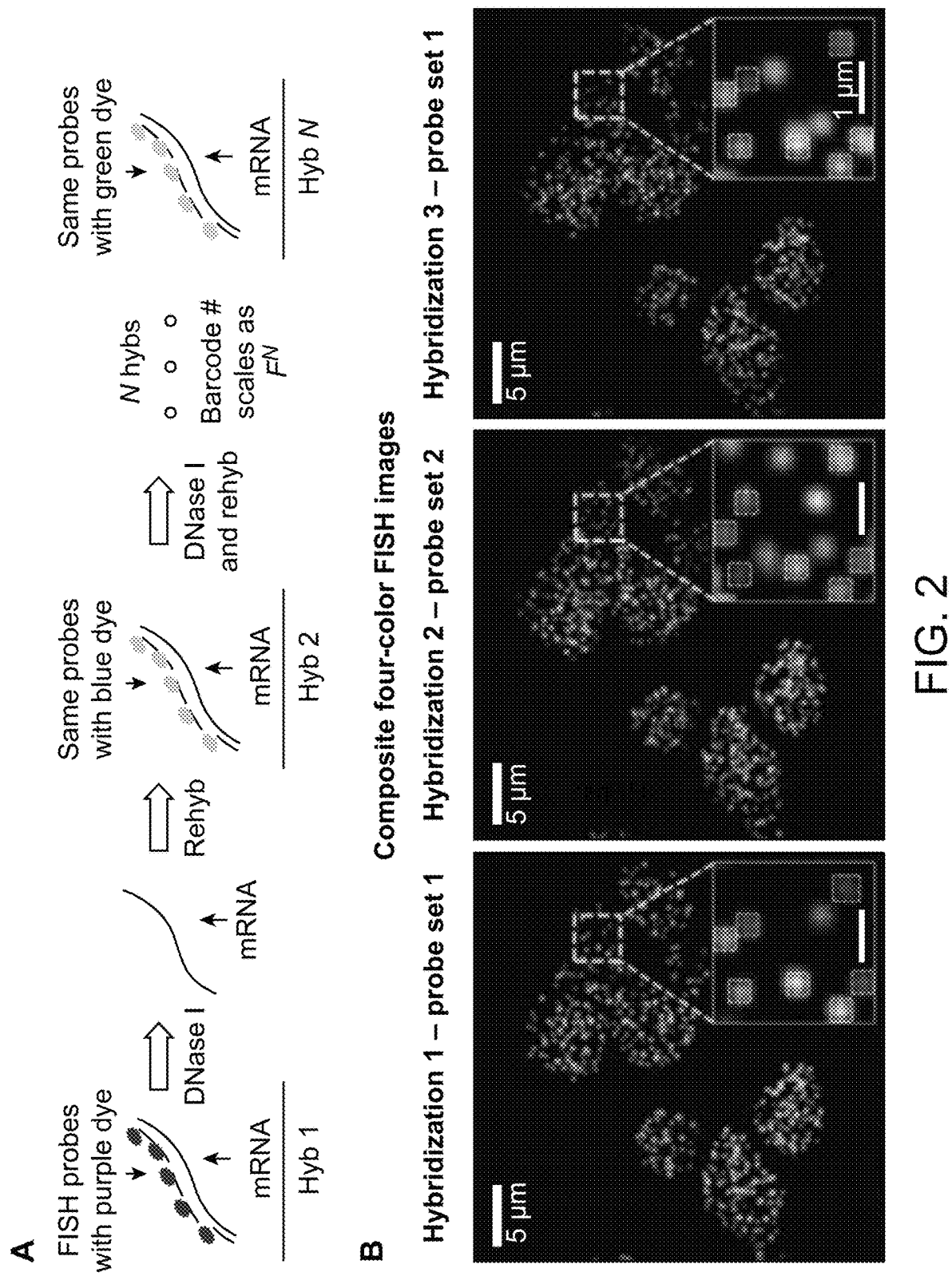
FIG. 2 depicts exemplary sequential barcoding of provided methods. (a) Schematic of sequential barcoding. In each round of hybridization, multiple probes (e.g., 24) were hybridized on each transcript, imaged and then stripped by DNase I treatment. The same probe sequences could be used in different rounds of hybridization, but probes were coupled to different fluorophores. (b) Composite four-color FISH Data from 3 rounds of hybridizations on multiple yeast cells. Twelve genes were encoded by 2 rounds of hybridization, with the third hybridization using the same probes as hybridization 1. The boxed regions were magnified in the bottom right corner of each image. The matching spots were shown and barcodes were extracted. Spots without co-localization, without the intention to be limited by theory, could be due to nonspecific binding of probes in the cell as well as mis-hybridization. The number of each barcode were quantified to provide the abundances of the corresponding transcripts in single cells. (c) Exemplary barcodes. mRNA 1: Yellow-Blue-Yellow; mRNA 2: Green-Purple-Green; mRNA 3: Purple-Blue-Purple; and mRNA 4: Blue-Purple-Blue.
Figure 2:
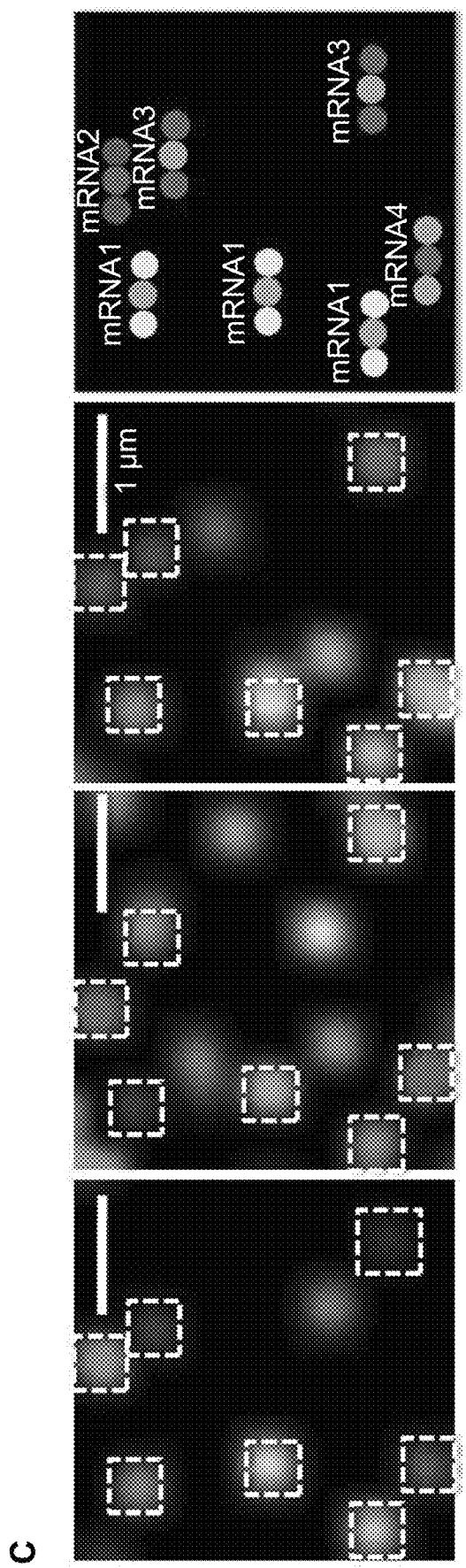

As shown in FIG. 2, a), in each round of hybridization, multiple probes (e.g., 20-30) were hybridized to each transcript, imaged and then stripped by DNase I treatment before another set of probes are used in the next round of hybridization. Probes with different binding sequences can be used in different rounds of hybridization. Also, the same probe sequences could be used in different rounds of hybridization, but probes were coupled to different fluorophores. A barcode for this mRNA is formed by combining the fluorescent colors associated with the probes in each round of hybridization according to the order or sequence by which the colors are detected. In the example illustrated in FIG. 2, a, the barcode for the mRNA in N rounds of hybridization will be {purple-blue . . . green}, with each color representing a particular hybridization round.

FIG. 2, b) illustrates exemplary composite four-color FISH images from 3 rounds of hybridizations on multiple yeast cells. As illustration, the same small region is magnified to reveal colored spots representing binding to probes to mRNA transcripts. Colored spots corresponding to the same target from different rounds of hybridization are matched to render a color barcode for the target. In each round of hybridization, the same spots were detected, but the dye associated with the transcript can change. The identity of an mRNA is encoded in the temporal sequence of dyes hybridized. For example, three rounds of hybridizations created the barcodes in FIG. 1, c): mRNA 1: Yellow-Blue-Yellow; mRNA 2: Green-Purple-Green; mRNA 3: Purple-Blue-Purple; and mRNA 4: Blue-Purple-Blue.

As noted above, the method of FIG. 1, c and FIG. 2 has significantly increased coding capacity. Based on 5 different visual signals and 7 rounds of hybridization experiments, a total of 78,125 targets (e.g., genes or mRNA transcripts) can be unique coded.

However, the types of color signals that can be used in these sequential hybridization experiments are limited. In order to encode the human genome, which includes about 20,000 protein encoding genes, at least 7 rounds of hybridization experiments are required. This many number of hybridization rounds result in long and complex barcodes that are hard to distinguish from each other, thus resulting in errors and inaccuracies. If one would like to include error correction in the barcodes, at least 8 rounds of hybridization experiments are needed, leading to even more complex barcodes and likelihood of more errors and inaccuracies.

Efforts made for creating more types of visual signals have not led to significant improvement. More improvements are need to increase coding capacities, enhance detection accuracies and sensitivities, and reduce errors.

In one aspect, a novel barcoding scheme is provided. Here, instead of developing different colors that are suitable for probe design, a counter-intuitive approach is adopted to create pseudo-colors to expand capacity of barcoding. Although the term "pseudo-color" is used, one is not limited to using colors in this new coding scheme, symbols, letters, numbers, 2D barcodes, 3D barcodes, and combinations thereof can be used to uniquely identify molecular targets. As disclosed herein the number of pseudo-colors far exceeds the number of actual colors that are associated with the detection probes used in the hybridization experiments.

Figure 3A:
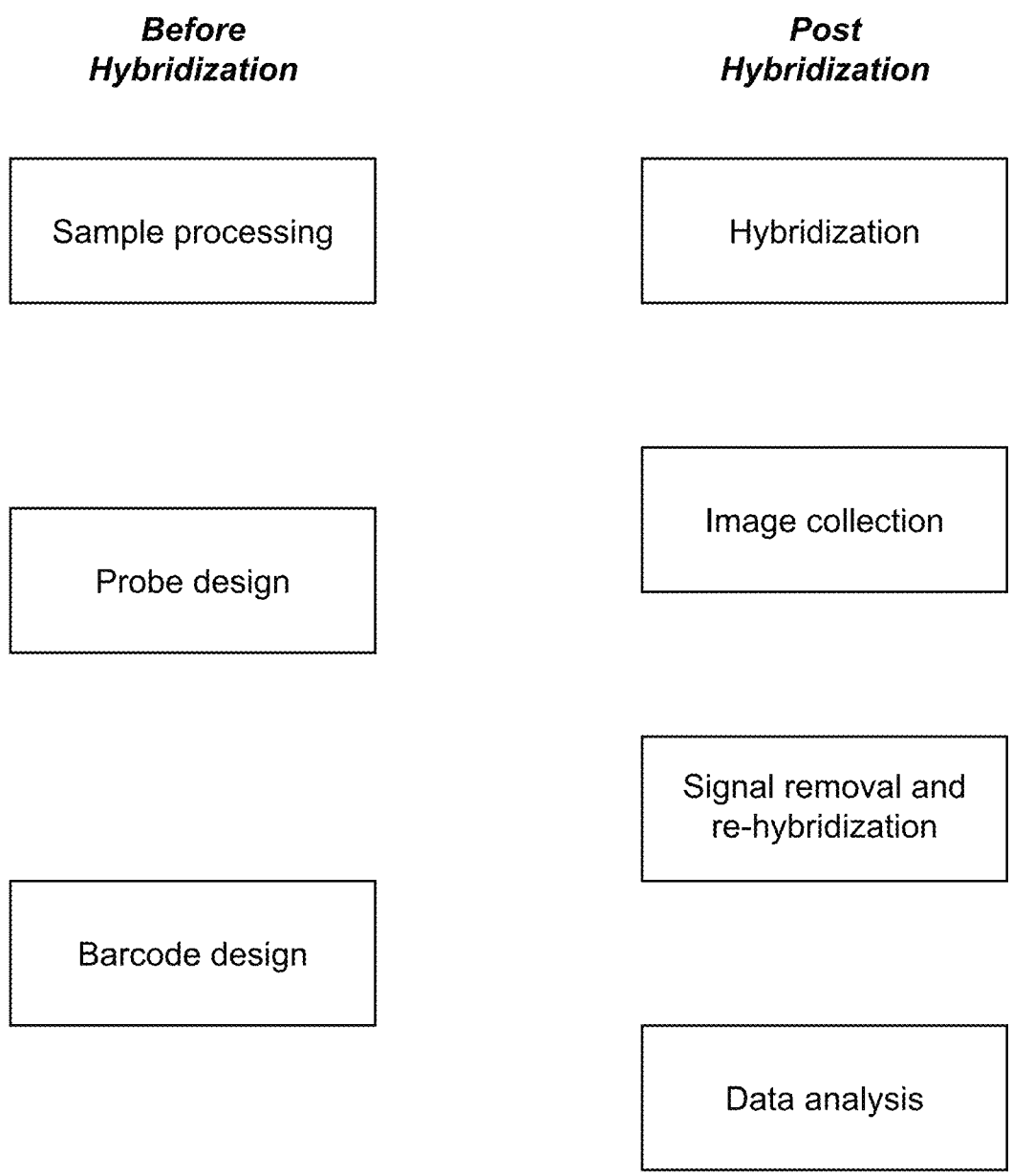
FIG. 3A illustrates aspects of an exemplary hybridization experiment.

FIG. 3A illustrates exemplary aspects that may contribute to error correction during a sequential hybridization process. Such aspects include but not limited to sample processing 302, probe design, barcode design, hybridization, image collection, signal removal and re-hybridization, and data analysis. In practice, any or all of these aspect can contribute to the quality of analysis.

Barcoding by sequential hybridization includes multiple rounds of hybridization. Each round of hybridization in turn is a multiple step process including most or all of the aspects outline above. Errors and inaccuracies can be introduced at any step during any round of hybridization. Such errors can lead to misidentification of target genes in a sample.

Prior to hybridization, samples that will be subject to analysis are processed. The main purpose of such processing is to immobilize target molecules; for example, mRNAs, chromosomal DNAs, and proteins. It is essential that the target molecules remain spatially fixed through different rounds of hybridization.

Figure 26:
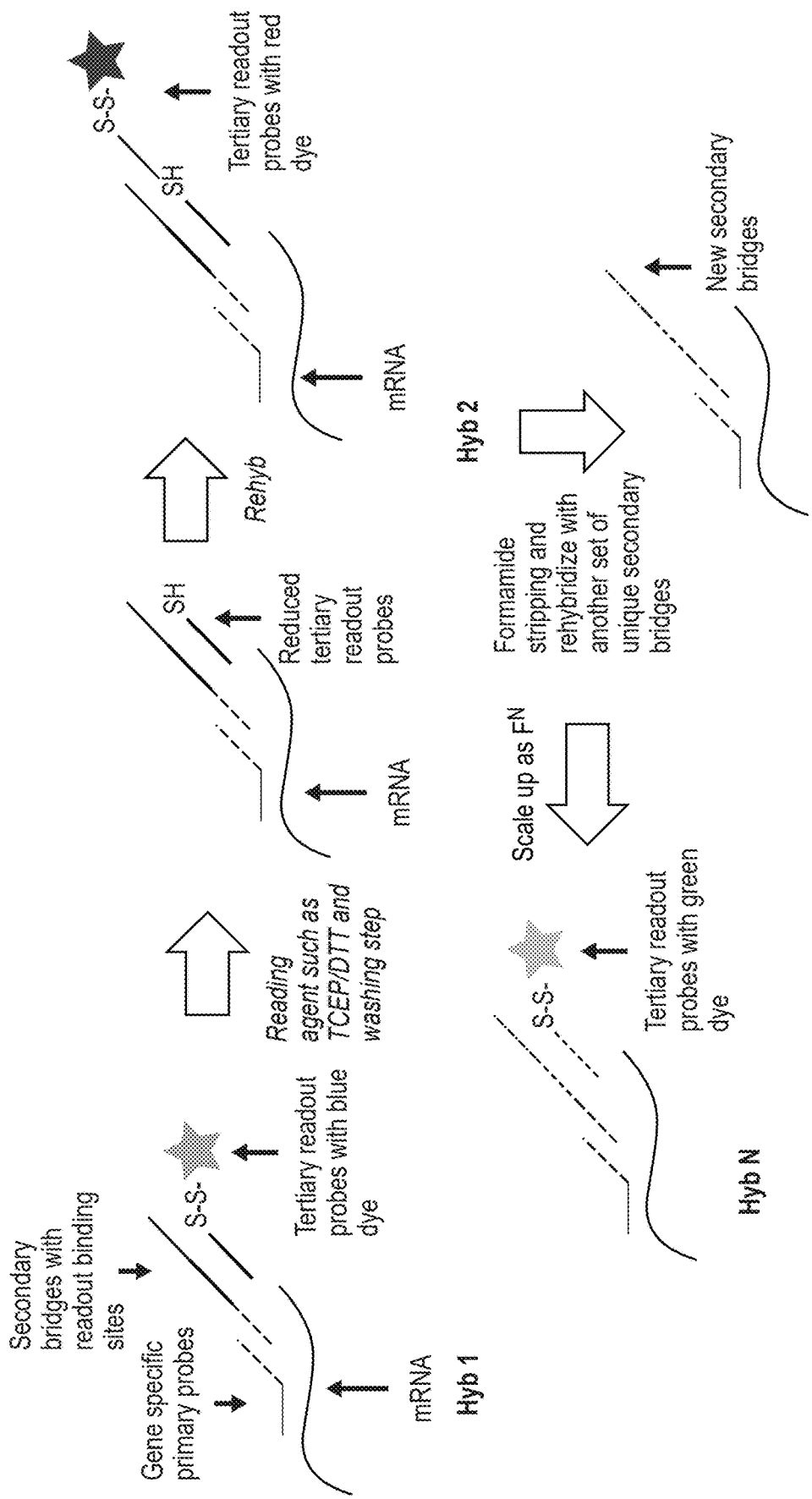
FIG. 26. An exemplary embodiment illustrating sequential barcoding using gene specific primary probes, secondary bridge probes and tertiary readout probes. (a) Sequential barcoding FISH (seqFISH) with DNA readout probes conjugated with dyes through disulfide linkage. The scheme begins with hybridization of gene specific primary probes, followed by secondary bridges with readout binding sites, and a unique tertiary readout probes with disulfide-linked dye. Once imaged, reducing agent such as TCEP/DTT is used to eliminate the fluorescent signals. Subsequent hybridization gives fluorescent signals which is not interfered by previous fluorescent spots. The secondary bridges can be stripped off by using high concentration of formamide, and replaced by a new set of secondary bridges. (b) An exemplary embodiment illustrating primary probes with two overhang sequences. One of the alternate designs of gene specific primary probes and secondary bridges. For example, with 2 overhangs on primary probes, each overhang can bind 1 secondary bridge which consists of 3 unique tertiary readout probes binding sites. By using 4 different colors of fluorophore, one can scale up the barcodes to 4⁶=4096 with this design.
Figure 26:
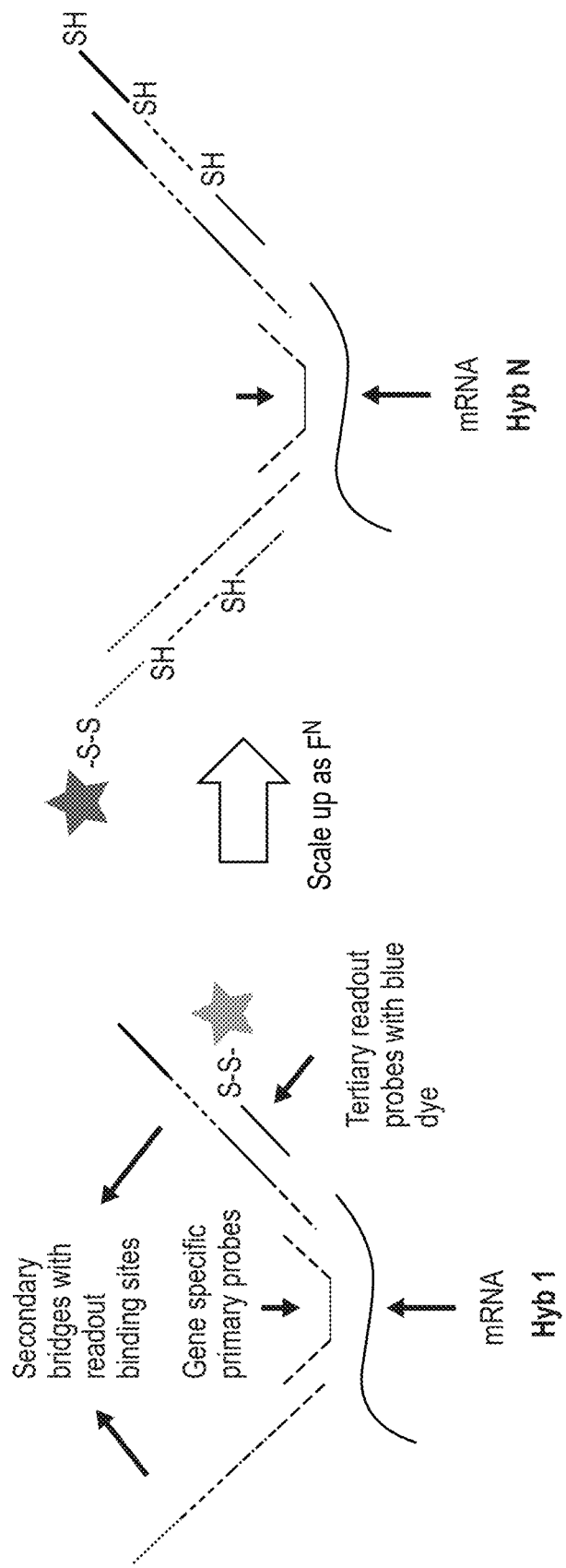

Probe design contributes to specificity of binding between the probes and target sequences. It is possible to apply hybridization chain reaction to allow multiple probes to bind at the same target sequence to amplify detectable signals. Additionally, as illustrated in FIGS. 26 and 27, it is possible to insert a cleavable linker between the binding sequence (that binds a target sequence) and signal moiety (that emits visible signals) of a probe. Here, error can be reduced because no removal of probes is needed for the next round of hybridization. Instead, only visible signals are switched.

Barcodes implemented during the analysis are unique. Nonspecific binding or other mistakes can render the results from one or more rounds of hybridization unreliable. A simple solution is to remove data that are unreliable. However, if data from one or more rounds of hybridization are eliminated from analysis, some of the barcodes would become indistinguishable from each other.

During and after hybridization of probes to target sequences, there are also aspects that are important for improving the quality of the sequential analysis. For example, the hybridization conditions should be designed to avoid non-specific bindings. This can also be achieved through sample processing and probe design. Similarly, image collection can also be affected by a number of factors including sample processing, probe design and barcode design. As described above, probes with too many types of color signal in many rounds of hybridization can lead to barcodes that are hard to resolve or even errors.

Between hybridization rounds, old probes can be removed before new probes are added. Here, the removal process can also be associated with errors. For example, if the removal condition is too harsh, immobilized biological samples can be disturbed. As a result, positions of visual signals in images from different rounds of hybridization experiments would change.

Some of the errors may be corrected or reduced by data analysis. For example, in most scenario, bindings between probes and target sequences are observed as colored bright spots over relatively darker background where no binding is observed. The spots are brightest in the center and fade away at the edges. Gaussian distribution analysis can be used to focus on the most significant portion of an image thus leading to better resolved image data. In addition, noise reduction can be used to reduce background signals.

Figure 3B:
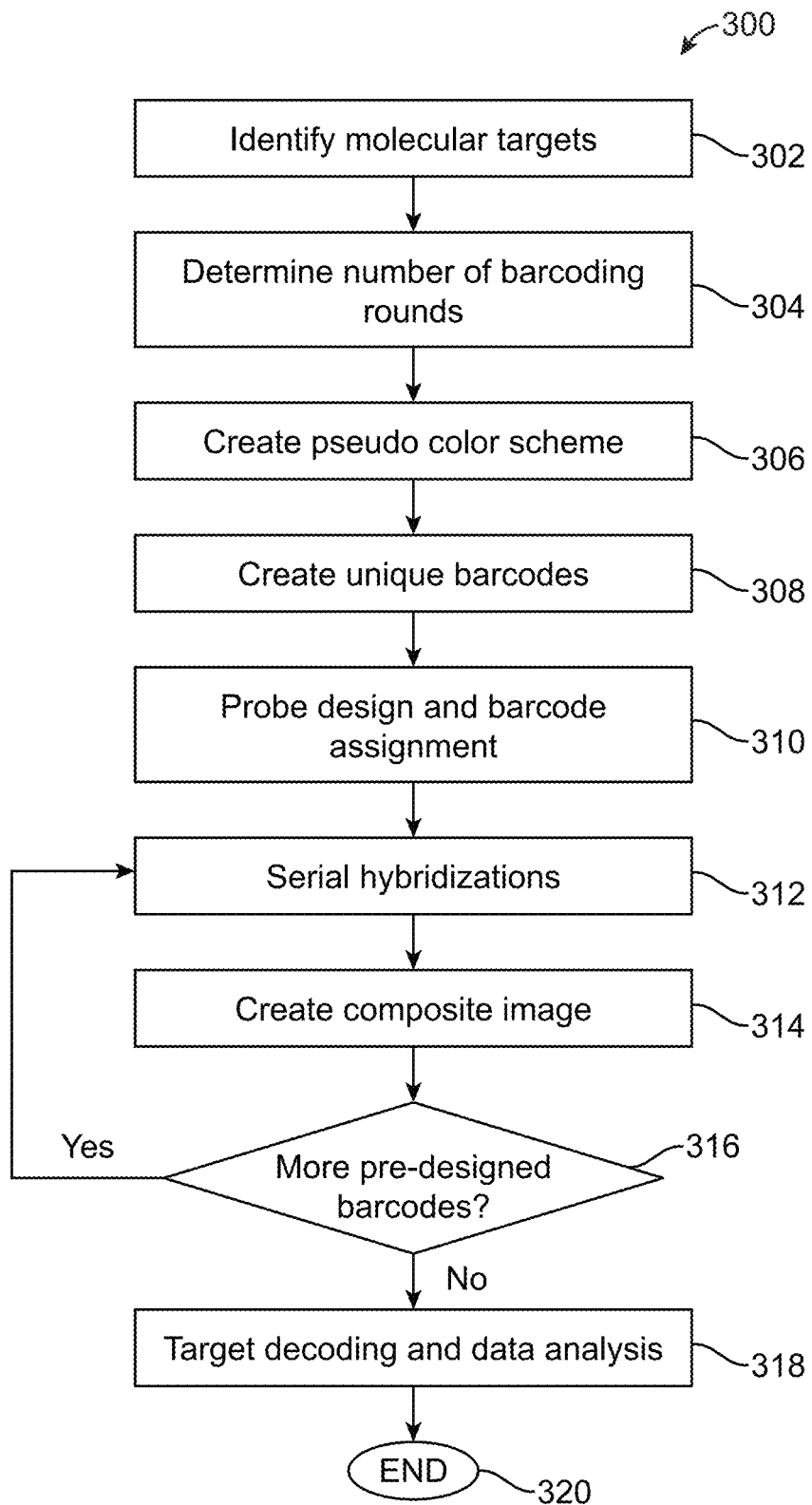
FIG. 3B depicts an exemplary process for performing a pseudo-color based barcoding scheme.

FIG. 3B depicts an exemplary process for performing a pseudo-color based barcoding scheme. Exemplary embodiment 300 provides an example of a pseudo-color based barcoding process. Here, instead of using a large number of actual detectable color signals, which are not available or impractical to obtain, a small number of color probes are repeatedly used in multiple serial hybridization experiments where non-overlapping sets of molecular targets are analyzed. Images from the serial hybridization experiment are combined to form a composite image representing a single barcoding round. In the composite image, at least some of the would-be redundant colors are replaced with predefined symbols in a pseudo-color based scheme. The process is repeated multiple times to produce the final multi-component barcodes.

At step 302 liquid molecular targets in a biological sample that needs to be barcoded will be identified. In particular, the number of the molecular targets and their respective identity, such as the name of the target and sequence information of the molecular target, will be identified to provide information that will be used for specific binding probe design.

Prior to actual hybridization experiments, the molecular targets in the biological sample will be immobilized; for example, on a glass cover slip. As disclosed herein, exemplary biological sample includes but is not limited to a tissue sample, a cell sample, a cell extract sample, a nucleic acid sample, a RNA transcript sample, a protein sample, or an mRNA sample.

At step 304, depending on the total number of the biological molecular targets, the number of barcoding rounds will be decided. Because the number of barcoding rounds corresponds to the size of the barcode that will result, the user should decide on how many rounds will be needed depending on the sample size of the molecular targets. In some embodiments, a user may take into consideration the types of color probes that are available. In some embodiment, three or more barcoding rounds will be used. In some embodiments, four or more barcoding rounds will be used. In some embodiments, five or more barcoding rounds will be used. In some embodiments, six or more barcoding rounds will be used. As disclosed air in one advantage of The method disclosed herein is providing relatively simpler barcodes that are more error resistant. In general, a five component barcode is more preferred then an eight component barcode.

At step 306, the number of symbols in a pseudo-color scheme will be determined based on the total number of the molecular targets (e.g., N>>2) and the intended number of barcoding rounds (e.g., n≥2). As disclosed here in the minimum number of pseudo-color symbols (e.g., S) can be determined according to the following equation:

$$S \geq \sqrt[n]{N}, \text{ where } S, n \text{ and } N \text{ are all integers.} \quad (1)$$

In some embodiments, one or more error correction coding rounds (e.g., x rounds where x≥1) will be implemented. As such, one may choose a higher number of pseudo-color symbols to avoid too many barcoding rounds. The minimum number of pseudo-color symbols, when one or more error reaction rounds, can be determined according to the following equation:

$$S \geq \sqrt[n-x]{N}, \text{ where } S, n, x, \text{ and } N \text{ are all integers.} \quad (2)$$

Although the term pseudo-color is used, the actual codes used in barcodes are not limited to colors. Any symbol or combination of symbols can be used as codes in a barcode so long as such symbol or combination of symbols are unique. Exemplary symbol or combination of symbols include but are not limited to colors, numbers, letters, shapes, or combinations thereof. It would be understood that a color based scheme would be preferred because At step 308, once the total number of symbols to be used in a pseudo-color barcoding scheme and the number of barcoding rounds are determined, non-redundant and unique barcodes will be created. For example, in a n-component barcode using S pseudo-color symbols, a barcode can be expressed as: $\{B_1, B_2, \ldots, B_n\}$, where each of $B_1$, $B_2$ through $B_n$ is selected from the S pseudo-color symbols. Standard code design algorithms can be used such that the results barcodes are unique.

During hybridization analysis, barcodes can be shortened due to loss of data from one or more rounds of hybridization, For example, after the loss of one round of hybridization, n-component barcodes can become n−1-component barcodes.

When error correction algorithm is not implemented during probe design, the resulting n−1-component barcodes may now include redundant codes, making it difficult or impossible to decode targets based on the coding scheme useless. In a more specific example using colors as symbols in a pseudo-color coding scheme, two distinct six-component barcodes: {Red-Blue-Green-Red-Yellow-Blue} and {Red-Blue-Green-Green-Yellow-Blue} can become {Red-Blue-Green-Yellow-Blue} and {Red-Blue-Green-Yellow-Blue} if data from the fourth hybridization round becomes unavailable. As a result, the results from the entire set of experiments will be discard, wasting time and resource.

The current disclosure also creates barcodes that are drop or error-resistant. In some embodiments, one or more rounds of error correction can be implemented. Additional code design algorithms can be applied such that the resulting barcodes are error resistant; for example, the loss of any one or more rounds of hybridization data would still lead to shortened barcodes. However, the shortened barcodes are still unique and can be used to specifically identify a molecular targets.

In some embodiments, implementing an error correction mechanism involves removing barcodes that are vulnerable to loss of data. As such, the number of targets that can be detected using the error-corrected scheme will be lower than that of the original scheme without error correction. To detect the same number of genes, more hybridization rounds would generally be needed.

The current method is advantageous in that it does not require additional hybridization rounds. Instead, coding capacity of the same number of hybridization rounds can be increased by designating more pseudo-color symbols.

At step 308, barcodes for an entire set of hybridization experiments will be created each corresponding to a particular molecular target. For example, a set of hybridization experiments including includes 4 barcoding rounds, each of which in turn including includes 4 serial hybridization experiments. In each hybridization experiment, 3 different detectable signals (such as three different fluorophores) will be associated with probes that bind to a set of molecular targets. Here, each detectable signal in the same serial hybridization experiment can be associated with multiple molecular targets; for example, hundreds or even more molecular targets. For example, 100 or more molecular targets can be assigned barcodes that start with the same pseudo-color symbol; i.e., all the molecular targets can be labeled with the same detectable signal. The unique identity of each molecular target will be reflected by symbols used in the subsequent three positions in the barcodes. To complete the barcoding in the example above will require that each target 3 molecular target will have a total of 48 hybridization experiments in four barcoding runs (see, FIG. 10). These 48 hybridization experiments can detect a total of 20,736 molecular target ($12^4$) based on 12 pseudo-colors. If one error correction round is implemented, only up to 1728 ($12^3$) molecular targets can be detected. If 1728 different mRNA transcripts are to be detected with error correction, 1728 unique barcodes with embedded error-correct mechanism for one round of data loss will be created. Actual hybridization experiments will be carried out based on these predesigned barcodes.

At step 310, after unique barcodes are generated, each identified molecular target will be assigned one of the unique barcodes. For example, for a five component barcode based on 12 pseudo-color symbols, the barcodes will be generated using the 12 symbols. The first code can be any one of the 12 symbols, but each subsequent symbol and each subsequent barcode will be generated taking into consideration the symbols and barcodes that have already been used in order to avoid redundant barcodes. In some embodiment, additional error correction algorithms are implemented in barcode design such that the resulting barcodes are resistant to mistakes such as the loss of data from an entire barcoding round.

In some embodiments, probes can be synthesized according to the predetermined probe designs. Each probe can include a binding sequence that specifically target a site in an intended molecular target. For each molecular targets, multiple probes with different binding sequences targeting different sites of the same molecular target can be synthesized. When probes with different binding sequences targeting the same molecular target are used in one hybridization rounds, the probes will be associated with the same detectable signal.

In some embodiments, a probe can include one or more readout sequences that can be connected, directly or indirectly, to either side of the binding sequence. In some embodiments, one or more readout sequences are directly connected to the binding sequence as one or more overhangs. In some embodiments, one or more readout sequences are indirectly connected to the binding sequence of the probe via one or more intermediate molecules; for example, as one or more overhangs of a bridge probe. Exemplary intermediate molecules include but are not limited to an RNA bridge probe, a DNA bridge probe, a protein bridge probe, a probe for hybridization chain reaction (HCR), a hairpin nucleic acid probe, an HCR initiator, an HCR polymer, other known amplification methods, or combinations thereof.

In some embodiments, the number of different readout sequences is the same as the number of barcoding rounds. In some embodiments, the number of readout sequences is greater than a number of barcoding rounds. In some and body months, each type of readout sequence, when activated, is capable of generating one color signal. In some embodiments, different readout sequence, when activated, are capable of generating the same color signal. Any detectable signals suitable for hybridization experiments can be used.

For five barcoding rounds, five groups of probes can be designed and synthesized for each molecular target. Probes in each group would increase binding sequences that target specific sequences within a molecular target. In some embodiments, probes in the same group will bind to the same target sequence. In other and more preferred embodiments, probes in the same group will bind to multiple target sequences. As disclosed herein, each barcoding around 1 to 100 probes can be used targeting a specific molecular target. In some embodiments, 100 or fewer, 80 or fewer, 60 or fewer, 50 or fewer, 40 or fewer, 30 or fewer, 20 or fewer, or 10 or fewer probes can be used. In some embodiments, between 5 and 40 probes are used.

In some embodiments, these probes will bind to two or more target sequences, three or more target sequences, four or more target sequences, five or more target sequences, or six or more target sequences in the same molecular target. And some embodiments, the probes will be concentrated in one area of the molecular target. In some embodiments the probes will be spread out along the entire length of the molecular target.

At step 310, all probes required to carry out the entire set of hybridization experiments will be synthesized, each associated via direct or indirect connection to a primary binding sequence. For example, a set of hybridization experiments including five barcoding round each including 12 serial hybridizations will have a total of 60 hybridization experiments. After step 310, all probes required for each hybridization will be designed and synthesized.

At step 312, serial hybridization experiments can be performed using probes synthesized in the previous step. Barcodes associated with these probes are stored in a database or library. Each probe will be associated with a code in the designated barcode for the molecular target of the probe. The number of hybridization experiments within a serial hybridization round will be determined based on the availability of different types of detectable signals (such as colors) and the total number of symbols in the pseudo-color barcoding scheme. As an example, hybridization experiments based on a 60 pseudo-color scheme will be carried out s using 4 different types of color signals. Then 5 rounds of barcoding with the 60 pseudo-color will be carried out for $60^5=7.776\times10^8$ number of barcodes. In some embodiments, in each barcoding round, 15 serial hybridization rounds will be performed. In each of the 15 hybridization round, all four color signals are used to each identify a different molecular target. Here, after the particular round of serial hybridization experiments, 60 unique molecular targets will be labeled with color signals. In some embodiments, 20 serials hybridization arounds will be performed using three of the four color signals, each color representing a different molecular target. Again, after the particular round of serial hybridization experiments, each 60 unique molecular targets are decoded and associated with a previously assigned pseudo-color symbol. In some embodiments, any combinations of three colors can be used in the serial hybridization experiments. In some embodiments, in each hybridization round, two to four color signals can be used, each representing each representing a different molecular target. In some embodiments, one color signals can be used in one or more hybridization experiments in a serial hybridization round. Here, one color must be present in separate hybridization experiments in order to represent different molecular targets. For example, if one is limited only one type of color signal, hybridization experiment can be carried out 60 times in each barcoding round. Each hybridization experiment identifies only one molecular target. It would be understood that performing a high number of hybridization experiments may not be desired because the biological sample being analyzed can be degraded, for example, by enzymes that digest nucleic acids.

In some embodiments, during each hybridization experiment in each serial hybridization round, reference visual signals are introduced. These reference visual signals are associated with one or more alignment references that are associated with a biological sample and do not change their positions between hybridization rounds. These alignment references can serve as standard for subsequent image analysis. They can be part of the biological sample or external material added to and immobilized with the biological sample. In some embodiments, alignment references are immobilized at the same time as the biological sample. In some embodiments, alignment references are immobilized at a different time from when the biological sample is immobilized. Exemplary alignment references include but are not limited to beads, oligonucleotide sequences immobilized on the coverslips and detected by a complementary oligo, microscopic objects (e.g., a metal bead, a gold bead, a polystyrene bead loaded with a dye), PCR handle sequences on the primary probe, or combinations thereof. As disclosed herein, the reference signals are fiducial markers for alignment between the different serial and barcoding hybridizations. They are present throughout all of the hybridizations. In some embodiments, at least one marker is present per image. They can be probes targeting all of the primary probes (as shown in FIG. 18, a, yellow probes), such that all the dots are observed in all of the hybridizations. In some embodiments, the reference signals can be produced from beads attached to the cover glass, or other molecules or particles. In some applications, where "super-resolution" capabilities are used, signals form the beads can be Gaussian fitted to nanometer resolution, and images between hybridizations can be aligned to that precision. In some embodiments, this becomes useful for the in situ application where Gaussian fitting allow more molecular targets to be detected in each pseudo-color and then collapsed into the composite image for barcoding.

At step 314, an image of visible probes bound to the biological sample will be taken after each hybridization experiment in a serial hybridization round. All images from hybridization experiment in a serial hybridization round will be aligned using reference visual signals to create a composite image.

At step 316, it will be determined whether there are one or more barcoding rounds remaining based on the barcodes pre-designed at step 308 If yes, the method returns to steps 312 and 314 and more serial hybridization experiments are carried out to constitute another barcoding round and produce another composite image.

If no, the hybridization portion of the analysis is complete and the method proceeds to step 318. Images and composite images will be subject to further data analysis. For example, in a sample with limited space, e.g., in a single cell, Gaussian localization analysis can be carried to generate, for example, more focused color spots each representing binding to a molecular target. Other data processing methods can also be used to enhance data quality, for example, a de-noise mechanism can be applied to reduce back signals.

The method concludes at step 320.

Figure 4:
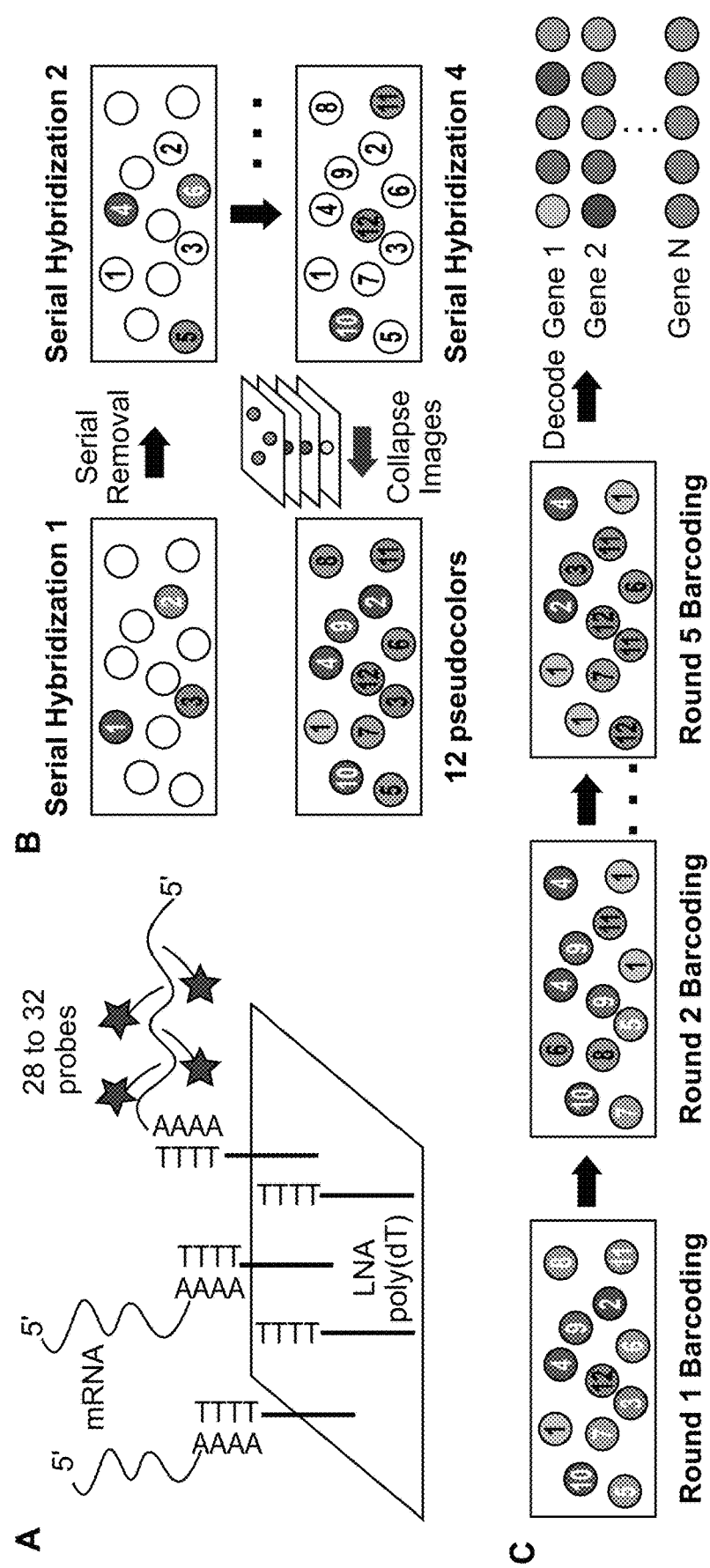
FIG. 4 depicts an overview illustrating a method for performing a pseudo-color based barcoding scheme: SPOTs (Sequential Probing Of Targets). (a) RNA molecules are captured on Locked Nucleic Acid (LNA) poly(dT) functionalized coverslips followed by hybridization of 28-32 gene specific primary probes. (b) Schematic to generate 12 pseudocolors used in decoding each RNA species. In each round of serial hybridizations, 3 'colors' are generated by imaging 3 unique readout probes conjugated with dye ALEXA FLUOR™ 647, ALEXA FLUOR™ 594, and Cy3b. After 4 rounds of serial hybridizations, the images are collapsed into 1 image to generate an image with 12 pseudo-colors. (c) Schematic of decoding 5 barcoded rounds based on 12 pseudo-colors coding scheme. (d) Digitized image of 12 pseudo-colors switching based on actual experimental image. After decoding 5 barcoded hyb, up to 20736 unique RNA species can be decoded with high accuracy and low error rates.
Figure 4:
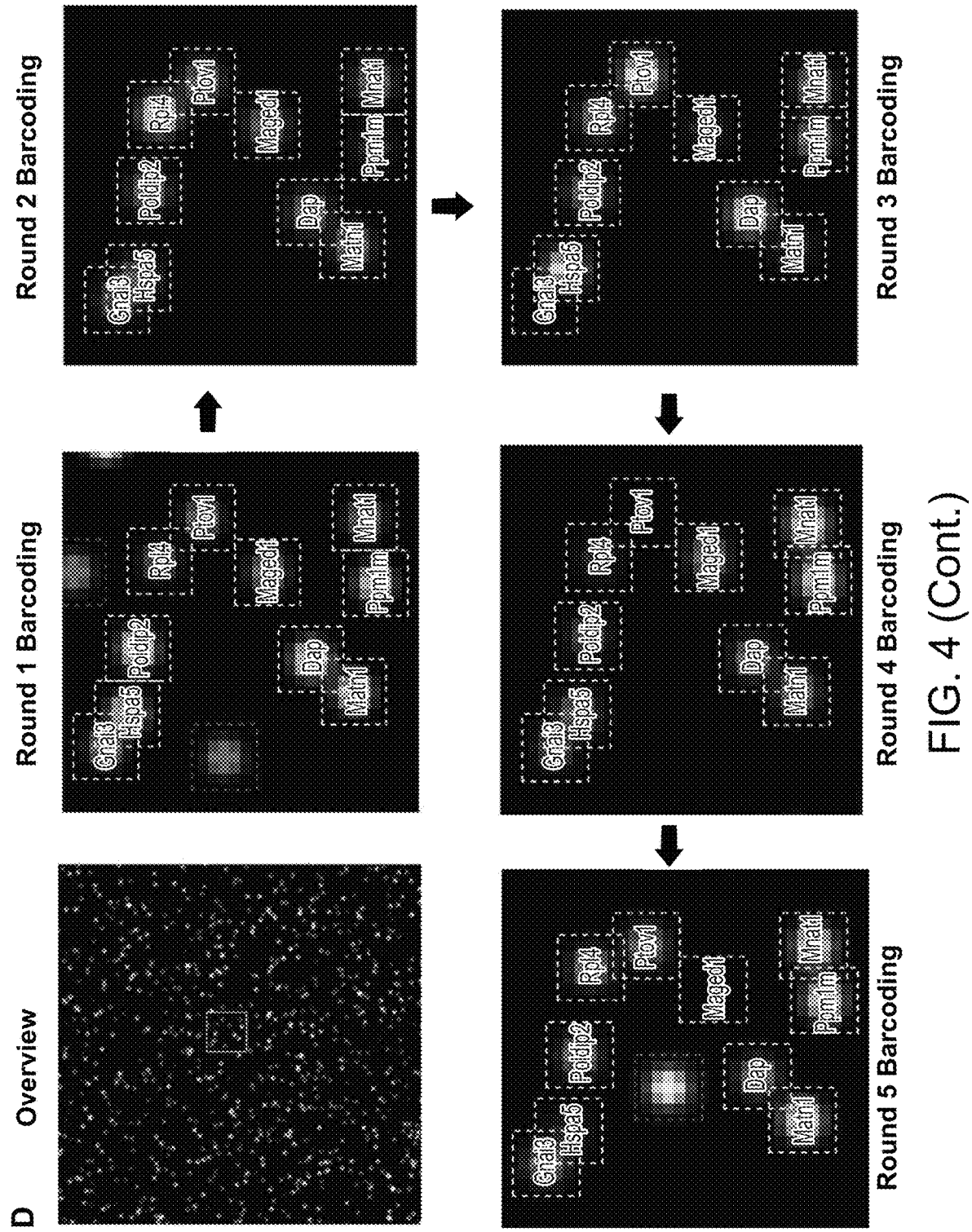

FIG. 4 depicts a schematic overview of Sequential Probing Of Targets (SPOTs), targeting RNA samples using a pseudo-color barcode scheme. The method performs transcriptome level profiling of mRNAs with single molecule sensitivity and high accuracy using a method based on sequential FISH (seqFISH) [Lubeck 2014]. The initial demonstration of seqFISH showed promising coding capacity to barcode a large number of molecular species in cells and tissues [Shah 2016]; however, a major limitation has been identified: when seqFISH is performed in cells, optical diffraction limit prevents many mRNAs to be resolved simultaneously due to the limited space in a cell.

As shown in FIG. 4, there are a total of 5 barcoding runs and each barcoding run has four serial hybridizations. Three different fluorophores (e.g., red, green and blue) are used in each serial hybridization experiment. For simplicity, each serial hybridization experiment in FIG. 4, b only shows one molecular target for each fluorophore. However, in practice, each fluorophore can represent tens, hundreds or even more molecular targets. In addition, unlike the illustration in FIG. 4, b which shows that the same number of targets are tagged in each serial hybridization, different numbers of molecular targets can be tagged in different serial hybridizations. For example, for a 1,500 mRNA experiment of 4 barcoding rounds, serial hybridization No. 1 of barcoding round 1 can tag 400 mRNA transcripts with three different fluorophores (e.g., red, green and blue). Serial hybridization No. 2 of the same barcoding round can tag 280 mRNA transcripts with the same three fluorophores. 320 mRNA transcripts can be tagged the same three fluorophores in serial hybridization No. 3. And 500 mRNA transcripts can be tagged the same three fluorophores in serial hybridization No. 4. As the numbers suggest, within each serial hybridization, multiple mRNA transcripts can be tagged with the same fluorophore. In some embodiments, a fluorophore is attached to a probe via multiple readout sequences, which in turn are connected to a primary binding sequence targeting a specific site in a molecular target. In some embodiments, the readout sequences can be connected directly to the primary sequence. In some embodiments, the readout sequences can be connected indirectly to the primary sequence, for example, via one or more intermediate molecules. In some embodiments, the one or more intermediate molecules comprise an RNA bridge probe, a DNA bridge probe, a protein bridge probe, a probe for hybridization chain reaction (HCR), a hairpin nucleic acid probe, an HCR initiator, an HCR polymer, or combinations thereof.

In addition, there can be different number of serial hybridizations in two different barcoding rounds. For example, in the example presented above, 4 serial hybridizations are included in barcoding round 1. Barcoding round 2 can have 4 or 6 or 3 serial hybridizations, so long as the results from the two sets of serial hybridizations can reveal the same 1,500 mRNA transcripts. For example, images from all serial hybridizations in the same barcoding round can be compiled into a composite image for the barcoding round. In this barcode scheme, 12 pseudo-colors are created, which can be assigned numbers as 1 through 12. In some embodiments, 12 different colors are assigned as symbols of the 12 pseudo-colors. After all 5 barcoding rounds are completed, the 1,500 mRNA transcripts will be fully coded.

In some embodiments, the total number of targets revealed in two different barcoding rounds can differ. For example, there are some problems and only 1,400 mRNA transcripts are tagged in in barcoding round 1 while 1,350 mRNA are tagged in barcoding run 2. Subsequent image and data analysis can reveal that only 1,200 of the mRNA transcripts overlap between the two barcoding rounds. And ultimately only 1,200 mRNA transcripts are fully coded in all 5 barcoding rounds.

The pseudo-color scheme can overcome this density problem in both in situ and in vitro applications. In the in vitro cases, implemented with SPOTS, capturing transcripts onto an oligonucleotide dT surface and adjusting the dilution factors can easily remove the optical crowding problems and allow the transcriptome to be imaged by seqFISH.

In addition, pseudo-color is more efficient in terms of imaging time than all existing imaging methods including expansion microscopy. For example, with 3 fluorophores, it takes $3^{(10-1)}=19,683$ to code for the transcriptome with one round of error correction. Thus, a total of 30 frames of imaging is required. In a pseudo-color scheme, 20 pseudo-colors can be used for 4 rounds of hybridization to code for $20^{(4-1)}=8000$ genes in each of the three fluorophore channels for a total of 24,000 genes. This requires 3×20×4-240 frames to image, a 8 fold increase in the imaging time. However, because the density of mRNA is effectively diluted into 3×20-60 pseudo-channels instead of 3 fluorophore without pseudo-color coding, the density problem is alleviated with a factor of 20. The target spots can be localized to nanometer precision by Gaussian fitting to decrease the density in each pseudo-color channel before barcode alignment. Thus, the benefit of pseudo-color coding is to decrease the density of the target spots in the cell, while saving imaging time compared to expansion microscopy, where expanding the sample by 20 folds requires an additional 20 fold increase in imaging time. Since imaging time is rate limiting in any sequential imaging method, pseudo-color solves a major problem in implementing transcriptome profiling in situ.

In some embodiments, for in situ experiments based on a pseudo-color scheme, fewer number of different detectable signals can be used so that they can be resolved from each other more clearly due to the limited amount of real estate within a cell. In some embodiments, with super resolution microscopy, even densely populated detectable signals can be resolved from each other.

As an example, three different color signals are used in an in situ experiment. In some embodiments, for each color, hybridization experiments can be repeated 20 times to generate a 20 pseudo-color image. Here, each 20 pseudo-color image is compiled from only 1 real color channel although multiple colors can be used. The single-color approach offers several advantages during imaging analysis. Significantly, there are chromatic aberrations in a microscope, and aligning images across different actual color channel can be difficult and lead to errors or inaccuracies. In the current embodiments, all 20 pseudo-color can be from the same color channel (e.g., the Cy5 channel) then all images are by definition aberration free.

Using an mRNA hybridization experiment as an example, mRNA transcripts bound to activated color probes are visualized as dots in the image. In some embodiments, Gaussian fitting is applied to localize the RNA dots in cells and generate a higher resolution image or less dense image of the cell. In some embodiments, Gaussian localization can take place at one or more time points; for example, for each image corresponding to a serial hybridization experiment, for the images from all serial hybridization experiments in a barcoding round; for each composite image corresponding to a barcoding round. In some embodiments, Gaussian localization can be repeated multiple times.

In some embodiments, color beads can be used to align the pseudo-color images to create composite images.

When multiple color probes are used (e.g., 4 or 5 colors), the resulting image can be too dense and it can be difficult or impossible to apply the Gaussian fitting process, which requires discrete dots. By virtually diluting the samples to 60 pseudo-color, then the density becomes much less of an issue. After the first barcoding round, DNAse can be used to strip the probes, which carries the RNA targeting sequence and one round of readout sequence. This ensures that when barcoding is done in cells (in situ), there is no nonspecific binding. A new set of probes with the 2nd barcode sequence is then hybridized. Another 20 rounds of serial hybridization with 3 colors is done. In some embodiments, images from the hybridization experiments are subject to Gaussian fit, and be compiled into 3 sets of 20 color pseudo-color images.

This process can be repeated 4 times to generate a 20×20×20×20 barcode in each color. So 8000 error corrected barcodes are available in each color, to encode a total of 24000 barcodes.

In this example, the barcode scheme can be actually 3 separate pieces of 8000 barcodes in each of the colors. There can be 60 readout sequences total. Because of the DNAse stripping step, the readout sequences used in the $2^{nd}$ barcoding hybridization can be the same as $1^{st}$ barcoding hybridization.

For in vitro analysis, all the readout sequences can be added onto the primary binding probes. In those cases, the readout sequences for the different barcoding hybridizations have to be different. The approach is possible in vitro because there is very little nonspecific binding, since the biological sample has often been extracted out of the cells. For in situ, more stringent conditions are needed to avoid nonspecific binding in cells.

An alternative approach is to generate 100 readout sequences all in one color and just code for 10,000 targets with 3 rounds of hybridization (100×100×100) with one round of error correction. As disclosed herein, any manageable number of readout sequences can be used; for example, 50 or fewer, 60 or fewer, 80 or fewer, 100 or fewer, 150 or fewer, 200 or fewer, 250 or fewer, 300 or fewer, 400 or fewer, or 500 or fewer. In some embodiments, more than 500 readout sequences can be used.

As disclosed herein, the pseudo-color scheme is better than expansion microscopy in solving the density issue. Expansion microscopy is a new technology for imaging biological samples with fine detail by physically making the samples bigger through a chemical process that preserves nanoscale isotropy. Expansion microscopy enables super-resolution imaging on a conventional light microscope. However, expansion is a complicated procedure and the sample can contract and expand during the rehybridization process, which makes aligning the barcodes hard. Also, if the tissue sample is expanded 10 times, the tissue will be imaged 10 times longer. So even though pseudo-color appears to require more hybridizations, the total imaging time is comparable or even more favorable compared to if one had to expand the sample. For example, the 60 pseudo-color scheme is basically 20× expansion compared to just a 3 color scheme.

In a seqFISH experiment, 10 rounds of hybridization are needed to encode 20,000 genes with error correction with 3 colors ($3^{(10-1)}$=19,683). As disclosed herein, the pseudo-color scheme use 20×4=80 rounds of hybridizations for each channel. Thus, the number of hybridizations gone up by 8 fold, but the density is diluted down by a factor of 20. Thus the current approach is more efficient than expansion microscopy. For example, one can also use 1 channel and 100 pseudo-color and three rounds of hybridization, which correspond to 33.3 fold (100 pseudo-colors/3 colors) improvement in dilution and only 10 fold increase in imaging time. As disclosed herein, 3 color signals and 20 pseudo-color in each channel have produced excellent results. In practice, one can balance the "dilution" factor with the number of targets being analyze to determine the number of the actual color signals and the number of pseudo-colors.

In some embodiments, the current approach can also be combined with correlation FISH (corrFISH, Coskun and Cai, Nature Methods 2016) to quantify the abundances of highly expressed mRNAs. corrFISH can be applied to decoding samples where the number of target dots are so high that they are individually resolvable. This approach can decode the abundance of the genes, but trade off in spatial resolution. As an example of implementing the corrFISH scheme in addition to the existing pseudocolor scheme, a 4th channel can be dedicated to barcode highly abundant transcripts by corrFISH in addition to the 3 colors channels used for generating the pseudo-colors. The 4th channels can generate 20 pseudo-color through 20 rounds of serial hybridization. Then corrFISH can be used to code for another 8000 genes, but highly expressed.

In some implementations, primary probes can be stripped and signals extinguished after the pseudocolor schemes and probes targeting another set of targets can be hybridized. The utility of this can be that multiple types of targets can be probed sequentially in the same cells. For example, 20,000 intronic RNAs can be first targeted through the pseudo-color scheme. Then 20,000 mRNAs can follow, with 20,000 proteins after that. Or alternatively, probes can be used to target specific highly expressed genes to measure their localizations in cells, especially cells with polarization, such as processes in neurons. Or probes can be used to target specific isoforms or combination of isoforms of specific targets.

As disclosed herein, the approached disclosed herein can also work with amplification methods, such as HCR, to implement this work robustly in tissues.

It will be noted that although the approach above is described in connection with an in situ experiment, one of more aspects of it can be applied to in vitro experiments as well.

Figure 25:
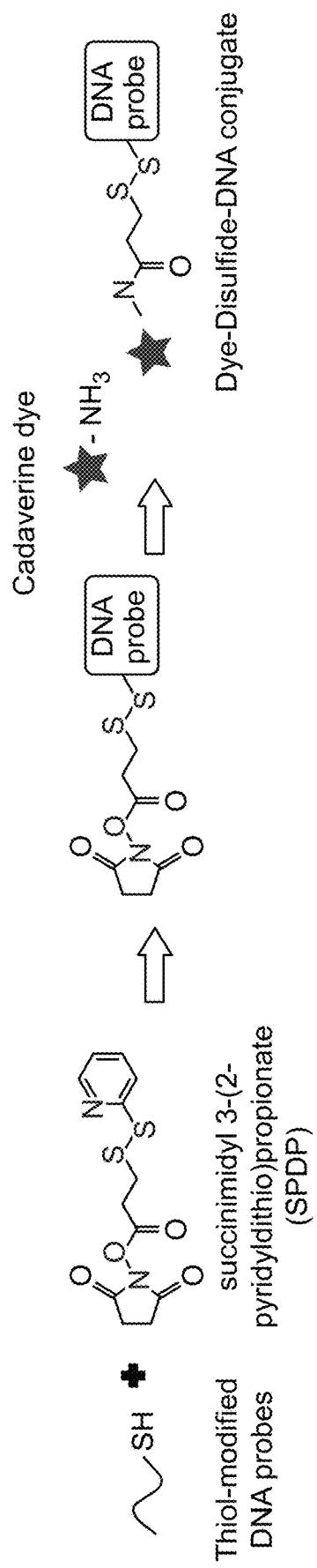
FIG. 25 depicts exemplary reaction scheme for synthesizing DNA probes conjugated to dye through cleavable disulfide linker.

In one aspect, disclosed herein are readout probes with cleavable linkers. FIG. 25 depicts exemplary chemical reactions for synthesizing a readout probe with a disulfide linker.

In one aspect, sequential barcoding FISH (seqFISH) is performed by using nucleic acid readout probes that are conjugated with a signal moiety via a cleavable linker. Any suitable cleavable linkers can be used, including but not limited to an enzyme cleavable linker, a nucleophile/base sensitive linker, reduction sensitive linker, a photo-cleavable linker, an electrophile/acid sensitive linker, a metal-assisted cleavable linker, or an oxidation sensitive linker. Exemplary linkers can be found in Leriche et al., 2012, "Cleavable linkers in chemical biology," Bioorganic & Medicinal Chemistry 20:571-582, which is hereby incorporated herein in its entirety.

In some embodiments, the cleavable linker is a disulfide linkage. In some embodiments, the cleavable linker is a nucleic acid restriction site. In some embodiments, the cleavable linker is a protease cleavage site.

An exemplary system utilizing nucleic acid readout probes is shown in FIG. 26. As depicted, a gene specific primary probe binds to a target site; e.g., in an mRNA molecule under an in situ or in vitro setting. Besides a binding sequence, the primary probe further includes an overhang sequence at one end of the binding sequence. In some embodiments, a second overhang sequence is included at the other end of the binding sequence.

In some embodiments, an overhang sequence includes one or more target sequences to which one or more nucleic acid readout probes bind. In some embodiments, each target sequence uniquely interacts with a set of readout probes with specific readout binding sequences. As disclosed herein, an overhang sequence may include two target sequences, three target sequences, five or fewer target sequences, seven or fewer target sequences, or ten or fewer target sequences. In some embodiments, an overhang sequence may include ten or more target sequences. Similar arrangements can be implemented where there are two overhang sequences.

In some embodiments, an overhang sequence binds to a bridge probe that provides target sequences for one or more readout probes to bind, as depicted in FIG. 26. A bridge probe can be interchangeably called an intermediate bridge probe or a secondary bridge probe. A bridge probe includes a binding sequence that binds to all or a portion of an overhang sequence in a primary probe. In some embodiments, a bridge probe further includes one or more readout binding targets that are connection in series and linked to the binding sequence.

In some embodiments, as depicted in FIG. 26, two bridge probes can bind to the same primary probe via two overhang sequences.

As disclosed herein, a bridge probe may include two readout binding targets, three readout binding targets, five or fewer readout binding targets, seven or fewer readout binding targets, or ten or fewer readout binding targets. In some embodiments, an overhang sequence may include ten or more readout binding targets. Similar arrangements can be implemented where there are two bridge probes bound to overhang sequences.

Exemplary rehybridization schemes utilizing the readout probes are illustrated in FIG. 26. For example, the first round of rehybridization (hyb1) begins with the hybridization of gene specific primary probes to the target mRNA. Each gene specific primary probes contains one or more "overhang" sequences that allows the secondary bridge probes to hybridize against. The secondary bridges contain two or more tertiary readouts binding sites which is the key to efficient and quick rehybridization. In the first hybridization, unique tertiary readout probes conjugated with blue dye are hybridized to their unique binding sites on the secondary bridge probe. Once imaged, the sample is treated with reducing agent such as TCEP or DTT to cleave off the disulfide-linked dyes. Then, the sample is washed with wash buffers. During the second round of hybridization, a second set of unique tertiary readout probes with red dye is hybridized to its unique binding site on the secondary bridge. After two rounds of hybridizations, a particular mRNA is then barcoded with a color barcode of red and blue. Additional rounds of hybridization can be applied to create more sophisticated barcoding sequences. Technically, the scaling factor of seqFISH with this rehybridization method depends on the number of available secondary bridges with its number of unique tertiary probes binding sites. For example, by incorporating 2 secondary bridges with total 8 unique tertiary readout binding sites (N=8), and with 4 fluorophores (F=4), one can generate up over 64,000 unique barcodes ($F^N=4^8=65,536$). Moreover, in embodiments where bridge probes are used, it is possible to strip off the secondary bridges with high concentration of formamide, and flow in another unique set of secondary bridges to continue the scaling process, which further increases the upper limit of the scaling factor.

Figure 27A:
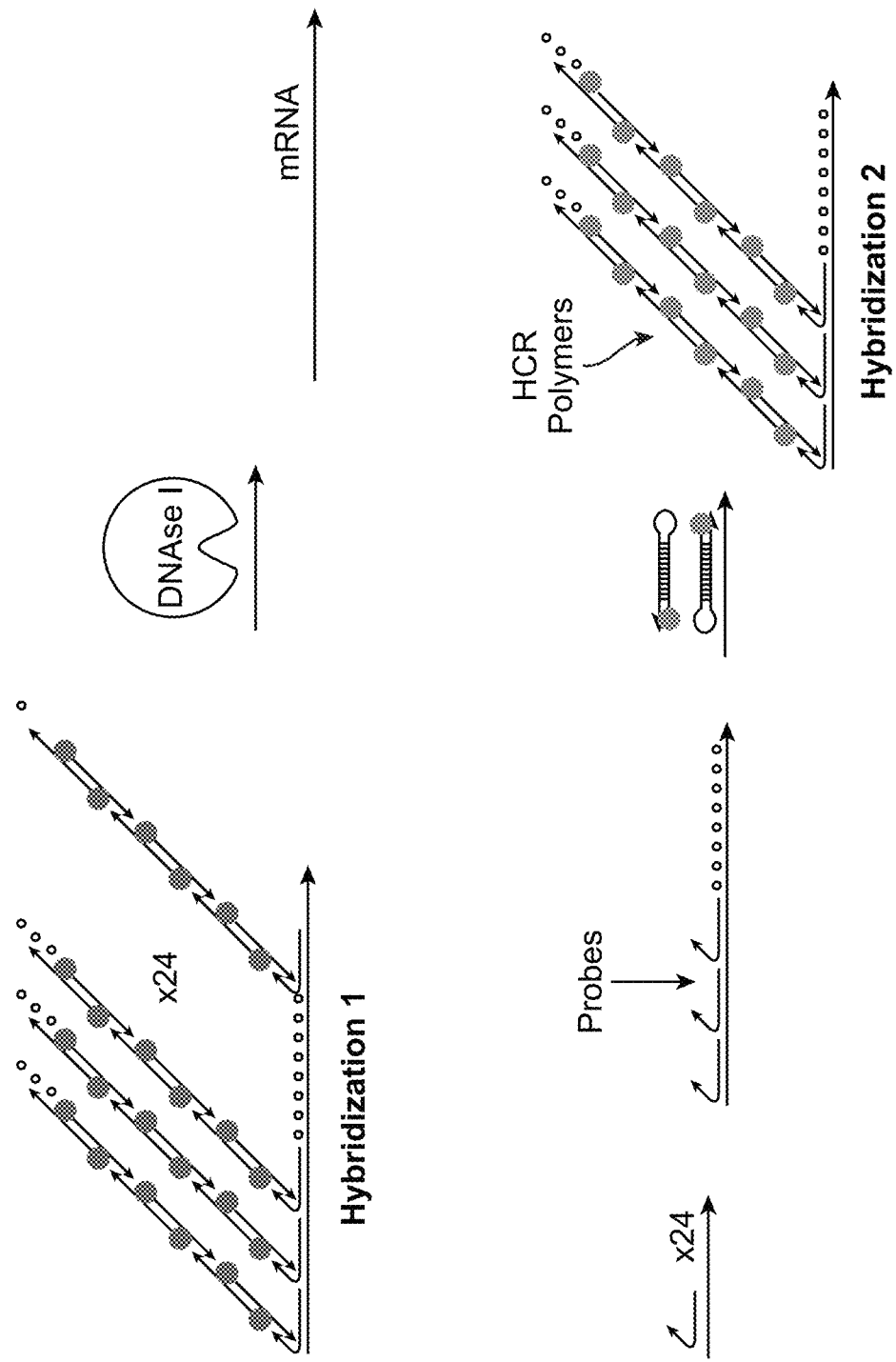
FIG. 27A depicts an exemplary hybridization chain reaction (HCR).

In one aspect, disclosed herein are methods and systems for amplifying visual signals during each round of hybridization during sequential hybridization reactions, based on hybridization chain reaction (HCR). An exemplary embodiment of HCR is illustrated in FIG. 27A. During hybridization round 1, probes with overhang initiator sequences are added to a nucleic acid target molecule such as an mRNA or a DNA. Also added are hairpin nucleic acid probes bearing sequences complementary to those of the initiator sequences. The presence of initiator sequences cause unfolding of the hairpin nucleic acid probes and result in chain reactions that lead to self-assembled extended HCR polymers. Because each hairpin nucleic acid probe bears a signal, self-assembled extended HCR polymers result in amplification of signals and better detection of target sites.

Figure 27B:
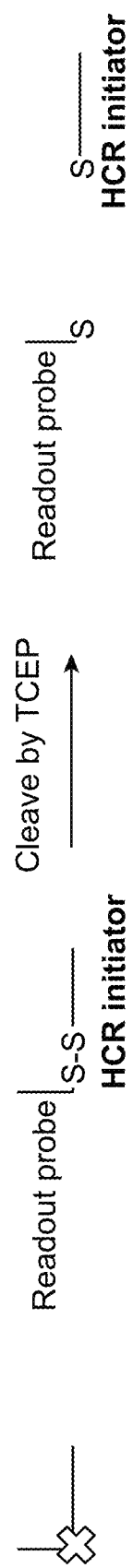
FIG. 27B depicts an exemplary readout probe.

FIG. 27B illustrates an exemplary readout probe embedded with a cleavable linker. Here, the cleavable linker is a disulfide bond. At one end of the cleavable linker, a readout probe as disclosed herein includes a binding sequence that allows it to bind to a specific nucleic acid target. In some embodiments, the nucleic acid target is an mRNA or a DNA. In some embodiments, the nucleic acid target is within an intact cell or as part of cell extract. In some embodiments, the nucleic acid target is within a primary binding probe that directly binds to a target site in an mRNA. In some embodiments, the nucleic acid target is within a secondary binding probe that binds to a primary binding probe that directly binds to a target site in an mRNA. In some embodiments, the nucleic acid target is within a tertiary or quaternary binding probe. One of skill in the art can apply the principle to any level of binding and interaction.

At the other end of the cleavable linker, a readout probe as disclosed herein further includes an HCR initiator sequence. When exposed to hairpin nucleic acids bearing partial or complete complementary sequences, the initiator sequence can trigger a chair reaction that allows a signal motif formed by multiple extender probes. Each extender probe includes a signal moiety. Aggregation of multiple extender probes enhances signal detection.

Figure 27C:
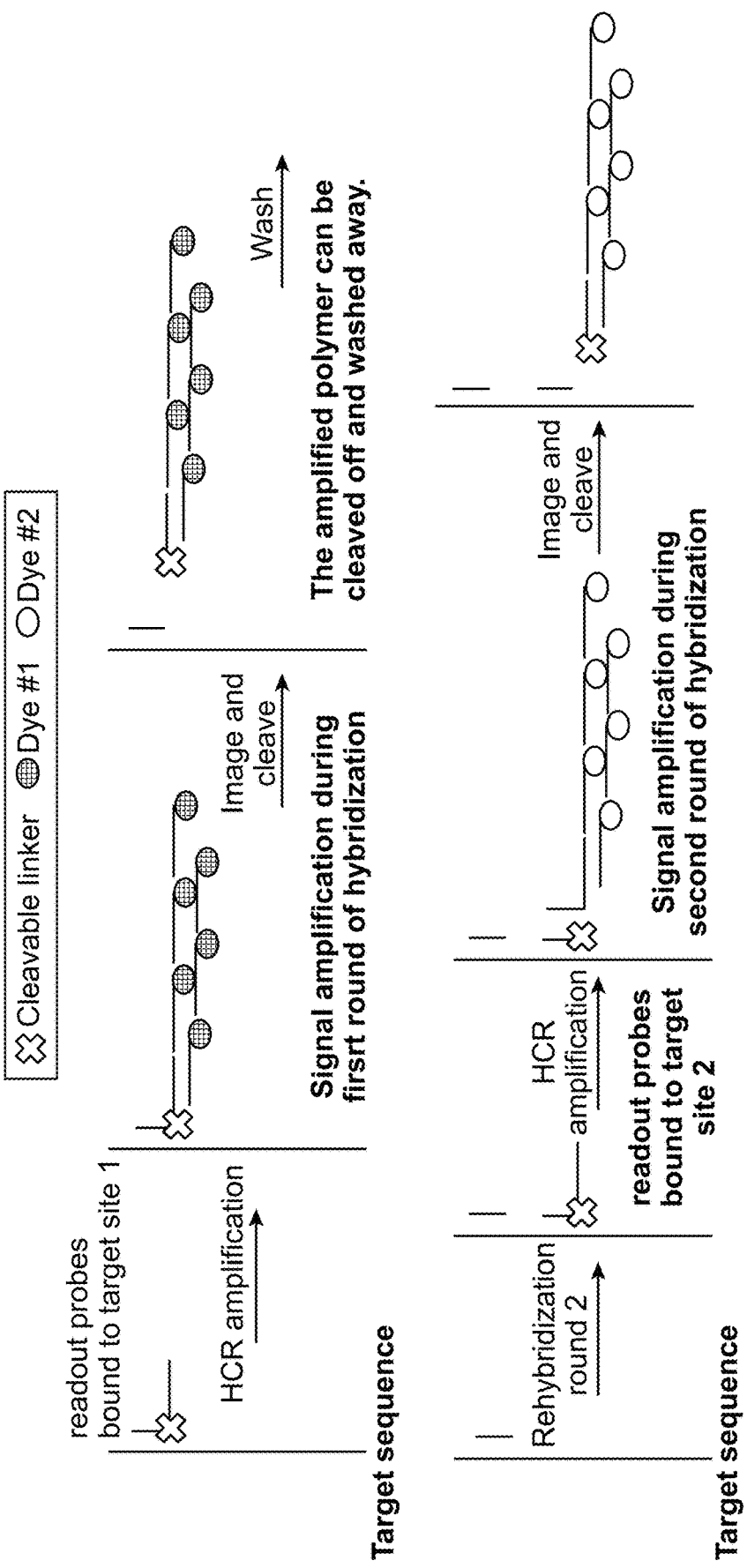
FIG. 27C depicts an exemplary hybridization chain reaction based on readout probes with cleavable linkers.

An exemplary scheme for forming a signal motif with multiple extender probes during a sequential hybridization process is illustrated in FIG. 27C. During the first round of hybridization, nucleic acid detection probes with embedded cleavable linkers binds to a first target site within a nucleic acid target sequence. In some embodiments, extender probes are added after the initial binding of nucleic acid detection probes to the first target sequences. In some embodiments, extender probes form an aggregate before the aggregated polymer is added to the reaction mix and binds to the imitator sequence in the nucleic acid detection probes.

In some embodiments, extender probes are standard hairpin probes each including a sequence that is partly or completely complementary to the initiator sequence in the readout probes. In these embodiments, extender probes are very similar or identical to each other. The size of the resulting extendible signal motif may be controlled by the concentration or absolute quantity of the extender probes added.

In some embodiments, extender probes including different types of nucleic acid sequences can be used to achieve controlled signal amplification. For example, the signal can be amplified five times if five populations of extender probes are used: $\{EP_1, EP_2, EP_3, EP_4, \text{ and } EP_5\}$. The first population of extender probes includes a binding sequence that binds to all or a part of the initiator sequence. The second population of extender probes includes a binding sequence that binds to a region in the first population of extender sequence. The third population of extender probes includes a binding sequence that binds to a region in the second population of extender sequence. The fourth population of extender probes includes a binding sequence that binds to a region in the third population of extender sequence. The fifth population of extender probes includes a binding sequence that binds to a region in the fourth population of extender sequence. In such embodiments of linear amplification, the size of the resulting extendible signal motif can be controlled by the number of populations of extender probes that are provided.

In some embodiments, an extender probe may include multiple binding sites for binding subsequent extender probes. For example, besides binding to the initiator sequence, $EP_1$ may include two or more binding sites for $EP_2$, thus allowing further amplification of the signal. This form of amplification may occur at any level. For example, in the example above, multiple binding sites for subsequent or downstream extender probes can be implemented in any one or combinations of $EP_1$, $EP_2$, $EP_3$, or $EP_4$. For example, extender probes from $EP_2$, $EP_3$, or $EP_4$ can all bind to target sites in $EP_1$, which in turn binds to the initiator sequence.

In some embodiments, the amplification occurs at multiple levels. Generally, when m populations of extender probes are present, multiple binding sites for subsequent or downstream extender probes cam be implemented in any one or combinations of $EP_1$, $EP_2$, . . . , or $EP_{m-1}$. Additionally, when multiple binding sites are present, they can be connected in series or arranged in a non-linear fashion (e.g., in a branched or circular arrangement). Depending on the number and configuration of the binding sites, the resulting extendible signal motif can be a stick, a ball, a net or in any other applicable form.

One of skill in the art would understand that any suitable number of populations of extender probes can be added to achieve an optimal signal to noise ratio for the best imaging effects. For example, the extender probes can include five or fewer, seven or few, 10 or fewer, 15 or fewer, 20 or fewer, 25 or fewer, 30 or fewer, 40 or fewer, 50 or fewer populations.

In some embodiments, the extender probes are mixed together prior to being mixed with the readout probes having the initiator sequence. In some embodiments, the extender probes are sequentially added to the readout probes having the initiator sequence where the readout probes are already bound to its nucleic acid targets.

As shown in FIG. 27C, after imaging analysis, a cleaving agent can be applied to sever the linker between the binding sequence and the imitator sequence in a readout probe. The amplified polymers can then be cleaved off and washed away.

During a second round of rehybridization, new nucleic acid detection probes are applied. The new nucleic acid detection probes include a different binding sequence that binds to a second and different target site in the nucleic acid target sequence. The new nucleic acid detection probes also include a cleavable linker and an initiator sequence. The initiator sequence can be the same as or different from the initiator sequence from the previous set of nucleic acid detection probes.

The new extender probes are used, as described hereinabove, to form amplified polymers to enhance signal detection. After imaging analysis, the new set of amplified polymers can be cleaved off and washed away. By using extender probes bearing a different type of visual signals, barcodes can be established for nucleic acid targets. Depending on the availability of target sites within a nucleic acid target, multiple rounds of hybridizations can be performed to create more complex barcodes. For example, there can be three rounds of hybridizations, four rounds of hybridizations, five rounds of hybridizations, seven or fewer rounds of hybridizations, 10 or fewer rounds of hybridizations, 12 or fewer rounds of hybridizations, 15 or fewer rounds of hybridizations, 20 or fewer rounds of hybridizations, 30 or fewer rounds of hybridizations, 40 or fewer rounds of hybridizations, or 50 or fewer rounds of hybridizations.

The compositions and methods disclosed herein can be used in sequential hybridizations to identify any suitable cellular targets within an intact cell or in an in vitro setting. In some embodiments, the cellular targets can be mRNAs or DNAs. In some embodiments, the cellular targets can be proteins. For example, the initial target-binding primary probe can be an antibody conjugated with nucleic acid sequence for subsequent bindings.

As exemplified herein, provided technologies work for a wide variety of samples. For example, HCR-seqFISH worked in brain slices and that SPIMs can robustly detect single mRNAs in CLARITY brain slices. In some embodiments, provided technologies are useful for profiling targets in mouse models of neurodegenerative diseases, or human brains. No other technology prior to the present invention can deliver the same quality and quantity of data.

Error Correction Mechanism

FIG. 3A illustrates general aspects of a sequential hybridization analysis that may contribute to quality of the analysis. Sequential hybridization includes multiple rounds of hybridization, where each round of hybridization is a multiple step process. Errors can be introduced at any step during any round of hybridization. Such errors can lead to misidentification of target genes in a sample.

Barcodes and Error Correction

In one aspect, disclosed herein are methods for designing barcodes with built-in error correction mechanisms such that the multi-component barcodes can withstand the loss of the data from one or more rounds of hybridization (i.e., drop-safe). As disclosed herein the terms "barcode" and "code" are used interchangeably.

As disclosed herein, by using probes that are associated with F detectable visual signals (F≥2), a sequential hybridization of N rounds (N≥2) can generate a total of $F^N$ combinations of visual signals. In some embodiments, these combinations of visual signals can be used as barcodes to uniquely identify cellular targets such as mRNA, DNA, or even protein.

FIG. 30 illustrates an exemplary process 3000 for generating drop safe barcodes.

At step 3010, the total number of genes that will be analyzed during the hybridization experiments is determined. This number sets the threshold values for the number of detectable visual signals (F) and the total number of rounds in the sequential hybridization (N).

Once the total number of genes is determined, steps 3020 and 3030 are performed simultaneously. The number of genes being analyzed must be smaller than the total number of possible combinations of visual signals ($F^N$). Practical aspects of the hybridization analysis need to be considered when selecting values for F and N. One would tend to reduce the number of rounds of hybridization to as few as possible. Theoretically, this can be achieved by using a high number of detectable visual signals (F). In practice, however, too many different types of visual signals may interfere with each other. For example, overlapping of visual signals can lead to barcode misidentification.

At step 3040, a library of drop-safe unique barcodes are generated by implementing one or more error correction mechanisms.

In some embodiments, a repeat round can be performed for any round during a sequential hybridization of N rounds, rendering a new sequential hybridization of (N+1) rounds. The extra repeat round can be an error correction round. The repeat round can be a duplicate of any round of the n rounds sequential hybridization. The repeat round can take place as any round during the sequential hybridization (N+1) rounds.

After the repeat, there are two rounds of hybridization that should be identical to each other. Consequently, the complete loss of one of the repeat rounds does not affect the outcome of the sequential hybridization. As such, either of the repeat rounds is a drop-safe round.

FIG. 2 illustrates an experiment where 3 rounds of hybridization using probes with 4 types of detectable visual signals (red: R, yellow: Y, green: G, and cyan: C) are used to create barcodes for 4 different mRNA molecules. Hybridization round 3 is a repeat of hybridization round 1, as summarized in Table 1 below.

TABLE 1

Illustration of the effect of repeat hybridization rounds.

| mRNA molecules | Color barcodes (3 rounds) | Color barcodes (dropping round 1) | Color barcodes (dropping round 3) |
|---|---|---|---|
| mRNA1 | Y-C-Y | C-Y | Y-C |
| mRNA2 | G-R-G | R-G | G-R |
| mRNA3 | R-C-R | C-R | R-C |
| mRNA4 | C-R-C | R-C | C-R |

As shown in the table above, data from one of the repeat rounds can be dropped completely in case of major experiment error, barcodes derived from the remaining rounds of hybridization still uniquely represent the mRNA molecules.

In some embodiments, even in a questionable hybridization round, most of the information is still reliable. Only some of the bindings between probes and target sequences include inaccurate information. In some embodiments, partial data from a questionable round of hybridization are used. For example, in the illustration above, binding signals can be missing or ambiguous for a particular location during hybridization round 1, which can produce an incomplete three letter barcode *-C-Y for the particular location, where * remains undetermined. In the scheme illustrated, the identity of * is not needed to decipher that the code is for mRNA1. Similarly, binding signals can be missing or ambiguous for a particular location during hybridization round 2, which can produce an incomplete three letter barcode R-*-R for the particular location, where * remains undetermined. Once again, the identity of * is not needed to decipher that the code is for mRNA3.

Additionally, data from repeat rounds can validate each other. For example, in FIG. 2, C, a circle highlights a cyan data point in the image corresponding to hybridization round 2. In the same location, the image corresponding to hybridization round 3 reveals a yellow data point. Based on only information from hybridization rounds 2 and 3, this location would be identified as part of mRNA1. However, no signals are identified at the location during hybridization round 1, which suggests that the highlighted data points may be due to non-specific binding.

In some embodiments, a sophisticated barcode generating algorithm is used such that the resulting barcodes can withstand the loss of any round or even multiple rounds of hybridization data. In some embodiments, a barcode generator is used to generate the drop-safe barcodes. For example, FIG. 32 illustrates an example, where probes with 5 different visual signals (blue, green, red, purple and yellow) are used in 4 rounds of hybridization. One of the hybridization round is an error correction round where barcodes are generated based on barcodes from the previous 3 rounds. The following is an example that illustrates how barcodes are generated.

Designing an error correction code to correct for m number of errors in a message of n length is analogous to packing as many spheres of radius m in a n dimensional cube. There are examples of "perfect codes" such as Golay and Hamming codes that can be as efficient as possible in this packing design. These perfect codes are important in digital communication because the word lengths are long, up to billions of letters for gigabytes of data, and many forms of errors can occur, including deletion and insertions. However, in the seqFISH experiments, as the code lengths are short, a perfect code correction system is not necessary, especially as the "correct" codes are already defined. One of the major source of error is deletions due to loss of a hybridization. Thus, it is possible to design simple correction schemes that are not completely efficient (i.e. obtain the tightest packing density for the n-spheres) but can achieve good error correction with just a few extra rounds of hybridization.

To design a barcode scheme that can tolerate loss of a single round of hybridization is akin to a problem where any n-dimensional hypercube is collapsed by 1 dimension to a n−1 dimensional hypercube without having any two points on the n-dimensional hypercube mapping to the same point. In order for this to be true, no two barcodes can be connected by a 1D line running parallel to any of the axes. There are many solutions to generate this 1 round loss tolerant code.

In this example, 4 rounds of hybridization is used. Here, 5 different visual signals (blue, green, red, purple and yellow) are assigned numerical values. In some embodiments, the numerical values are integers. For example, blue=1; green=2; red=3; purple=4; and yellow=5. It would be understood that these are mere sample values. Any non-redundant numerical values can be assigned to represent the different types of visual signals. In some embodiments, a barcode generator is used to generate the barcodes used in the experiment. In the exemplary embodiment, a drop-safe barcode for a particular target gene can be defined as a four-component linear array: {i, (i+j+k) mod 5, j, k}. Here, mod (modulo operation or modulus) finds the remainder after division of one number by another. For example, 8 mod 5 is 3. 5 mod 5 is 0, which is equivalent to 5.

In this example, I represents the numerical values corresponding to the visual signals observed for the particular target gene during the first round of hybridization. The scheme (i+j+k) mod 5 represents the numerical values corresponding to the visual signals observed for the particular target gene during the second round of hybridization. J represents the numerical values corresponding to the visual signals observed for the particular target gene during the third round of hybridization. K represents the numerical values corresponding to the visual signals observed for the particular target gene during the found round of hybridization. In this example, I, j, and k each can be 1, 2, 3, 4 or 5, or any one of the numerical values that have been assigned to the five types of visual signals used in the experiment.

In this example, (i+j+k) mod 5 is determined as the error correction round. However, once complete barcodes are generated, any of round 1 through round 4 can be dropped to yield unique 3-component barcodes. As such, the barcodes determined by this method can be used to correct errors in any round.

The following table illustrates how the 1 drop tolerant barcodes can be generated using the equation (i+j+k) mod 5.

TABLE 2

Illustration of the effect of repeat hybridization rounds.

| Genes | $1^{st}$ round of hyb* | $2^{nd}$ round of hyb | $3^{rd}$ round of hyb | $4^{th}$ round of hyb (i + j + k)mod 5 |
|---|---|---|---|---|
| mRNA1 | 1 | 2 | 4 | 2 |
| mRNA2 | 3 | 3 | 1 | 2 |
| mRNA 3 | 5 | 1 | 2 | 3 |
| mRNA 4 | 2 | 3 | 5 | 5 |
| ... | ... | ... | ... | ... |
| mRNA125 | 5 | 2 | 1 | 3 |

*The term "hyb." stands for hybridization.
Numerical values are assigned to color signals as follows: blue = 1; green = 2; red = 3; purple = 4; and yellow = 5.

*The term "hyb." Stands for hybridization. Numerical values are assigned to color signals as follows: blue=1; green=2; red=3; purple=4; and yellow=5.

As illustrated above, although the 4th round of hybridization is generated using an error correction algorithm, any one round of four rounds of hybridization in Table 2 can be dropped and still yield a unique set of barcodes for 125 genes.

More generally, a barcode that can resist the elimination of one round of hybridization can be defined as:

$$\{j_1, j_2, \ldots (a_1*j_1+a_2*j_2+ \ldots +a_n*j_n+C) \bmod F, \ldots j_n\} \quad (1)$$

where $j_1$ is a numerical value that corresponds the detectable visual signals used in the first round of hybridization, $j_2$ is a numerical value that corresponds the detectable visual signals used in the second round of hybridization, and $j_n$ is a numerical value that corresponds the detectable visual signals used in the nth round of hybridization. In some embodiments, $j_1, j_2, \ldots j_n$ are non-redundant integers. In some embodiments, $a_1, a_2, \ldots$ an can be any integers that are not none zero. In some embodiments, C is a constant integer. In some embodiments, C is zero. The remainder of F divided by F is 0 (F mod F=0), so F and 0 are equivalent. There is no limitation on the number of hybridization. One of such examples is shown in FIG. 37.

Array (1) is a general representation of a barcode that is safe against the drop or loss of one round of hybridization. Although $(@1*j_1+a_2*j_2+ \ldots +a_n*j_n+C) \bmod F$ is the designated error correction round, in some embodiments, the barcode is safe against the loss or drop of any round of hybridization.

As disclosed herein, array (1) consists of n-component, each corresponding to the visual signals from a particular round of hybridization. In some embodiments, probes binding to a particular gene are all associated with the same detectable visual signal, for example, red, green or blue. In some embodiments, probes binding to a particular gene are all associated with multiple types of detectable visual signal, for example, green+yellow or blue+red. Through combinations of visual signals, the total number of different types of detectable visual signals can be further expanded.

In some embodiments, barcodes can be designed such that drop or loss of data from two rounds of hybridization can be tolerated. Using 2 additional rounds of hybridization does not correct for all possible 2 drops, but it does correct for a large fraction of the 2 drops. For example, for detecting 100 genes with F=5 dyes, 3 rounds of hybridization are needed for basic barcoding of these genes. When adding two rounds of hybridization, the error correction code:

$$\{i,j,k,(i+j+k) \bmod F,(i-j) \bmod F\} \quad (2)$$

Such codes can correct for 2 drops all except dropping hybridization round 3 and round 4 together. Here, each component in the 5-member array represents one round of hybridization.

Similarly, an error correction code such as $$\{i,j,k,(i+j+k) \bmod F,(i-k) \bmod F\} \quad (3)$$

can correct for dropping hybridization round 2 and hybridization round 4 together. Again, each component in the 5-member array represents one round of hybridization.

For example, to code for most of the transcriptome, only 6 rounds of hybridization are needed when F=5 ($6^5$=15,625). When adding two rounds of hybridization, the following error correction code is generated:

$$\{i,j,k,l,m,n,(i+k+l+m+n) \bmod F,(i-j-k-l+n) \bmod F\} \quad (4)$$

There are a total of 28 combinations of how 2 rounds of hybridization can be lost or dropped. This type of code can correct for 24 out of the total 28 combinations. Here, each component in the 8-member array represents one round of hybridization. Similarly, the $1^{st}$ error correction round can be any liner combination of 5 out of 6 rounds of hybridization (e.g., without j) and $2^{nd}$ error correction can be a subset of the linear combination of 5 out of 6 rounds of hybridization (e.g., without m). In these embodiments, in the $2^{nd}$ error correction round, indices include different coefficients as long as the it is not exactly the same 5 indices used in the $1^{st}$ error correction round.

To correct for all combinations of drop or loss of 2 rounds of hybridization (2 drops) fully, 3 additional hybridizations are needed. Again for 6 rounds of hybridization with 5 types of detectable signals (F=5), three extra rounds of hybridizations are added to create the full 9-member error correction code:

$$\{i,j,k,l,m,n,(i+j+k+l+m+n) \bmod F, (i-j-k-l) \bmod F, (m-n-j+k) \bmod F\} \quad (5)$$

In some embodiments, there are many equivalent codes that can correct for 2 drops with 3 additional rounds of hybridization. They can be all empirically determined. The number of hybridization for any reasonable number can be simulated to determine the complete correcting barcode.

In some embodiments, three additional hybridization can correct for majority of the errors due to drop or loss of three rounds of hybridization. For example, for 6 rounds of hybridization with 5 types of detectable signals (F=5), three extra rounds of hybridizations are added to create the full 9-member error correction code:

$$\{i,j,k,l,m,n,(k+i-l+m-n) \bmod F, (i-l+j-k+m) \bmod F, (l-n-j-k+i) \bmod F\} \quad (6)$$

Similar to the previous example, 3 additional rounds of hybridizations can correct for a majority of the loss or drop of 3 rounds of hybridization. There are a total of 84 combinations how 3 rounds of hybridization can be lost or dropped. A 9-componenet code as illustrated in (6) can correct for 72 out of the 84 combinations.

In some embodiments, 4 additional rounds of hybridizations can correct for the drop or loss of all and any three rounds of hybridization. An example 10-component code is as follows:

$$\{i,j,k,l,m,n,(k+i+l+m+n) \bmod F, (i-l+j-k+m) \bmod F, (l-n-j-k+i) \bmod F, (n-k-i-j+m) \bmod F\} \quad (7)$$

It will be understood that there are many other solutions that can be determined empirically. For higher number of drops, similar correction schemes can be determined empirically.

For 16,000 species, this scheme allows 10 hybs with the ability to correct 3 drops. In comparison, in MERFISH, 16 hybs are needed to target 140 species, with only 2 round correction ability. Because the more round of hybridization one implements, the more mistakes can be made, keeping the number of hybs low is crucial. Thus, this error correction scheme is very powerful compared to the Hamming Distance scheme used in MERFISH. This is because hamming distance correction is used in telecommunications with binary numbers, which uses much longer strings of 0,1.

As described above, the design disclosed above can correct for loss of 1 hybridization for an arbitrarily long barcode sequence with minimal extra effort. In this example, only one round of error correction is needed in a total of 4 rounds of hybridization that analyzes 100 genes, which below the capacity of 54 (625).

For example, 7 rounds of hybridization with 5 colors can cover $5^7 = 78,125$ transcripts, more than the transcriptome, with 8 hybridizations the entire transcriptome can be coded with error correction using the barcoding system disclosed herein.

Another consideration in designing error-tolerant barcodes is that the mechanism of re-hybridization should guide the robustness of error correction. In the merFISH implementation of seqFISH (Chen 2015), null signal, or "0", along with "1" which is cy5 fluorescence, is used to form a binary barcode. However, it is difficult to determine whether no signal is due to mis-hybridization or actual null signal. In the seqFISH implementation using positive signals as readouts during each round of hybridization reduces the need for error correction because false positive signal is unlikely to re-occur in the same position during another hybridization due to DNAse stripping between hybridizations. Thus, implementation of seqFISH with 5 colors and 1 extra round of hybridization to error correct is both efficient and accurate, and allows imaging of a large tissue sections since imaging time is ultimately limiting in multiplexing experiments.

At step 3050, sequential hybridization is carried out to associate or assign barcodes from step 3040 to target genes in a sample. As disclosed herein, the sample can be immobilized mRNAs, DNAs, chromosomal DNAs, and combinations thereof. For example, in the 100-gene sequential hybridization example (see FIG. 32 and FIG. 40), 4 rounds of hybridization are carried out using probes associated with 5 different types of visual signals. Barcodes are assigned through selection of probes during the 4 rounds of hybridization experiment on immobilized nucleic acid samples.

At step 3060, after hybridization, visual signals are collected and used in further analysis. For example, images are collected from different hybridization are used to readout the barcodes for specific locations on the immobilized nucleic acid samples. Such barcodes can then be used to decipher the identity of the nucleic acid targets (see, for example, FIGS. 2, 32, 33, 40 and 41).

In one aspect, sequential hybridization and serial hybridization are combined for gene identification. In serial hybridization, only one round of hybridization is used to identify target genes. The method is particularly helpful when analyzing genes whose expression level is too high. In some embodiments, genes that are highly expressed, if included in hybridization analysis with genes that are not so highly expressed, would overpower the signals for the genes that are not so highly expression. In some embodiment, the method can also applied to genes whose expression level is too low.

In some embodiments, expression levels of genes are pre-determined. For example, gene expression levels (e.g., measured by mRNA transcription level) can be already available for certain species. It is possible to identify highly expressed genes by mining publically available data, thus obviating the need to conduct additional experiments to measure expression level.

In some embodiments, initial experiments are performed to determine relative expression level of candidate genes. In some embodiments, genes are grouped according to their expression levels. For example, genes with moderate or low expression levels can be grouped together and subject to sequential hybridization analysis. Genes that are highly expressed can be subject to serial hybridization analysis. In some embodiments, expression levels of different genes are compared to the same control gene to derive a relative expression level. For example, the expression level of actin can be used as a control. It will be understood that gene expression level may vary by organisms and can change with respect to different internal and environmental controls. In some embodiments, data from existing expression analysis can be used in identifying highly expressed gene. In some embodiments, preliminary expression analysis is carried out before sequential and/or serial hybridization analysis.

In some embodiments, a threshold value is set for high expression. Any genes having expression level above the threshold will be excluded from sequential hybridization.

Depending on types of detectable visual signals that are available, a serial hybridization experiment can detect as many target genes as the number of types of detectable visual signals. For example, in the experiment illustrated in FIGS. 32 and 40, 5 genes are analyzed at the same time during one serial hybridization experiment.

In some embodiments, when multiple target genes are present in one serial hybridization round, the number of probes that recognize each target gene is selected such that overlapping of signals is minimize or avoided. In some embodiments, the concentration of probes are selected to avoid or minimize overlapping of detectable signals.

Computer System

FIG. 31 depicts a diagram of an example system architecture for implementing the features and processes of the method disclosed herein, in particular the barcode design functionalities with embedded error correct mechanism.

In one aspect, some embodiments can employ a computer system (such as the computer system 3100) to perform methods in accordance with various embodiments of the invention. An exemplary embodiment of computer system 3100, includes a bus 3102, one or more processors 3112, one or more storage devices 3114, at least an input device 3116, at least an output device 3118, a communication subsystem 3120, working memory 3130 which includes an operating system 3132, device drivers, executable libraries, and/or other code, such as one or more application(s) 3134 (one or more for implementing the methods disclosed herein).

According to a set of embodiments, some or all of the procedures of such methods are performed by the computer system 3100 in response to processor 3112 executing one or more sequences of one or more instructions (which might be incorporated into operating system 3132 and/or other code, such as an application program 3134) contained in working memory 3130. Such instructions can be read into the working memory 3130 from another computer-readable medium, such as one or more of storage device(s) 3114. Merely by way of example, execution of the sequences of instructions contained in working memory 3130 might cause processor (s) 3112 to perform one or more procedures of the methods described herein. Additionally or alternatively, portions of the methods described herein can be executed through specialized hardware. Merely by way of example, a portion of one or more procedures described with respect to the method(s) discussed above, such as method 3000, and methods illustrated in FIGS. 3B and 30, might be implemented by processor 3112.

In some embodiments, computer system 3100 can further include (and/or be in communication with) one or more non-transitory storage devices 3114, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices can be configured to implement any appropriate data stores, including without limitation, various file systems, database structures, and/or the like. In some embodiments, the storage device 3114 can be example of local database of a user device, or the server database of a server.

In some embodiments, computer system 3100 can further include one or more input devices 3116, which can comprise, without limitation, any input device that allows a computer device to receive commands from a user such as a request for barcode design.

In some embodiments, computer system 3100 can further include one or more input output devices 3118, which can comprise, without limitation, any output device that can receive information from a computer device and communicate such information to a user, to another computer device, to the environment of the computer device, or to a functional component communicably connected with the computer device. Examples of input devices include but are not limited to a display, a keyboard, a mouse and etc. For example, the results of the barcoding analysis can be presented on any one or more of the output devices, for example, as two dimensional heat map, cluster map, a list, a table, and etc.

It would be understood that any applicable input/output devices or components, such as those disclosed in connection with one or more user device or server, can be applied to input device 3116 and output device 3118.

In some embodiments, computer system 3100 might also include a communications subsystem 3120, which can include without limitation a modem, a network card (wireless or wired), an infrared communication device, a wireless communication device, and/or a chipset (such as a Bluetooth™ device, an 802.11 device, a WiFi device, a WiMax device, cellular communication facilities, etc.), and/or the like. Communications subsystem 620 can include one or more input and/or output communication interfaces to permit data to be exchanged with a network, other computer systems, and/or any other electrical devices/peripherals. In many embodiments, computer system 3100 will further comprise a working memory 3130, which can include a RAM or ROM device, as described above.

In some embodiments, computer system 3100 also can comprise software elements, shown as being currently located within the working memory 3130, including an operating system 3132, device drivers, executable libraries, and/or other code, such as one or more application(s) 3134, which can comprise computer programs provided by various embodiments, and/or can be designed to implement methods, and/or configure systems, provided by other embodiments, as described herein. Merely by way of example, a portion of one or more procedures described with respect to the method(s) discussed above, such as the methods described in relation to FIG. 30, can be implemented as code and/or instructions executable by a computer (and/or a processing unit within a computer); in an aspect, then, such code and/or instructions can be used to configure. And/or adapt a general purpose computer (or other device) to perform one or more operations in accordance with the described methods.

A set of these instructions and/or code might be stored on a non-transitory computer-readable storage medium, such as storage device(s) 3114 described above. In some cases, the storage medium might be incorporated within a computer system, such as computer system 3100. In other embodiments, the storage medium might be separate from a computer system (e.g., a removable medium, such as an optical disc), and/or provided in an installation package, such that the storage medium can be used to program, configure, and/or adapt a general purpose computer with the instructions/code stored thereon. These instructions might take the form of executable code, which is executable by computer system 3100 and/or might take the form of source and/or installable code, which, upon compilation and/or installation on the computer system 3100 (e.g., using any of a variety of generally available compilers, installation programs, compression/decompression utilities, etc.), then takes the form of executable code.

It will be apparent to those skilled in the art that substantial variations can be made in accordance with specific requirements. For example, customized hardware might also be used, and/or particular elements might be implemented in hardware, software (including portable software, such as applets, etc.), or both. Further, connection to other computing devices such as network input/output devices can be employed.

The terms "machine-readable medium" and "computer-readable medium," as used herein, refer to any medium that participates in providing data that causes a machine to operate in a specific fashion. In an embodiment implemented using computer system 3100, various computer-readable media might be involved in providing instructions/code to processor(s) 3112 for execution and/or might be used to store and/or carry such instructions/code. In many implementations, a computer-readable medium is a physical and/or tangible storage medium. Such a medium can take the form of a non-volatile media or volatile media. Non-volatile media include, for example, optical and/or magnetic disks, such as storage device(s) 3114. Volatile media include, without limitation, dynamic memory, such as working memory 3130.

Common forms of physical and/or tangible computer-readable media include, for example, a floppy disk, a flexible disk, hard disk, magnetic tape, or any other magnetic medium, a CD-ROM, any other optical medium, any other physical medium with patterns of holes, a RAM, a PROM, EPROM, a FLASH-EPROM, any other memory chip or cartridge, or any other medium from which a computer can read instructions and/or code.

Various forms of computer-readable media can be involved in carrying one or more sequences of one or more instructions to processor(s) 3112 for execution. Merely by way of example, the instructions can initially be carried on a magnetic disk and/or optical disc of a remote computer. A remote computer might load the instructions into its dynamic memory and send the instructions as signals over a transmission medium to be received and/or executed by computer system 3100.

Communications subsystem 3120 (and/or components thereof) generally will receive signals, and bus 3102 then might carry the signals (and/or the data, instructions, etc. carried by the signals) to working memory 3130, from which processor(s) 3112 retrieves and executes the instructions. The instructions received by working memory 1330 can optionally be stored on non-transitory storage device 3114 either before or after execution by processor(s) 3112.

The methods and systems are provided by way of illustration only. They should in no way limit the scope of the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXEMPLIFICATION

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

Example 1

Pseudo-Color Based Barcoding

Sample Preparation

Figure 5:
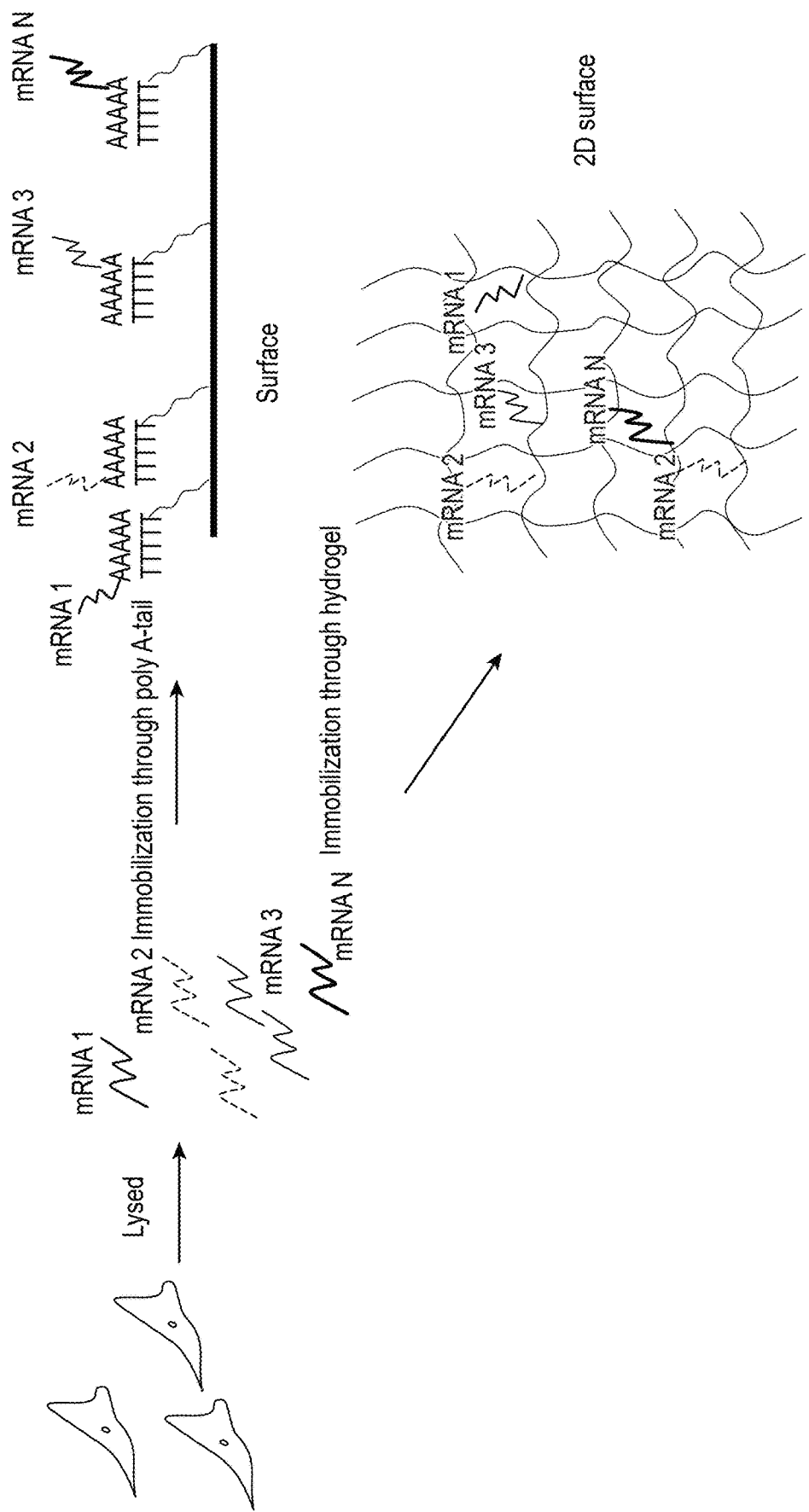
FIG. 5 illustrates mRNA transcripts immobilized on a surface through poly-A-tail or hydrogel embedment.

FIG. 5 illustrates mRNA transcripts immobilized on a surface through poly-A-tail or hydrogel embedment. Once cells are lysed, the cell lysate or purified total RNA can be immobilized on a surface through a coverslips functionalized by DNA or LNA Poly-T by capturing the poly-A tail of mRNA. Alternatively, the mRNA can be mixed with hydrogel such as polyacrylamide gel and allowed gelation on a coverslips surface which the pore size formed would trap the mRNA molecules on the surface.

Design of Primary Probes

Figure 6:
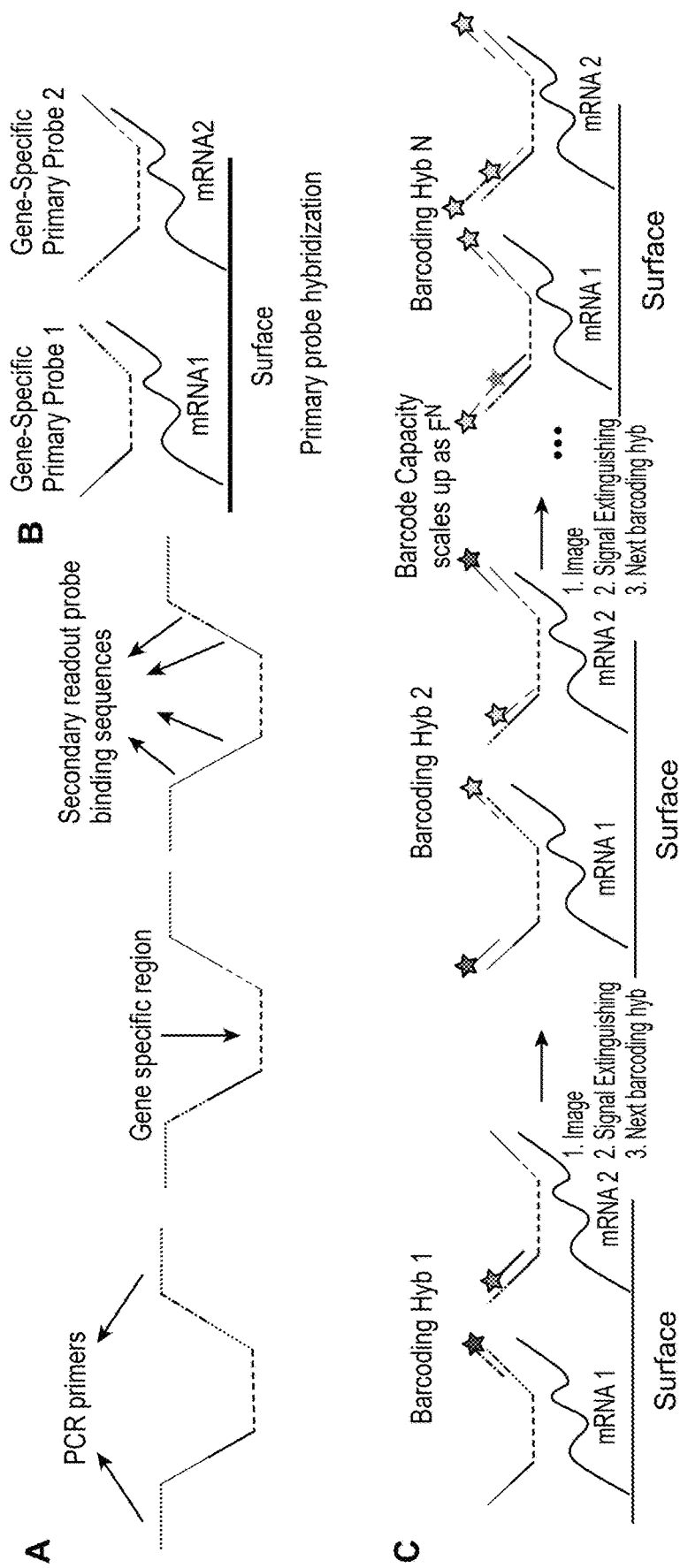
FIG. 6 illustrates an exemplary embodiment of gene specific primary probes design and sequential barcoding hybridization on mRNA immobilized on a surface. (a) Design of gene specific primary probe. (b) primary probe hybridizations on mRNA on the surface, alternatively, the primary probes hybridizations can also be done in solution. (c) sequential barcoding hybridization on the surface. One or multiple 18-30mers secondary readout probes conjugated with fluorophore will hybridize to the primary probes during each round of hybridization.

FIG. 6 illustrates an exemplary embodiment of gene specific primary probes design and sequential barcoding hybridization on mRNA immobilized on a surface. In particular, FIG. 6, a, shows that primary probes are not directly labeled with fluorophore. The primary probe contains (i) a gene specific targeting region of the mRNA which is 20 nt to 35 nt, (ii) one or multiple secondary readout probe binding sites, (iii) PCR primer pairs, and optionally (iv) a restriction enzyme cutting sites and (v) spacers nucleotides. Each target mRNA requires at least 20 or more primary probes. These primary probes are synthesized from a complex oligo pool which later is amplified by the unique PCR primers to obtain a complete set of probes. The primary probes can be attached to target sequence either on the surface or in solution (FIG. 6, b). Different primary binding sequences are associated with different readout sequences, which can be selectively turned on during hybridization rounds.

In this case, mRNA 1 is barcoded with red color and mRNA 2 is barcoded with blue color in the first round of hybridization. After imaging, a signal extinguishing step is performed, followed by the next round of barcoding hybridization. Each mRNA will receive 4 colors in total which gives their unique identity to differentiate between each other. The barcode capacity scales up as $F^N$, with F is the number of fluorophore and N is the number of barcoding hybridization (FIG. 6, c).

Arrangement of Secondary Probe Binding Sites

Figure 7:
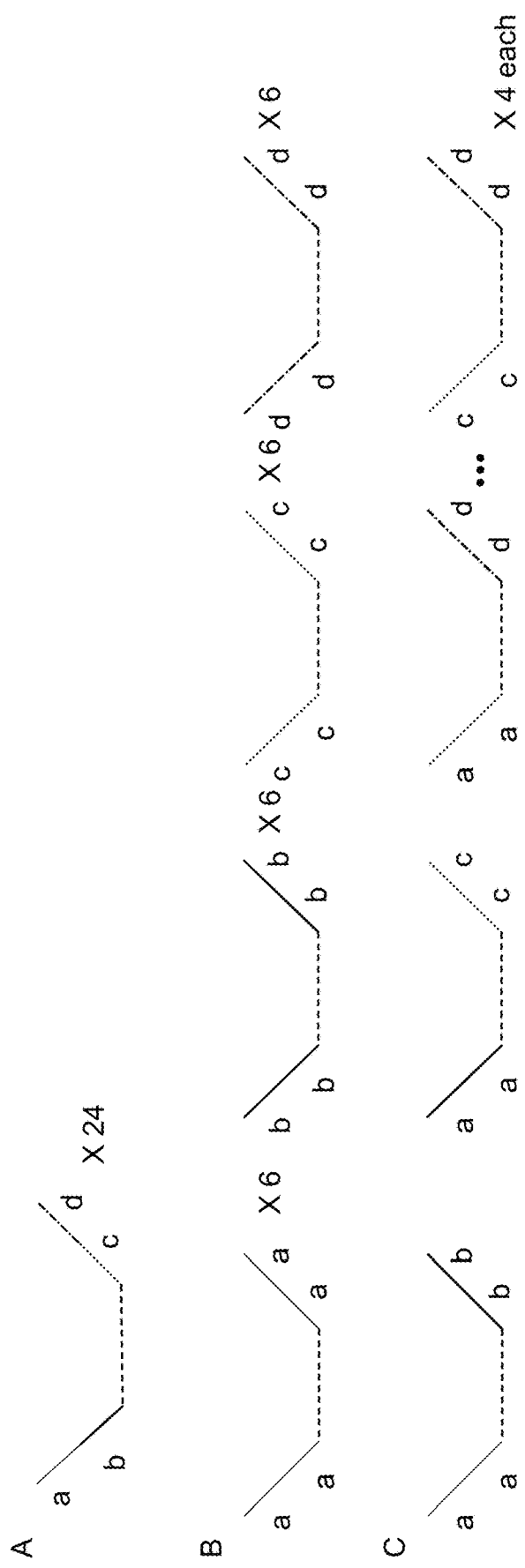
FIG. 7 illustrates different arrangements of secondary probe binding sites on primary probes. Assume 24 primary probes are used for each gene, 4 rounds of barcoding hybridization with 4 different unique secondary probe binding sequences, there are various combinations of arranging the secondary probe binding sequences on the primary probe. (a) all 4 unique binding sequences a, b, c, d are placed on all 24 primary probes. (b) each unique binding sequence are placed separately into each primary probe. In this case, 6 primary probes have unique binding sequence a, 6 primary probes will get unique binding sequence b, 6 primary probes will have unique binding sequence c, and 6 primary probes will have unique binding sequence d. (c). a combination of unique binding sequences is placed on different primary probes for a gene. In this case, the unique binding sequences combination can be (a,b),(a,c),(a,d),(b,c),(b,d),(c,d) on each 4 primary probes.

FIG. 7 illustrates different arrangements of secondary probe binding sites on primary probes. Assume 24 primary probes are used for each gene, 4 rounds of barcoding hybridization with 4 different unique secondary probe binding sequences, there are various combinations of arranging the secondary probe binding sequences on the primary probe. Multiple or all unique secondary probe binding sequences can be found in one probe; for example, as overhang sequences connected to the primary binding sequence in various combinations (FIG. 7, a-c).

Signal Extinguishing Steps

Figure 8:
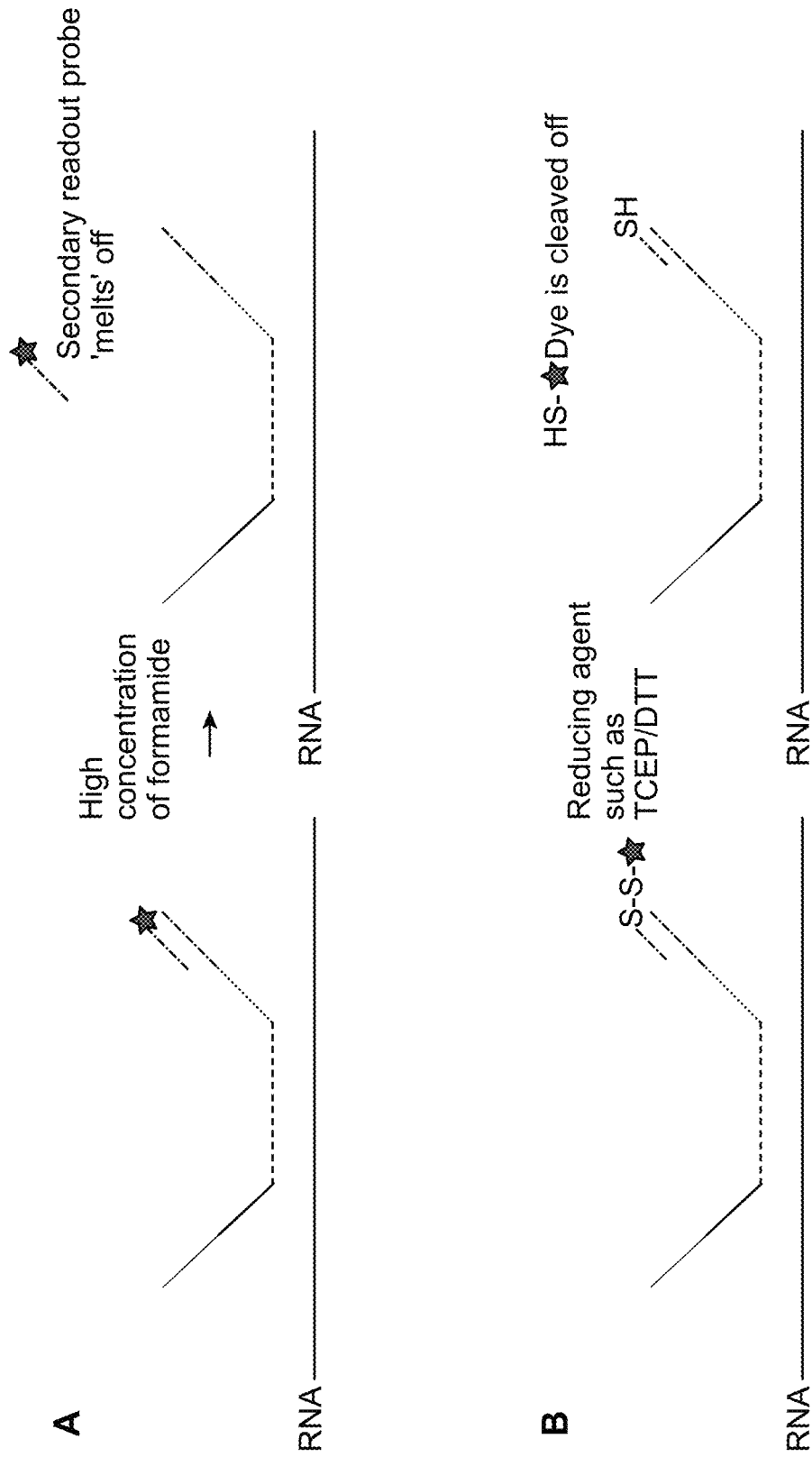
FIG. 8 depicts possible ways to extinguish fluorescent signals via (a) flowing in high concentration of formamide to 'melt' off the secondary readout probe or (b) chemical cleavage.

FIG. 8 depicts possible ways to extinguish fluorescent signals. For example either high concentration of formamide can be introduced to 'melt' or strip off the secondary readout probe (FIG. 8, a). Alternatively, chemical cleavage can be applied (FIG. 8, b); for example, one implementation can be disulfide conjugated dye on secondary readout probes can be reduced by TCEP or DTT and other reducing agents to cleave off the linker, and thus getting rid the fluorophore from the primary probe.

Scaling Up the Number of 'Fluorophore' by Serial Hybridization

FIG. 10 depicts a table showing possible barcodes obtained using the pseudo-color barcode scheme. In this example, 3 different color signals, 4 serial hybridization rounds and 4 barcoding rounds were used. In this implementation, 16 rounds of imaging will be implemented with a total of 48 unique secondary readout adapters conjugated to one of the 3 fluorophores.

One can adjust F, n, and N to achieve the best strategy to generate a desired barcode capacity. For example, in order to reduce the number of barcoding rounds to 3, 30 unique secondary readout sequences are needed at each round of barcoding, as $30^3=27,000$. This scheme can allow lower density of targets detected per channel in each hybridization round, allowing a larger number of genes to be detected in situ.

Time Efficient Error Correction Scheme

A time efficient error correction scheme can be implemented in the current coding scheme to tolerate 1 drop of 'color' in decoding the whole color codes due to loss of hybridization. It is possible to design a highly efficient correction schemes that are not perfect by obtaining the tightest packing density for the n-spheres. A barcode generator (I, (i+j+k) mod 5,j,k) can be used to generate barcodes that can tolerate 1 round of mis-hybridization. For example, 6 rounds of hybridization with 5 color can cover 15625 genes, one can design the barcode scheme to have an extra round of hybridization to still be able to identify the 15625 genes even though any one round of hybridizations is lost in the barcode. More rounds can be corrected with additional error correction hybridization rounds. For example, barcodes can be designed such that shortened barcodes are still unique after data for two or more rounds of hybridizations are lost.

Hybridization Experiment

To show the entire idea works, we targeted 64 genes in mouse NIH3T3 cells (FIG. 10). These 64 genes were chosen randomly with a range of FPKM values from bulk RNA-sequencing data. A set of 24 primary probes for 1 gene were designed as illustrated in FIG. 2 which contain 35 nt of gene specific targeting region, 3 unique secondary readout binding sequences, a pair of PCR primers, and a 1nucleotide-'T' spacer. The primary probes were synthesized in a complex oligo pool and were amplified by PCR. The barcodes were generated as $4^3=64$, without implementing an error correction scheme. 3 fluorophores were used: Cy3b, ALEXA FLUOR™ 594, and ALEXA FLUOR™ 647 and the number of fluorophores were scaled up as described in FIG. 4 with slight variation. Briefly, in each round of barcoding hybridization, 4 unique secondary readout probes were coupled to the 3 fluorophores+one of the fluorophores hybridized in a later hybridization. In this experiment, the fourth unique secondary readout probes in each barcoding hybridization were coupled to ALEXA FLUOR™ 647, ALEXA FLUOR™ 594, and Cy3B so that only one extra round of imaging is needed to scale up the number of 'fluorophores'. The length of readout probes used in this proof-of-concept experiment is 18mers. These secondary readout probes were conjugated to dye through an amine-NHS reaction. The fluorescent signals in each hybridization was extinguished by high concentration of formamide (60% formamide).

This proof-of-principle shows that the secondary probe readout scheme using a combination of serial and barcoding steps can be scaled up to perform whole transcriptome profiling. Probes can be designed to target over 20,000 genes in the transcriptome and can be readout with 4 barcoded rounds of hybridization with 12 based "colors", performed in similar fashion as this 64-gene experiment.

Figure 11:
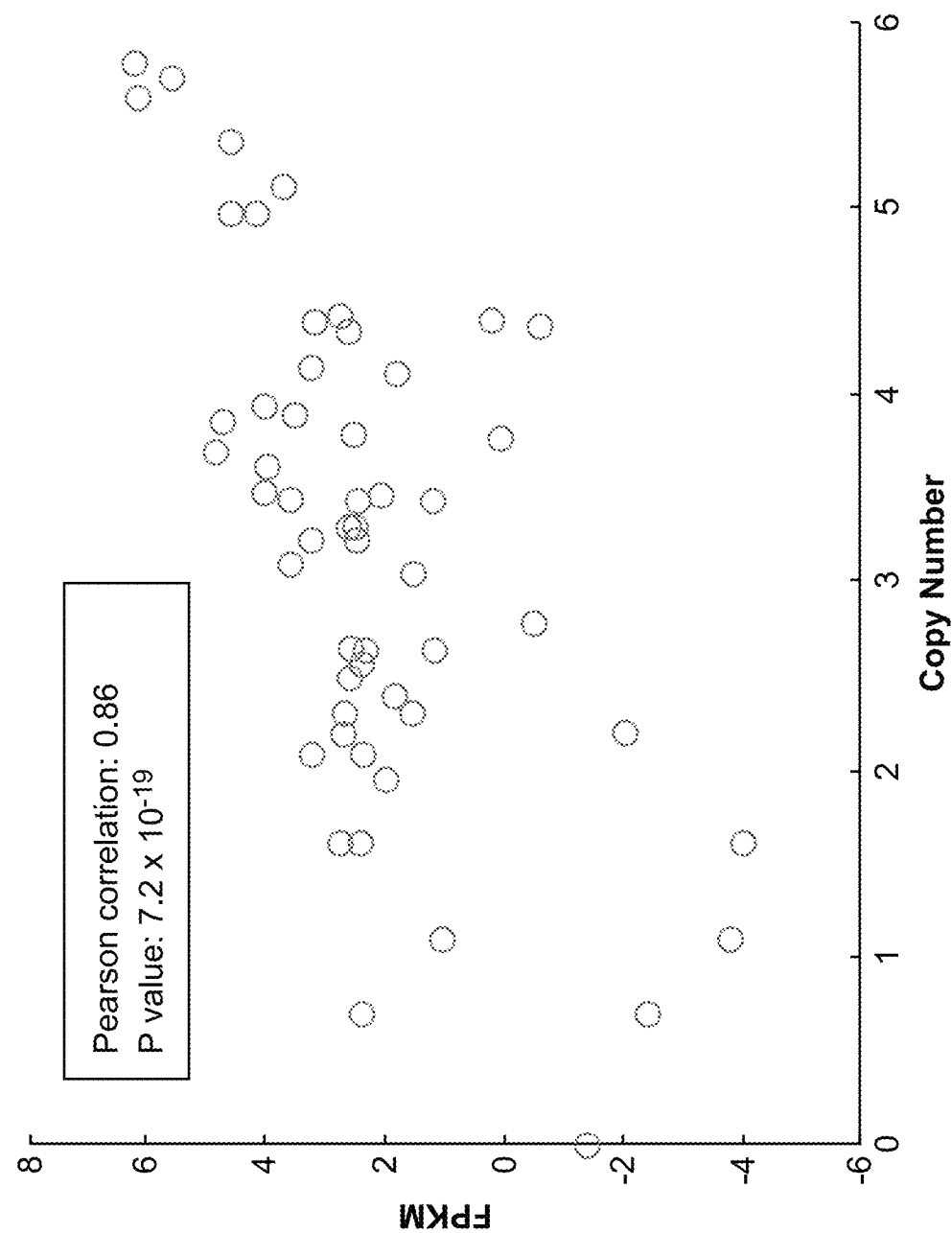
FIG. 11 depicts an exemplary embodiment of data analysis.

FIG. 11 depicts an exemplary embodiment of data analysis. Pearson's correlation plot between the copy number determined by this technology vs FPKM values determined from bulk RNA-seq. This shows that the measurements by the sequential hybridization barcoding experiments are highly accurate.

Figure 9:
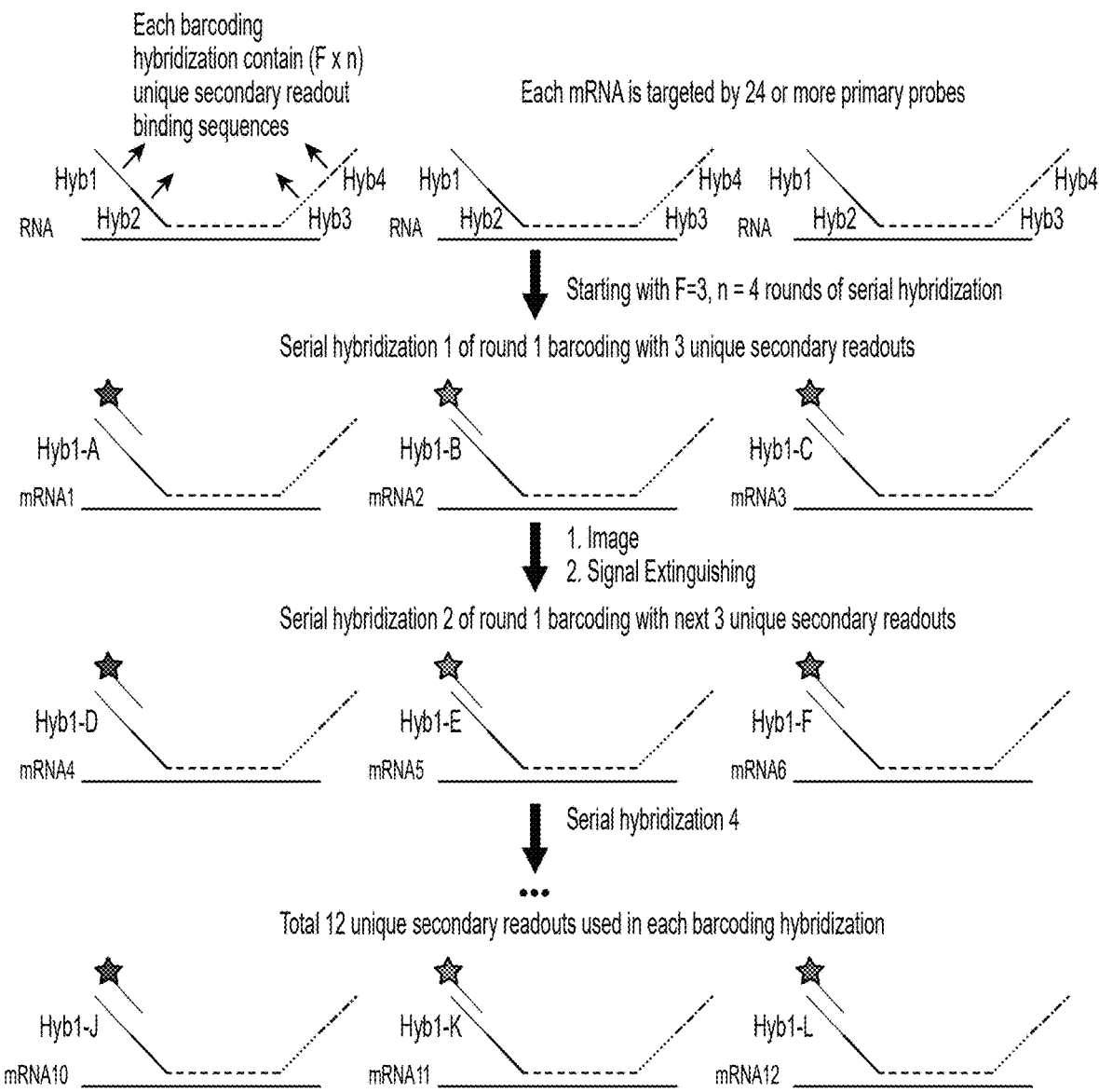
FIG. 9 depicts a schematic illustration of serial hybridization to scale up the number of available 'fluorophore'. For example, by using 3 fluorophores, and a total of 12 unique secondary readout sequences, 3 unique secondary readout probes were serially flown in. The probes code for hyb1 at a time, image, and then extinguish the signal. Then, another 3 unique secondary readout probes were be flowed in and undergo the same process. With a total of 4 rounds of serial hybridizations (n=4), 12 unique secondary readouts with 3 colors are used to generate the barcode color for hyb1. The same process was repeated for barcoding hyb 2, . . . to hyb N. Essentially, a combination of serial hybridization and sequential barcoding hybridization allows us increase the number of fluorophore (F) from 3 to 12, and if number of barcoding hybridization (N)=4, the barcode capacity will be $(3 \times 4)^4 = 20736$ which can cover almost the entire transcriptome.

The barcoding scheme illustrates in FIGS. 8 and 9 were used for multiplex detection of 1000 different transcription factors mRNAs with in vitro RNA SPOTs. First, NIH3T3 cells were grown on a 6-well plate until 60% to 80% confluency. Then the cells were lysed and purified according to QIAGEN Rneasy® Mini Kit. Then, 100 ng of total RNA in RNA Binding Buffer consists of 1M LiCl, 40 mM pH7.5 Tris-HCl, 2 mM EDTA, 0.1% Triton X-100, and 20 units of SUPERase Inhibitor (ThermoFischer) was captured on a LNA functionalized coverslips for overnight at room temperature. The capturing time and amount of total RNA can be modified to adjust the dots density on a coverslip in one frame of view. Next, primary probes (1 nM/probe) which consists of a gene specific binding region, 4 barcoded secondary readouts regions, spacers, and primers pair for a thousand genes were allowed to hybridize to the mRNA target in 30% hybridization buffer made from 10% Dextran Sulfate, 2×SSC, and 30% formamide at 37° C. overnight. Each gene is targeted by a minimum of 24 probes. After washing, RNA SPOTs began with the first round of hybridization by flowing in 10 nM readout probes for each color (3 colors in one round of hybridization) and the hybridization was allowed to happen for 30 minutes at room temperature. After a brief wash, anti-bleaching buffer was flowed into the flow cell, and the fluorescent signals were imaged. Then, the fluorescent signals were extinguished by reduction of 50 mM TCEP in 2×SSC with 0.1% Triton X-100 at room temperature for 15 mins. The process was repeated until the last round of hybridization.

In this implementation, 16 rounds of imaging was implemented with a total of 48 unique secondary readout adapters conjugated to one of the 3 fluorophores. The coding space consists of one round of error correction for up to 1728 different targets. In this experiment, a thousand different mRNAs were encoded with the scheme described in FIG. 10. The target mRNAs were chosen from a list of transcription factors (master regulators of gene expression) that are conserved between mouse and humans.

Figure 12:
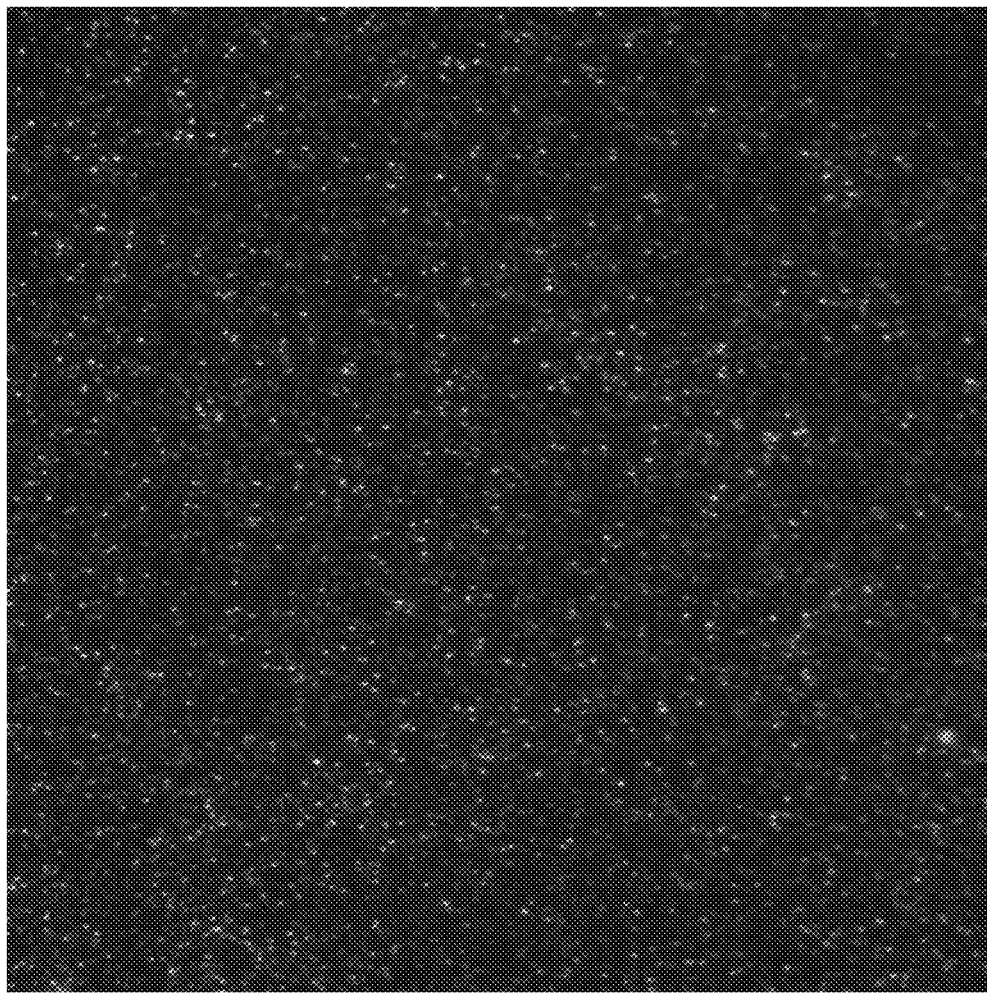
FIG. 12 depicts an exemplary a raw image from a barcoding experiment.

FIG. 12 depicts an exemplary a raw image from a barcoding experiment. The raw image shows the results from one of the hybridization round in the 1000 transcription factor genes experiment. The images of each serial hybridizations were first aligned to obtain the 12 'color' barcodes. Then the dots were decoded based on the error correction barcode scheme.

Figure 13:
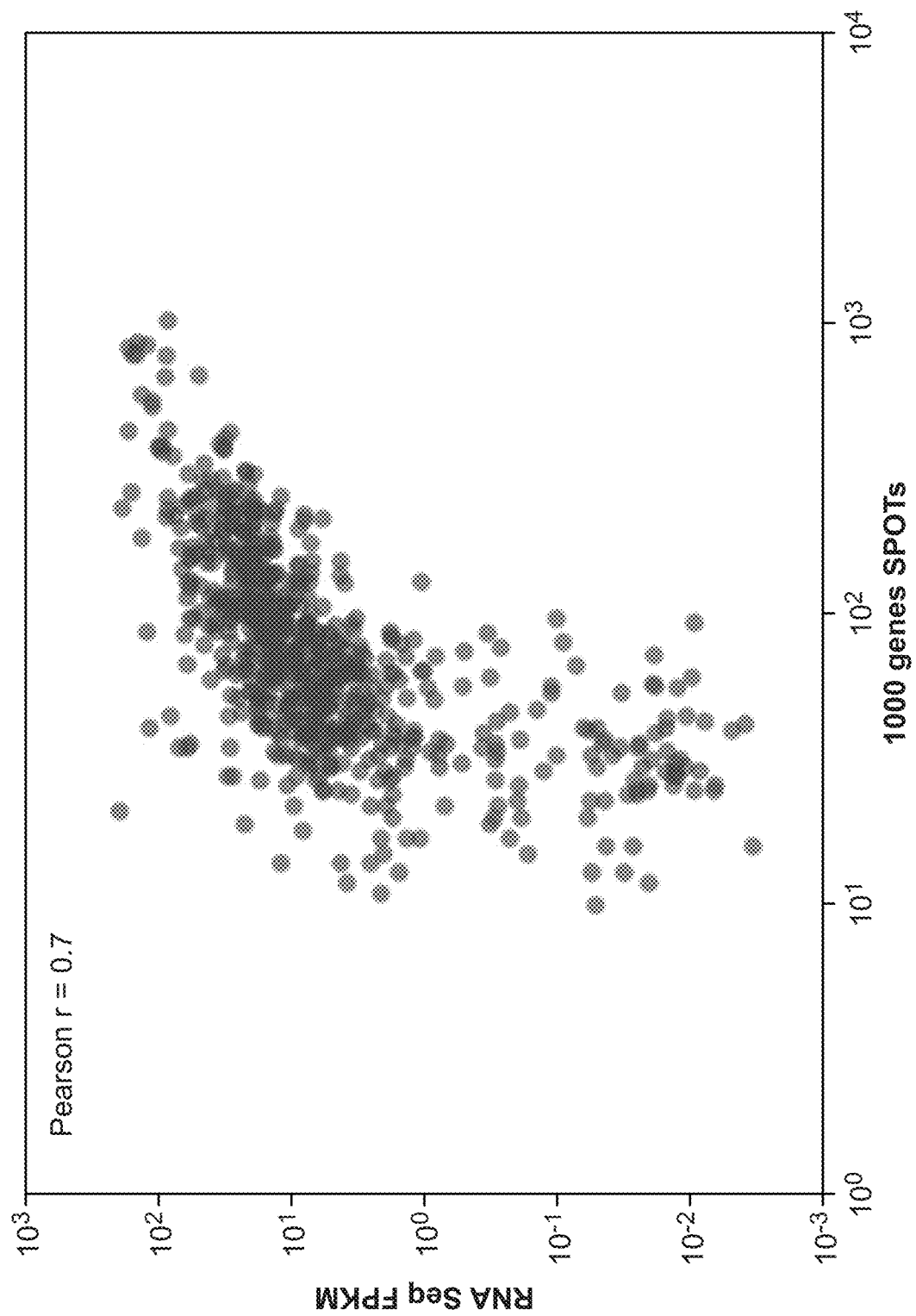
FIG. 13 depicts exemplary results from data analysis.

FIG. 13 depicts exemplary results from data analysis, showing decoded 1000 different RNA counts with RNA SPOTs on coverslip and correlate with bulk RNA-Seq Fragments per Kilobase Million (FPKM) for NIH3T3 cells. 753 genes which have a non-zero value of FPKM and a non-zero value of SPOTs are chosen for this correlation. Note that genes with low FPKM values are well detected by RNA SPOTs.

Figure 14:
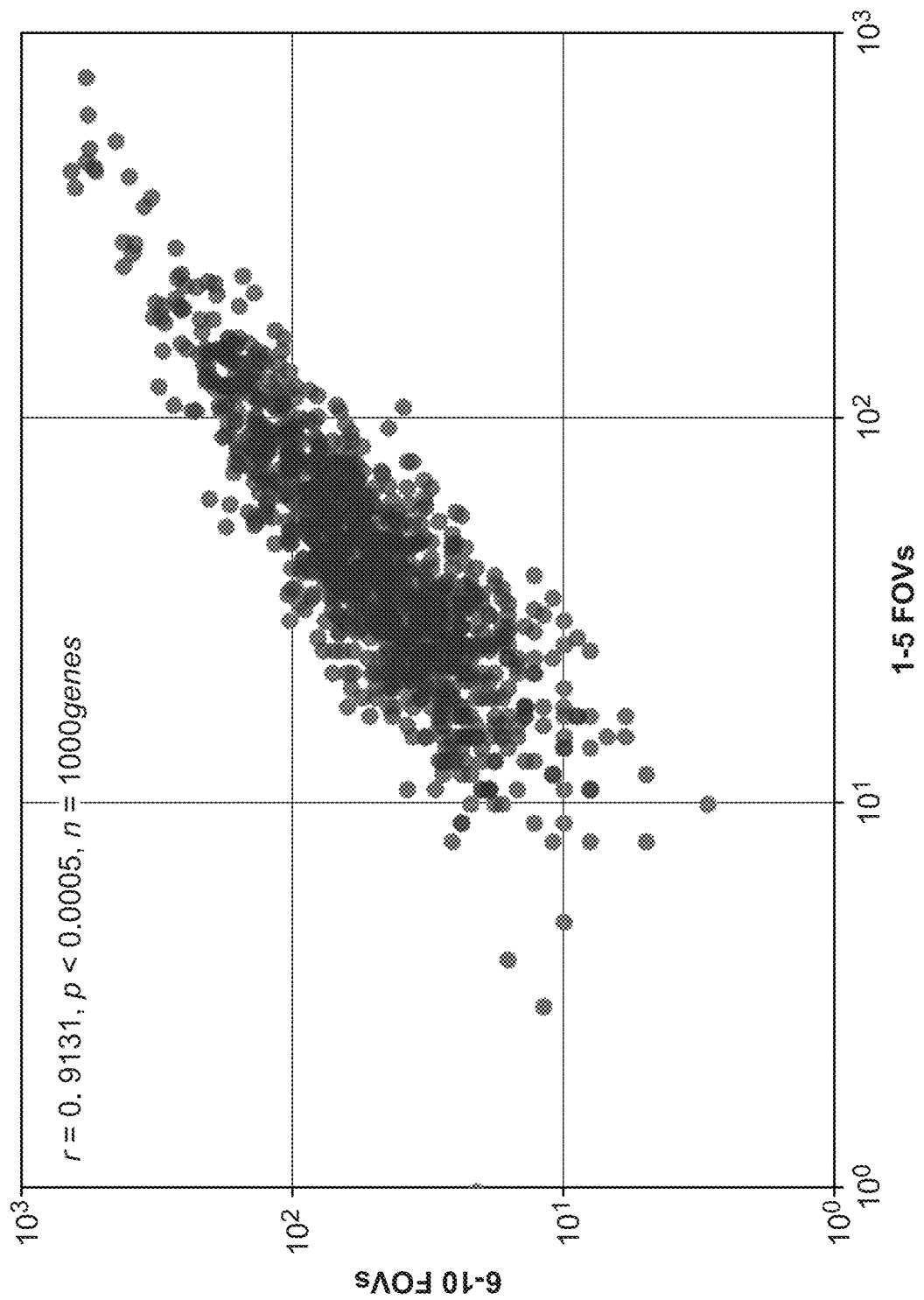
FIG. 14 depicts exemplary results from data analysis.

FIG. 14 depicts exemplary results from data analysis, showing correlation between RNA counts from different field of views (FOV) s. Each dot is a single gene with its x value the total number of transcript counted for that gene in FOV 1-5, the y value the counts for FOV 6-10. A high Pearson's correlation coefficient of 0.9131 is observed. This shows that a few FOV is sufficient to accurately quantify transcript abundance.

Imaging-Based Translational Profiling, the RiboCounter

Intact ribosomes contain 28S rRNA and 18S rRNA. By probing against these rRNA after the initial RNA SPOTs experiment to decode the mRNA identity, one can estimate the number of ribosomes on each mRNA molecule and infers the translational state of the mRNA molecules. By combining this method and RNA SPOTs, we develop the imaging-based polysome profiling to infer the translational state of each detected mRNA molecules by probing against the 28S and 18S rRNA followed by decoding their identity through RNA SPOTs.

Experimental Design: Cells were lysed and captured on LNA coverslips. Then, by using fluorescence probes either with direct 20mer smFISH or using primary probes, followed by secondary readouts to target the 18S and/or 28S rRNA before RNA SPOTs, one can obtain the intensity for the ribosomes on each mRNA molecules. The identity of each RNA molecules were decoded by RNA SPOTs as described above.

Figure 15:
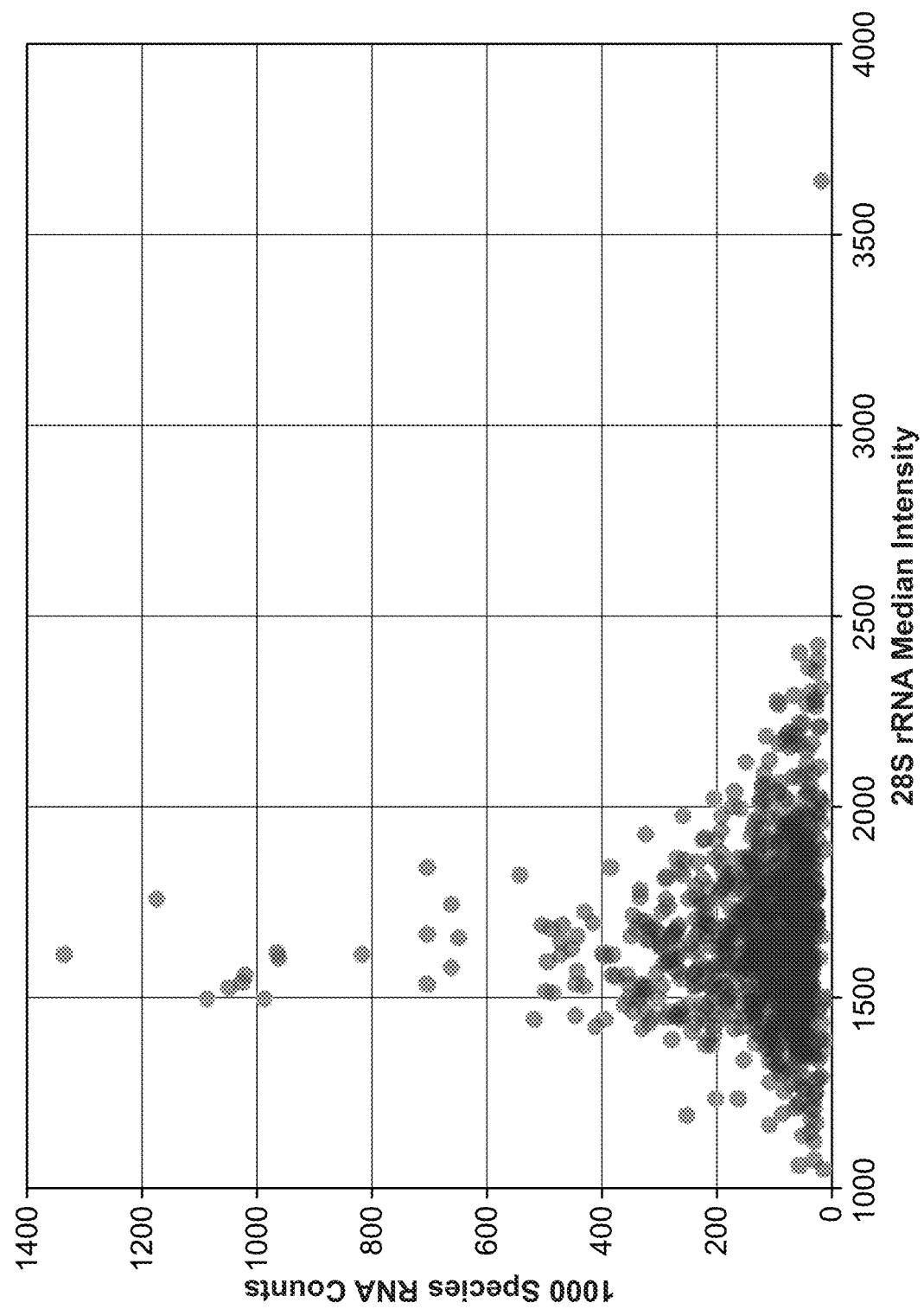
FIG. 15 depicts exemplary results from translational profiling analysis.

Results: FIG. 15 depicts exemplary results from translational profiling analysis showing the 28S rRNA median intensity extracted from each mRNA molecules of the thousand RNA species. The 28S rRNA intensity for all the 1000 transcription factor genes were all obtained.

Figure 16:
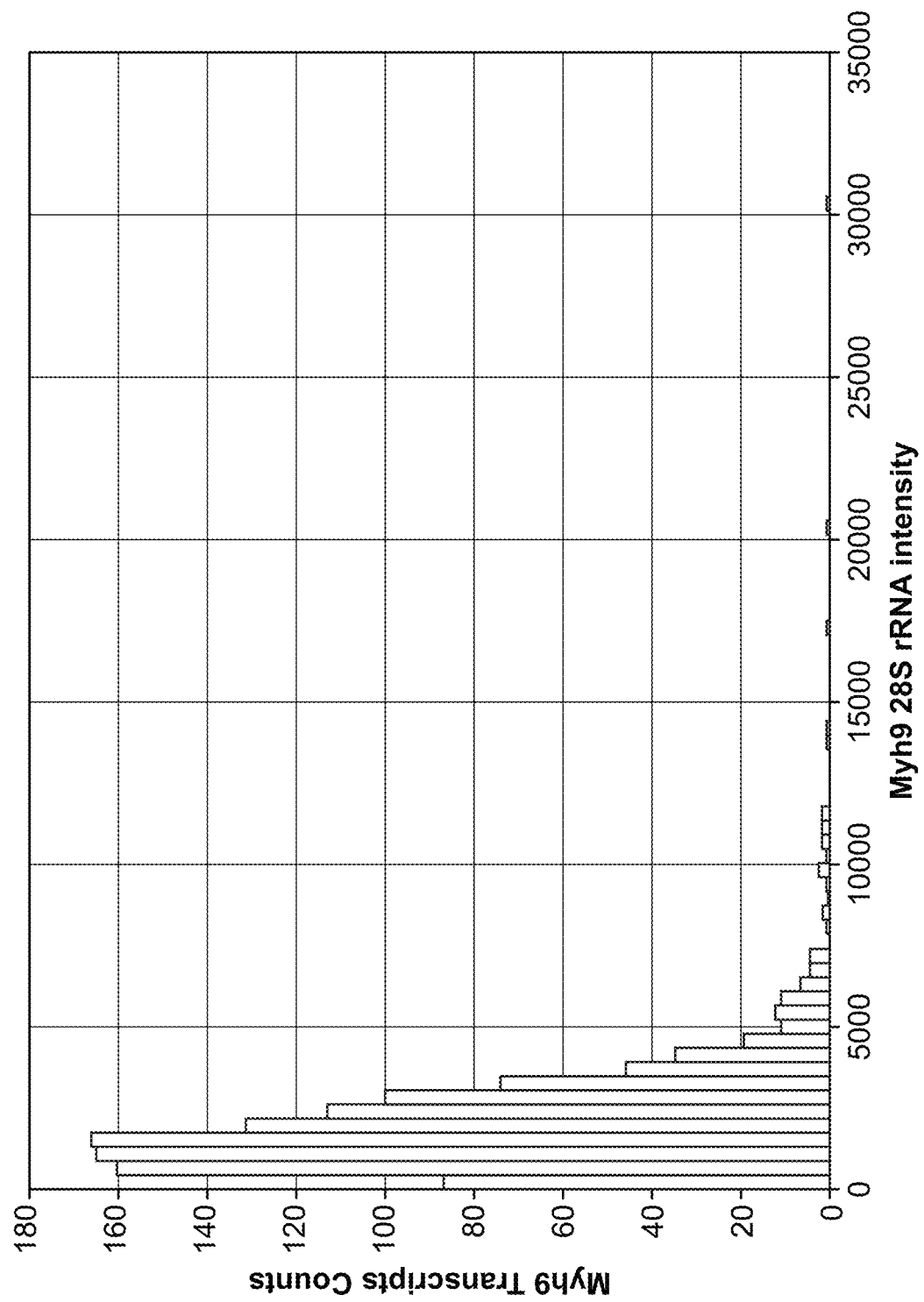
FIG. 16 depicts exemplary results from translational profiling analysis.

FIG. 16 depicts exemplary results from translational profiling analysis, showing the distribution of 28S rRNA median intensity of the gene Myh9 on each mRNA transcripts. The total number of Myh9 transcripts detected are 1169.

RNA SPOTs of the transcriptome To implement RNA SPOTs at the transcriptome level, probes were designed targeting the coding regions of 10,212 mRNAs with 28 to 32 probes each gene for a total of 323,156 probes. Probes were stringently designed to avoid off-target and cross hybridization (Supplementary information). The primary probes directly hybridize to the mRNAs captured on a Locked Nucleic Acid (LNA) poly(dT) functionalized coverslip and contains a set of overhang sequences that specifies the barcode unique to each transcript (FIG. 4, A). A 12 "pseudo-color" based scheme was used such that 4 rounds of barcoding are sufficient to cover the transcriptome ($12^4$=20,736), with an additional round of error correction to compensate for one drop in any round of barcoding [Shah et al, 2016].

This design minimizes the barcode length to avoid errors from using long barcodes. The 12 base "pseudo-colors" in each round of barcoding is encoded by a set of 12 readout oligos. Three of the readout oligos were hybridized at a time, imaged in the Cy3b, ALEXA FLUOR™ 594 and ALEXA FLUOR™ 647 fluorescence channels, and repeated 4 times to iterate through all 12 readout sequences. After each round of hybridization and imaging, the fluorophores are removed by di-sulfide cleavage and followed by the next round of hybridization. A total of 60 readout oligos in 20 rounds of hybridization were used to decode the 10,212 genes targeted. Every four rounds of hybridization were collapsed onto a single image with 12 pseudo-colors. The barcodes were determined from aligning the 12-color images. A common sequence is present in all primary probes and targeted by an oligo labeled with ALEXA FLUOR™ 488 to serve as an alignment marker through all 20 rounds of hybridization. The switching and rehybridization time is fast, with the overall speed limited by imaging speed. Typically, 100 fields of view containing 106 mRNAs can be imaged with 20 rounds of hybridization in a 14-hour period through an automated fluidics system.

To determine the accuracy of the transcriptome level measurements, we compare the decoded RNA SPOTs data with RNAseq data in fibroblasts and mESCs, and found that they correlated with R=0.86 and R=0.9 respectively. In addition, RNA SPOTs correlated with the gold standard smFISH quantitation with a correlation of R=0.86 in mESCs (23 genes) [Singer 2014] and R=0.88 in fibroblasts (7 genes). Between two replicates of RNA SPOTs in fibroblasts, the results agree with R=0.94, indicating that RNA SPOTs is a highly robust and reproducible measurement method. Lastly, comparing genes that were differentially expressed in fibroblasts versus mESCs, we observed the same trend as those detected by RNAseq. For example, pluripotency factors such as Rex1, Esrrb and Sox2 are highly expressed in mESCs but not expressed in fibroblasts as determined by RNA SPOTs (FIG. 19), similar to the differences observed by RNAseq.

Figure 19:
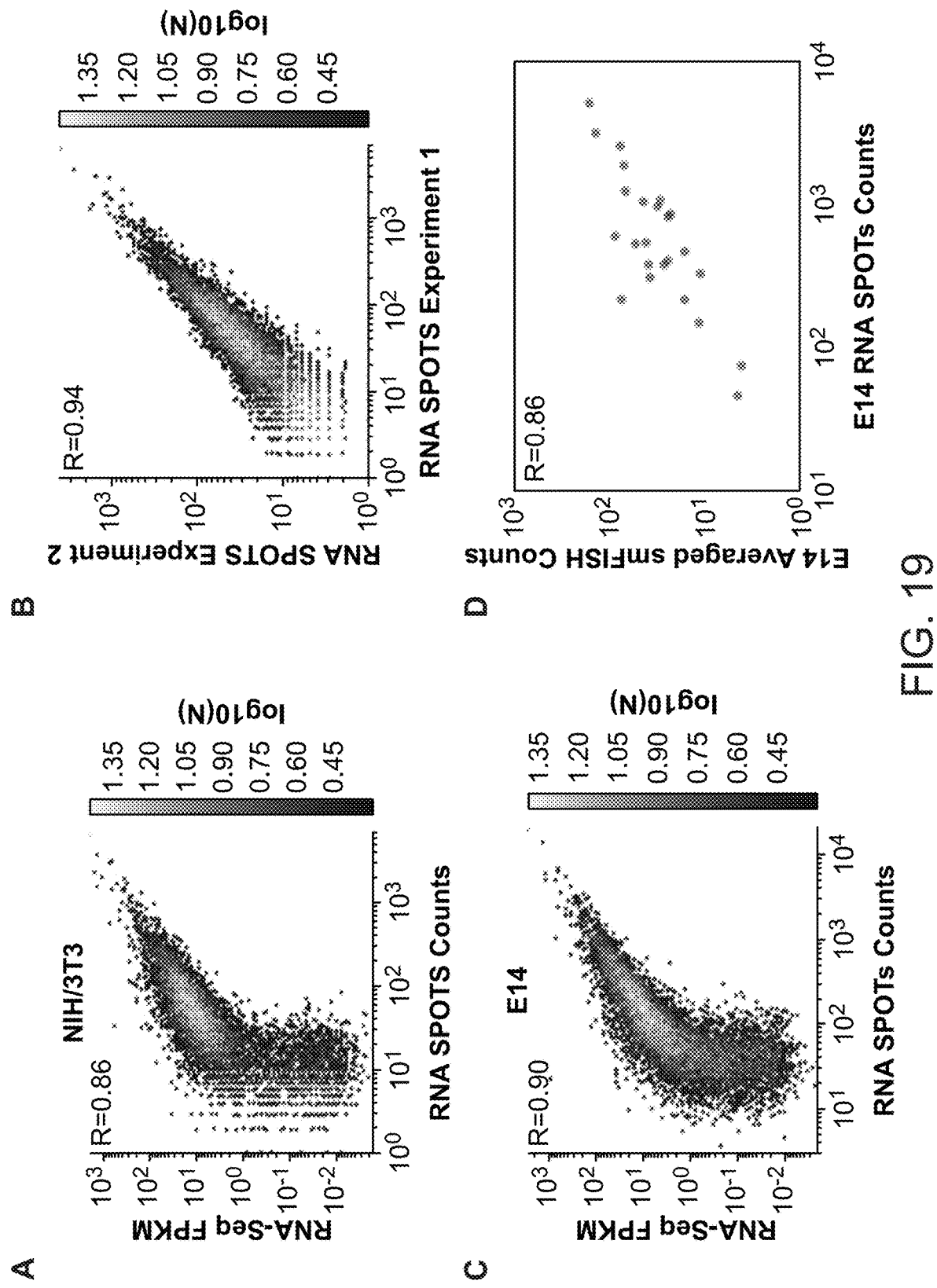
FIG. 19 illustrates RNA Sequential Probing Of Targets (SPOTs) measurement of 10,212 genes. Correlation of RNA SPOTs with RNAseq in fibroblasts with Pearson r coefficient of 0.86. (b Two SPOTs replicate experiments, signifies its high reproducibility (c) Correlation of RNA SPOTs measurement with RNAseq in mESCs, with Pearson r coefficient of 0.90. (d) Correlation of averaged smFISH counts for 24 genes in mESCs. RNA SPOTs has single molecule sensitivity and highly accurate in transcriptome profiling.
Figure 20:
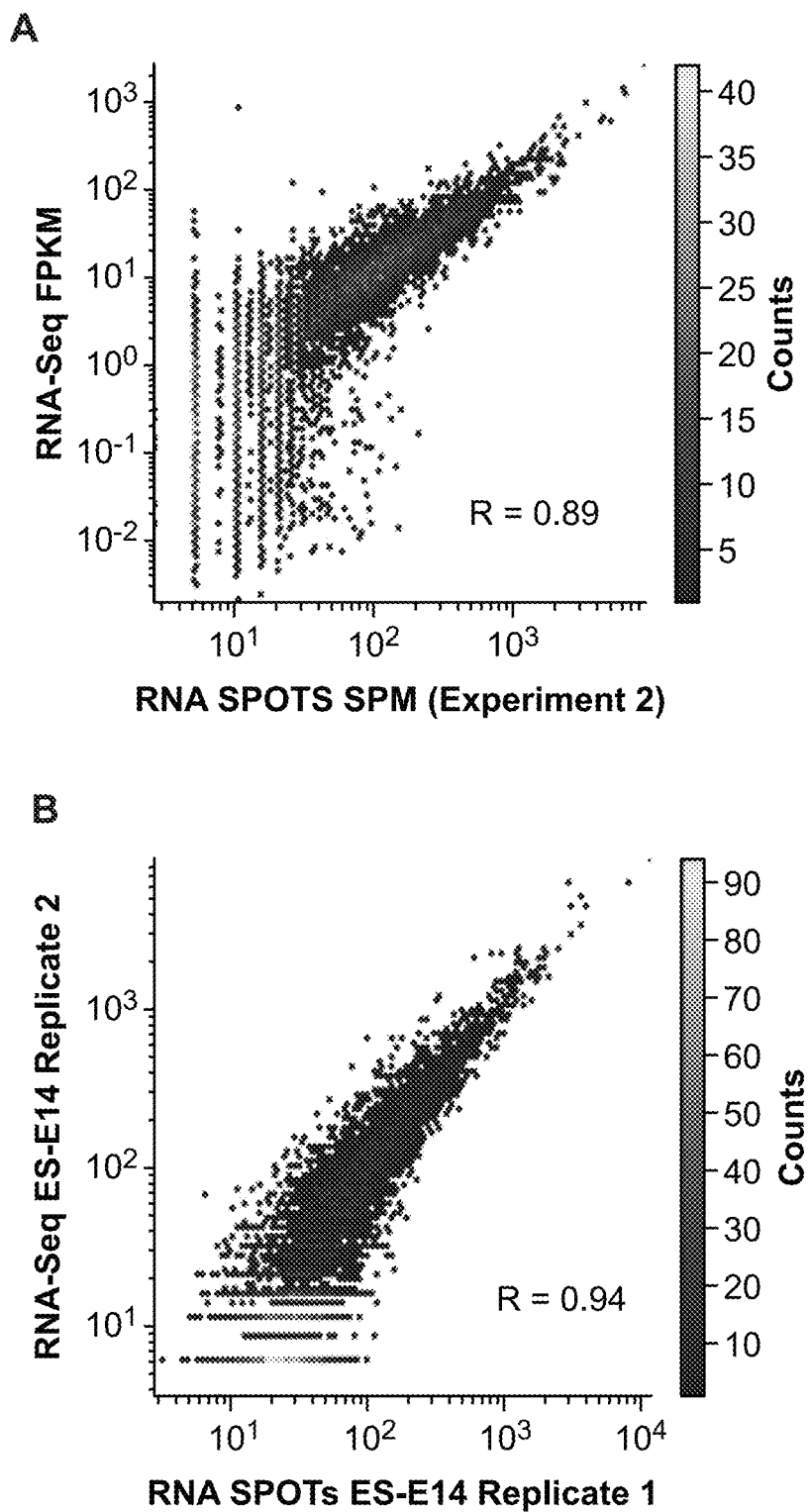
FIG. 20 illustrates RNA SPOTs analysis at lower depth. (a) Correlation between RNA-seq FPKM and RNA SPOTs SPM from another replicate is high when a total of 376,781 spots are counted. SPM, spots per million; FPKM, fragments per kilobase per million reads. (b) High reproducibility of RNA SPOTs between the two replicates in profiling ES-E14 cell gene expression (n1=376,781 spots, n2=1,688, 747 spots).
Figure 21:
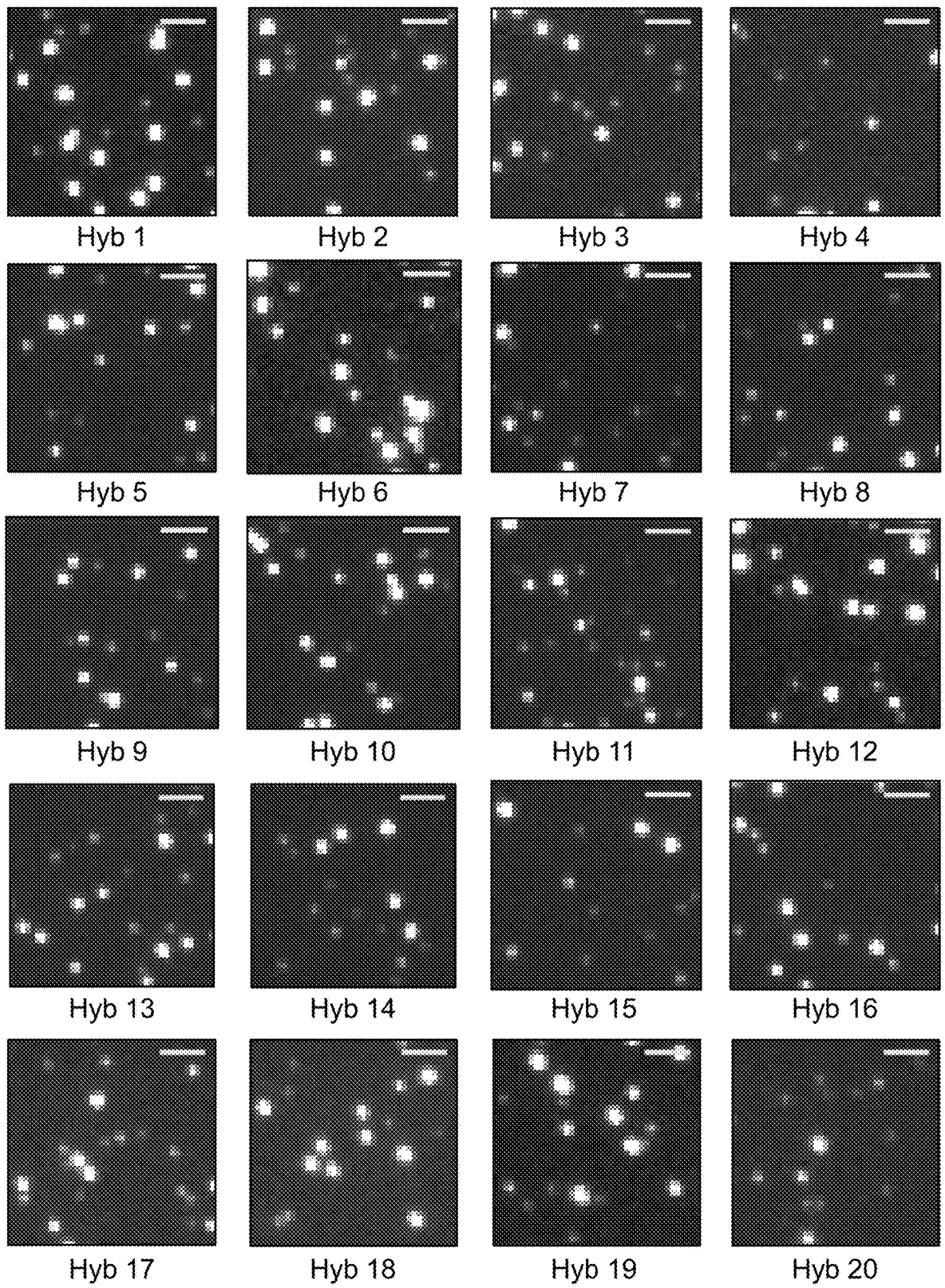
FIG. 21 shows raw images of 20 rounds of fluorescent switching in channel 647. Bright dots are the real targets while dim dots are due to nonspecific binding. The switching between each round of hybridization is complete, with minimal retention of fluorescent signals from previous round. (Scale bars: 2 μm.)
Figure 22:
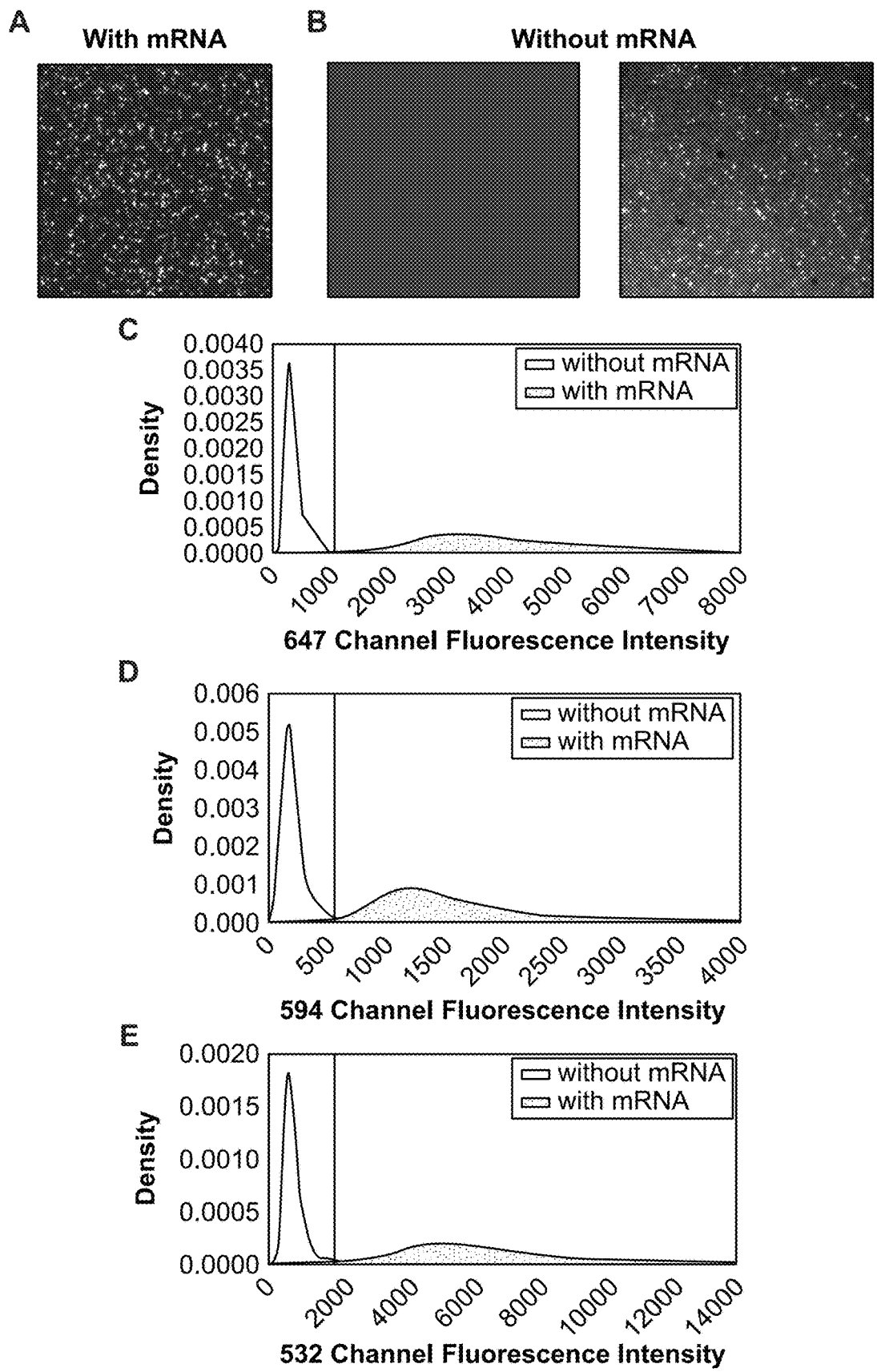
FIG. 22 depicts assessment of primary probes non-specific binding. (a) Raw images of 532 channel with the presence of mRNA on coverslips through LNA poly(d)T capturing. (b) No bright fluorescent signals is observed in the absence of mRNA on coverslips as a control. The left image has the same contrast as (a) while the right image contrast has been increased 4.5 fold to illustrate better the non-specific fluorescent signals. (c) Quantitative measurement of fluorescent intensity in channel 647 with and without the presence of mRNA. A threshold can be set to distinguish between the two populations to identify the real signals. (d) & (e) same as (c) but for channel 594 and channel 532.
Figure 24:
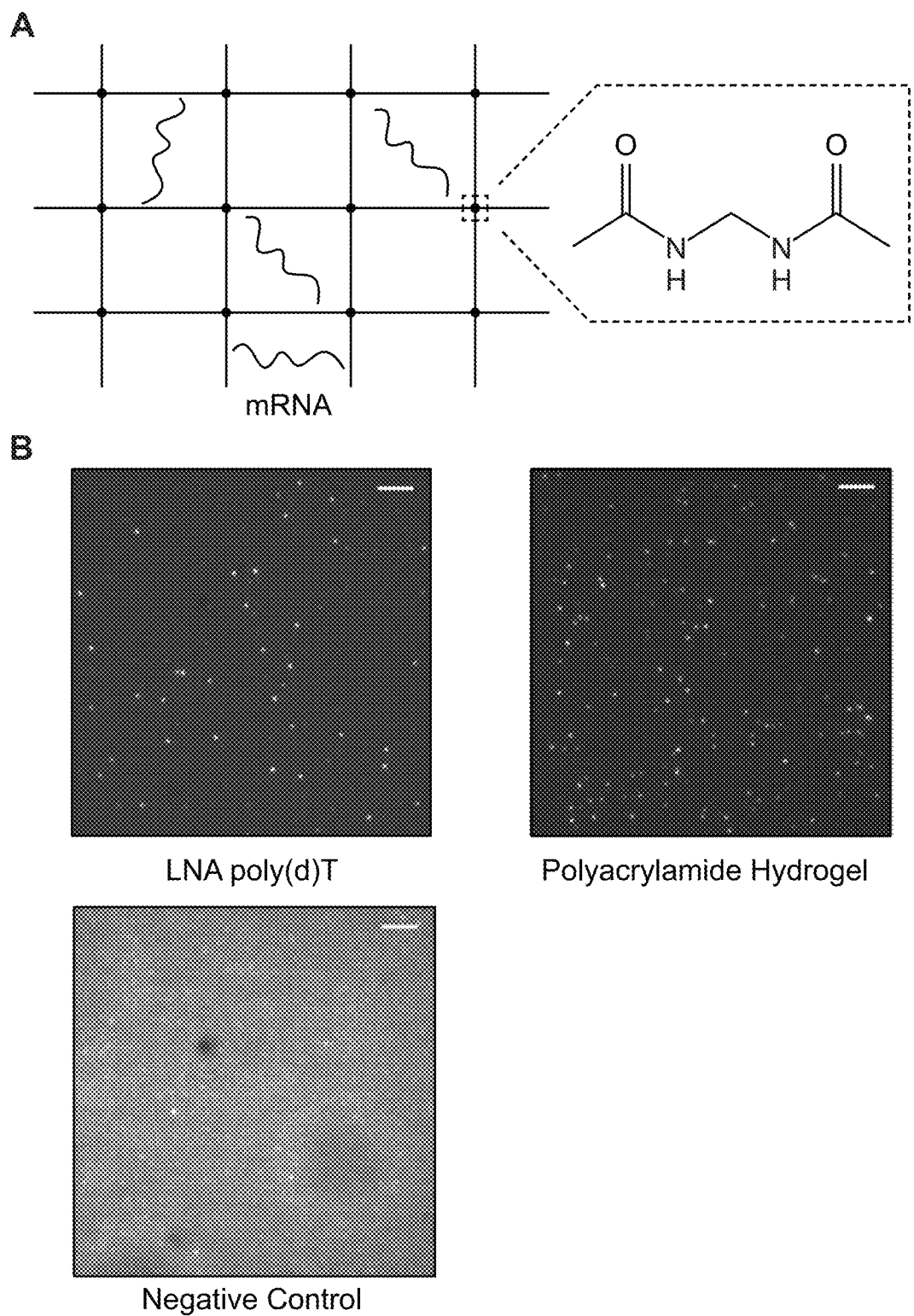
FIG. 24 depicts that mRNA can be immobilized by polyacrylamide hydrogel on a bind-silane treated coverslips. (a) mRNA is trapped in the hydrogel mesh once acrylamide and bis-acrylamide monomers crosslink completely on the coverslip. (b) smFISH detection of ACTB once the total RNA is captured on a coverslip through LNA poly(d)T capturing (left) or polyacrylamide hydrogel (right). Negative control (channel 488) shows that the fluorescent signals are not coming from nonspecific sources. (Scale bars: 5 μm.)

Several genes were observed to be outliers in the RNA SPOTs to RNAseq comparison (FIG. 19). When we examined the genes in cells directly by single molecule FISH, we observed that their expression levels matched those determined with RNA SPOTs. This indicates that either hybridization efficiency on these genes were low or they were over-detected by RNAseq.

An advantage of RNA SPOTs is that specific sets of genes can be profiled selectively simply by designing probe sets targeting those genes. In this fashion, ribosomal RNA and highly expressed housekeeping genes can be avoided simply by eliminating those probes from the gene set. As each dot detected in our assay corresponds to a single mRNA, RNA SPOTs is more efficient in term of imaging compared to RNAseq, where many sequencing reads are needed to determine the abundance of a transcript.

RNA SPOTs can be scaled down to single cell in combination with microfluidics tools to trap and lyse cells [Bose 2015] or with split-pool molecular indexing methods [Cao 2017, Rosenberg 2017]. With targeted RNA SPOTs, we can choose to probe only for the 2000 transcription factors [Fulton 2009] or 1000 landmark informative genes [Donner 2012, Duan 2016] in single cells, instead of profiling the transcriptome, to capture the essential information in cells and to increase the number of cells sampled.

RNA SPOTs can enable many additional methods beyond expression profiling to study RNA variants [Levesque 2013], modifications [Mellis 2017], RNA binding proteins [Buenrostro 2014] and profile ribosomes occupancy [Ingolia 2009] directly on the captured RNA. Lastly, noncoding RNAs and other RNAs without polyA tails can be captured in hydrogels rather than with dT oligos. As cost of sequencing is a major limiting factor in genomics experiments, SPOTs enable an accurate and low-cost alternative to sequencing with many further applications beyond RNA to DNA and proteins.

Example 2

Readout Probes and Rehybridization in Mouse Embryonic Stem Cells

Synthesis of DNA Probes-Disulfide-Dye Conjugates

An exemplary scheme for synthesizing readout probes-dye conjugates connected by a disulfide bond. Thiol-modified DNA probes were ordered from Integrated DNA Technologies in their oxidized form. 10 nmoles of thiol-modified DNA probes was treated with 10 mM TCEP at 37° C. for 30 minutes. After reduction step and gel column purified, the DNA probes were mixed with 50 equivalents of 3-(2-Pyridyldithio) propionic acid N-hydroxysuccinimide ester (SPDP) linker in 1×PBS solution containing 10 mM EDTA. The mixture was allowed to react at room temperature for at least 2 hours. Immediately after the reaction, the mixture was spin column purified and was re-suspended in 60 μL of 1×PBS containing 100 ug of cadaverine dyes. The reaction was allowed to proceed at room temperature for at least 4 hours before subjected to ethanol-precipitation purification and HPLC purified. The concentration of the final product was determined using Nanodrop.

Rehybridization in Mouse Embryonic Stem Cells (mESCs).

Figure 28:
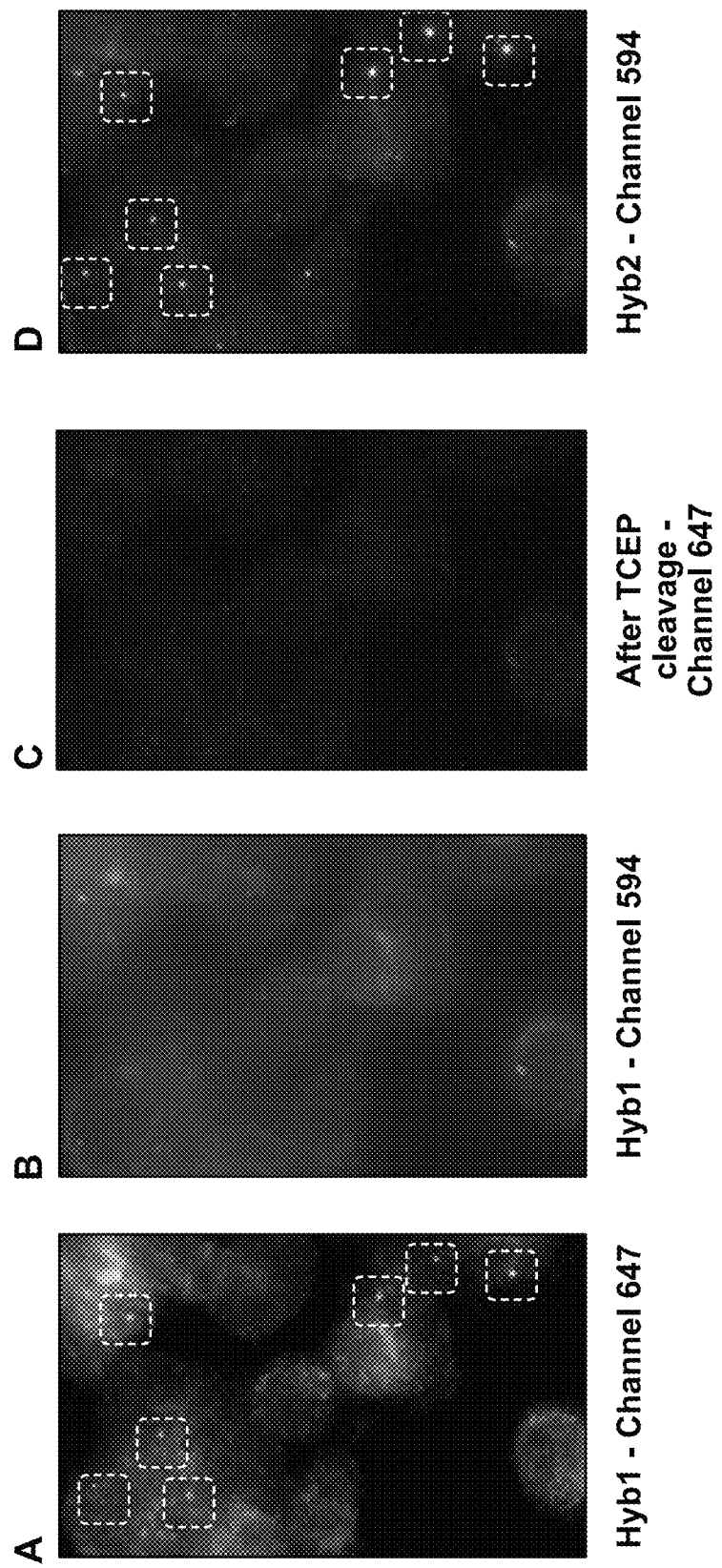
FIG. 28 depicts an exemplary embodiment illustrating rehybridization in mouse embryonic stem cells (mESCs). (a) First hybridization with tertiary readout probes conjugated with A647. Real fluorescent spots are shown in red dashed box. (b) No fluorescent spots are observed in channel 594 during the first hybridization. (c) After TCEP treatment and washing steps, channel 647 is reimaged. The observed dim dots are non-specific sticking of dyes which does not interfere with subsequent real fluorescent spots identification. (d) Second unique readout probes are hybridized to the secondary bridge binding sites to give real fluorescent spots that appear as the same positions in (a).

FIG. 28 illustrates rehybridization reactions in mouse embryonic stem cells (mESCs). To verify the scheme works in both cells and on coverslips, we perform a proof of concept experiments in mouse embryonic stem cells (mESCs) targeting introns of pgk1 gene. During first round of hybridization, tertiary readout probes conjugated with A647 were applied to identify specific target sequences in mRNAs via secondary bridge binding sites. Real fluorescent spots are shown in red dashed box (28A). As a control, fluorescence presence in channel 594 was also measured during the first hybridization: no fluorescent spots were observed (28B). After TCEP treatment and washing steps, channel 647 was reimaged. The observed dim dots are non-specific binding of dyes which does not interfere with subsequent real fluorescent spots identification (28C). During a second round of hybridization, unique readout probes bearing 594 dye were used to hybridize with the secondary bridge binding sites to give real fluorescent spots (28D). These spots confirmed the positions observed previous when readout probes with A647 were used (28A).

In Vitro Rehybridization with Readout Probes

Transcribed polyA-tailed dCAS9-EGFP mRNA were captured on a dT20 Locked Nucleic Acid (LNA) surface-modified coverslips to show the rehybridization scheme works in vitro on the coverslips. Once again, specific binding was observed. When tertiary probes conjugated with A647 were used: specific signals were observed in channel 647 while there were few signals observed in channel 594 (FIG. 29, top row). After TCEP treatment and wash of the first set of tertiary probes, a second set of tertiary probes conjugated with 594 dye were applied during the set round of hybridization reaction. Consequently, specific signals were observed in channel 594 while there were few signals observed in channel 647 (FIG. 29, bottom row).

Technically, any heterobifunctional cross-linking reagent that can connect between the dye and thiol-modified DNA probes will work for this rehybridization scheme. DNA probes-disulfide-dye conjugates were synthesized using 3-(2-pyridyldithio) propionyl hydrazide (PDPH) linker and NHS ester dyes which work equally well as former conjugates.

Example 3

Brain Slice Analysis

As an illustration, barcodes generated using the error correction mechanisms disclosed herein are used for in situ transcription profiling of single cells reveals spatial organization of cells in the mouse hippocampus.

Identifying the spatial organization of tissues at cellular resolution from single cell gene expression profiles is essential to understanding many biological systems. In particular, there exist conflicting evidence on whether the hippocampus is organized into transcriptionally distinct subregions. Here, a generalizable in situ 3D multiplexed imaging method was applied to quantify hundreds of genes with single cell resolution via Sequential barcoded Fluorescence in situ hybridization (seqFISH) (Lubeck et al., 2014). seqFISH was used to identify unique transcriptional states by quantifying and clustering up to 249 genes in 16,958 cells. By visualizing these clustered cells in situ, we identified distinct layers in the dentate gyrus corresponding to the granule cell layer, composed of predominantly a single cell class, and the subgranular zone, which contains cells involved in adult neurogenesis. Furthermore, it was discovered that distinct subregions within the CA1 and CA3 are composed of unique combinations of cells in different transcriptional states, instead of a single state in each sub-region as previously proposed. In addition, it was revealed that while the dorsal region of the CA1 is relatively homogeneous at the single cell level, the ventral part of the CA1 has a high degree of cellular heterogeneity. These structures and patterns are observed in sections from different mice, as well as in seqFISH experiments with different sets of genes. Together, these results demonstrate the power of seqFISH in transcriptional profiling of complex tissues.

The mouse brain contains about $10^8$ cells arranged into distinct anatomical structures. While cells in these complex structures have been traditionally classified by morphology and electrophysiology, their characterization has been recently aided by gene expression studies. In particular, the Allen Brain Atlas (ABA) provides a systematic gene expression database using in situ hybridization (ISH) of the entire mouse brain one gene at a time (Dong et al., 2009; Fanselow and Dong, 2010; Thompson et al., 2008). This comprehensive reference provides regional gene expression information, but lacks the ability to correlate the expression of different genes in the same cell. More recently, single cell RNA sequencing (RNA-seq) has identified many cell types based on gene expression profiles (Darmanis et al., 2015; Tasic et al., 2016; Zeisel et al., 2015). However, while single cell RNA-seq provides useful information on multiple genes in individual cells, it has relatively low detection efficiencies and requires cells to be removed from their native environment resulting in the loss of spatial information. These different approaches can lead to contradictory descriptions of cellular organization in the brain and other biological systems.

In the hippocampus, recent RNA-seq data suggests that CA1 is composed of cells with a continuum of expression states (Cembrowski et al., 2016, Zeisel et al 2015), while ABA analysis indicates that sub-regions within the CA1 have distinct expression profiles (Thompson et al, 2008). To resolve the two conflicting descriptions of hippocampal organization, a method to profile transcription in situ in the hippocampus with single cell resolution is needed. Here, we demonstrate a general method that enables the mapping of cells and their transcription profiles with single molecule resolution in tissue, allowing an unprecedented resolution of cellular transcription states for molecular neuroscience (FIG. 32, A).

A great deal of progress has been made recently in developing highly quantitative methods to profile the transcriptome of single cells. Building upon single molecule fluorescence in situ hybridization (smFISH) (Femino et al., 1998; Raj et al., 2006, Lubeck et al. devised a general method to highly multiplex single molecule in situ mRNA imaging irrespective of transcript density using super-resolution microscopy (Betzig et al., 2006; Rust et al., 2006; Lubeck and Cai, 2012). However, the spectral barcoding methods used in these previous works is difficult to scale up beyond 20-30 genes because of limited number of fluorophores (Fan et al., 2001; Lubeck and Cai, 2012).

To overcome the scalability problem, a temporal barcoding scheme was developed that uses a limited set of fluorophores and scales exponentially with time (Lubeck et al., 2014). Specifically, by using sequential rounds of probe hybridizations on the mRNAs in fixed cells to impart a unique pre-defined temporal sequence of colors, different mRNAs can be uniquely identified in situ. The multiplex capacity scales as FA, where F is the number of fluorophores and N is the number of rounds of hybridization. Thus, one can increase the multiplex capacity by increasing the number of rounds of hybridization with a limited pool of fluorophores. This approach is called Sequential barcoded Fluorescence in situ Hybridization (seqFISH) (Lubeck et al., 2014). In parallel, in situ sequencing methods were developed to directly sequence transcripts in tissue sections, but these methods suffer from low detection efficiency (<1%) (Ke et al., 2013; Lee et al., 2014). Recently, Chen et al. expanded the error correction method in the original seqFISH demonstration by using a Hamming distance 2 based error correcting barcode system, called merFISH. However, this implementation requires larger transcripts (>6 kb) and many more rounds of hybridization than the method described here (Chen et al., 2015b). Furthermore, seqFISH and its variants have only been applied in cell culture systems due to the difficulty of smFISH detection in tissue. Here, an improved version of seqFISH in complex tissues by including signal amplification and a time-efficient error correction scheme (FIG. 32, A-D, and FIG. 40) were demonstrated to resolve the structural organization of the hippocampus with single cell resolution.

Example 4

Brain Slice Analysis with Error Correction
Signal Amplification and Error Correction Enable Robust Detection of mRNAs in Tissues.

To overcome the autofluorescence and scattering inherent to brain tissues, we used an amplified version of smFISH, called single molecule Hybridization Chain Reaction (smHCR) (FIG. 32, E) (Shah et al., 2016). Single molecule HCR amplified signal 22.1±11.5 (mean #s.d., n=1288, FIG. 38, B) fold compared to smFISH, enabling robust and rapid detection of individual mRNA molecules in tissues and facile alignment of spots between hybridizations (FIG. 38, A). Single transcripts can be detected and localized in 3D with just 24 probes in tissues, enabling detection of transcripts <1 kb in size, with a fidelity comparable to the smFISH gold standard (FIG. 41, C-D) but with signals 20-fold brighter (Shah et al., 2016). Single molecule HCR DNA polymers can also be digested by DNAse and re-hybridized in brain slices, allowing HCR-seqFISH to be robustly implemented (FIG. 33, A). We note the smHCR enables true 3D imaging in tissues, whereas the previous sequential FISH demonstrations (Lubeck et al., 2014, Chen et al., 2015) were performed only in flat cell cultures.

Furthermore, we improved upon our existing barcode system by implementing a time-efficient error correction scheme. The major source of error in seqFISH is the loss of signal due to mis-hybridization, which increases with the numbers of hybridization. We introduced an extra round of hybridization to correct loss of signal during any round of hybridization (FIG. 32, D). By minimizing the number of hybridizations, this error correction scheme is efficient in practical implementation. For example, using 5 fluorophores and 4 rounds (instead of 3 rounds) of hybridization to code for 125 genes, we can still uniquely assign barcodes to genes even when signal from any single round of hybridization is missing. Although merFISH can tolerate 2 errors in the barcodes, it requires 16 rounds of hybridization to code 140 genes (Chen et al. 2015). As increasing the number of hybridizations can potentially lead to more experimental error and analysis complexity, our simple error correction method corrects for the most common error, dropped signal. Also, the fewer rounds of hybridizations decreases the total imaging time, which is rate-limiting for tissue experiments. HCR-seqFISH with simpler error-correction scheme allows efficient and accurate quantification of transcription profiles in tissues.

Using this HCR-seqFISH method, we surveyed the regional and sub-regional transcriptional heterogeneity within the temporal and parietal cortex and hippocampus of the mouse brain by imaging similar coronal sections collected from 3 different animals. Two similar sections from separate mice were profiled with probes for 125 genes, while one additional brain slice was imaged for 249 genes. In each of the coronal slices, between 60-80 fields of view were imaged, each 216 μm×216 μm×15 μm, in the cortex and hippocampus (FIG. 32, A and FIG. 41, E). For the 125 gene set, 56 of the genes (FIG. 32, D, and FIG. 40) were selected because they showed spatially heterogeneous expression based on the ABA (Lein et al., 2007), another 44 were selected from a list of transcription factors, and 25 marker genes were selected from single cell RNA-seq datasets (Zeisel et al., 2015). One hundred of these genes were barcoded by 4 rounds of hybridization (FIG. 32, B). The remaining 25 high abundance genes were measured individually using 5-color smHCR in 5 serial rounds of hybridizations (FIG. 32, C). This hybrid approach of measuring medium expression genes with barcoding seqFISH and high copy number genes serially in subsequent hybridizations allows a large dynamic range of transcripts to be profiled in the same cell.

seqFISH is an Accurate and Efficient Method to Multiplex RNA In Situ.

To determine the accuracy of the seqFISH method in quantifying mRNA levels in single cells in tissue, we compared the copy number of 5 of the 100 target genes measured by barcoding to the copy number found by colocalized smHCR detection in the same cell (FIG. 33, B, and FIG. 42, A) in 15 μm brain sections. We found that the copy number of the RNAs per cell as measured by barcoding and smHCR agreed with an R-value of 0.85 and a slope of 0.84 (N=3851). As colocalized smHCR matches smFISH transcript quantitation (Shah et al., 2016), the barcoded seqFISH method can quantify mRNA molecules in single cells with 84% efficiency compared to the gold standard of smFISH. In comparison, single cell RNA-seq measurements are 5-20% efficient based on spike-in controls and in situ sequencing is less than 1% efficient (Darmanis et al., 2015; Klein et al., 2015; Lee et al., 2014; Macosko et al., 2015; Tasic et al., 2016; Zeisel et al., 2015; Ståhl et al., 2016). This high efficiency of detection results from a low transcript drop rate and a high barcode recovery rate due to the error correction round of hybridization. In our experiment, 78.9% of barcodes (N=2,115,477 barcodes) were found in all 4 hybridization rounds and 21.1% were identified in 3 out of the 4 hybridizations (FIG. 33, C), indicating that the probability of detecting a given mRNA molecule is 94% in each round of hybridization (FIG. 42, B).

To quantify the amount of false positive signal due to misalignment of barcodes and nonspecific binding of probes, the amount of off-target barcodes that were detected was measured. With four rounds of hybridizations and 5 fluorophores, there were $5^4=625$ unique codes. 100 of these barcodes were assigned to measure mRNAs detected at 914.8±570.5 counts per cell (mean±s.d., N=3439). In comparison, the 525 remaining off-target barcodes that were not used were detected at 4.6±4.7 (mean±s.e., N=3439) counts per cell (FIG. 33, D). False positives, due to chance alignment of nonspecifically bound spots, contributed minimally to the barcode readouts because of this three order of magnitude difference in detected barcodes (on target vs. off target). The false positives we observe fall only on barcodes hamming distance one away from on-target barcodes, yet minimally contribute to undercounting on-target barcodes (FIG. 33, E). Furthermore, even the most frequent off-target barcode was observed 65.57 times less frequently than the most infrequent mRNA coding barcode (FIG. 33, E, and FIG. 42). Even though during each round of hybridization, 24.8±0.4% (mean±s.e., N=4 rounds of hybridization) of the spots were nonspecifically bound probes, barcode missassignments did not occur frequently because non-specifically bound probes do not reappear in the same location after digestion with DNAse and re-hybridization (FIG. 33, A). Together the quantifications of false positive and false negative barcodes demonstrate that this method is highly efficient and accurate at detecting RNAs in situ in single cells within tissues.

Cell Clusters are Based on Combinatorial Expression Profiles.

We imaged the expression of 125 genes in coronal sections from two mice for a total of 14,908 cells (FIG. 41, E). Cortical and hippocampal cells were segmented based on DAPI and Nissl staining. A tessellation algorithm was developed to accurately segment densely packed cells in the hippocampus. To avoid capturing mRNA from neighboring cells, we contracted by 10% the borders of cells determined by the segmentation algorithm.

To group the single cell data into distinct transcriptional states, we Z-score normalized the copy number of each transcript in every cell (FIG. 34, A) and hierarchically clustered the cells to identify cells with similar expression patterns (FIG. 43). Many of these clusters, based on overall expression patterns, contain clear transcriptional markers of known cell types previously identified by single cell RNA-seq (FIG. 34, B) (Zeisel et al., 2015, Tasic et al 2016). Cell clusters 12 and 13 contained clear expression of Gja1 which marks out astrocytes (Zeisel et al., 2015, Tasic et al 2016). Cluster 12 also expresses Mfge8 while cluster 13 did not, indicating two distinct population of astrocytes (FIG. 34, B). There are further subclusters within each of the astrocyte populations with different spatial localization patterns (FIG. 43, C). Cluster 11 cells expressed Laptm5, a known microglia marker (Zeisel et al., 2015, Tasic et al 2016). Cluster 3 expressed interneuron genes while cluster 1-2 and 4-5 expressed genes associated with pyramidal neurons (Zeisel et al., 2015, Tasic et al 2016). Some clusters contained many distinct subclusters, such as Amigo2 enriched Mural cells (cluster 9.4) or Omg expressing oligodendrocytes (cluster 10.4 and 10.5). The major clusters were robust to downsampling the number of cells used in clustering (FIG. 44), with some of the hippocampal pyramidal and glia clusters robustly defined even with 400 cells. Similarly, principal component analysis (PCA) visualization of the data (FIG. 43, F) recapitulated the major clusters that corresponded to astrocyte, microglia, cortical pyramidal, hippocampal pyramidal, dentate gyrus (DG) granule, and interneuron cells.

Cell Clusters Show Distinct Regional Localization

Many neuronal clusters mapped to distinct regions in the brain (FIG. 34, B). Several classes of pyramidal cells (cluster 1-2) showed exclusive localization to the hippocampus, while other classes (4-5) showed predominantly cortical localization. There were also a class of cells (cluster 7) that were almost exclusively present in the DG. Interestingly, these clusters segregated based solely on gene expression profiles without adding any spatial information into the clustering algorithm. These differences in transcriptional states of neurons could be due to intrinsic differences in the cells or due to different local environment and activity patterns.

In contrast, astrocyte, microglia and other non-neuronal cell clusters were generally uniformly present in all areas of the brain (FIG. 34, B). However, subclusters of astrocytes did localize to different regions of the brain preferentially (FIG. 43, C), with subcluster 12.3 localized preferentially to the cortex, while 12.1 subcluster was uniformly distributed. Similarly, cluster 9 cells contain subclusters (9.3, 9.5 and 9.6) that localize exclusively to the DG, while other subcluster (9.1) localize almost exclusively to the cortex. The regional localization of neurons are especially pronounced with cluster 1 and 2 localized almost exclusively to the hippocampus, with some of the subclusters localized predominantly to the CA3. Furthermore, while pyramidal cell clusters 4 and 5 are preferentially cortically localized, the few hippocampal cells in these clusters form their own subclusters (4.4 and 5.4) (FIG. 43, C). In cluster 6 cells, many subclusters with distinct expression profiles are localized almost exclusively in the CA1, CA3 or the DG (FIG. 34, C, and FIG. 43, C). In contrast, cluster 7 cells show a relatively homogenous regionalization pattern, but further subdivide based on combinatorial expression patterns (FIG. 34, D). Subclusters of cluster 9 also show significant regionalization where subclusters 9.1, 9.3, 9.5, and 9.6 show localization to the SGZ (FIG. 43, C). Overall, cell clusters with similar expression profiles exhibited similar spatial localizations across the brain with a correlation coefficient of 0.67 (FIG. 43, E), indicating the existence of archetypal regional expression patterns and potential spatial markers in the brain. These results show that the tissue-optimized HCR seqFISH approach can directly identify a variety of transcriptional states and quantify broad spatial patterns of expression.

Combinatorial Expression Patterns Define Fine Clusters.

While certain cell clusters contain strong expression of marker genes, not all clusters are defined based on a few genes. How much power do individual genes or groups of genes have in explaining the observed cell clusters? To understand this, we examined whether subsets of genes can recapitulate the observed clusters (FIG. 34, E). We found that any set of 25 genes recovers about half of the correlation structure in the cell-to-cell correlation map (FIG. 34, (E), FIG. 45, (B-C), and FIG. 44, N=10 bootstrap replicates). The fact that the selection of any 25 genes can explain the gross patterns in the data is likely due to the high correlations amongst the expression patterns of genes, as shown in the gene-to-gene correlation map (FIG. 45, A). Thus, a small subset of the measured genes can provides sufficient information to infer the gross transcriptional states of the cells. Interestingly, this may be the same reason why low-coverage single cell sequencing methods such as drop-seq and inDrop (Klein et al., 2015; Macosko et al., 2015) can capture the large distinction of cell types, because many highly expressed genes are correlated to other genes that collectively define cell types.

At the same time, the finer correlation structure in the data, required to define the cell clusters accurately, can only be captured with more genes (FIG. 34, (F), and FIG. 45, (B-C)). Consistent with this, using a "random-forest" machine learning algorithm (Breiman, 2001) to classify cell clusters, we found that 75 genes are needed to classify cells with 50% accuracy, indicating that correct cluster assignment requires more detailed information from many genes (FIG. 34, E). Supporting this view, the first 10 principal components (PC) explained 59.5% of the variation in the data, while the rest of the variation required the remaining 115 PCs (FIG. 34, (F), and FIG. 43, (D)). The "random forest" algorithm required 10 PCs to predict the cell cluster assignments with 50% accuracy (FIG. 34, F), but accuracy steadily increased with more PCs. These observation indicated two levels of information in the data: a coarse level, where large distinctions in cell clusters are observable by a few genes, and a fine level, where subtle distinctions require many more genes.

These results suggest two points experimentally. First, multiplexing at the level of 20 genes by seqFISH can give broad cell cluster identification that is not available with 2-3 gene smFISH experiments. Although single marker genes are useful for inference, we find that they frequently are not sufficient for cell classification. For example, all DG specific granule cells (clusters 7) have Gpc4 and Vps13c as their enriched marker genes (FIG. 34, B); yet, Gpc4 and Vps13c are also strongly expressed in other hippocampal cells outside of the DG, as seen in both our experiments and the ABA. Thus, smFISH against Gpc4 and Vps13c alone would not be sufficient to uniquely identify the DG granule cells. Furthermore, even the strongly bimodal markers that are known to define cell types (i.e. Mgfe8, Gja1, etc.) are correlated enough to overall expression profiles that cells fall into the appropriate cluster even when these genes are excluded. This point suggests that while marker genes can be essential in assigning a cell to a known cell type, they are not necessary to identify unique clusters in the dataset provided enough measurements are made. Second, accurate measurement of combinatorial expression of many genes enabled by seqFISH can allow for more specific cell cluster identification. As a comparison, in single cell RNAseq data, CA1 pyramidal cells are clustered into a single cluster (Zeisel et. Al, 2015; Habib et. Al 2016) potentially because of the relatively lower detection efficiency of the method. In our seqFISH experiments, measuring hundreds of genes quantitatively, we can resolve several clusters and subclusters with robust regionalization within the CA1 (FIG. 34, (B), and FIG. 43, (C)).

Cells are Patterned in the Dentate Gyrus.

To further visualize the spatial organization of cells, we mapped cluster definitions of cells back into the images. In the DG, we observed a striking lamina layering of cell classes. The two blades of the DG (FIG. 35, A-B) showed mirror arrangements of cells, with cluster 9 cells, forming the subgranular zone (SGZ), leading into a granule cell layer (GCL) dominated by a single cluster of granule cells (cluster 7) (FIG. 34, B). In the 125 gene data set, the cells of the GCL were found to be dominated by expression of Gpc4 and Vps13c matching ISH data from the ABA (FIG. 48, B). Cluster 7 was found to be further subdivided into 6 subclusters (FIG. 40, C). These subclusters were found to have varying levels of calbindin D-28K (Calb1) expression which is known to increase with granule cell maturation (FIG. 34, D) (Yang et al., 2015). On the other hand, the cells of the SGZ were found to be significantly enriched in astrocyte markers such as Mfge8 and Mertk, which has been also been observed previously (Miller et al, 2013) and in the ABA data. However, these cells do not cluster with typical astrocytes (cluster 12 and 13) because their combinatorial expression patterns are different from astrocytes, consistent with their classification as a completely different population of cells.

In the fork region of the DG, the layer of cluster 9 cells appeared on the interior surface of the fork, followed by a layer of granule cells (cluster 7) (FIG. 35, C). A different layering pattern is seen at the crest of the DG, where astrocytes, microglia, and some other glial cells line the exterior of the crest ensheathing the GCL (FIG. 35, D). In both brains of the 125 gene experiments, the same cell clusters and spatial arrangements are observed. Furthermore, because the mRNAs are imaged in 3D in the 10-15 um brain slices, we can obtain a 3D view of the expression profiles, shown in the fork regions of the DG (FIG. 35, F).

Distinct Regions of CA1 and CA3 are Composed of Different Combination of Cell Clusters.

While each region of the DG contains similar compositions of cells, distinct subregions within the CA1 and CA3 contained different combinations of cell classes (FIG. 36, and FIG. 46, (F)). In the CA1, there were 3 distinct regions defined by their individual cellular compositions. In the dorsal region of CA1 (CA1d), neuron cluster 6 (enriched in Nell1, a protein kinase C binding protein) was the major cell type in the pyramidal layer, with astrocyte, microglia and other cells (clusters 10-13) intercalating into the stratum pyramidale (SP) (FIG. 36, A-C). Transitioning into the CA1 intermediate region (CA1i) (FIG. 36, D), pyramidal cell cluster 4 displaced cell cluster 6 as the dominant cell, with the co-appearance of cluster 1 and 2 pyramidal cells.

As the middle of the CA1i region was reached, a small amount of cluster 4 pyramidal cells remain, while cluster 1 and 2 pyramidal cells dominate (FIG. 36, E-F). Cluster 1 and 2 are enriched in Nell1 (EGF like protein), Npy2r (neuropeptide Y receptor), Slc4a8 (sodium bicarbonate transporter) and B3gat2 (glucuronosyltransferase). The CA1i region displayed a characteristic spatial organization where glial cells line the outermost regions, while pyramidal cell cluster 1 and 2 longitudinally partitioned the pyramidal layer. This separation of the inner versus the outer layers of CA1 matches those observed in previously (Dong et al., 2008). Furthermore, interneurons (cluster 3) were found to preferentially line the inner edge of the pyramidal layer in the CA1i region (FIG. 36, E-F). This patterning of interneurons, particularly subcluster 3.1 cells which were enriched in Slc5a7, a choline transporter, was consistent with the patterning of cholinergic interneurons observed with ChAT-GFP labeling (Yi et al., 2015). Finally, the largest amount of heterogeneity in the CA1 was seen in the ventral CA1 region (CA1v), where cell clusters 3, 5, and 10 began to mix in with clusters 1 and 2 (FIG. 36, G-I).

Similarly, the CA3 was found to have four transcriptionally distinct regions with different pyramidal cell compositions and abrupt transitions. The ventral most region of CA3 contained a high level of heterogeneity of pyramidal cell clusters (FIG. 36, J-K), while the intermediate region of CA3 contain a mixture of cell clusters 1 and 2 (FIG. 36, L-M). As the CA3 progressed towards the hilus of the DG, the cell types transitioned first to primarily cluster 4 neurons (enriched in dcx, doublecortin, and Col5a1, a collagen), and then to almost exclusively cluster 6 neurons in the region most proximal to the DG hilus (FIG. 36, O-P). It is interesting to note that while cluster 6 cells appear in both the CA1 (subcluster 6.8) and CA3 (subclusters 6.1 and 6.4), sub-clusters of 6 show distant regional localization (FIG. 43, C), suggesting that the gene expression differences in CA1 and CA3 cells are captured in the seqFISH data.

The regionalized expression patterns we observed in the hippocampus match closely to those observed in previous literature (Thompson et al Neuron 2008 and Dong et al PNAS 2009). For example, CA1d, CA1i, CA1v boundaries correspond to the boundaries shown in FIG. 2B in Dong et al. In CA3, the subregions observed in our experiment match the CA3 subregion 4-7 in Thompson et al. (Thompson et al., 2008).

Lastly, we note that the two slices from two different mice in the 125 gene experiment show not only the same subregional structure (FIGS. 35-37), but also the same clusters of cells (FIGS. 36 and 37) in the different subregions of the hippocampus (FIG. 46). In both brains, the CA1d consists of relatively homogenous population of cluster 6 cells, which transition to a mixture of 1 and 2 cells in CA1i, and finally to a mixture of 1-6 and 10 cells in the CA1v (FIG. 46, F). These results together show that the sub-regions of the hippocampus are a robust feature in the organization of CA1 and CA3, consisting of cells classes with distinct expression profiles. The stereotypical nature of the spatial arrangement of these structures suggest further experiments with seqFISH and other functional assays to probe the distinct functions of the different cell clusters in the CA1 and CA3.

249 Gene Multiplex Experiments Show the Same Hippocampal Subregions

To further show that the sub-regional structure of the hippocampus is independent of the target genes, we performed a 249 gene seqFISH experiment on a third coronal section. Of these 249 genes, only 22 genes overlapped with the 125 gene experiment set. For this set of genes, 214 were selected from a list of transcription factors and signaling pathway components and the remaining 35 were selected from cell identity markers from another single cell RNAseq dataset (Tasic et al, 2016). The 214 genes were barcoded by 5 rounds of hybridization, while the remaining genes were imaged in 7 rounds of non-barcoding serial hybridization. To quantify the efficiency of this experiment, 4 genes in the barcoding set (Smarca4, Sin3a, Npas3, and Neurod4) were re-probed with smHCR. The barcoding efficiency of the 249 gene probe set was found to be 71% with and R value of 0.80 (FIG. 46, D). In single cells, we detect on average 2807±1660 (mean±s.d., N=2050 cells) total barcoded barcodes.

The same arrangement in the DG was observed in the 249 gene experiment, despite different genes used, indicating robust identification of the layering in the DG by seqFISH (FIG. 38, S-T). In particular, the cells in the SGZ are clustered independently from cells in the GCL, similar to the layers observed in the 125 gene experiment. In the SGZ cells, we observed enrichment of Sox11, a key transcription factor in neurogenesis (Miller et al, 2013). Other transcription factors involved in neurogenesis, NFIA and Tbr1 are also enriched in the SGZ cells as seen in our data and the ABA images (FIG. 48, A). The observations of this distinct layer in both the 249 and 125 gene experiment and the combined gene enrichment pattern (increased Sox11, Sox9, NFIA, and Tbr1 in the 249 gene experiment and increased Mertk and Mfge8 in the 125 gene experiment) suggests that many cells in this layer are involved in adult neurogenesis in the SGZ.

In addition, the same regionalized cellular patterns are observed in CA1d, CA1i, and CA1v, where different sub-regions utilize different cell classes in characteristic ratios (FIG. 46, F). As seen with the 125 gene experiment, while the CA1d uses only a few cell classes and is relatively homogeneous, while the CA1v region is made up of many different cell classes resulting in a high level of cellular heterogeneity. Furthermore, the distinction between CA1 and CA3 cell clusters are more clear in the 249 gene experiment suggesting more resolving power of spatial patterns (FIG. 38, A-K). The 249 gene experiment also suggests that the CA3 may be composed of 3-4 subregions based on cell cluster composition (FIG. 38, L-R). The cellular heterogeneity of the CA3 is again shown to mirror that of the CA1, where the cellular heterogeneity increases along the dorsal to ventral axis. Cells with distinctive marker gene expression in the hippocampus are shown in supplementary FIG. 38, A.

Single Cell Data Resolves Cellular Organizations in the Sub-Regions of the CA1 and CA3.

Two conflicting views of the cell types in the hippocampus have been proposed based on the analysis of the Allen Brain Atlas data (Thompson 2008) as well as recent RNA-seq data (Cembrowski et al., 2016, Zeisel et al 2015). Analysis of the ABA in situ data showed that distinct subregions of the hippocampus expressed different molecular markers, indicating that the CA1 and CA3 are "regionalized" into distinct sub-structures (Fanselow and Dong, 2010; Thompson et al., 2008). However, recent bulk RNA-seq experiments on the CA1 found that gene expression patterns changed gradually along the dorsal to ventral axis, contradicting the sharp boundaries observed in the ABA analysis (Cembrowski et al., 2016). Further supporting this "continuous" cell type view of the hippocampus, analysis of the single cell RNA-seq data (Zeisel et al, 2015) identified a single continuous population of cells in the CA1 region.

Our data provides a single cell resolution picture of the spatial organization of cells in the hippocampus and reconciles both the RNA-seq and the ABA data. While our data mostly supports a regionalized view of the hippocampus, we observe that a single cell class does not in general define CA1 and CA3 sub-regions. Instead, we observed that different subregions of CA1 and CA3 are composed of distinct combinations of cell clusters (FIGS. 33-35). For example, CA1d consists primarily of cluster 6 pyramidal cells (FIG. 36, A-C), in addition to the cluster 1, 2, 10, and 12 cells, while CA1v consists of a large set of cell classes including cluster 1-6 and 10 cells, but at different relative abundances (FIGS. 36-37, FIG. 46, F-G). Due to this intermixing of cell classes in each sub-region, a bulk measurement of transcription profiles would find a lack of regionalization, but single cell analysis with spatial resolution would identify these distinct regions based on their unique cell class compositions. Indeed, when we averaged the single cell expression profile within each sub-region of the CA1, we can reproduce the continuous correlation profiles found by bulk RNA-seq between CA1v, CA1i, and CA1d (FIG. 39) (Cembrowski et al., 2016). The bulk RNA-seq observation that CA1i lacked specific marker genes can also be explained. This is in fact consistent with our findings that CA1i contained cell classes present in both CA1d and CA1v (FIGS. 36-38).

This organization of cell classes is observed in both the 125 gene experiments as well as in the 249 gene experiment. It is worth noting that the complexity of cell populations observed in the CA1d versus the CA1v matches the functional differences in CA1. CA1d is responsible for spatial learning and navigation and contains a higher concentration of place cells and send projections to dorsal subiculum and cortical retrosplenial area (Cenquizca and Swanson, 2007; Jung et al., 1994; Risold et al, 1997; O'Keefe and Dostrovsky, 1971). We observed that CA1d is composed of a relatively homogeneous population of cells, predominantly of cluster 6 cells. In contrast, the ventral region is involved in a variety of cognitive tasks, such as stress response, emotional and social behavior (Cenquizca and Swanson, 2007; Jung et al., 1994; Fanselow and Dong, 2010; Kishi et al., 2006; Muller et al., 1996; Petrovich et al., 2001; Pitkänen et al., 2000; Saunders et al., 1988; Witter and Amaral, 1991; Yi et al., 2015). Correspondingly, we observed a large set of cell classes in the CA1v regions. It is intriguing to hypothesize that the different cell classes identified based on molecular profiles may correspond to neurons with distinct connectivity and functional patterns. This hypothesis can be investigated in future experiments combining anterograde tracing as well as electrophysiological recording followed by seqFISH.

A list of the 249 genes being analyzed can be found in the following Table 3.

| Name of Genes being analyzed |
|---|
| Tal1 |
| Dmbx1 |
| Emx2 |
| Uncx |
| Paxip1 |
| Ctnnb1 |
| Prdm1 |
| Rybp |
| Nfkb2 |
| Tfdp2 |
| Grhl1 |
| Sp8 |
| Irf2 |
| Zfp287 |
| Esr2 |
| Zfp128 |
| Vav1 |
| Sp1 |
| Ppargc1b |
| Sp7 |
| Pin1 |
| Nfya |
| Vsx1 |
| Klf1 |
| Vsx2 |
| Mybl1 |
| Mybl2 |
| Rnf2 |
| Blzf1 |
| Topors |
| Nr3c2 |
| Nfia |
| Taf6l |
| Nr4a3 |
| Hoxd12 |
| Hoxd13 |
| Ttf1 |
| Sox9 |
| Nr2e1 |
| Polr2b |
| Hltf |
| Sox6 |
| Pbx3 |
| Sox5 |
| Foxa1 |
| Cdc5l |
| Cebpg |
| Ciita |
| Rest |
| Ets1 |
| Mafk |

-continued

| Name of Genes being analyzed |
|---|
| Tbx15 |
| Scml2 |
| Myb |
| Clock |
| Rbpj |
| Foxc1 |
| Zfp422 |
| Pias3 |
| Runx1 |
| Ppara |
| Relb |
| Vdr |
| Cdc6 |
| Arid3a |
| Lhx1 |
| Hoxb8 |
| Hoxb9 |
| Hic1 |
| Lhx6 |
| Six4 |
| Hoxb3 |
| Zfp263 |
| Cbfa2t3 |
| Ehf |
| Nhlh1 |
| Gata6 |
| Gata4 |
| Gata5 |
| Lpp |
| Nfe2l3 |
| Nfe2l2 |
| Tmf1 |
| Gli1 |
| Tbx2 |
| En1 |
| En2 |
| Hnf1a |
| Tbx4 |
| Zfp423 |
| Elf1 |
| Foxb1 |
| Elf2 |
| Elf4 |
| Mxd1 |
| Wt1 |
| Rfx4 |
| Bhlhe41 |
| Sox13 |
| Taf4b |
| Rfx2 |
| Sox17 |
| Ahr |
| Sall4 |
| Med14 |
| Smyd1 |
| Sall3 |
| Arid2 |
| Zfp64 |
| Pgr |
| Trps1 |
| Hoxa1 |
| Bach2 |
| Bach1 |
| Notch3 |
| Pknox1 |
| Pknox2 |
| Sin3a |
| Etv3 |
| Smad9 |
| Smad5 |
| Alx1 |
| Egf |
| Mn1 |
| Nkx3-1 |
| Rbak |
| Gabpa |
| Nfkbiz |

| Name of Genes being analyzed |
|---|
| Zscan21 |
| Trp73 |
| E2f7 |
| Esrrg |
| Rbpjl |
| Nfatc4 |
| Nr5a1 |
| Neurod4 |
| Esrrb |
| Tbx21 |
| Rorc |
| Mitf |
| Pax7 |
| Pax6 |
| Pax1 |
| Pax3 |
| Pax2 |
| Pax9 |
| Zkscan17 |
| Gfi1 |
| Mzf1 |
| Runx3 |
| Smarca4 |
| Foxd4 |
| Foxd3 |
| Creb1 |
| Srebf1 |
| Sox11 |
| Gmeb2 |
| Irx4 |
| Pou3f2 |
| Ikzf1 |
| Tcf23 |
| Mtf2 |
| Npas3 |
| Nfatc3 |
| Nfil3 |
| Phox2b |
| Plag1 |
| E2f2 |
| Ddx3x |
| Taf2 |
| Pou4f1 |
| Trim33 |
| Tsc2 |
| Lmx1a |
| Nr2f2 |
| Eomes |
| Wwtr1 |
| Foxo1 |
| Ar |
| Zfp354a |
| Elk4 |
| Foxo4 |
| Sall1 |
| Mycn |
| Maml3 |
| Foxp3 |
| Atm |
| Uaca |
| Tbr1 |
| Pml |
| Lhx3 |
| Atr |
| Zbtb33 |
| Ptch1 |
| Lhx5 |
| Barhl1 |
| Irx5 |
| Tfap2b |
| Tfap2e |
| Rxra |
| Rxrb |
| Gli2 |
| Gli3 |
| Zic4 |
| Zic5 |

| Name of Genes being analyzed |
|---|
| Zic2 |
| Zic3 |
| Satb1 |
| Onecut2 |
| Foxn4 |
| Mnat1 |
| Foxn1 |
| Dlx2 |
| Vezf1 |
| sncg |
| sst |
| th |
| vip |
| xdh |
| slc17a8 |
| slc5a7 |
| slc6a3 |
| slc6a8 |
| smad3 |
| opalin |
| pdgfra |
| palvb |
| reln |
| slc17a7 |
| lyve |
| mfge8 |
| mog |
| myl14 |
| ndnf |
| ctss |
| foxj1 |
| gad1 |
| htr3a |
| igtP |
| acta2 |
| alldh1l1 |
| camk2 |
| chat |
| cldn5 |
| ngef |
| tiam1 |
| slc1a2 |
| gja1 |
| fbll1 | seqFISH Provides a Generalized Method to Multiplex mRNA Imaging in Tissues seqFISH with amplification and error correction provides a highly quantitative method to profile hundreds of mRNA species directly in single cells within their native anatomical context. Our method of stripping the probes from the RNA has many advantages. DNAse digestion of probes allows false positives to be rejected as nonspecifically bound probes do not colocalize between different rounds of hybridization (FIG. 33, A). In addition, the same region of the transcript can be hybridized in every round, allowing seqFISH to efficiently target mRNAs shorter than 1 kb, enabling targeting of most genes. Lastly, seqFISH allows exponential scaling of barcode numbers, thus 4-5 rounds of hybridization can code for hundreds of transcripts with a simple error correction scheme. Theoretically, the entire transcriptome can be coded for with error correction by using 8-9 rounds of hybridization with seqFISH. These advantages of HCR seqFISH allows robust multiplexed RNA detection in tissues, shown here in the mouse brain.

Ultimately, the multiplexing capability of seqFISH is limited by the amount of optical space within a cell, and not by the coding capacity of the method (supplementary text). We showed previously that super-resolution microscopy can significantly increase the optical space available in the cell for transcription profile imaging, but super-resolution microscopy experiments proved difficult to image in samples thicker than 1 µm, and were experimentally cumbersome and time consuming to image (Lubeck and Cai, 2012). A recent development in expansion microscopy as well as correlation methods (Coskun et al., 2016) however offers promise for multiplexing to levels of high transcript density (Chen et al., 2015a; Treweek et al., 2015, Chen et al., 2016). In addition, by labeling subcellular components (i.e., dendrites and axons) with antibodies, the local transcriptome in compartments of the cell can be measured.

It was observed that, because expression patterns amongst genes are highly correlated, the distinction between large classes of cells can be determined from 10-20 genes, while a finer classification of cell clusters depends on the quantitative measurement of the combinatorial expression patterns of many genes (FIGS. 34, E and F). This correlation amongst genes can be used to "stitch" our seqFISH data with single cell RNAseq data, similar to the approach explored with single cell RNAseq and ISH in Satija et al (Satija et al., 2015). By correlating seqFISH data to single cell RNA-seq expression data, cells types identified based on RNA-seq can be "mapped" back into our seqFISH data.

As shown here, seqFISH with hundreds of genes in tissues can become a general and widely used tool to answer a wide range of fundamental questions in biology and medicine. For neuroscience, by combining the insights into the spatial organization of transcription provided by seqFISH with connectomics and electrophysiological measurements, we can obtain a comprehensive understanding of the molecular basis of the neuroanatomy of the brain.

Example 5

Supplementary Experimental Procedure for Brain Slide Analysis

Probe Design. Genes were selected from the Allen Brain Atlas database. We identified genes that are heterogeneously expressed in coronal sections containing the hippocampus at Bregma coordinates-2.68 mm anterior. Using the ABA region definitions, we break down the voxels representing the ABA data in those brain sections into 160 distinct regions and average the expression values within each region. We selected 100 genes that had high variances across these distinct regions and that also had low-medium expression levels. These genes included transcription factors and signaling pathways components as well as ion channels and other functional genes. Lastly, we chose 25 genes from single cell RNA-seq data that were enriched in certain cell types. Briefly, the design criteria used were 1) constant regions of all spliced isoforms were identified, 2) Masked regions of UCSC genome were removed from possible probe design, 3) 35mer sequences were tiled 4 nt apart, 4) sets of non-overlapping probes with tightest GC range around 55% were found, 5) probes were blasted for off-target hits. Any probe with an expected total off-target copy number of more than 5000 was dropped. Once all possible probes for every target gene was acquired, the probe set oligo-pool was optimized using the following criteria: 1) Expected # of off-target hits for entire probe pool was calculated, 2) probes were sequentially dropped from genes until any off-target gene was hit by no more than 6 probes from entire pool, 3) HCR adapters were added to designed probes and 10 nt in either direction of the adapter junction was blasted and screened for off-target hits, 4) probe pools were searched for regions of 18mer complementary, 5) the probe sets for a given transcript was refined down to 24 probes by dropping probes in order of the expected number of off-target hits, 6) Cutting sites and hybridization specific primers were added to probes.

Probe Generation. All oligoarray pools were purchased as 92k synthesis from Customarray Inc. Probes were amplified from array-synthesized oligo pool), with the following modifications: (i) a 35 nt RNA-targeting sequence for in situ hybridization, (ii) a 35 nt HCR initiator sequence designed to initiate one color of 5 possible HCR polymers, (iii) two hybridization specific flanking primer sequences to allow PCR amplification of the probe set and (iv) EcoRI (5'-GAATTC-3') and KpnI (5'-GGTACC-3') sites for cutting out flanking primers to reduce probe size. Ethanol precipitation was used to purify the final digested probes.

Brain extraction and sample mounting. C57BL/6 with Ai6 Cre-reporter (uncrossed) (Jackson Labs, SN: 007906) female mice aged 50-80 days were anesthetized with isoflurane according to institute protocols (protocol #1701-14). No randomization of mice was used and blinding was not necessary as the study was exploratory. Mice were perfused for 8 minutes with perfusion buffer (10 U/ml heparin, 0.5% $NaNO_2$ (w/v) in 0.1M PBS at 4° C.). Mice were then perfused with fresh 4% PFA\0.1M PBS buffer at 4 C for 8 minutes. The mouse brain was dissected out of the skull and immediately placed in a 4% PFA buffer for 2 hours at room temperature under gentle mixing. The brain was then immersed in 4 C 30% RNAse-free Sucrose (Amresco 0335-2.5 KG) \1×PBS until the brain sank. After the brain sank, the brain was frozen in an dry ice\isopropanol bath in OCT media and stored at −80 C. Fifteen micron sections were cut using a cryotome and immediately placed on an aminosilane modified coverslip.

Sample permeabilization, hybridization, and Imaging. Brain sections mounted to coverslips were permeabilized in 4 C 70% EtOH for 12-18 hours. Brains were further permeabilized by the addition of mase-free 8% SDS (Ambion AM9822) for 10 minutes. Samples were rinsed to remove SDS, desiccated and a hybridization chamber (Grace Bio-Labs 621505) was adhered around the brain section. Samples were hybridized overnight at 37 C with Split Color PGK1 Probes in Hybridization Buffer (2×SSC (INVITROGEN™ 15557-036), 10% Formaldehyde (v/v) (Ambion AM9344), 10% Dextran Sulfate (Sigma D8906), 2 mM Vanadyl Ribonucleoside Complex (VRC; NEB S1402S) in Ultrapure water (INVITROGEN™ 10977-015)). Samples were washed in 30% Wash Buffer (WBT: 2×SSC, 30% Formaldehyde (v/v)] 10% Dextran Sulfate, 0.1% Triton-X 100 (Sigma X-100), 2 mM VRC in Ultrapure water) for 30 minutes. While washing aliquoted HCR hairpins (Molecular Instruments Inc) were heated to 95 C for 1.5 minutes and allowed to cool to RT for 30 minutes. HCR hairpins were diluted to a concentration of 120 nM per hairpin in amplification buffer (2×SSC, 10% Dextran Sulfate) and added to washed tissue for 45 minutes. Following amplification, samples were washed in the same 30% WBT for at least 10 minutes to remove excess hairpins. Samples were stained with DAPI and submerged in pyranose oxidase antibleaching buffer. Sample port covers were closed with a glass coverslip or a transparent polycarbonate sheet to exclude oxygen.

Samples were imaged using a standard epifluorescence microscope (Nikon Ti Eclipse with custom built laser assembly) for the 125-gene experiment. Exposures times were 200 ms for cy7 and ALEXA FLUOR™ 488 channels and 100 ms for ALEXA FLUOR™ 647, ALEXA FLUOR™ 594, and cy3b channels. For the 249-gene experiment, a Yokogawa CSU-W1 spinning disk confocal unit attached to an Olympus IX-81 base was used for imaging. The exposure times were 500 ms for each channel. At this stage, intact and accessible mRNA should always appear in two channels. If the RNA was deemed to be intact, DAPI data was collected in this hybridization. Samples were digested with DNAse I (Roche 04716728001) for 4 hours at room temperature on the scope. Following DNAse I the sample was washed several times with 30% WBT and hybridized overnight with 70% Formamide HB and the experiment probes at 1 nM concentration per probe sequence at room temperature. Samples were again washed and amplified as before. Barcode digits were developed by repeating this cycle with the appropriate probes for each hybridization. Fluorescent Nissl stain (ThermoFisher N-21480) was collected at the end of the experiment along with images of multispectral beads to aid chromatic aberration corrections.

Image Processing. To remove the effects of chromatic aberration, the multispectral beads were first used to create geometric transforms to align all fluorescence channels. Next, the background illumination profile of every fluorescence channel was mapped using a morphological image opening with a large structuring element. These illumination profile maps were used to flatten the illumination in post-processing resulting in relatively uniform background intensity and preservation of the intensity profile of fluorescent points. The background signal was then subtracted using the imagej rolling ball background subtraction algorithm with a radius of 3 pixels. Finally, the calculated geometric transforms were applied to each channel respectively. The 150 pixel border region around the image was ignored in all analysis to avoid errors from edge effects of illumination.

Image Registration. The processed images were then registered by first taking a maximum intensity projection along the z direction in each channel. All of the maximum projections of the channels of a single hybridization were then collapsed resulting in 4 composite images containing all the points in a particular round of hybridization. Each of these composite images of hybridization 1-3 were then cross-correlated individually with the composite image of hybridization 4 and the position of the maxima of the cross-correlation was used as the translation factor to align hybridizations 1-3 to hybridization 4.

Cell Segmentation. For cells in the cortex, the cells were segmented manually using the DAPI images taken in the first round of hybridization and the fluorescent nissl stain taken at the end of the experiment. Furthermore, the density of the point cloud surrounding a cell was taken into account when forming cell boundaries, especially in cells that did not stain with the nissl stain. For the hippocampus, the cells were segmented by first manually selecting the centroid in 3D of each DAPI signal of every cell. Transcripts were first assigned based on nearest centroids. These point clouds were then used to refine the centroid estimate and create a 3D voronoi tessellation with a 10% boundary-shrinking factor to eliminate ambiguous mRNA assignments from neighboring cells.

Barcode calling. The potential mRNA signals were then found by LOG filtering the registered images and finding points of local maxima above a specified threshold value. Once all potential points in all channels of all hybridizations were obtained, dots were matched to potential barcode partners in all other channels of all other hybridizations using a 1 pixel search radius to find symmetric nearest neighbors. Point combinations that constructed only a single barcode were immediately matched to the on-target barcode set. For points that matched to construct multiple barcodes, first the point sets were filtered by calculating the residual spatial distance of each potential barcode point set and only the point sets giving the minimum residuals were used to match to a barcode. If multiple barcodes were still possible, the point was matched to its closest on-target barcode with a hamming distance of 1. If multiple on target barcodes were still possible, then the point was dropped from the analysis as an ambiguous barcode. This procedure was repeated using each hybridization as a seed for barcode finding and only barcodes that were called similarly in at least 3 out of 4 rounds were used in the analysis. The number of each barcode was then counted in each of the assigned cell volumes and transcript numbers were assigned based on the number of on-target barcodes present in the cell volume. All image processing and image analysis code can be obtained upon request.

Clustering. To cluster the dataset with 14,908 cells and 125 genes profiled, we first z-score normalized the data based on gene expression. Once the single cell gene expression data is converted into z-scores, we compute a matrix of cell-to-cell correlations using Pearson correlation coefficients. Then hierarchical clustering with Ward linkage is performed on the cell-to-cell correlation data with cells in the center field of view. The cluster definitions are then propagated to the remaining cells using a random forest machine learning algorithm. To analyze the robustness of individual clusters, a random forest model was trained using varying subsets of the data and used to predict the cluster assignment of the remaining cells. A bootstrap analysis by dropping different sets of cells was performed in increments (FIG. 42). To determine the effect of dropping out genes on the accuracy of the clustering analysis, we used a random forest decision tree to learn the cluster definition based on the 125 gene data. Then we ask the decision tree to re-compute the cluster assignment on cell-to-cell correlation matrices with fewer and fewer genes (FIG. 34, F, green line). Bootstrap resampling was also performed with this analysis (FIG. 34, F, bluelines). The PCA and tSNE analysis were performed using the same cell-to-cell z-scored Pearson correlation matrix. The cell-to-cell correlation in FIG. 34, E was calculated with increasing number of principal components dropped (have their eigenvalues set to zero). The cluster assignment accuracy is again computed through the random forest decision tree.

Optical Space for Barcodes in Cells. The theoretical upper limit for the number of barcodes that can be identified accurately within a cells primarily depends on the volume of the cell. As mRNA spots are diffraction limited, if a microscope is configured to have sub-diffraction limited pixel size, the ability to identify smFISH signal without any super-resolution would require no two mRNA signals to be immediately adjacent to each other in x, y or z dimension. These minimum required voxels are called "coding voxels." The absolute upper limit of the number of transcripts that can be coded unambiguously without any super-resolution methods is solely a function of the number of coding voxels present in a cell Assuming a diffraction limit of $\lambda$ µm and a resolution of z um in the z direction, there exists $$\frac{V}{(3\lambda)^2 z}$$

coding voxels per cell, where V is the volume of the cell in microns. In the seqFISH method, we use 5 or more channels to hold mRNA spots which would increase the total number of coding voxels by a multiplicative factor equal to the number of channels used for barcoding. Therefore, $$\#B = \frac{FV}{(3\lambda)^2 z}$$

where #B is the maximum number of unambiguous barcodes a cell can hold, and F is the number of channels used. As mammalian cells range from about 500-4000 microns in volume, these cells can accommodate roughly between 6100-49,000 barcodes assuming 5 fluorescence channels are being used, the diffraction limit is 0.3 um, and the z resolution is 0.5 um. In principle, this calculation would provide the total number of perfectly discernible spots a cell can accommodate. In our actual experimental data, we have some amount of dropped barcodes due to ambiguity in barcode assignment due to spot overlaps. This is one of the main factors that reduces the efficiency of seqFISH as compared to single transcript detection (i.e., smFISH or smHCR). Expansion microscopy could further increase the number of coding voxels in a cell by the expansion factor leading to fewer drops and imaging of denser transcripts.

Additional background information can be found in the following references, each of which is hereby incorporated by reference in its entirety.

Beliveau, B. J., Joyce, E. F., Apostolopoulos, N., Yilmaz, F., Fonseka, C. Y., McCole, R. B., Chang, Y., Li, J. B., Senaratne, T. N., Williams, B. R., et al. (2012). Versatile design and synthesis platform for visualizing genomes with Oligopaint FISH probes. Proc. Natl. Acad. Sci. U.S.A 109, 21301-21306.

Betzig, E., Patterson, G. H., Sougrat, R., Lindwasser, O. W., Olenych, S., Bonifacino, J. S., Davidson, M. W., Lippincott-Schwartz, J., and Hess, H. F. (2006). Imaging Intracellular Fluorescent Proteins at Nanometer Resolution. Science 313, 1642-1645.

Breiman, L. (2001). Random Forests. Mach. Learn. 45, 5-32.

Bose S, Wan Z, Carr A, Rizvi A H, Vieira G, Pe'er D, Sims P A. Scalable microfluidics for single-cell RNA printing and sequencing. Genome Biol. 2015 Jun. 6; 16:120.

Buenrostro J D, Araya C L, Chircus L M, Layton C J, Chang H Y, Snyder M P, Greenleaf W J. Quantitative analysis of RNA-protein interactions on a massively parallel array reveals biophysical and evolutionary landscapes. Nat Biotechnol. 2014 June; 32 (6): 562-8.

Cajigas, I. J., Tushev, G., Will, T. J., Dieck, S. tom, Fuerst, N., and Schuman, E. M. (2012). The Local Transcriptome in the Synaptic Neuropil Revealed by Deep Sequencing and High-Resolution Imaging. Neuron 74, 453-466.

Junyue Cao, Jonathan S. Packer, Vijay Ramani, Darren A. Cusanovich, Chau Huynh, Riza Daza, Xiaojie Qiu, Choli Lee, Scott N. Furlan, Frank J. Steemers, Andrew Adey, Robert H. Waterston, Cole Trapnell, Jay Shendure. Comprehensive single cell transcriptional profiling of a multicellular organism by combinatorial indexing. bioRxiv 104844; doi: https://doi.org/10.1101/104844

Cembrowski, M. S., Bachman, J. L., Wang, L., Sugino, K., Shields, B. C., and Spruston, N. (2016). Spatial Gene-Expression Gradients Underlie Prominent Heterogeneity of CA1 Pyramidal Neurons. Neuron 89, 351-368.

Cenquizca, L. A., and Swanson, L. W. (2007). Spatial organization of direct hippocampal field CA1 axonal projections to the rest of the cerebral cortex. Brain Res. Rev. 56, 1-26.

Chen, F., Tillberg, P. W., and Boyden, E. S. (2015a). Expansion microscopy. Science 347, 543-548.

Chen, F., Wassie, A. T., Cote, A. J., Sinha, A., Alon, S., Asano, S., Daugharthy, E. R., Chang, J.-B., Marblestone, A., Church, G. M., Raj, A., Boyden, E. S., 2016. Nanoscale imaging of RNA with expansion microscopy. Nat Meth advance online publication.

Chen, K. H., Boettiger, A. N., Moffitt, J. R., Wang, S., and Zhuang, X. (2015b). Spatially resolved, highly multiplexed RNA profiling in single cells. Science 348, aaa6090.

Choi, H. M. T., Beck, V. A., and Pierce, N. A. (2014). Next-Generation in Situ Hybridization Chain Reaction: Higher Gain, Lower Cost, Greater Durability. ACS Nano 8, 4284-4294.

Darmanis, S., Sloan, S. A., Zhang, Y., Enge, M., Caneda, C., Shuer, L. M., Gephart, M. G. H., Barres, B. A., and Quake, S. R. (2015). A survey of human brain transcriptome diversity at the single cell level. Proc. Natl. Acad. Sci. 112, 7285-7290.

Dong, H.-W., Swanson, L. W., Chen, L., Fanselow, M. S., and Toga, A. W. (2009). Genomic-anatomic evidence for distinct functional domains in hippocampal field CA1. Proc. Natl. Acad. Sci. 106, 11794-11799.

Donner Y, Feng T, Benoist C, Koller D. Imputing gene expression from selectively reduced probe sets. Nat Methods. 2012 November; 9 (11): 1120-5.

Duan et al. L1000CDS2: LINCS L1000 characteristic direction signatures search engine. npj Systems Biology and Applications (2016) 2, 16015;

Fan, Y., Braut, S. A., Lin, Q., Singer, R. H., and Skoultchi, A. I. (2001). Determination of transgenic loci by expression FISH. Genomics 71, 66-69.

Fanselow, M. S., and Dong, H.-W. (2010). Are the dorsal and ventral hippocampus functionally distinct structures? Neuron 65, 7-19.

Femino, A. M., Fay, F. S., Fogarty, K., and Singer, R. H. (1998). Visualization of Single RNA Transcripts in Situ. Science 280, 585-590.

Fulton D L, Sundararajan S, Badis G, Hughes T R, Wasserman W W, Roach J C, Sladek R. TFCat: the curated catalog of mouse and human transcription factors. Genome Biol. 2009; 10 (3): R29. doi: 10.1186/gb-2009-10-3-r29.

Habib, N., Li, Y., Heidenreich, M., Swiech, L., Trombetta, J. J., Zhang, F., Regev, A., 2016. Div-Seq: A single nucleus RNA-Seq method reveals dynamics of rare adult newborn neurons in the CNS. bioRxiv 045989.

Ingolia N T, Ghaemmaghami S, Newman J R, Weissman J S. Genome-wide analysis in vivo of translation with nucleotide resolution using ribosome profiling. Science. 2009 Apr. 10; 324 (5924): 218-23.

Jung, M. W., Wiener, S. I., and McNaughton, B. L. (1994). Comparison of spatial firing characteristics of units in dorsal and ventral hippocampus of the rat. J. Neurosci. 14, 7347-7356.

Ke, R., Mignardi, M., Pacureanu, A., Svedlund, J., Botling, J., Wählby, C., and Nilsson, M. (2013). In situ sequencing for RNA analysis in preserved tissue and cells. Nat. Methods 10, 857-860.

Kishi, T., Tsumori, T., Yokota, S., and Yasui, Y. (2006). Topographical projection from the hippocampal formation to the amygdala: A combined anterograde and retrograde tracing study in the rat. J. Comp. Neurol. 496, 349-368.

Klein, A. M., Mazutis, L., Akartuna, I., Tallapragada, N., Veres, A., Li, V., Peshkin, L., Weitz, D. A., and Kirschner, M. W. (2015). Droplet Barcoding for Single-Cell Transcriptomics Applied to Embryonic Stem Cells. Cell 161, 1187-1201.

Lee, J. H., Daugharthy, E. R., Scheiman, J., Kalhor, R., Yang, J. L., Ferrante, T. C., Terry, R., Jeanty, S. S. F., Li, C., Amamoto, R., et al. (2014). Highly Multiplexed Subcellular RNA Sequencing in Situ. Science 343, 1360-1363.

Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.

Levesque M J, Ginart P, Wei Y, Raj A. Visualizing SNVs to quantify
allele-specific expression in single cells. Nat Methods. 2013 September; 10 (9): 865-867.

Lubeck, E., and Cai, L. (2012). Single-cell systems biology by super-resolution imaging and combinatorial labeling. Nat. Methods 9, 743-748.

Lubeck, E., Coskun, A. F., Zhiyentayev, T., Ahmad, M., and Cai, L. (2014). Single-cell in situ RNA profiling by sequential hybridization. Nat. Methods 11, 360-361.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 161, 1202-1214.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nat. Neurosci. 13, 133-140.

Madisen, L., Mao, T., Koch, H., Zhuo, J., Berenyi, A., Fujisawa, S., Hsu, Y.-W. A., Iii, A. J. G., Gu, X., Zanella, S., et al. (2012). A toolbox of Cre-dependent optogenetic transgenic mice for light-induced activation and silencing. Nat. Neurosci. 15, 793-802.

Mellis I A, Gupte R, Raj A, Rouhanifard S H. Visualizing adenosine-to-inosine RNA editing in single mammalian cells. Nat Methods. 2017 Jun. 12. doi: 10.1038/nmeth.4332.

Miller, JA. Jason Nathanson, Daniel Franjic, Sungbo Shim, Rachel A. Dalley, Sheila Shapouri, Kimberly A. Smith, Susan M. Sunkin, Amy Bernard, Jeffrey L. Bennett, Chang-Kyu Lee, Michael J. Hawrylycz, Allan R. Jones, David G. Amaral, Nenad Sestan, Fred H. Gage, Ed S. Lein (2013). Conserved molecular signatures of neurogenesis in the hippocampal subgranular zone of rodents and primates. Development. 140 (22): 4633-4644.

Mortazavi A, Williams B A, McCue K, Schaeffer L, Wold B. Mapping and quantifying mammalian transcriptomes by RNA-Seq. Nat Methods. 2008 July; 5 (7): 621-628.

Muller, R., Stead, M., and Pach, J. (1996). The hippocampus as a cognitive graph. J. Gen. Physiol. 107, 663-694.

Nagalakshmi, U. et al. The transcriptional landscape of the yeast genome defined by RNA sequencing. Science 320, 1344-1349 (2008).

O'Keefe, J., and Dostrovsky, J. (1971). The hippocampus as a spatial map. Preliminary evidence from unit activity in the freely-moving rat. Brain Res. 34, 171-175.

Petrovich, G. D., Canteras, N. S., and Swanson, L. W. (2001). Combinatorial amygdalar inputs to hippocampal domains and hypothalamic behavior systems. Brain Res. Brain Res. Rev. 38, 247-289.

Pitkänen, A., Pikkarainen, M., Nurminen, N., and Ylinen, A. (2000). Reciprocal Connections between the Amygdala and the Hippocampal Formation, Perirhinal Cortex, and Postrhinal Cortex in Rat: A Review. Ann. N. Y. Acad. Sci. 911, 369-391.

Raj, A., Peskin, C. S., Tranchina, D., Vargas, D. Y., and Tyagi, S. (2006). Stochastic mRNA Synthesis in Mammalian Cells. PLOS Biol 4, e309.

Risold, P. Y., and Swanson, L. W. (1996). Structural evidence for functional domains in the rat hippocampus. Science 272, 1484-1486.

Alexander B Rosenberg, Charles Roco, Richard A Muscat, Anna Kuchina, Sumit Mukherjee, Wei Chen, David J Peeler, Zizhen Yao, Bosiljka Tasic, Drew L Sellers, Suzie H Pun, Georg Seelig. Scaling single cell transcriptomics through split pool barcoding bioRxiv 105163; doi: https://doi.org/10.1101/105163

Rust, M. J., Bates, M., and Zhuang, X. (2006). Sub-diffraction-limit imaging by stochastic optical reconstruction microscopy (STORM). Nat Meth 3, 793-796.

Satija, R., Farrell, J. A., Gennert, D., Schier, A. F., Regev, A., 2015. Spatial reconstruction of single-cell gene expression data. Nat Biotech 33, 495-502.

Saunders, R. C., Rosene, D. L., and Van Hoesen, G. W. (1988). Comparison of the efferents of the amygdala and the hippocampal formation in the rhesus monkey: II. Reciprocal and non-reciprocal connections. J. Comp. Neurol. 271, 185-207.

S. Shah, E. Lubeck, W. Zhou, L. Cai, In Situ Transcription Profiling of Single Cells Reveals Spatial Organization of Cells in the Mouse Hippocampus. Neuron 92, 342-357 (2016).

Singer Z S, Yong J, Tischler J, Hackett J A, Altinok A, Surani M A, Cai L, Elowitz M B. Dynamic heterogeneity and DNA methylation in embryonic stem cells. Mol Cell. 2014 Jul. 17; 55 (2): 319-31.

Shah, S., Lubeck, E., Schwarzkopf, M., He, T., Greenbaum, A., Sohn, C. ho, Lignell, A., Choi, H. M. T., Gradinaru, V., Pierce, N. A., Cai, L., 2016. Single-molecule RNA detection at depth via hybridization chain reaction and tissue hydrogel embedding and clearing. Development dev. 138560. doi: 10.1242/dev.138560

Ståhl, P. L., Salmén, F., Vickovic, S., Lundmark, A., Navarro, J. F., Magnusson, J., Giacomello, S., Asp, M., Westholm, J. O., Huss, M., Mollbrink, A., Linnarsson, S., Codeluppi, S., Borg, Å., Pontén, F., Costea, P. I., Sahlén, P., Mulder, J., Bergmann, O., Lundeberg, J., Frisén, J., 2016. Visualization and analysis of gene expression in tissue sections by spatial transcriptomics. Science 353, 78-82. doi: 10.1126/science.aaf2403

Tasic, B., Menon, V., Nguyen, T. N., Kim, T. K., Jarsky, T., Yao, Z., Levi, B., Gray, L. T., Sorensen, S. A., Dolbeare, T., et al. (2016). Adult mouse cortical cell taxonomy revealed by single cell transcriptomics. Nat. Neurosci. advance online publication.

Thompson, C. L., Pathak, S. D., Jeromin, A., Ng, L. L., MacPherson, C. R., Mortrud, M. T., Cusick, A., Riley, Z. L., Sunkin, S. M., Bernard, A., et al. (2008). Genomic Anatomy of the Hippocampus. Neuron 60, 1010-1021.

Treweek, J. B., Chan, K. Y., Flytzanis, N.C., Yang, B., Deverman, B. E., Greenbaum, A., Lignell, A., Xiao, C., Cai, L., Ladinsky, M. S., et al. (2015). Whole-body tissue stabilization and selective extractions via tissue-hydrogel hybrids for high-resolution intact circuit mapping and phenotyping. Nat. Protoc. 10, 1860-1896.

Van der Maaten, L., and Hinton, G. (2008). Visualizing data using t-SNE. J. Mach. Learn. Res. 9, 85.

Witter, M. P. (1993). Organization of the entorhinal-hippocampal system: A review of current anatomical data. Hippocampus 3, 28-44.

Witter, M. P., and Amaral, D. G. (1991). Entorhinal cortex of the monkey: V. Projections to the dentate gyrus, hippocampus, and subicular complex. J. Comp. Neurol. 307, 437-459.

Yang, B., Treweek, J. B., Kulkarni, R. P., Deverman, B. E., Chen, C.-K., Lubeck, E., Shah, S., Cai, L., and Gradinaru, V. (2014). Single-Cell Phenotyping within Transparent Intact Tissue through Whole-Body Clearing. Cell.

Yang S M, Alvarez D D, Schinder A F. (2015). Reliable Genetic Labeling of Adult-Born Dentate Granule Cells Using Ascl1 CreERT2 and Glast CreERT2 Murine Lines. J Neurosci. 35 (46): 15379-90.

Yi, F., Catudio-Garrett, E., Gabriel, R., Wilhelm, M., Erdelyi, F., Szabo, G., Deisseroth, K., and Lawrence, J. (2015). Hippocampal "cholinergic interneurons" visualized with the choline acetyltransferase promoter: anatomical distribution, intrinsic membrane properties, neurochemical characteristics, and capacity for cholinergic modulation. Front. Synaptic Neurosci. 7.

Zeisel, A., Manchado, A. B. M., Codeluppi, S., Lönnerberg, P., Manno, G. L., Juréus, A., Marques, S., Munguba, H., He, L., Betsholtz, C., et al. (2015). Cell types in the mouse cortex and hippocampus revealed by single-cell RNA-seq. Science aaa1934.

EQUIVALENTS

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A method of barcoding molecular targets in a cell, comprising:
    (a) identifying N molecular targets in a cell, wherein N is greater than 500;
    (b) performing n sequential barcoding rounds, wherein n≥2, and wherein each barcoding round comprises m serial hybridizations of probes collectively hybridized to the N molecular targets, and wherein m≥2, and wherein m serial hybridizations of probes in each barcoding round are generated by:
        (i) contacting one or more groups of probes to a subset of the N molecular targets, the total number of groups of probes corresponding to the number of molecular targets in the subset, wherein probes in each group comprise one or more binding sequences capable of hybridizing to the molecular targets in the subset, wherein each probe is capable of generating at least one detectable signal representing hybridizations of the probes to the molecular targets in the subset, and wherein probes in the one or more groups generate one or more different detectable signals corresponding to the number of molecular targets in the subset;
        (ii) detecting detectable visual signals corresponding to the hybridizations between the one or more groups of probes and the subset of the N molecular targets in an image;
        (iii) super-localizing the detectable visual signals in the image;
        (iv) removing the detectable visual signals, prior to the next serial hybridization;
        (v) repeating steps (i)-(iv), each time with a new group of probes capable of hybridizing to a new subset of the N molecular targets;
    (c) for each barcoding round in n sequential barcoding rounds, generating a composite image by superimposing m images corresponding to m serial hybridizations, wherein m≥2, and wherein the m images are aligned based on one or more alignment references whose positions remain constant relative to the cell, and wherein the detectable signals in the composite image corresponding to the molecular targets are assigned S pseudo-color symbols;
    (d) combining the S pseudo-color symbols from each barcoding round in n sequential barcoding rounds to generate barcodes for the molecular targets, wherein the barcode to each molecular target consists of u unique components, and wherein u≥2, and wherein each unique component in the u unique components is assigned from S unique pseudo-color symbols, and wherein S is an integer that is equal to or greater than $$\sqrt[u]{N},$$

and wherein the molecular targets can be differentiated by one or more differences in their barcodes.

2. The method of claim 1, wherein the one or more alignment references are selected from the group consisting of an oligonucleotide sequence immobilized on a coverslip and detected by a complementary oligo, a common sequence within all probes, a microscopic object, a metal bead, a gold bead, a polystyrene bead, a PCR handle sequence on a primary binding probe, and combinations thereof.

3. The method of claim 1, wherein the n sequential barcoding rounds includes x error correction rounds, where x is an integer equal or greater than 1, and wherein assigning barcodes for the N molecular targets requires S unique pseudo-color symbols, wherein S is an integer equal or greater than $$^{n-x}\sqrt{N}.$$

4. The method of claim 1, wherein the molecular targets comprise nucleic acids, RNA transcripts, proteins, mRNAs, DNA molecules, RNA and DNA isoform molecules, single nucleotide polymorphism molecules, or combinations thereof.

5. The method of claim 4, wherein the molecular targets comprise RNA transcripts and protein molecules.

6. The method of claim 1, further comprising:
identifying secondary molecular targets interacting with the N molecular targets by contacting the cell with molecules capable of binding to the secondary molecular targets.

7. The method of claim 6, wherein the secondary molecular targets comprises RNA binding proteins, ribosomes, DNA binding proteins, transcription factors, chromatin binding proteins, protein binding molecules, scaffold proteins, or combinations thereof.

8. The method of claim 1, wherein the probes in the one or more groups of probes further comprise:
one or more binding sequences, each binding sequence capable of hybridizing to one or more sites on a molecular target;
one or more readout probe binding sequences, wherein in each barcoding round, only one readout probe binding sequence is associated with a detectable signal for a molecular target, and wherein each readout probe binding sequence is capable of hybridizing a readout probe.

9. The method of claim 8, wherein each probe comprises one or more readout probe binding sequences.

10. The method of claim 9, wherein the binding sequence comprises an overhang sequence.

11. The method of claim 10, wherein the readout probe binding sequences hybridize to readout probes through one or more intermediate molecules.

12. The method of claim 11, wherein the one or more intermediate molecules are selected from the group consisting of RNA bridge probes, DNA bridge probes, protein bridge probes, hybridization chain reaction (HCR) probes, hairpin nucleic acid probes, HCR initiators, HCR polymers, and combinations thereof.

13. The method of claim 8, wherein the one or more binding sequences specifically bind to one or more non-nucleic acid sites on the molecular targets.

14. The method of claim 1, wherein the one or more binding sequences hybridize to different binding sites within the same molecular target.

15. The method of claim 1, wherein the one or more binding sequences hybridize to different binding sites within different molecular targets.

16. The method of claim 1, wherein a signal moiety is linked to the binding sequence of a probe or an intermediate molecule via a cleavable linker.

17. The method of claim 1, wherein the S pseudo-color symbols comprise colors, numbers, letters, shapes, or combinations thereof.

18. The method of claim 1, wherein, for each serial hybridization, the one or more groups of probes hybridize to non-overlapping subsets of the N molecular targets.

19. The method of claim 1, wherein one of the S unique pseudo-color symbols is a null signal.

20. The method of claim 1, wherein N is greater than 720; 1,728; 10,312; 20,736; or 78,125 targets.

21. The method of claim 1, wherein the probes comprise oligonucleotides and at least one of antibodies or antibody fragments.

22. A method of barcoding molecular targets in a cell, comprising:
(a) identifying N molecular targets in a cell, wherein N is greater than 500;
(b) performing n sequential barcoding rounds, wherein n≥2, and wherein each barcoding round comprises m serial bindings of probes collectively bound to the N molecular targets, and wherein m≥2, and wherein m serial bindings of probes in each barcoding round are generated by:
  i. contacting one or more groups of probes to a subset of the N molecular targets, the total number of groups of probes corresponding to the number of molecular targets in the subset, wherein probes in each group comprise one or more binding sequences capable of binding to the molecular targets in the subset, wherein each probe is capable of generating at least one detectable signal representing bindings of the probes to the molecular targets in the subset, and wherein probes in the one or more groups generate one or more different detectable signals corresponding to the number of molecular targets in the subset;
  ii. detecting detectable visual signals corresponding to the bindings between the one or more groups of probes and the subset of the N molecular targets in an image;
  iii. super-localizing the detectable visual signals in the image;
  iv. removing the detectable visual signals, prior to the next serial bindings;
  v. repeating steps (i)-(iv), each time with a new group of probes capable of binding to a new subset of the N molecular targets;
(c) for each barcoding round in n sequential barcoding rounds, generating a composite image by superimposing m images corresponding to m serial bindings, wherein m≥2, and wherein the m images are aligned based on one or more alignment references whose positions remain constant relative to the cell, and wherein the detectable signals in the composite image corresponding to the molecular targets are assigned S pseudo-color symbols;
(e) combining the S pseudo-color symbols from each barcoding round in n sequential barcoding rounds to generate barcodes for the molecular targets, wherein the barcode to each molecular target consists of u unique components, and wherein u≥2, and wherein each unique component in the u unique components is assigned from S unique pseudo-color symbols, and wherein S is an integer that is equal to or greater than $\sqrt[n]{N}$, and wherein the molecular targets can be differentiated by one or more differences in their barcodes.

23. The method of claim 22, wherein the molecular targets comprise nucleic acids, RNA transcripts, proteins, mRNAs, DNA molecules, RNA and DNA isoform molecules, single nucleotide polymorphism molecules, or combinations thereof.

24. The method of claim 23, wherein the molecular targets comprise RNA transcripts and protein molecules.

25. The method of claim 22, wherein the probes are selected from proteins, antibodies, antibody fragments, oligonucleotides, and combinations thereof.

26. The method of claim 25, wherein the probes comprise oligonucleotides and at least one of antibodies or antibody fragments.

27. A method of barcoding molecular targets in a cell, comprising:
  (a) identifying N molecular targets in a cell;
  (b) performing n sequential barcoding rounds, wherein $n \geq 2$, and wherein each barcoding round comprises m serial bindings of probes collectively bound to the N molecular targets, and wherein $m \geq 2$, and wherein m serial bindings of probes in each barcoding round are generated by:
    i. contacting one or more groups of probes to a subset of the N molecular targets, the total number of groups of probes corresponding to the number of molecular targets in the subset, wherein probes in each group comprise one or more binding sequences capable of binding to the molecular targets in the subset, wherein each probe is capable of generating at least one detectable signal representing bindings of the probes to the molecular targets in the subset, and wherein probes in the one or more groups generate one or more different detectable signals corresponding to the number of molecular targets in the subset;
    ii. detecting detectable visual signals corresponding to the bindings between the one or more groups of probes and the subset of the N molecular targets in an image;
    iii. removing the detectable visual signals, prior to the next serial bindings;
    iv. repeating steps (i)-(iii), each time with a new group of probes capable of binding to a new subset of the N molecular targets;
  (c) for each barcoding round in n sequential barcoding rounds, generating a composite image by superimposing m images corresponding to m serial bindings, wherein $m \geq 2$, and wherein the m images are aligned based on one or more alignment references whose positions remain constant relative to the cell, and wherein the detectable signals in the composite image corresponding to the molecular targets are assigned S pseudo-color symbols;
  (f) combining the S pseudo-color symbols from each barcoding round in n sequential barcoding rounds to generate barcodes for the molecular targets, wherein the barcode to each molecular target consists of u unique components, and wherein $u \geq 2$, and wherein each unique component in the u unique components is assigned from S unique pseudo-color symbols, and wherein S is an integer that is equal to or greater than $\sqrt[u]{N}$, and wherein the molecular targets can be differentiated by one or more differences in their barcodes.

* * * * *